United States Patent

[19]

Nova et al.

[11] Patent Number: 6,136,274
[45] Date of Patent: Oct. 24, 2000

[54] MATRICES WITH MEMORIES IN AUTOMATED DRUG DISCOVERY AND UNITS THEREFOR

[75] Inventors: Michael P. Nova, Rancho Santa Fe; John E. Lillig, Poway; Kanchana Sanjaya Gunesekera Karunaratne, San Diego; Donald O'Neil, San Diego; William Ewing, San Diego; Yozo Satoda, San Diego, all of Calif.

[73] Assignee: IRORI, San Diego, Calif.

[21] Appl. No.: 08/958,254

[22] Filed: Oct. 7, 1997

Related U.S. Application Data

[63] Continuation-in-part of application No. 08/912,998, Aug. 11, 1997, which is a continuation-in-part of application No. 08/826,253, Mar. 27, 1997, which is a continuation-in-part of application No. 08/857,800, Jan. 22, 1997, which is a continuation-in-part of application No. 08/788,594, Jan. 23, 1997, abandoned, which is a continuation-in-part of application No. 08/741,685, Oct. 31, 1996, abandoned, which is a continuation-in-part of application No. 08/743,984, Oct. 28, 1996, which is a continuation-in-part of application No. 08/726,703, Oct. 7, 1996, abandoned.

[51] Int. Cl.[7] ........................................................ B01L 3/00
[52] U.S. Cl. ........................... 422/102; 422/101; 422/104; 435/288.4; 435/288.5; 435/297.1; 435/303.1; 435/305.2; 935/88
[58] Field of Search ..................................... 422/101, 102, 422/104; 935/88; 435/288.4, 288.5, 297.1, 303.1, 305.2

[56] References Cited

U.S. PATENT DOCUMENTS

| | | |
|---|---|---|
| 4,020,830 | 5/1977 | Johnson et al. . |
| 4,133,642 | 1/1979 | Nosaka et al. . |
| 4,176,260 | 11/1979 | Ward et al. . |
| 4,177,253 | 12/1979 | Davies et al. . |
| 4,297,337 | 10/1981 | Mansfield . |
| 4,452,773 | 6/1984 | Molday . |
| 4,680,268 | 7/1987 | Clark, Jr. . |
| 4,784,162 | 11/1988 | Ricks et al. . |

(List continued on next page.)

FOREIGN PATENT DOCUMENTS

| | | |
|---|---|---|
| 0226979 A2 | 12/1986 | European Pat. Off. . |
| 0420177 A1 | 9/1990 | European Pat. Off. . |

(List continued on next page.)

OTHER PUBLICATIONS

Baldwin et al., Synthesis of a small molecule combinatorial library encoded with molecular tags, *J. Am. Chem. Soc.* 117:5588 (1995.

(List continued on next page.)

*Primary Examiner*—Jan Ludlow
*Attorney, Agent, or Firm*—Brown, Martin, Haller & McClain

[57] ABSTRACT

Automated drug discovery protocols, or partially automated protocols, in which matrices-with-memories serve as the platform on which all manipulations are performed or serve as the repository of information that is transferred to other memories as the synthesized compounds are processed and screened. Also provided are automated drug discovery units for use in the protocols. The units provide for seamless data tracking and include instrumentation and vials with memories for information transfer to other memories in a unit. The units, which are provided herein, include some or all of the following: an automated or manual sorter, microreactors and microvessels, which contain memories, an automated or semi-automated synthesizer, a microreactor washer/dryer, a manual or automated cleaver with a valved U-tube outlet for removing compounds from the matrix-with-memory microreactors, and associated software. The memories may be any of any type, including electromagnetically encodable memories and optical memories, or combinations thereof. The memories may be pre-encoded or may be encodable during, after or before processing. Also provided are manual and automated methods for sorting matrices with memories.

18 Claims, 47 Drawing Sheets

U.S. PATENT DOCUMENTS

| | | |
|---|---|---|
| 4,816,513 | 3/1989 | Bidgham et al. . |
| 4,821,920 | 4/1989 | Lin et al. . |
| 4,848,559 | 7/1989 | Hoppmann et al. . |
| 4,855,583 | 8/1989 | Fraser et al. . |
| 4,855,909 | 8/1989 | Vincent et al. . |
| 4,857,893 | 8/1989 | Carroll . |
| 4,915,564 | 4/1990 | Eror et al. . |
| 4,966,154 | 10/1990 | Cooper et al. . |
| 4,975,647 | 12/1990 | Downer et al. . |
| 4,995,467 | 2/1991 | Niemann . |
| 5,043,222 | 8/1991 | Cherukuri . |
| 5,046,496 | 9/1991 | Betts et al. . |
| 5,047,371 | 9/1991 | Cherukuri . |
| 5,053,115 | 10/1991 | Wienberger et al. . |
| 5,075,077 | 12/1991 | Durley, III et al. . |
| 5,093,982 | 3/1992 | Gussman . |
| 5,108,819 | 4/1992 | Heller et al. . |
| 5,128,528 | 7/1992 | Heninger . |
| 5,130,362 | 7/1992 | Prasad et al. . |
| 5,149,629 | 9/1992 | Rishpon et al. . |
| 5,152,758 | 10/1992 | Kaetsu et al. . |
| 5,156,810 | 10/1992 | Ribi . |
| 5,157,262 | 10/1992 | Marsoner et al. . |
| 5,184,003 | 2/1993 | McMillan et al. . |
| 5,186,336 | 2/1993 | Pippin et al. . |
| 5,211,129 | 5/1993 | Taylor et al. . |
| 5,262,305 | 11/1993 | Heller et al. . |
| 5,267,151 | 11/1993 | Ham et al. . |
| 5,268,862 | 12/1993 | Rentzepis . |
| 5,273,715 | 12/1993 | Bridgham et al. . |
| 5,273,905 | 12/1993 | Muller et al. . |
| 5,314,058 | 5/1994 | Graham . |
| 5,318,676 | 6/1994 | Sailor et al. . |
| 5,360,728 | 11/1994 | Prasher . |
| 5,380,589 | 1/1995 | Goodman et al. . |
| 5,405,783 | 4/1995 | Pirrung et al. . |
| 5,411,647 | 5/1995 | Johnson et al. . |
| 5,415,999 | 5/1995 | Saul et al. . |
| 5,421,816 | 6/1995 | Lipkovker . |
| 5,422,266 | 6/1995 | Cormier et al. . |
| 5,431,691 | 7/1995 | Snell et al. . |
| 5,435,937 | 7/1995 | Bell et al. . |
| 5,437,284 | 8/1995 | Trimble . |
| 5,443,953 | 8/1995 | Hansen et al. . |
| 5,447,533 | 9/1995 | Vachon et al. . |
| 5,482,867 | 1/1996 | Barrett et al. . |
| 5,498,545 | 3/1996 | Vestal . |
| 5,516,491 | 5/1996 | Kath et al. ............................... 422/102 |
| 5,521,601 | 5/1996 | Kandlur et al. . |
| 5,541,061 | 7/1996 | Fodor et al. . |
| 5,545,531 | 8/1996 | Rava et al. . |
| 5,634,562 | 6/1997 | Isaacs . |
| 5,751,629 | 5/1998 | Nova et al. . |
| 5,770,157 | 6/1998 | Cargill et al. ............................. 422/99 |
| 5,888,830 | 3/1999 | Mohan et al. .......................... 436/174 |

FOREIGN PATENT DOCUMENTS

| | | |
|---|---|---|
| 0410688 A2 | 1/1991 | European Pat. Off. . |
| 0554955 A1 | 8/1993 | European Pat. Off. . |
| 0569215 A3 | 11/1993 | European Pat. Off. . |
| 0633468 | 5/1994 | European Pat. Off. . |
| 4313807 | 4/1993 | Germany . |
| 4213065 A1 | 10/1993 | Germany . |
| 4301401 A1 | 7/1994 | Germany . |
| 2129551 | 5/1984 | United Kingdom . |
| WO 9400602 | 1/1994 | WIPO . |
| WO 9424642 | 10/1994 | WIPO . |
| WO 9501569 | 1/1995 | WIPO . |
| WO 9529473 | 11/1995 | WIPO . |
| WO 9624061 | 8/1996 | WIPO . |
| WO 9720073 | 6/1997 | WIPO . |

OTHER PUBLICATIONS

Combinatorial chemistry—playing electronic tag, *Chem. & Indust. Magaz. News*, Nov. 6, 1995.

Czarnik et al., No static at all, *Chemistry in Britain*, pp. 39–41 (Oct., 1996).

Ohlmeyer et al., "Complex synthetic chemical libraries indexed with molecular tags", *Proc. Natl. Acad. Sci.* 90:10922–10926, (1993).

Service, Memory enhanced microreactor chemistry, *Science* 270:577 (1995).

Xiao–yi et al., Combinatorial chemistry with laser optical encoding, *Angew Chem. Int. Ed. Engl.* 36(7): 780–782 (1997).

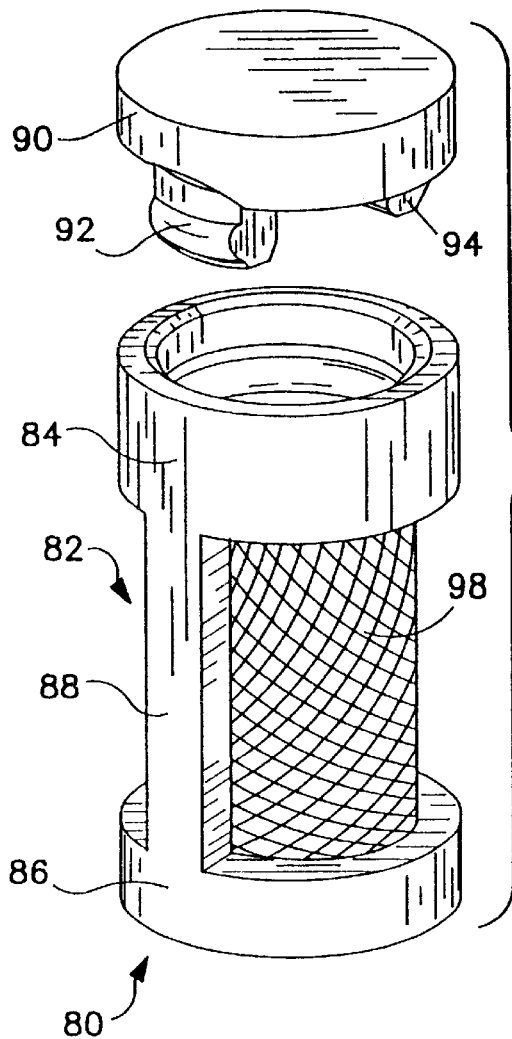
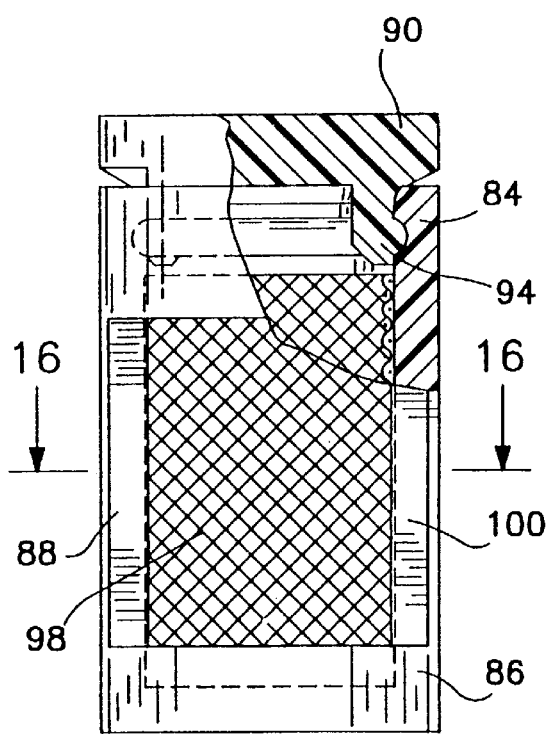
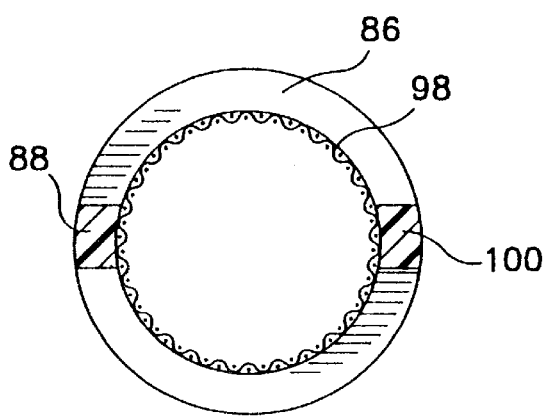
FIG. 2
FIG. 3
FIG. 4

FIG. 30

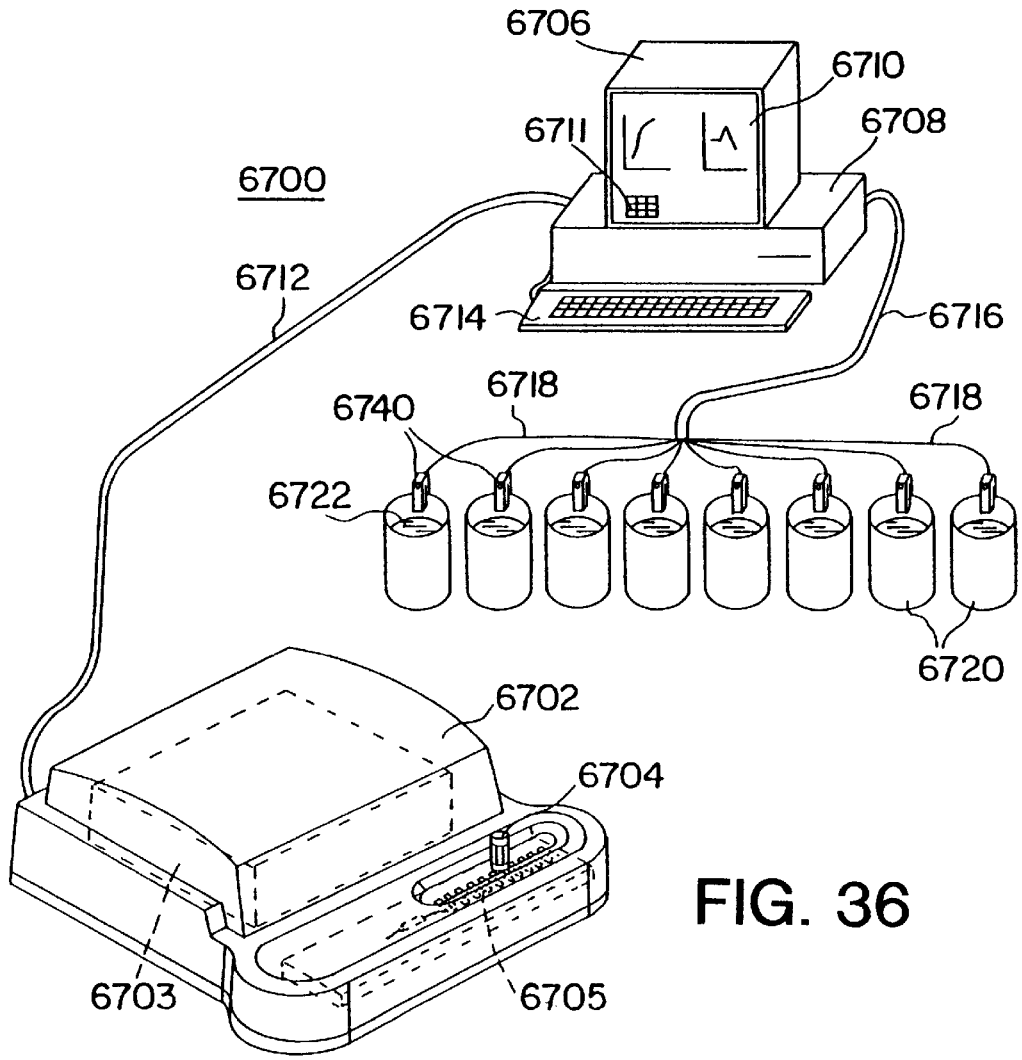
FIG. 36
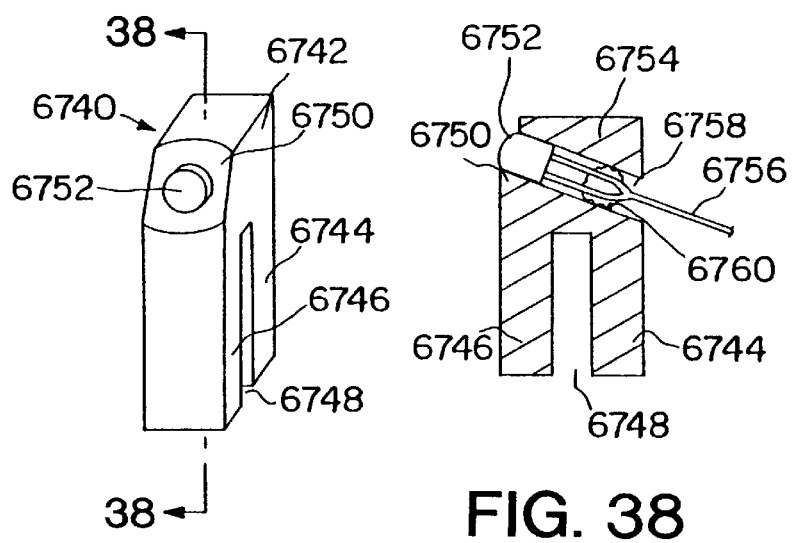
FIG. 37
FIG. 38

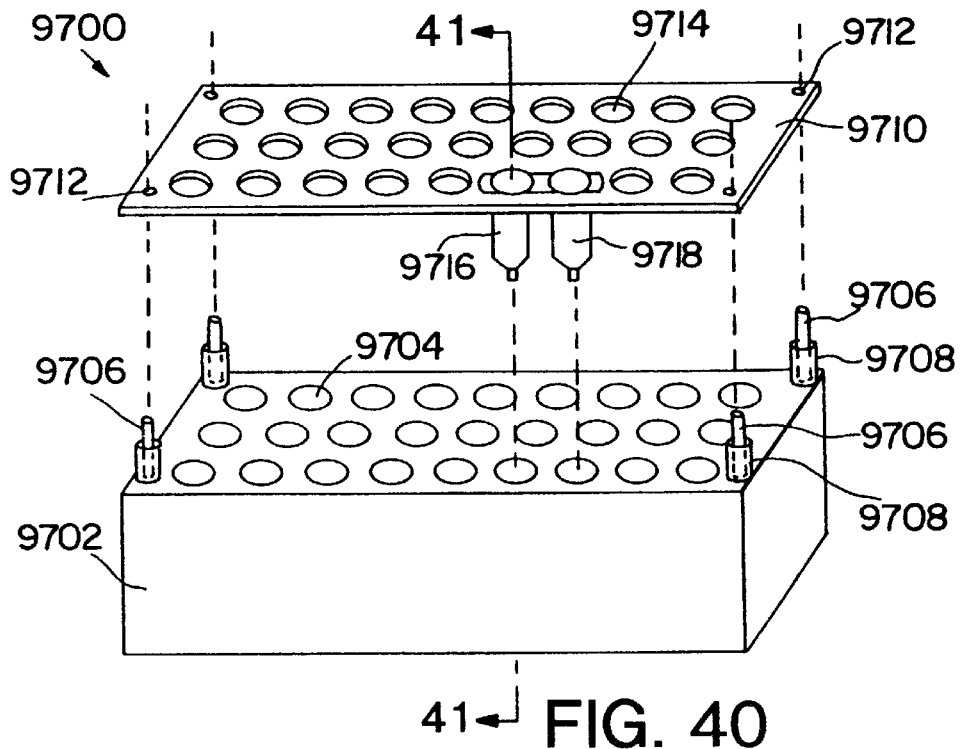
FIG. 40
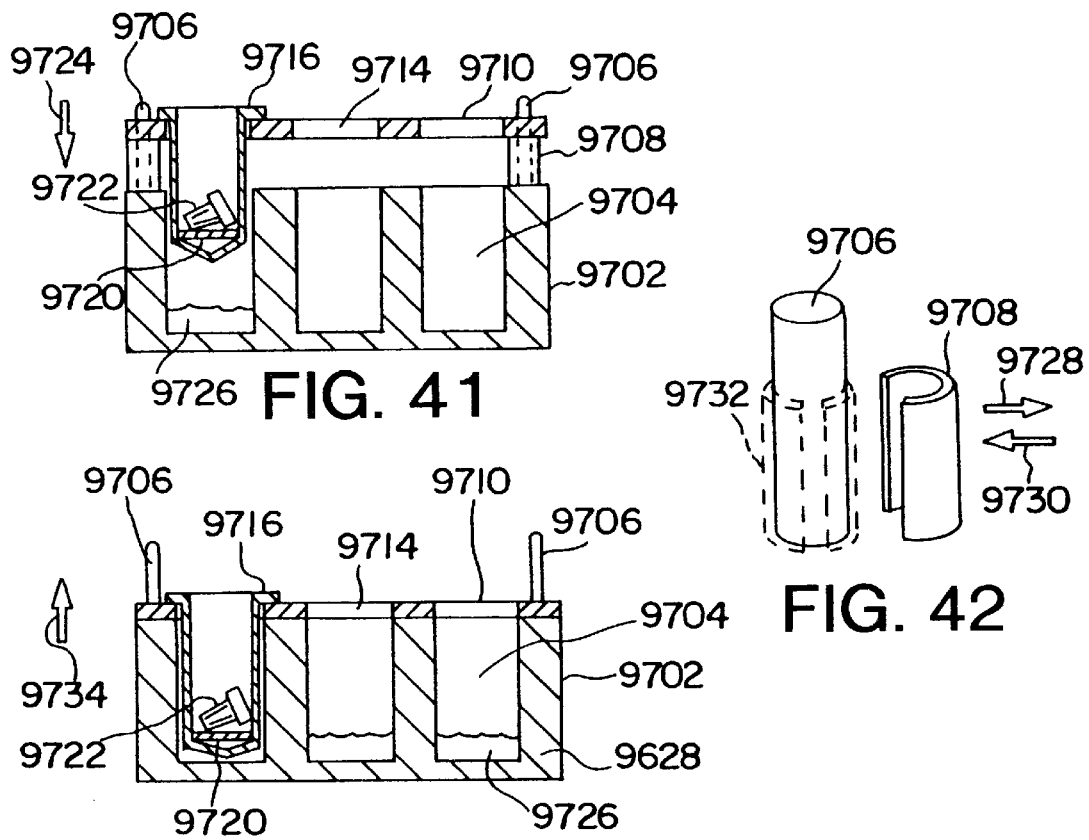
FIG. 41
FIG. 42
FIG. 43

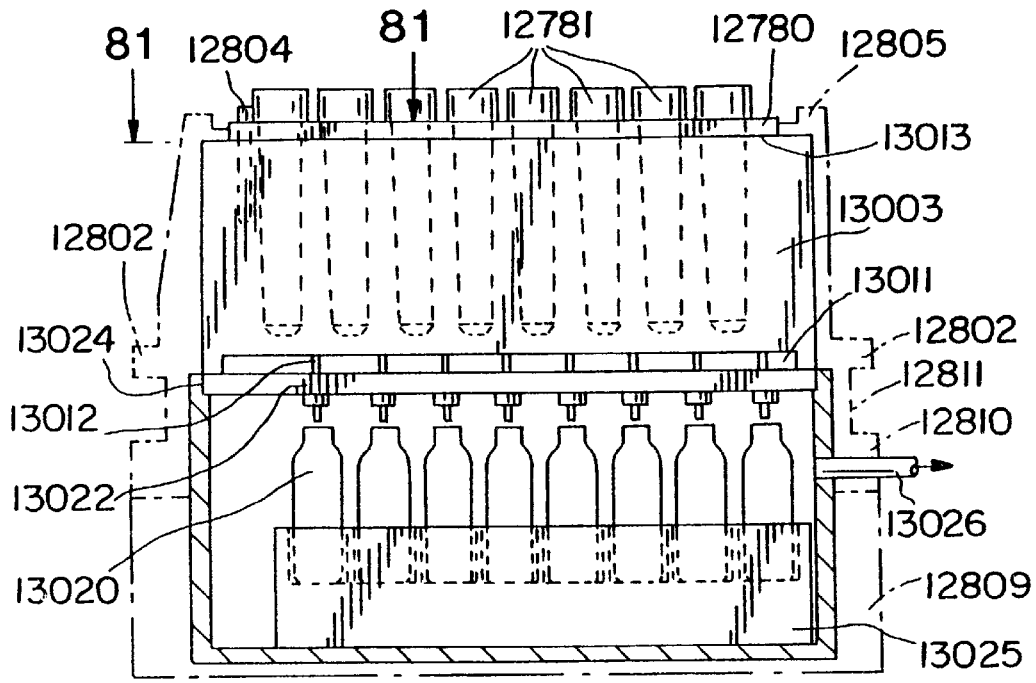
FIG. 80
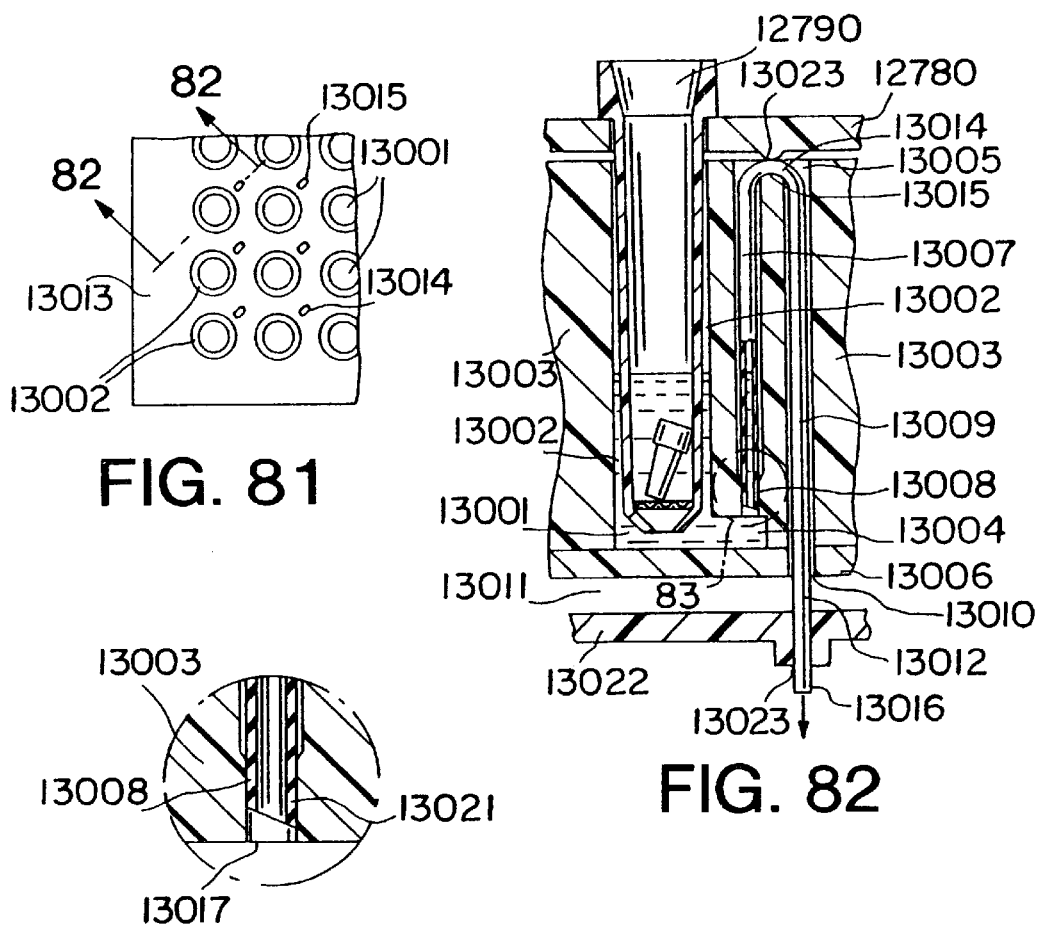
FIG. 81
FIG. 82
FIG. 83

MATRICES WITH MEMORIES IN AUTOMATED DRUG DISCOVERY AND UNITS THEREFOR

RELATED APPLICATIONS

For any U.S. National Stage purposes this application is a continuation-in-part of U.S. application Ser. No. 08/912,998, filed Aug. 11, 1997, which is a continuation-in-part of U.S. application Ser. No. 08/826,253, filed Mar. 27, 1997 which is a continuation-in-part of U.S. application Ser. Nos. 08/857,800 filed Jan. 22, 1997 and 08/788,594 (now abandoned) filed Jan. 23, 1997 which are continuations-in-part of U.S. application Ser. No. 08/741,685, filed Oct. 31, 1996 now abandoned, which is a continuation-in-part of U.S. application Ser. No. 08/743,984, filed Oct. 28, 1996, which is a continuation-in-part of U.S. application Ser. No. 08/726,703, entitled "SORTING MATRICES WITH MEMORIES, SENSORS WITH MEMORIES AND USES THEREOF", filed Oct. 7, 1996, now abandoned.

For international purposes priority to each of the above-noted applications is claimed herein:

This application is also related to U.S. application Ser. No. 08/881,248, filed Jun. 24, 1997, now abandoned, International PCT application No. PCT/US96/15999, published as WO 97/12680, filed as an International PCT application in the US/RO on Oct. 3, 1996; U.S. application Ser. No. 08/723,423, filed on Sep. 30, 1996, now U.S. Pat. No 5,961,923; U.S. application Ser. No. 08/709,435, filed on Sep. 6, 1996, now U.S. Pat. No. 6,017,496; U.S. application Ser. No. 08/711,426, filed on Sep. 5, 1996; U.S. application Ser. No. 08/669,252, filed on Jun. 24, 1996; U.S. application Ser. No. 08/633,410, filed on Jun. 10, 1996; International PCT application No. PCT/US96/06145 which designates the U.S. and which was filed on Apr. 25, 1996 and published as WO 96/36436; and U.S. application Ser. No. 08/639,813, filed Apr. 2, 1996 and now abandoned.

This application is also related to U.S. application Ser. No. 08/567,746, filed Dec. 5, 1995; and U.S. application Ser. No. 08/538,387, filed Oct. 3, 1995 now issued as U.S. Pat. No. 5,874,214. This application is also related to each of U.S. applications Ser. Nos. 08/428,662, filed Apr. 25, 1995, now U.S. Pat. No. 5,741,462; 08/473,660, filed Jun. 7, 1995; 08/480,147, filed Jun. 7, 1995; 08/480,196, filed Jun. 7, 1995, now U.S. Pat. No. 5,925,562; 08/484,504, filed Jun. 7, 1995, now U.S. Pat. No. 5,751,629; and 08/484,486, filed Jun. 7, 1995.

Where permitted, the subject matter of each of above-noted U.S. applications and International PCT applications is incorporated herein by reference in its entirety.

REFERENCE TO COMPUTER APPENDICES

For U.S. purposes, a five Computer Appendices containing computer program source code for programs described herein has been submitted concurrently with the filing of this application. The Computer Appendices will be converted to a Microfiche Appendices pursuant to 37 C.F.R. 1.96(b). The Computer Appendices, which are referred to hereafter as the "Microfiche Appendix I", "Microfiche Appendix II", "Microfiche Appendix III", "Microfiche Appendix IV" and Microfiche Appendix V", are each incorporated herein by reference in its entirety.

Thus, a portion of the disclosure of this patent document contains material that is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention relates to the application of information and data storage and retrieval technology to drug discovery, including molecular tracking and identification and to biological, chemical, immunological and biochemical assays. The methods, combinations, and devices provided herein permit synthetic chemistry to be linked to analysis and high throughput screening on the same platform with seamless remote informatics management.

BACKGROUND OF THE INVENTION

Drug Discovery

Drug discovery relies on the ability to identify compounds that interact with a selected target, such as cells, an antibody, receptor, enzyme, transcription factor or the like. Traditional drug discovery relied on collections or "libraries" obtained from proprietary databases of compounds accumulated over many years, natural products, fermentation broths, and rational drug design. Recent advances in molecular biology, chemistry and automation have resulted in the development of rapid, High throughput screening (HTS) protocols to screen these collection. In connection with HTS, methods for generating molecular diversity and for detecting, identifying and quantifying biological or chemical material have been developed. These advances have been facilitated by fundamental developments in chemistry, including the development of highly sensitive analytical methods, solid state chemical synthesis, and sensitive and specific biological assay systems.

Analyses of biological interactions and chemical reactions, however, require the use of labels or tags to track and identify the results of such analyses. Typically biological reactions, such as binding, catalytic, hybridization and signaling reactions, are monitored by labels, such as radioactive, fluorescent, photoabsorptive, luminescent and other such labels, or by direct or indirect enzyme labels. Chemical reactions are also monitored by direct or indirect means, such as by linking the reactions to a second reaction in which a colored, fluorescent, chemiluminescent or other such product results. These analytical methods, however, are often time consuming, tedious and, when practiced in vivo, invasive. In addition, each reaction is typically measured individually, in a separate assay. There is, thus, a need to develop alternative and convenient methods for tracking and identifying analytes in biological interactions and the reactants and products of chemical reactions.

Combinatorial Libraries

The provision and maintenance of compounds to support HTS have become critical. New methods for the lead generation and lead optimization have emerged to address this need for diversity. Among these methods is combinatorial chemistry, which has become a powerful tool in drug discovery and materials science. Methods and strategies for generating diverse libraries, primarily peptide- and nucleotide-based oligomer libraries, have been developed using molecular biology methods and/or simultaneous chemical synthesis methodologies [see, e.g., Dower et al. (1991) *Annu. Rep. Med. Chem.* 26:271–280; Fodor et al. (1991) *Science* 251:767–773; Jung et al. (1992) *Angew. Chem. Ind. Ed. Engl.* 31:367–383; Zuckerman et al. (1992) *Proc. Natl. Acad. Sci. USA* 89:4505–4509; Scott et al. (1990) *Science* 249:386–390; Devlin et al. (1990) *Science* 249:404–406; Cwirla et al. (1990) *Proc. Natl. Acad. Sci.*

USA 87:6378–6382; and Gallop et al. (1994) *J. Medicinal Chemistry* 37:1233–1251]. The resulting combinatorial libraries potentially contain millions of pharmaceutically relevant compounds and that can be screened to identify compounds that exhibit a selected activity.

The libraries fall into roughly three categories: fusion-protein-displayed peptide libraries in which random peptides or proteins are presented on the surface of phage particles or proteins expressed from plasmids; support-bound synthetic chemical libraries in which individual compounds or mixtures of compounds are presented on insoluble matrices, such as resin beads [see, e.g., Lam et al. (1991) *Nature* 354:82–84] and cotton supports [see, e.g., Eichler et al. (1993) *Biochemistry* 32:11035–11041]; and methods in which the compounds are used in solution [see, e.g., Houghten et al. (1991) *Nature* 354:84–86, Houghten et al. (1992) *BioTechniques* 313:412–421; and Scott et al. (1994) *Curr. Opin. Biotechnol.* 5:40–48]. There are numerous examples of synthetic peptide and oligonucleotide combinatorial libraries. The present direction in this area is to produce combinatorial libraries that contain non-peptidic small organic molecules. Such libraries are based on either a basis set of monomers that can be combined to form mixtures of diverse organic molecules or that can be combined to form a library based upon a selected pharmacophore monomer.

There are three critical aspects in any combinatorial library: (i) the chemical units of which the library is composed; (ii) generation and categorization of the library, and (iii) identification of library members that interact with the target of interest, and tracking intermediary synthesis products and the multitude of molecules in a single vessel. The generation of such libraries often relies on the use of solid phase synthesis methods, as well as solution phase methods, to produce collections containing tens of millions of compounds that can be screened in diagnostically or pharmacologically relevant in vitro assay systems. In generating large numbers of diverse molecules by stepwise synthesis, the resulting library is a complex mixture in which a particular compound is present at very low concentrations, so that it is difficult or impossible to determine its chemical structure. Various methods exist for ordered synthesis by sequential addition of particular moieties, or by identifying molecules based on spacial positioning on a chip. These methods are cumbersome and ultimately impossible to apply to highly diverse and large libraries. Identification of library members that interact with a target of interest, and tracking intermediary synthesis products and the multitude of molecules in a single vessel is also a problem. While considerable efforts have been devoted to the development of solid support chemistry, the choice of methods for structural elucidation has been limited to spatial addressing, mixture deconvolution, direct microanalysis and chemical tagging [see, e.g., Metzger et al. (1994) *Jung, Anal. Biochem.* 219:261; Brown et al. (1995) *Mol. Diversity* 1:4; Youngquist et al. (1995) *J. Am. Chem. Soc.* 177:3900; Brummel et al. (1994) *Science* 264:399; Brenner et al. (1992) *Proc. Natl. Acad. Sci. U.S.A.* 89: 5381; Needles et al. (1993) *Proc. Natl. Acad. Sci. U.S.A.* 90:10700; Ohimeyer et al. *Proc. Natl. Acad. Sci. U.S.A.* 90: 10922; Eckes (1994) *Angew. Chem. Int. Ed. Engl.* 33:1573; Ni et al. (1996) *J. Med. Chem.* 39:1601]. Tagging, especially non-chemical, non-invasive tagging, is potentially the most efficient and reliable structural tracking method.

High Throughput Screening

In addition, exploitation of this diversity requires development of methods for rapidly screening compounds. Advances in instrumentation, molecular biology and protein chemistry and the adaptation of biochemical activity screens into microplate formats, has made it possible to screen of large numbers of compounds. Also, because compound screening has been successful in areas of significance for the pharmaceutical industry, high throughput screening (HTS) protocols have assumed importance. Presently, there are hundreds of HTS systems operating throughout the world, which are used, not only for compound screening for drug discovery, but also for immunoassays, cell-based assays and receptor-binding assays.

An essential element of high throughput screening for drug discovery process and areas in which molecules are identified and tracked, is the ability to extract the information made available during synthesis and screening of a library, identification of the active components of intermediary structures, and the reactants and products of assays. While there are several techniques for identification of intermediary products and final products, nanosequencing protocols that provide exact structures are only applicable on mass to naturally occurring linear oligomers such as peptides and amino acids. Mass spectrographic [MS] analysis is sufficiently sensitive to determine the exact mass and fragmentation patterns of individual synthesis steps, but complex analytical mass spectrographic strategies are not readily automated nor conveniently performed. Also, mass spectrographic analysis provides at best simple connectivity information, but no stereoisomeric information, and generally cannot discriminate among isomeric monomers. Another problem with mass spectrographic analysis is that it requires pure compounds; structural determinations on complex mixtures is either difficult or impossible. Finally, mass spectrographic analysis is tedious and time consuming. Thus, although there are a multitude of solutions to the generation of libraries and to screening protocols, there are no ideal solutions to the problems of identification, tracking and categorization.

These problems arise in any screening or analytical process in which large numbers of molecules or biological entities are screened. In any system, once a desired molecule (s) has been isolated, it must be identified. Simple means for identification do not exist. Because of the problems inherent in any labeling procedure, it would be desirable to have alternative means for tracking and quantitating chemical and biological reactions during synthesis and/or screening processes, and for automating such tracking and quantitating.

Therefore, it is an object herein to provide methods for identification, tracking and categorization of the components of complex mixtures of diverse molecules. It is also an object herein to provide products for such identification, tracking and categorization and to provide assays, diagnostics and screening protocols that use such products. It is of particular interest herein to provide means to track and identify compounds and to perform HTS protocols.

SUMMARY OF THE INVENTION

Drug discovery units for effecting drug discovery protocols are provided. The drug discovery protocols and integrated software therefor are also provided. A drug discovery unit provides a means for seamless data tracking between and among the components of the units in which all critical components, including instrumentation and vials contain are associated with memories. The memories provide the means for seamless transfer information to other memories in a unit. The units and protocols, which are automated protocols, or partially automated protocols, rely on the use matrices-with-memories as the platform on which all manipulations are performed and/or as the repository of information that is transferred to other memories as synthesized compounds are processed and screened are provided. Protocols in which a series of matrices with memories are used and information is transferred from one memory to another are also provided. In particular, protocols in which all steps, including synthesis and screening or assaying, are performed on a single platform are provided herein. The units [see, e.g., FIGS. 25–27 for diagrammatic representations], which are provided herein, include some or all of the following: an automated or manual sorter, matrices-with-memories, which contain memories, an automated or semi-automated synthesizer, a matrix-with memory washer/dryer, a manual or automated cleaver for removing compounds from the matrices-with-memories, and a host computer associated software. The memories may be any of any type, including electromagnetically encodable/readable memories and optical memories, or combinations thereof. The memories may be pre-encoded or may be encodable during, after or before processing. Memories which may be remotely encoded are presently preferred. In some embodiments, however, memories associated with certain of the components, such as instrumentation or vials used therewith, may be pre-encoded for convenience and ease of reuse.

The drug discovery unit can encompass an entire laboratory that is augmented with memories linked to or proximate to every container, instrument, and device, from reagent bottle to collected fraction, used in a particular protocol, whereby a sample may be tracked. Software that integrates and provides communication links among the devices and instruments will also be included. The information that is stored will include information regarding the identity of a sample and/or source of the sample. Information can be transferred from one container, instrument, vessel, etc., during synthesis and screening.

Combinations of matrix materials with programmable data storage or recording devices or other memory means, herein referred to as memories, and assays using these combinations are provided. The combinations are referred to herein as matrices-with-memories. These combinations serve as a common platform for all aspects of drug discovery, including synthesis, screening and storage. Detailed descriptions of the matrices-with-memories, their preparation and use, including numerous assay protocols, have been described in the copending and allowed applications enumerated above, including U.S. application Ser. Nos. 08/428,662, 08/480,147, 08/484,486, 08/484,504, 08/480,196, 08/473,660, 08/538,387, 08/567,746, 08/639, 813, 08/711,426, 08/709,435, 08/723,423, 08/633,410, 08/669,252, 08/726,703, 08/743,984, 08/741,685, 08/857, 800, 08/826,253 and 08/912,998, as well as published International PCT application Nos. WO 96/36436 and WO 97/12680.

Of particular interest herein, are multiprotocol applications (such as multiplexed assays or coupled synthetic and assay protocols) in which the matrices with memories are used in a series (more than one) of reactions, a series [more than one] of assays, and/or a series of more or more reactions and one or more assays, typically on a single platform or coupled via automated analysis instrumentation. As a result synthesis, particularly combinatorial syntheses of libraries, is coupled to screening, including compound identification and analysis, where needed.

Manual, and/or automated or partially automated systems are provided for directing synthesis and screening, or other protocols. Such systems include apparatus and software to provide protocols and to implement the protocols. In one embodiment, a manual system includes a sorter, a device for reading and/or writing to the memories of the matrices-with-memories, and a host computer for storing identification data and for running operational and, in some cases, analytical software. The manual sorter includes an apparatus to assist the user in identifying a particular matrix-with-memory and its intended destination by generating an indication, such as visual or audio cue, corresponding to the proper destination of the matrix-with-memory, thus simplifying, expediting and improving the accuracy of the synthetic and screening protocols.

The host computer includes a database with identifying information and software for directing the selected protocol (s). The identifying information may include the source of the particular matrix-with-memory, the identity of linked molecules or biological particles, and the destination of that matrix-with-memory. Once the destination of the matrix-with-memory has been determined, the computer system generates a cue to indicate the proper destination of the matrix-with-memory, directing the user to manually place the matrix-with-memory at the designated destination.

In another embodiment, an automated sorting device loads, reads from and/or writes to the matrix-with-memory, and automatically moves the matrix-with-memory to the proper location as indicated by the protocols. The host computer includes all software necessary for implementing the protocols and for controlling the loading, reading/ writing, and positioning operations of the sorter. The loading operation of the sorter is implemented using a feeder with a vessel which holds a plurality of matrices-with-memories. The feeder, such as a vibratory feeder, takes the matrices-with-memories from the vessel and feeds them one at a time to a singulator which dispenses a matrix-with-memory after a pre-determined delay to a positioner. The positioner includes a release gate which, when a release command is received from the host computer, opens to release the matrix-with-memory. A read/write station is located within a reading distance from the positioner for reading from or writing to the matrix-with-memory. A translator moves the positioner to a destination that is pre-determined by the host computer once the identity of the matrix-with-memory has been established. The destination is a container selected from an array of containers within a sorter tray that has addressable coordinates.

Automated and manual cleavers for cleaving compounds and molecules from matrices-with-memories are provided for use separately or in combination with the sorting devices. In one embodiment, the automated cleaver includes a cleaving block with a least one vessel with a drain. A vacuum chamber is attached to the cleaving block for drawing fluid through the vessel into a fluid communication means such as a tube or channel which extends from the vessel drain to a well within a container enclosed in the vacuum chamber. The cleaved fluid is captured within the well for subsequent analysis. The fluid communication means includes an inverted U-tube which has one end attached to the drain and another end positioned above the well. A fluid trap is provided below the vessel to prevent fluid from flowing through the U-tube in the absence of a partial vacuum within the vacuum chamber.

Also provided are robotic methods for synthesizing and screening compounds using the matrices-with-memories provided herein for supports and the assays provided herein for screening. The robotic methods incorporate the automated sorting device and software such as that provided herein. The robotic methods also can incorporate the methods in which one memory with matrix is used to transmit information to another memory. Also provided herein, is the fully automated and communicating laboratory in which all aspects of synthesis and screening are automated and/or communicated from one container or instrument to another, thereby tracking and following the synthesis, screening and storage and subsequent use of compounds synthesized on matrices with memories as provided herein.

Software for the units and directed sorting, in particular, is provided herein. Software that aids in the design, synthesis and archiving of synthetic libraries and other collections of compounds is provided. In an exemplified embodiment, the software includes: a repository for the chemical synthesis information—primarily the building blocks and reaction steps, and also, if desired, storage for other information, such a pre-reaction procedures and reaction work-up procedures, explicit directions for sorting microreactors between each reaction step to ensure that all compounds, and no duplicates, are synthesized; an interface from the chemical synthesis environment and format (individual compounds in microreactors) to the biological screening environment and screening format, such as cleaved compounds in 96-well microplates.

Also provided is an improvement of the robotic methods for synthesis and screening, such as the methods set forth in U.S. Pat. No. 5,463,564, is provided herein. As provided herein, all instrumentation and devices include memory devices, such as RF tags or optical memories, 2-D optical bar codes or combinations thereof, whereby identifying information is stored. All vials, glassware, flasks, beakers, tubes and other containers in which the compounds are synthesized and assayed and all synthesis and assays are performed as provided herein by coupling each vial and assay step to a memory. The information can be transferred, manually or, preferably automatically, from one memory device to another as a sample is processed. In particular, automated methods for generating and screening a plurality of compounds are provided. The methods include the steps of robotically synthesizing, in accordance with robotic synthesis instructions, a plurality of chemical compounds linked to a memory with matrix; and (2) robotically analyzing the chemical compounds to obtain structure-activity data pertaining thereto. The matrices with memories will be sorted preferably using the automated sorting methods and systems provided herein. Software integrating all steps in the synthesis and processing steps will be used, and substantially all instrumentation and containers will include memories to store information regarding the associated compounds. The methods can also include one or more of the steps of comparing, under computer control, the structure-activity data of the chemical compounds against the prescribed set of properties to identify any of the chemical compounds substantially conforming to the prescribed set of properties; classifying, under computer control, the identified chemical compounds as lead compounds; analyzing, under computer control, the structure-activity data of the compounds and historical structure-activity data pertaining to compounds synthesized and analyzed in the past to derive structure-activity models having enhanced predictive and discriminating capabilities; identifying, under computer control and in accordance with the structure-activity models, reagents from a reagent database that, when combined, will produce a set of compounds predicted to exhibit activity/properties more closely matching the prescribed set of properties; generating, under computer control, robotic synthesis instructions that, when executed, enable robotic synthesis of the set of compounds; (8) repeating steps (1)–(7), where step (1) is repeated using the generated robotic synthesis instructions. At all steps, relevant information and/or parameters will be stored in the memories associated with each compound.

DESCRIPTION OF THE DRAWINGS

FIG. 2 is a perspective view of an exemplary embodiment of a microvessel for retaining matrix materials, with the end cap separated.

FIG. 3 is a side elevation view of the microvessel of FIG. 14, with a portion cut away.

FIG. 4 is a sectional view taken along line 16—16 of FIG. 15.

FIG. 30 is a diagram of an exemplary view screen produced by the SYNTHESIS MANAGER™ software for the step of defining building blocks;

FIG. 36 is a perspective view of a preferred embodiment of a manual sorting device, including an identification station, a computer, and a visual cue for each destination.

FIG. 37 is a perspective view of the LED bracket showing the LED and the slot positionable over the rim of a beaker.

FIG. 38 is a cross-sectional view of the LED bracket taken along line 38—38 in FIG. 37 showing the orientation of the LED within the bracket, and the electrical connections extending out the rear portion of the bracket.

FIG. 40 is a perspective view of a manual cleaving station.

FIG. 41 is a cross-sectional view of the manual cleaving station of FIG. 40 taken along line 41—41, and showing the top plate separated from the cleaving block.

FIG. 42 is a detail view of the standoff of FIG. 40, detailing the operation of the standoff to suspend the top plate from the cleaving block.

FIG. 43 is a cross sectional view of the manual cleaving station of FIG. 40, showing the top plate adjacent to the cleaving block to rinse the MICROKAN microreactor.

FIG. 80 is a side view of the cleaving assembly with its external housing indicated in broken line and a portion in section to show the relationship between the various components.

FIG. 81 is a sectional view of the cleaving block taken along line 81—81 of FIG. 80.

FIG. 82 is an enlarged sectional view taken on line 82—82 of FIG. 81.

FIG. 83 is an enlargement of the portion circled on FIG. 82.

DETAILED DESCRIPTION OF PREFERRED EMBODIMENTS

A. Definitions

Figure 1:
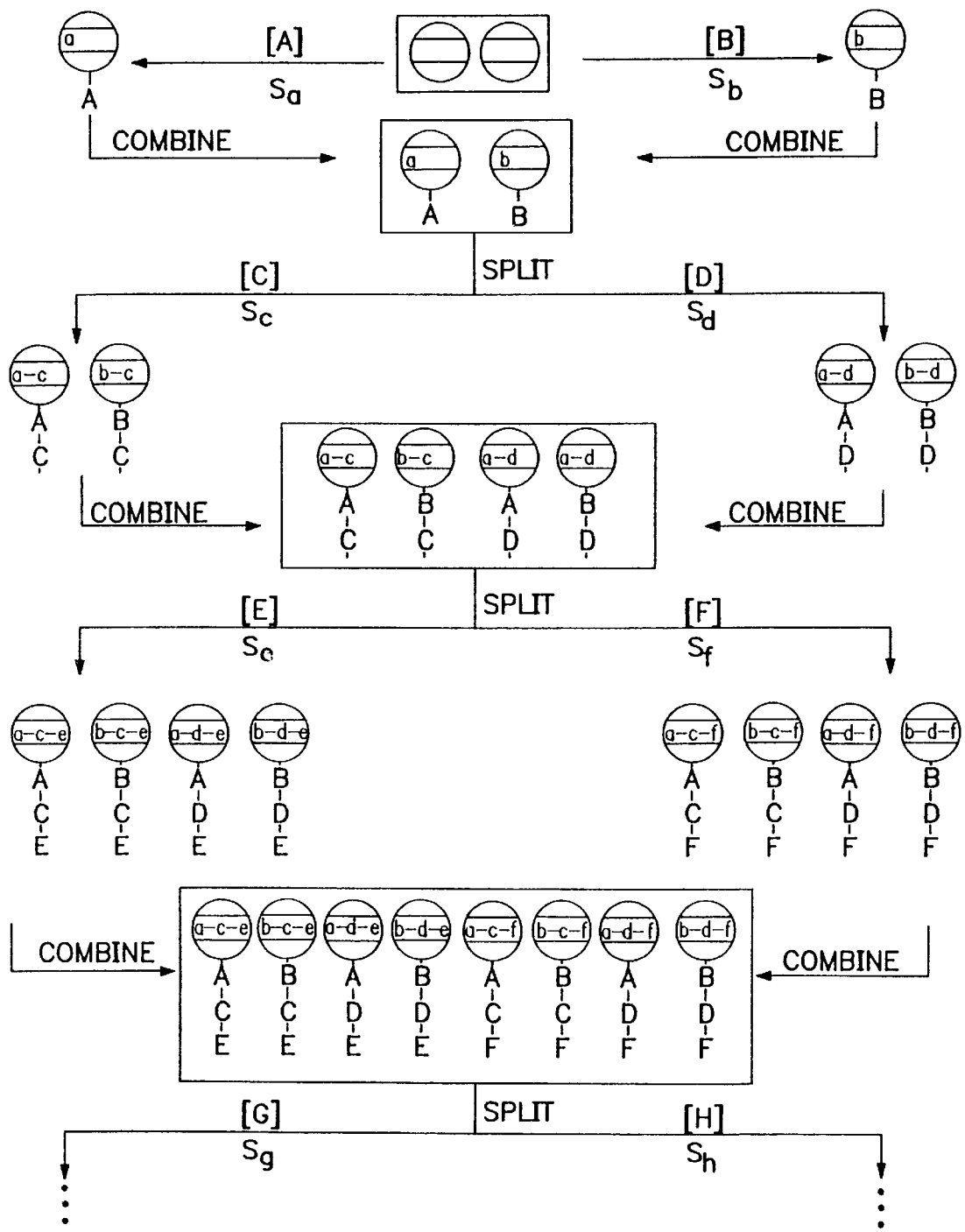
FIG. 1 depicts combinatorial synthesis of chemical libraries on matrix supports with memories. A, B, C . . . represent the chemical building blocks; a, b, c . . . represent the codes stored in memory that correspond to each of A, B, C, . . . , respectively. $S_a$, $S_b$, $S_c$ . . . represent respective signals sent to memory.

Unless defined otherwise, all technical and scientific terms used herein have the same meaning as is commonly understood by one of skill in the art to which this invention belongs. All patents and publications referred to herein are, unless noted otherwise, incorporated by reference in their entirety. In the event a definition in this section is not consistent with definitions elsewhere, the definition set forth in this section will control.

As used herein, a matrix-with-memory refers to a combination of a particulate, continous surface or container with a memory, any means for storing information. Matrix with memory combinations are described in the copending and allowed applications enumerated above, including U.S. application Ser. Nos. 08/428,662, 08/480,147, 08/484,486, 08/484,504, 08/480,196, 08/473,660, 08/538,387, 08/567, 746, 08/639,813, 08/711,426, 08/709,435, 08/723,423, 08/633,410, 08/669,252, 08/726,703, 08/743,984, 08/741, 685, 08/857,800, 08/826,253 and 08/912,998, as well as published International PCT application Nos. WO 96/36436 and WO 97/12680. as well as published International PCT application Nos. WO 96/36436 and WO 97/12680. Memories include, miniature recording device that stores multiple bits of data by which the matrix may be identified, preferably in a non-volatile memory that can be written to and read from by transmission of electromagnetic radiation from a remote host, such as a computer. By miniature is meant of a size less than about 10–20 mm in the largest dimension. Preferred memory devices or data storage units are miniature and are preferably smaller than 20 mm dimension, more preferably less than 10 mm, most preferably about 5 mm or smaller. Alternatively, the memory may be fabricated as part of the matrix material or may be a chemical or biological-based memory means, such as those described herein, including the rhodopsin based memories and 3-D optical memories based on photochromic materials [see, e.g., U.S. Pat. Nos. 5,268,862, 5,130,362, 5,325,324; see, also, Dvornikov et al. (1996) *Opt. Commun.* 128:205–210; Dvornikov et al. (1996) *Res. Chem. Intermed.* 22:115–28; Dvornikov et al. (1994) *Proc. SPIE-Int. Soc. Opt. Eng.* 2297:447–51; Dvornikov et al. (1994) *Mol. Cryst. Liq. Cryst. Sci. Technol., Sect. A* 246:379–88; Dvornikov et al. (1994) *J. Phys. Chem.* 98:6746–52; Ford et al. (1993) *Proc. SPIE-Int. Soc. Opt.* 2026:604–613; Ford et al. *Proc. SPIE-Int. Soc. Opt. Eng.* 1853:5–13; Malkin et al. *Res. Chem. Intermed. 19:159–89;* Dvornikov et al. (1993) *Proc. SPIE-Int. Soc. Opt. Eng.* 1852:243–52; Dvornikov et al. (1992) *Proc. SPIE-Int. Soc. Opt. Eng.* 1662:197–204; Prasad et al. (1996) *Mater. Res. Soc. Symp. Proc.* 413:203–213]. Alternatively, the memory may be an optical bar code, such as the 2-D optical bar codes described herein. Thus, the term memory with matrix refers generically to any combination [association] between a matrix and any means for storing information.

The matrices-with-memories serve as the platform on which all manipulations are performed or serve as the repository of information that is transferred to other memories as the synthesized compounds are processed and screened.

As used herein, a memory is a data storage unit [or medium] with programmable memory, preferably a non-volatile memory; or alternatively is a symbology on a surface, such as a bar code, whose identity and as for which associate information is stored in a remote memory, such as a computer memory.

As used herein, a bar codes refers any array of optically readable marks of any desired size and shape that are arranged in a reference context or frame of, preferably, although not necessarily, one or more columns and one or more rows. For purposes herein, the bar code refers to any symbology, not necessary "bar" but may include dots, characters or any symbol or symbols.

As used herein, an optical memory refers to the symbology and the surface on which it is engraved or otherwise imprinted or refers to other optical devices. For purposes herein, an optical memory also includes from optical recording media that may be appropriate for use in the recording devices and combinations herein and include, but are not limited to, optical discs, magneto-optical materials, photochromic materials, photoferroelectric materials, and photoconductive electro-optic materials. Optical memories also include memories, such as 2-D and 3-D optical memories that use optics, such as lasers, for writing and/or reading.

As used herein, an optical memory device [OMD] refers to a surface that is encoded with a code, preferably the 2-D bar code provided herein. For use herein, such devices include at least two surfaces, one of which is treated or formed from a matrix material treated to render it suitable for use as a support to which molecules or biological particles are linked, such as in chemical syntheses or as supports in assays, and the other that includes a code that can be optically read and then compared with information in a computer or other memory to interpret its meaning.

As used herein, symbology refers to the code, such as a bar code, that is engraved or imprinted on the OMD. The symbology is any code known or designed by the user. The symbols are associated with information stored in a remote computer or memory or other such device or means. For example, each OMD can be uniquely identified with an encoded symbology. The process steps or additions or manipulations to the associated molecules or biological particles can be recorded in a remote memory and associated with the code.

As used herein, a matrix refers to any solid or semisolid or insoluble support on which a code is imprinted or engraved and to which the memory device and/or the molecule of interest, typically a biological molecule, organic molecule or biospecific ligand is linked or contacted. Typically a matrix is a substrate material having a rigid or semi-rigid surface. In many embodiments, at least one surface of the substrate will be substantially flat, although in some embodiments it may be desirable to physically separate synthesis regions for different polymers with, for example, wells, raised regions, etched trenches, or other such topology. Matrix materials include any materials that, when suitably treated, are used as affinity matrices or supports for chemical and biological molecule syntheses and analyses, such as, but are not limited to: polystyrene, polycarbonate, polypropylene, nylon, glass, dextran, chitin, sand, pumice, polytetrafluoroethylene, agarose, polysaccharides, dendrimers, buckyballs, polyacrylamide, Kieselguhr-polyacrlamide non-covalent composite, polystyrene-polyacrylamide covalent composite, polystyrene-PEG [polyethyleneglycol] composite, silicon, rubber, and other materials used as supports for solid phase syntheses, affinity separations and purifications, hybridization reactions, immunoassays and other such applications. The matrix herein may be particulate or may be in the form of a container, such as a microtiter dish or well, or in the form of a continous surface such as a derivatized glass slide, a silicon chip with a surface adapted for linking of biological particles or molecules, a nitrocellulose sheet, nylon mesh, or other such materials, or a hollow or solid surface on which molecules or biological particles are linked (e.g., MICRO-TUBE™ microreactors, sold by IRORI, La Jolla Calif., and Chiron "pins" modified by inclusion of a memory as described herein).

When particulate, typically the particles have at least one dimension in the 5–10 mm range or smaller, generally on the order of 1 $\mu$m–1000 $\mu$m. Such particles, referred collectively herein as "beads", are often, but not necessarily, spherical. Such reference, however, does not constrain the geometry of the matrix, which may be any shape, including random shapes, needles, fibers, elongated, and any other desired or suitable geometry. The "beads" may include additional components, such as magnetic or paramagnetic particles [see, e.g., Dyna beads (Dynal, Oslo, Norway)] for separation using magnets, fluorophores and other scintillants, as long as the additional components do not interfere with chemical reactions, data entry or retrieval from the memory.

Significantly, it is noted, however, that many surfaces, such as glass, require modification to render them suitable for use as supports. Any such surface must be treated to render it suitable for chemical syntheses or for adsorption of biological particles. Chemical syntheses require a support that not only has the proper surface characteristics (organic solvent wettability, chemical kinetics, etc.), but that also has a high density of functional groups. An untreated glass surface contains only a very small amount [less than 1 nmol/sq. mm] of hydroxy groups. It is also very hydrophilic and not very suitable for reactions in organic media. Therefore, the glass surface has to be modified to achieve high functional group density (~>10 nmol/mm$^2$) and proper hydrophobicity. Thus, as used herein, matrix refers to materials that have been so-treated. Therefore, a transponder in which the memory device is encased in a glass capsule for instance is not usable as is, but must be treated, either by coating at least one surface with a polymer, such as by grafting, derivatizing or otherwise activating the surface.

The matrices may also be containers, such as microtiter plates [e.g., plates made from polystyrene or polycarbonate or derivatives thereof commercially available from Perkin Elmer Cetus and numerous other sources, and Covalink trays [Nunc], microtiter plate lids or a test tube, such as a 1 ml Eppendorf tube or smaller versions, such as 500 $\mu$l, 200 $\mu$l or smaller.

Matrices that are in the form of containers refers to containers, such as test tubes and microplates and vials that are typically used for solid phase syntheses of combinatorial libraries or as pouches, vessels, bags, and other containers for screening and diagnostic assays or as containers for samples, such as patient samples. Thus, a container used for chemical syntheses refers to a container that typically has a volume of about 1 liter, generally 100 ml, and more often 10 ml or less, 5 ml or less, preferably 1 ml or less, and as small as about 50 $\mu$l–500 $\mu$l, such as 100 $\mu$l or 250 $\mu$l or 200 $\mu$l. This also refers to multi-well plates, such as microtiter plates [96 well, 384 well, 1536 well or other higher density format]. Such microplate will typically contain a memory device in, on, or otherwise in contact with in each of a plurality of wells. The matrices may also be in the form of continous surfaces that generally encase the memory.

Also contemplated herein, are the combination of "chips" or arrays that contain hundreds of thousands of probes [see, e.g., U.S. Pat. No. 5,525,531] linked to a matrix with a surface suitable for linking probes or other selected molecules or biological particles.

As used herein, a microreactor refers generally to combinations of matrices-with-memories, and particularly matrices-with-memories with associated, such as linked or proximate, biological particles or molecules. It is produced, for example, when the molecule is linked thereto or synthesized thereon. It is then used in subsequent protocols, such as immunoassays and scintillation proximity assays. The term microreactor is used to refer to the device upon which solid phase synthesis and screening is performed.

As used herein, a combination herein called a microvessel [e.g., a microvessel such as the MICROKAN™ microreactor, sold by IRORI, La Jolla, Calif.] refers to a combination in which a single device [or more than one device] and a plurality of particles are sealed in a porous or semi-permeable inert material, such as polytetrafluoroethylene or polypropylene or membrane that is permeable to the components of the medium, but retains the particles and memory, or are sealed in a small closable container that has at least one dimension that is porous or semi-permeable. Typically such microvessels, which preferably have at least one end that can be opened and sealed or closed tightly, has a volume of about 200–500 mm$^3$, with preferred dimensions of about 1–10 mm in diameter and 5 to 20 mm in height, more preferably about 5 mm by 15 mm. The porous wall should be non-collapsible with a pore size in the range of 70 $\mu$M to about 100 $\mu$M, but can be selected to be semi-permeable for selected components of the reaction medium.

As used herein, programming refers to the process by which data or information is entered and stored in a memory. A memory that is programmed is a memory that contains retrievable information.

As used herein, remotely programmable, means that the memory can be programmed (read from and written to) without direct physical or electrical contact or can be programmed from a distance, typically at least about 10 mm, although shorter distances may also be used, such as instances in which the information comes from surface or proximal reactions or from an adjacent memory or in instances, such as embodiments in which the memories are very close to each other, as in microtiter plate wells or in an array.

As used herein, a recording device [or memory device] is an apparatus that includes the data storage unit with programmable memory, and, if necessary, means for receiving information and for transmitting information that has been recorded. It includes any means needed or used for writing to and reading from the memory. The recording devices intended for use herein, are miniature devices that preferably are smaller than 10–20 mm$^3$ [or 10–20 mm in their largest dimension], and more preferably are closer in size to 1 mm$^3$ or smaller that contain at least one such memory and means for receiving and transmitting data to and from the memory. The data storage device also includes optical memories, such as bar codes, on devices such as OMDs.

As used herein, a data storage unit with programmable memory includes any data storage means having the ability to record multiple discrete bits of data, which discrete bits of data may be individually accessed [read] after one or more recording operations. Thus, a matrix with memory is a combination of a matrix material with a data storage unit.

As used herein, programmable means capable of storing unique data points. Addressable means having unique locations that may be selected for storing the unique data points.

As used herein, a host computer or decoder/encoder instrument is an instrument that has been programmed with or includes information [i.e., a key] specifying the code used to encode or decode the memory devices. This instrument or one linked thereto transmits the information and signals to the recording device and it, or another instrument, receives the information transmitted from the recording device upon receipt of the appropriate signal. This instrument thus creates the appropriate signal to transmit to the recording device and can interpret transmitted signals. For example, if a "1" is stored at position 1,1 in the memory of the recording device means, upon receipt of this information, this instrument or computer can determine that this means the linked molecule is, for example, a peptide containing alanine at the N-terminus, an organic group, organic molecule, oligonucleotide, or whatever this information has been predetermined to mean. Alternatively, the information sent to and transmitted from the recording device can be encoded into the appropriate form by a person.

Figure 17:
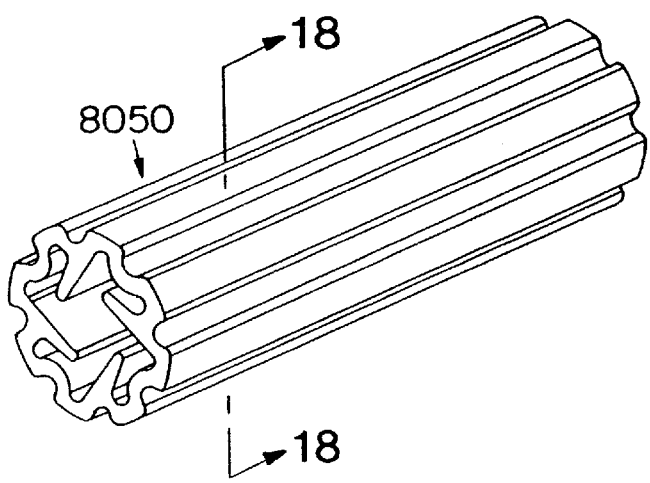
FIG. 17 is a perspective view of an alternative embodiment of a microreactor.
Figure 67:
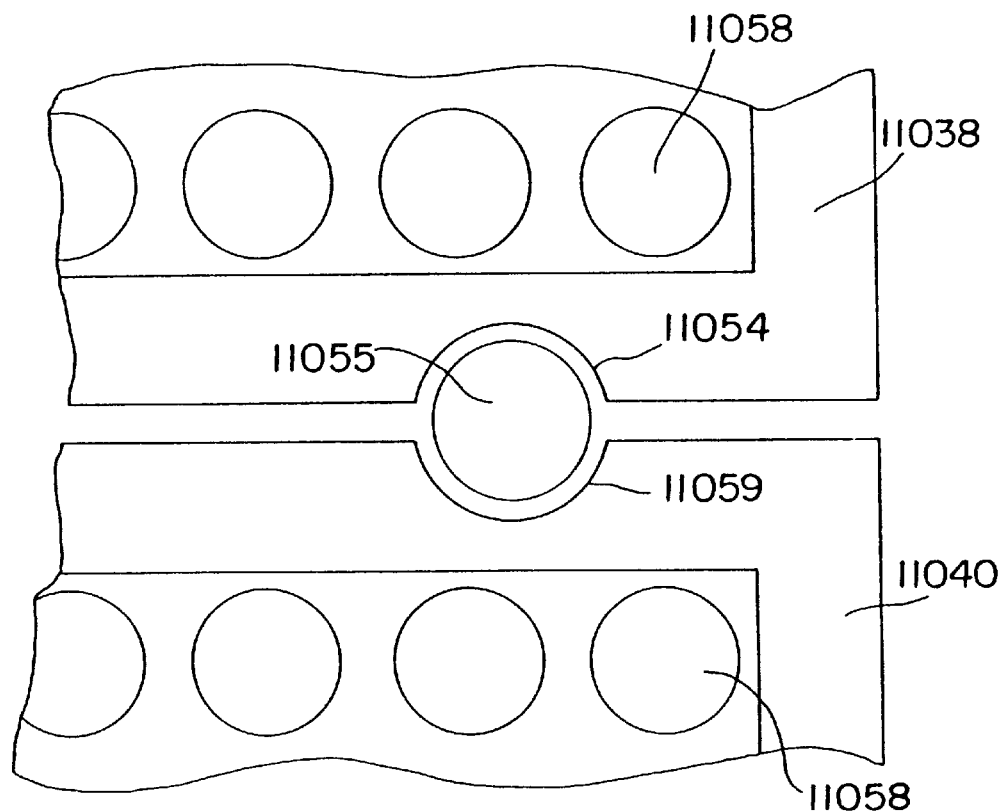
FIG. 67 is an enlarged view of a typical collection rack showing one embodiment of keying the individual vial racks for placement on a unique position within the collection rack.

As used herein, an identification station refers to a device that reads memories and includes any such components and software necessary to effect such reading and communication of information to the user or to other devices, such as a host computer. An exemplary identification station is depicted in FIGS. 17 and 67.

As used herein, an electromagnetic tag or electronic tag is a recording device that has a memory that contains unique data points that correspond to information that identifies molecules or biological particles linked to, directly or indirectly, in physical contact with or in proximity [or associated with] to the device. Thus, electromagnetic tagging is the process by which identifying or tracking information is transmitted [by any means and to any recording device memory, including optical and magnetic storage media] to the recording device. As used herein, a cue refers to any detectable signal, such as an audio, visual, electronic or other signal, generated in the automated and manual sorting systems provided herein. In the manual system, the signal is detected by the user; and in the automated system, by means that transport matrices with memories to their destination.

As used herein, proximity means within a very short distance, generally less than 0.5 inch, typically less than 0.2 inches. In particular, stating that the matrix material and memory, or the biological particle or molecule and matrix with memory are in proximity means that, they are at least or at least were in the same reaction vessel or, if the memory is removed from the reaction vessel, the identity of the vessel containing the molecules or biological particles with which the memory was proximate or linked is tracked or otherwise known.

As used herein, associated with means that the memory must remain in proximity to the molecule or biological particle or must in some manner be traceable to the molecule or biological particle. For example, if a molecule is cleaved from the support with memory, the memory must in some manner be identified as having been linked to the cleaved molecule. Thus, a molecule or biological particle that had been linked to or in proximity to a matrix with memory is associated with the matrix or memory if it can be identified by querying the memory.

As used herein, antifuse, which is intended for use in the recording devices described herein, refers to an electrical device that is initially an open circuit that becomes a closed circuit during programming, thereby providing for non-volatile memory means and, when accompanied by appropriate transceiver and rectification circuitry, permitting remote programming and, hence identification. In practice, an antifuse is a substantially nonconductive structure that is capable of becoming substantially conductive upon application of a predetermined voltage, which exceeds a threshold voltage. An antifuse memory does not require a constant voltage source for refreshing the memory and, therefore, may be incorporated in a passive device. Other memories that may be used include, but are not limited to: EEPROMS, DRAMS and flash memories.

As used herein, flash memory is memory that retains information when power is removed [see, e.g., U.S. Pat. No. 5,452,311, U.S. Pat. No. 5,452,251 and U.S. Pat. No. 5,449,941]. Flash memory can be rewritten by electrically and collectively erasing the stored data, and then by programming.

As used herein, passive device refers to an electrical device which does not have its own voltage source and relies upon a transmitted signal to provide voltage for operation.

As used herein, electromagnetic [EM] radiation refers to radiation understood by skilled artisans to be EM radiation and includes, but is not limited to radio frequency [RF; low kilohertz (80 KHz) up to about 800 MHz –1 GHz], infrared

[IR], visible, ultraviolet [UV], radiation, microwave [i.e., 800 MegaHz–300 GHz (corresponding to wavelengths of 1 meter to 1 mm), preferably just beyond the RF range], sonic waves, X-rays, and laser light.

As used herein, information identifying or tracking a biological particle or molecule, refers to any information that identifies the molecule or biological particle, such as, but not limited to the identity particle [i.e. its chemical formula or name], its sequence, its type, its class, its purity, its properties, such as its binding affinity for a particular ligand. Tracking means the ability to follow a molecule or biological particle through synthesis and/or process steps. The memory devices herein store unique indicators that represent any of this information.

As used herein, combinatorial chemistry is a synthetic strategy that produces diverse, usually large, chemical libraries. It is the systematic and repetitive, covalent connection of a set, the basis set, of different monomeric building blocks of varying structure to each other to produce an array of diverse molecules [see, e.g., Gallop et al. (1994) *J. Medicinal Chemistry* 37:1233–1251]. It also encompasses other chemical modifications, such as cyclizations, eliminations, cleavages, etc., that are carried in manner that generates permutations and thereby collections of diverse molecules.

As used herein, a biological particle refers to a virus, such as a viral vector or viral capsid with or without packaged nucleic acid, phage, including a phage vector or phage capsid, with or without encapsulated nucleotide acid, a single cell, including eukaryotic and prokaryotic cells or fragments thereof, a liposome or micellar agent or other packaging particle, and other such biological materials. Biological particles are distinct from molecules, defined below, in that do not include synthetic macromolecules.

As used herein, compounds refer generally to biological particles, molecules or mixtures thereof.

As used herein, a molecule refers to any molecule that is linked to the solid support. Typically such molecules are macromolecules or components or precursors thereof, such as peptides, proteins, small organics, oligonucleotides or monomeric units of the peptides, organics, nucleic acids and other macromolecules. A monomeric unit refers to one of the constituents from which the resulting compound is built. Thus, monomeric units include, nucleotides, amino acids, and pharmacophores from which small organic molecules are synthesized.

As used herein, the molecules in the combinations include any molecule, including nucleic acids, amino acids, other biopolymers, and other organic molecules, including peptidomimetics and monomers or polymers of small organic molecular constituents of non-peptidic libraries, that may be identified by the methods here and/or synthesized on matrices with memories as described herein.

As used herein, the term "library" refers to a collection of substantially random compounds or biological particles expressing random peptides or proteins or to a collection of diverse compounds. Of particular interest are bio-oligomers, biopolymers, or diverse organic compounds or a set of compounds prepared from monomers based on a selected pharmacophore.

As used herein, an analyte is any substance that is analyzed or assayed in the reaction of interest. Thus, analytes include the substrates, products and intermediates in the reaction, as well as the enzymes and cofactors.

As used herein, multianalyte analysis is the ability to measure many analytes in a single specimen or to perform multiple tests from a single specimen. The methods and combinations herein provide means to identify or track individual analytes from among a mixture of such analytes.

As used herein, complete coupling means that the coupling reaction is driven substantially to completion despite or regardless of the differences in the coupling rates of individual components of the reaction, such as amino acids. In addition, the amino acids, or whatever is being coupled, are coupled to substantially all available coupling sites on the solid phase support so that each solid phase support will contain essentially only one species of peptide.

As used herein, the biological activity or bioactivity of a particular compound includes any activity induced, potentiated or influenced by the compound in vivo or in vitro. It also includes the abilities, such as the ability of certain molecules to bind to particular receptors and to induce [or modulate] a functional response. It may be assessed by in vivo assays or by in vitro assays, such as those exemplified herein. Biological activity, thus, encompasses therapeutic effects and pharmaceutical activity of such compounds, compositions and mixtures.

As used herein, multiplexing refers to performing a series of synthetic and processing steps and/or assaying steps on the same platform [i.e. solid support or matrix] or coupled together as part of the same automated coupled protocol, including one or more of the following, synthesis, preferably accompanied by writing to the linked memories to identify linked compounds, screening, including using protocols with matrices with memories, and compound identification by querying the memories of matrices associated with the selected compounds. Thus, the platform refers system in which all manipulations are performed. In general it means that several protocols are coupled and performed sequentially or simultaneously.

As used herein, a platform refers to the instrumentation or devices in which on which a reaction or series of reactions is(are) performed.

As used herein, cleaving refers to the process by which linked molecules or biological particles are removed from a support matrix. A cleaving agent is a compound or composition that effects such cleavage.

As used herein a luminescent moiety refers to a scintillant or fluorophore used in scintillation proximity assays or in non-radioactive energy transfer assays, such as HTRF assays.

As used herein, scintillants include, 2,5-diphenyloxazole [PPO], anthracene, 2-(4'-tert-butylphenyl)-5-(4"-biphenyl)-1,3,4-oxadiazole [butyl-PBD]; 1-phenyl-3-mesityl-2-pyrazoline [PMP], with or without frequency shifters, such as 1,4,-bis[5-phenyl(oxazolyl)benzene] [POPOP]; p-bis-o-methylstyrylbenzene [bis-MSB]. Combinations of these fluors, such as PPO and POPOP or PPO and bis-MSB, in suitable solvents, such as benzyltoluene [see, e.g., , U.S. Pat. No. 5,410,155], are referred to as scintillation cocktails.

As used herein, fluorescent resonance energy transfer [FRET] is an art-recognized term meaning that one fluorophore [the acceptor] can be promoted to an excited electronic state through quantum mechanical coupling with and receipt of energy from an electronically excited second fluorophore [the donor]. This transfer of energy results in a decrease in visible fluorescence emission by the donor and an increase in fluorescent energy emission by the acceptor. Significant energy transfer can only occur when the donor and acceptor are sufficiently closely positioned since the efficiency of energy transfer is highly dependent upon the distance between donor and acceptor fluorophores.

B. Matrices-With-Memories

FIG. 1 depicts a representative schematic of a combinatorial synthesis of chemical libraries on matrices-withmemories. A, B, C . . . represent the chemical building blocks; a, b, c . . . represent the codes stored in memory that correspond to each of A, B, C, . . . , respectively. $S_a$, $S_b$, $S_c$ . . . represent respective signals sent to memory. Descriptions of the support matrices and the memory devices associated therewith are provided in this section. Any of the described matrix-with-memory combinations may be used in such synthesis procedures.

As noted above, copending and allowed applications enumerated above, U.S. application Ser. Nos. 08/428,662 now U.S. Pat. No. 5,741,462, 08/480,147, 08/484,486, now U.S. Pat. No. 5,751,620, 08/484,504, 08/480,196, 08/473,660, 08/538,387, now U.S. Pat. No. 5,874,387, 08/567,746, 08/639,813, 08/711,426, 08/709,435, 08/723,423, 08/633,410, 08/669,252, 08/726,703, 08/743,984, 08/741,685, 08/857,800, 08/826,253 and 08/912,998, as well as published International PCT application Nos. WO 96/36436 and WO 97/12680 describe the preparation and use of matrices-with-memories. These combinations of matrix materials with memories and combinations of matrices with memories and molecules or biological particles may be used in any application in which support-bound molecules or biological particles are used. Such applications include, but are not limited to diagnostics, such as immunoassays, drug screening assays, combinatorial chemistry protocols and other such uses. These matrices with memories can be used to tag cells for uses in cell sorting, to identify molecules in combinatorial syntheses, to label monoclonal antibodies, to tag constituent members of phage displays, affinity separation procedures, to label DNA and RNA, in nucleic acid amplification reactions [see, e.g., U.S. Pat. No. 5,403,484; U.S. Pat. No. 5,386,024; U.S. Pat. No. 4,683,202 and, for example International PCT Application WO/94 02634, which describes the use of solid supports in connection with nucleic acid amplification methods], to label known compounds, particularly mixtures of known compounds in multianalyte analyses], to thereby identify unknown compounds, or to label or track unknowns and thereby identify the unknown by virtue of reaction with a known. Thus, the matrices with memories are particularly suited for high throughput screening applications and for multianalyte analyses.

In preferred embodiments, the matrix-with-memory combinations contain (i) a recording device that includes a memory or memories comprised of one or more programmable data storage devices and/or an engraved or imprinted optically readable code or a 3-D optical memory, that can be remotely read and in preferred embodiments also remotely programmed; and (ii) a matrix, such as a particulate support used in chemical syntheses.

Compositions, i.e. libraries, containing a plurality of combinations of matrices-with-memories with linked molecules and biological particles are contemplated for use in the units and systems provided herein. In particular, optically coded or electronically tagged libraries of oligonucleotides, peptides, proteins, non-peptide organic molecules, phage display, viruses and cells are provided. Particulate matrices, such as polystyrene beads, with attached memories, and continuous matrices, such as microtiter plates or slabs or polymer, with a plurality of embedded or attached memories are may be used in the systems and units herein.

It is also contemplated that memories will be associated by contacting or incorporation into the material of laboratory instruments, container or other analytical tool or engraved thereon are also provided. The memories may be used in combination with instruments, including, but not limited to HPLC, gas chromatographs (GC), mass spectrometers (MS), NMR instruments, GC-MS, stir bars spectrometers, including fluorimeters, luminometers, and capillary electrophoresis and electrophoresis instruments and tubes and plates used therefor. Thus, an entire laboratory may be augmented with memories linked to or proximate to every container, instrument, and device, from reagent bottle to collected fraction, used in a particular protocol, whereby a sample may be tracked. Software that integrates and provides communication links among the devices and instruments will also be included. The information that is stored will include information regarding the identity of a sample and/or source of the sample.

1. Memories (a) Electromagnetically Programmable Devices

The programmable devices intended for use herein, include any device that can record or store data. A preferred device will be remotely programmable using electromagnetic radiation, such as radio frequency (RF) signals or laser light, and will be small, typically on the order of 20 mm in its largest dimension] or, preferably smaller. The presently preferred devices are on the order of 1–10 mm in the largest dimension. Any means for remote programming and data storage, such as semiconductors and optical storage media are intended for use herein.

In a preferred embodiment herein, the data storage unit includes a semiconductor chip with integrated circuits formed thereon including a memory and its supporting circuitry. These memory devices can be written to and interrogated from a distance. A radio frequency transmitter/receiver system supplies power to program and retrieve data. Devices that are programmable in the microwave range are among the preferred devices. In particular, the data storage unit preferably includes a programmable read only semiconductor memory [PROM], preferably a non-volatile memory or other memory that can store data for future retrieval. The data will include information describing or identifying the molecules or biological particles linked to or in proximity to the matrix. Such information can include the identity of a phage and viral particles, bacteria, cells and fragments thereof, or it can be a history of the synthesis of the molecule, or information, such as a batch number, quality control data, reaction number, and/or identity of the linked entity. Information to be written into the memory need not be detailed since the data stored in the memory is primarily acting as an identification marker that is traceable to a more detailed record stored in the host computer memory, independent of the memory associated with the matrix support or tagged molecule or biological particle. The memory can be programmed, before, during or, preferably, after, each step of synthesis and can thereafter be read, thereby identifying the molecule or its components and sequence of addition, or process of synthesis.

The data storage units or recording devices may be active, containing a power source such as a battery, or passive, which does not include a power source. In a passive device, which has no independent power source, the transmitter/receiver system, which transfers the data between the recording device and a host computer and which is preferably integrated on the same substrate as the memory, also supplies the power to program and retrieve the data stored in the memory.

Among the particularly preferred devices are chips [particularly, the IPTT-100, Bio Medic Data Systems, Inc., Maywood, N.J.; see, also U.S. Pat. Nos. 5,422,636, 5,420,579, 5,262,772, 5,252,962, 5,724,080 5,767,792 and 5,250,962] that can be remotely encoded and remotely read. The devices, such as the IPTT-100 transponders that are about 8 mm long, include a recording device, such as an EEPROM, a passive transponder for receiving an input signal and transmitting an output signal in response. In some embodiments, the devices are modified for use by altering the geometry. They are folded in half and the antenna wrapped around the resulting folded structure to make them sufficiently compact to permit insertion into microreactors or in to use in other combinations.

The preferred devices include a power antenna means [see, e.g., U.S. Pat. No. 5,250,944 and U.S. Pat. No. 5,420,579] for receiving the input signal, frequency generator and modulator means for receiving the input signal from the receive antenna means and for generating the output signal in response thereto. The output signal has a second frequency that is a multiple (>1×) of the first frequency. The device also includes a transmitting antenna means for receiving the output signal from the frequency generator and modulator means and transmitting the output signal. Data are stored within the transponder within a reprogrammable memory circuit that is programmed by the user [see, e.g., U.S. Pat. No. 5,422,636 and EP 0 526 173 A3]. A transponder scanner for scanning and programming the transponder is also available [Bio Medic Data Systems Inc. DAS-5001 CONSOLE™ System, e.g., U.S. Pat. No. 5,252,962 and U.S. Pat. No. 5,262,772].

Other appropriate devices include a 4 mm chip with an onboard antenna and an EEPROM [Dimensional Technology International, Germany] or ID tags available from IDTAG™ Inc, particularly the IDT150 read/write transponder [ITDAG™ Ltd. Bracknell, Berks RG12 3XQ, UK]. These devices can be written to and read from remotely.

Among other tags for use herein are magnetoelastic tags, which contain a metallic glass whose nuclei resonate and give off a radio signal when the tag passes through an oscillating magnetic field. Such tags are manufactured by Sensormatic Electronics Corporation, Deerfield Beach, Fla. [see, e.g., U.S. Pat. Nos. 5,594,420, 5,321,412, 5,218,371, 5,051,726, 5,517,195, 4,999,641, 5,006,856].

As smaller semiconductor and electronic or optical devices become available, the capacity of the memory can be increased and/or the size of the particles can be decreased. For example, while current semiconductor technology uses 0.5 micron gate semiconductor devices, 0.025 micron gate technology is under development, which will increase device speed as well as shrinking the overall size of the memory device.

Alternatively, smaller monolithic (single chip) devices may be used. Such devices can be programmed and/or read at microwave frequencies, for faster recording/reading than with previously described RF tags. For example, a 2.45 GHz tag can communicate 360 times faster than a 6.78 MHz tag and $2 \times 10^4$ times faster than a 125 KHz (RF) tag. A microwave tag contains an antenna, which can be a dipole- or loop-type antenna which is integrated with or bonded to the chip. A rectifier circuit is included for converting the incoming microwave signal to a DC level to power the chip is included, connected to a power capacitor which stores the charge for powering the chip. Analog circuitry detects code transitions and amplifies signals up to proper digital communication levels, and digital circuitry provides digital processing, modulates communication codes, communicates and controls memory. An EPROM is used to store permanent information, and a RAM holds variable information, such as write information that is transmitted to the chip from external transmission sources. These devices are described in International PCT application No. WO 97/12680; see, also, U.S. Pat. No. 4,857,893, and U.S. Pat. No. 5,345,231 for descriptions of the electronics. The antenna for use with these particular electronics can be tuned to a desired resonant frequency, including 125 kHz, but also in the higher frequency RF-microwave range (300 MHz and higher) and preferably microwave range (800 MHz to 300 GHz, corresponding to wavelengths of 1 meter to 1 mm).

(b) Optical Memories

Optical memories can be used as means for storing identification and/or other information. Appropriate optical memories can include optical bar codes, particularly two-dimensional bar codes, or other types of optical memories, such as memories that rely on changes in chemical or physical properties of particular molecules for writing to the medium. Optical memories which comprise bar codes or other optically-readable symbologies are herein referred to as matrices with codes, optical memory devices [OMDs], or optical memory microreactors. Optical memory devices can be read/write devices, or can be read-only precoded devices. Typically, the actual memory in which is stored detailed information about the matrix and any processes to which it has been exposed, may be remote from the matrix. Remote storage is particularly used in instances in which the memory device is precoded [or pre-encoded] with a mark or identifier, or the matrix is encoded with a bar code. The identity [i.e., the mark or code] of each device is written to a memory, which may be part of a host computer, a piece of paper, or other recording means. Information associated with each matrix is stored in the remote memory and linked to or associated with the code or other identifier, i.e., a "look-up table.

2. Matrices and Materials Therefor

The term "matrices" refer broadly to the supports used in solid phase syntheses and screening protocols to retain molecules and biological particles, and containers, such as microplates and test tubes. Matrices used for supports will be derivatized or are otherwise suitable for retaining molecules or biological particles. Containers will either be derivatized or otherwise suitable for retaining molecules or biological particles or will be suitable for containing molecules and biological particles. At least some portion of the matrix is adapted for linking biological particles or molecules.

For purposes herein, three configurations of matrices are contemplated: (1) matrices that are in the form of beads or particles, such as Merrifield resin beads; (2) matrices the form a continuous surface larger than the particles, such as a tube or a ball, on which molecules and/or biological particles are linked on the outside; and (3) containers, such as test tubes, vials, and microtiter plates in which molecules can be in solution (or other composition) or that can be used as the solid support. In all instances when used as a support for linking molecules or biological particles, the matrix material is adapted, i.e., treated or derivatized, to render all or a portion thereof suitable for linking. When the matrix material is particulate the particles are typically contained in a rigid or semi-rigid porous receptacle. The matrices are tagged with an optical and/or electronic memory.

a. Matrix Materials

The matrices may be engraved with an optical bar code, or may have a memory device, such as the RF or microwave tags described above, contained, embedded or otherwise retained in or on the matrix. Matrices include containers, laboratory equipment and other such devices.

Matrices are generally insoluble materials that are used to immobilize ligands and other molecules, having applications in many chemical syntheses, assays and separations. Matrices are used in affinity chromatography, in the immobilization of biologically active materials for assays, and during chemical syntheses of macromolecules, including proteins, amino acids and other organic molecules and polymers. The preparation of and use of matrices is well known to those of skill in this art; there are many such materials and preparations thereof known. For example, naturally-occurring matrix materials, such as agarose and cellulose, may be isolated from their respective sources, and processed according to known protocols, and synthetic materials may be prepared in accord with known protocols.

The matrix materials can be any materials that are routinely used in chemical and biochemical synthesis. The matrix materials are typically polymeric materials that are compatible with chemical and biological syntheses and assays, and include, glasses, silicates, celluloses, polystyrenes, polysaccharides, polypropylenes, sand, and synthetic resins and polymers, including acrylamides, particularly cross-linked polymers, cotton, and other such materials.

Matrices include any material that can act as a support matrix for attachment of the molecules or biological particles of interest and can be in contact with or proximity to or associated with, preferably encasing or coating, the data storage device with programmable memory. Any matrix composed of material that is compatible with and upon or in which chemical syntheses are performed, including biocompatible polymers, is suitable for use herein. The matrix material should be selected so that it does not interfere with the chemistry or biological reaction of interest during the time which the molecule or particle is linked to, or in proximity therewith [see, e.g., U.S. Pat. No. 4,006,403]. The matrix may also be a relatively inert polymer, which can be grafted by ionizing radiation. Generally, the matrices include any material to which a data storage device with memory or optical code can be attached, placed in proximity thereof, impregnated, encased or otherwise connected, linked or physically contacted. Such materials are known to those of skill in this art, and include those that are used as a support matrix. These materials include, but are not limited to, inorganics, natural polymers, and synthetic polymers, including, but are not limited to: cellulose, cellulose derivatives, acrylic resins, glass that is derivatized to render it suitable for use a support, silica gels, polystyrene, gelatin, polyvinyl pyrrolidone, co-polymers of vinyl and acrylamide, polystyrene cross-linked with divinylbenzene or the like [see, e.g., Merrifield (1964) Biochemistry 3:1385–1390], polyacrylamides, latex gels, polystyrene, dextran, polyacrylamides, rubber, silicon, plastics, nitrocellulose, celluloses, natural sponges, and many others. Among the preferred particulate matrices are polymeric beads, such as the TENTAGEL™ resins and derivatives thereof and derivatives thereof [sold by Rapp Polymere, Tubingen, Germany; see, U.S. Pat. No. 4,908,405 and U.S. Pat. No. 5,292,814; see, also Butz et al. (1994) *Peptide Res.* 7:20–23; Kleine et al. (1994) *Immunobiol.* 190:53–66; see, also Piskin et al. (1994), Chapter 18 "Nondegradable and Biodegradable Polymeric Particles" in *Diagnostic Biosensor Polymers*, ACS Symp. Series 556, Usmani et al. Eds, American Chemical Society, Washington, D.C.], which are designed for solid phase chemistry and for affinity separations and purifications. See, also Bayer et al. (1994) in *Pept.: Chem., Struct. Biol., Proc. Am. Pent. Symp.*, 13th; Hodges, et al. eds., pp.156–158; Zhang et al. (1993) *Pept.* 1992, *Proc. Eur. Pept. Symp.*, 22nd, Schneider, et al., eds. pp. 432–433; Ilg et al. (1994) *Macromolecules*, pp. 2778–83; Zeppezauer et al. (1993) *Z. Naturforsch., B: Chem. Sci.* 48:1801–1806; Rapp et al. (1992) *Pept. Chem.* 1992, *Proc. Jpn. Symp., 2nd*, Yanaihara, ed., pp. 7–10; Nokihara et al. (1993) *Shimadzu Hyoron* 50:25–31; Wright et al. (1993) *Tetrahedron Lett.* 34:3373–3376; Bayer et al. (1992) *Poly(Ethylene Glycol) Chem.* Harris, ed., pp. 325–45; Rapp et al. (1990) *Innovation Perspect. Solid Phase Synth. Collect. Pap., Int. Symp., 1st*, Epton, ed., pp. 205–10; Rapp et al. (1992) *Pept.: Chem. Biol., Proc. Am. Pept. Symp., 12th*, Smith et al., eds., pp. 529–530; Rapp et al. (1989) *Pent., Proc. Eur. Pept. Symp., 20th*, Jung et al., ed., pp. 199–201; Bayer et al. (1986) *Chem. Pept. Proteins* 3: 3–8; Bayer et al. (1983) *Pent.: Struct. Funct., Proc. Am. Pept. Symp., 8th*, Hruby et al. eds., pp. 87–90 for descriptions of preparation of such beads and use thereof in synthetic chemistry. Matrices that are also contemplated for use herein include fluophore-containing or—impregnated matrices, such as microplates and beads [commercially available, for example, from Amersham, Arlington Heights, Ill.; plastic scintillation beads from NE (Nuclear Technology, Inc., San Carlos, Calif.), Packard, Meriden, Conn.].

Where the matrix particles are macroscopic in size, e.g., at least 1 mm in at least one dimension, such bead or matrix particle or continuous matrix may contain one or more memories.

The matrices are typically insoluble substrates that are solid, porous, deformable, or hard, and have any required structure and geometry, including, but not limited to: beads, pellets, disks, capillaries, hollow fibers, needles, solid fibers, random shapes, thin films and membranes. For purposes herein, the support material will typically encase or be in contact with the data storage device, linked or in proximity to one memory or matrix with memory, such as the microreactors, which retain a matrix-with-memory within their interiors. Typically, when the matrix is particulate, with particles at least about 10–2000 $\mu$M, more than one particle is in disposed in close proximity to a memory. Each memory will be in associated with, in contact with, or proximity to at least one matrix particle, and may be in contact with more than one.

Naturally-occurring supports include, but are not limited to gels, including agarose, other polysaccharides, collagen, celluloses and derivatives thereof, glass, silica, and alumina. Methods for isolation, modification and treatment to render them suitable for use as supports is well known to those of skill in this art [see, e.g., Hermanson et al. (1992) *Immobilized Affinity Ligand Techniques*, Academic Press, Inc., San Diego]. Gels, such as agarose, can be readily adapted for use herein. Natural polymers such as polypeptides, proteins and carbohydrates; semiconductor, such as silicon and germanium, and compound semiconductors, as long as they do not interfere with operation of the data storage device may also be adapted for use herein. Also, metals such as platinum, gold, nickel, copper, zinc, tin, palladium, silver, again as long as the combination of the data storage device with memory, matrix support with molecule or biological particle does not interfere with operation of the device with memory, may be adapted for use herein. Other matrices of interest include oxides of the metal and metalloids, such as, but not limited to, Pt—PtO, Si—SiO, Au—AuO, $TiO_2$ and Cu—CuO.

b. Configuration

The matrices can be either particulate of a size that is roughly about 1 to 20 $mm^3$ [or 1–20 mm in its largest dimension], preferably about 10 $mm^3$ or smaller, preferably 1 $mm^3$ or smaller, such as minute particulates, typically on the order of 500 $\mu$m or less. In some embodiments, the matrices may be in the form of a continuous surface, such as a tube, which encases a recording device. The continuous surface embodiments refer to those in which the outer surface is used as the support matrix, and all or a portion of the outer surface is adapted for linking biological particles or molecules.

In other embodiments, the matrices are in the form of a container, such as a microtiter plate, or other multi-well plate, or plastic or other solid polymeric vial or glass vial or catheter-tube [for drug delivery] or such container or device conventionally used in chemistry and biological syntheses and reactions. In these embodiments, the matrices either hold a solution (or other mixture) of the molecules and biological particles or the inner surface or a portion thereof is adapted for linking biological particles or molecules.

(1) Particles

Where the matrix material is one or more particles, the matrix material can be retained within a container together with one or more remotely accessible memory devices. The container can have an optically encoded memory, such as a 2-dimensional bar code, on its outer surfaces. Such containers, which include the category known as microvessels, are formed from an inert material which is at least partially porous. The pore size is selected to be semi-permeable for selected components of the medium in which the microvessel is placed. Microvessels can be formed in a number of different geometries including cylindrical, conical, square or rectangular boxes, or other shapes. The microvessels are commonly formed as relatively rigid containers with mesh side walls, however, a sealed pouch or bag fabricated from a porous material can be used. Typically, the inert material will be polytetrafluoroethylene [marketed under the trademark TEFLON™ (Trademark, E. I. DuPont)] or polypropylene prepared with pores.

FIGS. 2–4 illustrate an exemplary embodiment of a microvessel contemplated for use with the sorting and cleaving devices and drug discovery unites provided herein. The microvessel retains particulate matrix materials and can be imprinted with a symbology and/or will contain one or more recording devices (not illustrated). The body of the microvessel has a single-piece solid material frame 82, including a top ring 84, two support ribs 88, 100 disposed diametrically opposite each other and a bottom cap 86. The solid material frame 82 may be constructed of any material which is non-reactive with the solutions with which the microvessel will come into contact. Such appropriate materials include, for example, plastic, polytetrafluoroethylene (hereinafter, PTFE), TEFLON or polypropylene, and formation may be by molding or machining of the selected material, with the former being preferred for economy of manufacture.

The sidewall 98 of the microvessel is formed of porous or semi-permeable non-reactive material, such as PTFE mesh, preferably having a 70 $\mu$M pore size. The sidewall is preferably attached to the top ring 84 and bottom cap 86 of the solid material frame 82.

The microvessel is configured with a removable end cap 90. The end cap 90 is preferably constructed of the same material as the solid material frame 82. A snap ring, or, as illustrated, projections 92, 94 extend downward from the inside surface of the top ring 84. The projections 92, 94 have a flange which mates with a groove 96 formed in the inner wall of top ring 84 when pressed into the top ring to releasable secure the end cap 90 to the microvessel 80.

Figure 5:
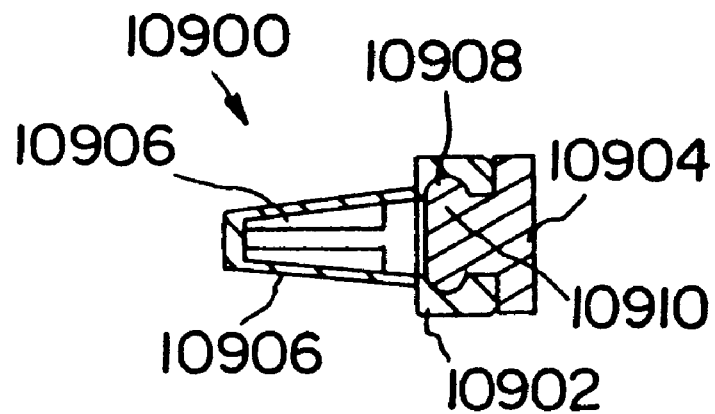
FIG. 5 is a cross-sectional view of an exemplary microreactor or microvessel with a removable cap.

Another embodiment of a microreactor or microvessel, designated the double-bodied microvessel 10900, is shown in cross-section in FIG. 5. Microvessel 10900 includes a body 10902 and a cap 10904. Body 10902 is formed with porous portions 10906 which are intended to permit the free diffusion of solutions through the body while retaining the synthesis resins within the microvessel. Cap 10904 is press fit into the upper open portion of body 10902, with an interference fit being created between tab portion 10910 of cap 10904 and channel portion 10908 in body 10902.

Figure 6:
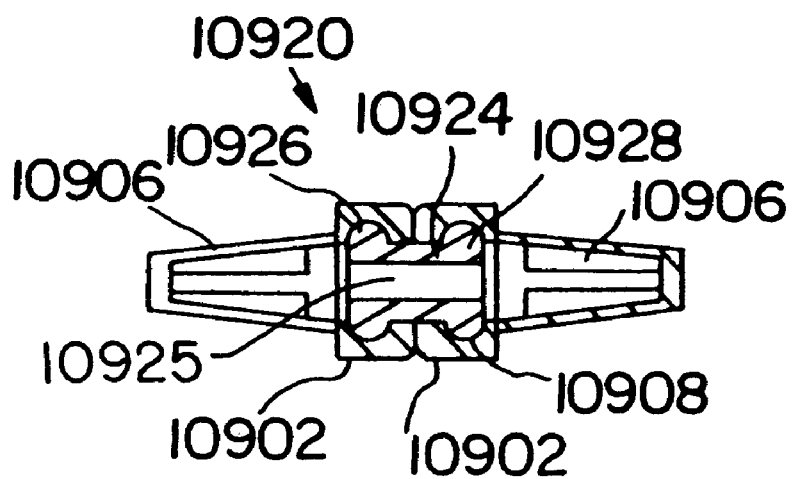
FIG. 6 is a cross-sectional view of a back-to-back microreactor or microvessel with a removable coupler.

Referring to FIG. 6, a variation of the microvessel of FIG. 5 is shown in cross-section. The double-bodied, or back-to-back, microvessel 10920 is formed by joining two bodies 10902 together using a coupler 10924. Coupler 10924 has a junction tube 10925 extending through it to permit the free flow of reagents and resin particles between the two bodies 10902. Coupler 10924 is press fit into the tops of each of the bodies 10902 so that the bodies are held together by an interference fit in a manner similar to cap 10904 of the single-bodied microvessel 10900. Coupler 10924 has tab portions 10926 and 10928 which engage channel portions 10908 in bodies 10902. The double-bodied configuration permits two microvessels to be combined to be introduced to the same solution after each microvessel has separately been exposed to other reagents.

(2) Continuous Surfaces

Any continuous surface or device in which the outer surface is used as the solid support is contemplated for use herein. The device may be hollow or solid or any combination thereof. All or a portion of the outer surface is adapted for linking or otherwise retaining molecules or biological particles.

In preferred embodiments, there surfaces are formed from inert polymers that are treated such as by radiation grafting. The solid continuous surfaces that form the tubular (or other geometry) embodiments, [or other geometry] have been physically coated or grafted with suitable materials that are used as a solid support for any other methods disclosed herein, including organic syntheses and assays. Fluorophores, scintillants and other such compounds may also be incorporated into the surface or linked thereto. These tubular or hollow or continuous surfaces include those that contain the memory encased either permanently or removably, or that include an imprinted symbology on an outer surface.

(a) Hollow Devices with Electronic Recording Devices

Matrices can also be formed as tubular or other geometry devices in which a recording device is enclosed or encased in a solid polymer which is then suitably treated, such as by radiation grafting with selected monomers to produce a surface suitable for chemical synthesis and linkage of molecules or biological particles. The may be sealed or open and retain the device by friction or crimping the outer surface.

These tubular hollow devices, such as the tube microvessels (or microreactors) may contain a recording device and/or may have a code engraved or otherwise imprinted on the surface. Appropriate polymers for the tubular devices include TEFLON™ [polytetrafluoroethylene (PFTE)], polyethylene, high density polyethylene, polypropylene, polystyrene, polyester, ceramic, composites of any of these materials and other such materials. Relatively long tubes (or other shapes) of material [e.g., about 1–5 cms] permit synthesis to be performed, after which they can be cut into small [millimeter] pieces and put in various assays, or the product can be cleaved into a microplate well.

In other embodiments, the surface of the matrix material that is treated or adapted for linking biological particles or molecules may include linkers for effecting the linkage. In certain embodiments, a variety of linkers with differential cleavage properties may be used, thereby providing a means to selectively cleave linked molecules after synthesis and/or screening and linked biological particles before or after screening. The matrix-with-memory tubes (tubular or hollow continuous surfaces) can serve as a reaction "flask" on which assays can be conducted, as storage vial for storing materials, and as a microtiter plate well by differentially loading the "tube".

Prior to introducing and/or sealing the recording device inside, the tube or encasing material is treated to render all or a portion of the surface suitable for linking molecules or biological particles, such as by radiation grafting by ionizing radiation to render the surface suitable for grafting selected monomers, such as styrene [see, e.g., Maeji et al. (1994) *Reactive Polymers* 22:203–212; Ang et al. in Chapter 10: Application of Radiation Grafting in Reagent Insolubilization, pp 223–247; and Berg et al. (1989) *J. Am. Chem. Soc.* 111:8024–8026].

In certain embodiments, the tubes (tubular or hollow continuous surfaces) are hollow and retain a memory by virtue of friction, or alternatively, the ends or insides are crimped to retain any memory device (typically at concentrations of from about 0.01–0.5M). A method for further increasing loading by machining (i.e., using a lathe to render the surface ridged or making the surface rough) the grafted surface. In other embodiments, the continuous surfaces are sealed and retain the recording device therein. Exemplary devices that are designed to retain the recording device by friction and/or interference fit are depicted in FIGS. 7–24.

Recording device(s) is(are) introduced inside the material or the material is wrapped around the device and the resulting matrix-with-memory "tubes" are used for chemical synthesis or linkage of selected molecules or biological particles. These "tubes" are preferably synthesized from an inert resin, such as a polypropylene resin [e.g., a Moplen resin, V29G PP resin from Montell, Newark Del., a distributor for Himont, Italy] or TEFLON or other such polymer. Any inert matrix that can then be functionalized, or to which derivatizable monomers can be grafted, or that can otherwise be derivitized or adapted for linking molecules and biological particles is suitable. Preferably herein, polypropylene surfaces are grafted and then formed into tubes or other suitable shape and the recording device inserted inside. The resulting "tubes" with grafted monomers are then used for synthesis, and/or for assays or for multiplexed processes, including synthesis and assays or other multistep procedures. Although denoted a "tube", the device may be any shape formed from a continuous surface fabricated from an inert polymer, enclosing a hollow space comprising about 5 ml or less and including at least one orifice. Thus, the "tube" is hollow with an interior volume of less than about 5 ml, typically less than 1 or 2 mls; and the inert polymer is inert with respect to solvents used for protein synthesis, oligonucleotide synthesis, or organic synthesis or any assays for biological or pharmacological activity.

The "tubes" may have no lids and instead retain any memory device by virtue of friction. Hollow and open "tubes" are presently preferred. They may have a nonuniform coating on the surface so that differential loading may be achieved or so different portions are suitable for different assays. They may be designed to be readily segmented into pieces so the portion with a memory serves to store the linked molecules or biological particles as bits or pieces of the device are introduced into various assays or used for other purposes.

The "tubes", which serve as the reaction matrices, may be formed with a number of different physical modifications to increase the interior and/or exterior the loading capacity thereof. Several different examples are illustrated in FIGS. 7 through 20.

Figure 7:
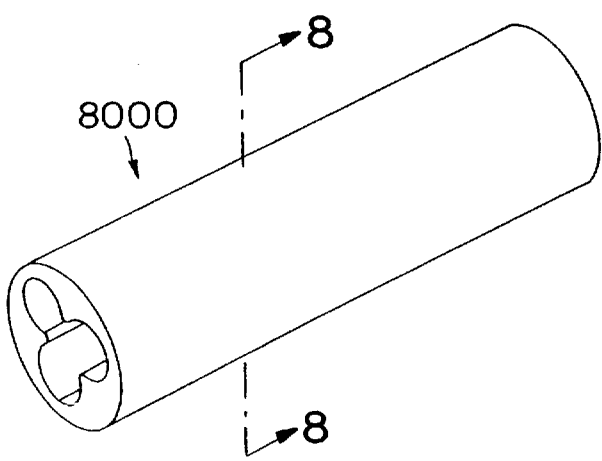
FIG. 7 is a perspective view of an alternative embodiment of a tubular-type (continuous surface) microreactor.
Figure 8:
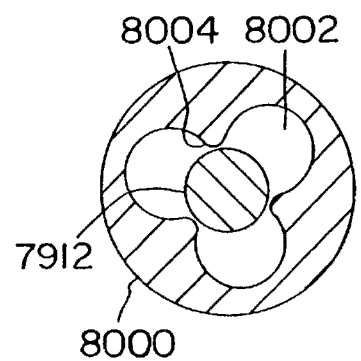
FIG. 8 is a cross-sectional view of the microreactor of FIG. 7 taken along line 8—8.
Figure 9:
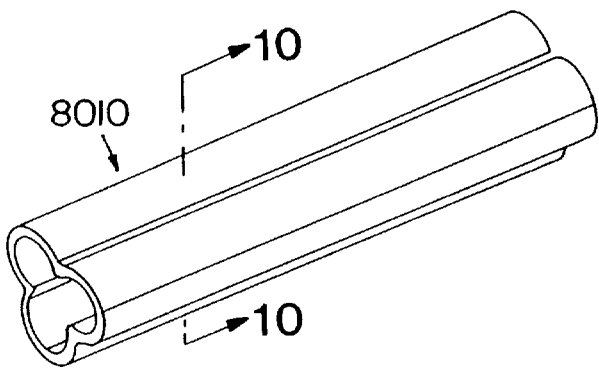
FIG. 9 is a perspective view of an alternative embodiment of a microreactor.
Figure 10:
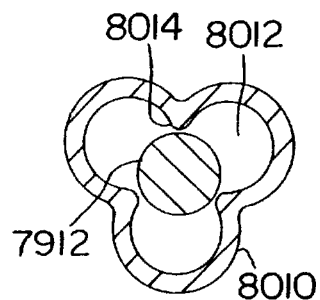
FIG. 10 is a cross-sectional view of the microreactor of FIG. 9 taken along line 10—10.

The embodiment of FIGS. 7 and 8 includes three interior flow channels 8002. Two adjacent channels 8002 intersect to form an interior ridge 8004 projecting toward the axial center of the tube 8000. Ridges 8004 combine to frictionally retain memory device 7912 within the axial center of tube 8000. The embodiment of FIGS. 9 and 10 is similar to that of the previous embodiment, however, the exterior surface of tube 8010 is configured to conform to the interior channels 8012, thus increasing the exterior surface area as well as the interior surface area as compared to the simple cylindrical tube. The combined ridges 8014 frictionally retain memory device 7912, as in the previous embodiment.

Figure 11:
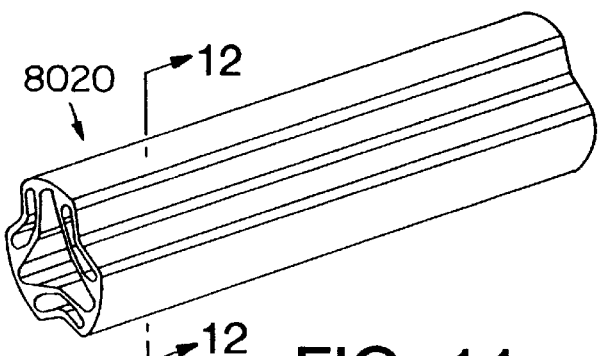
FIG. 11 is a perspective view of an alternative embodiment of a microreactor.
Figure 12:
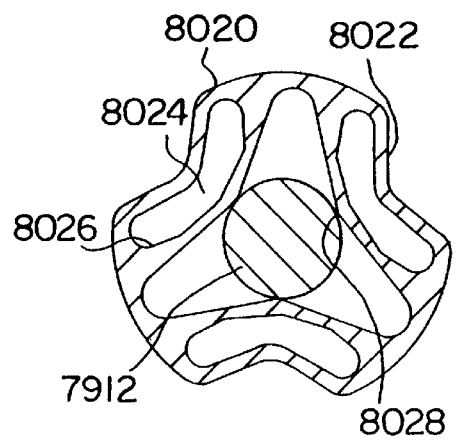
FIG. 12 is a cross-sectional view of the microreactor of FIG. 11 taken along line 12—12.

FIGS. 11 and 12 show tube 8020, which has U-cross-sectional shape interior flow channels 8024 providing interior surface areas 8026 in addition to the primary interior volume of the tube. Memory device 7912 is frictionally retained within the primary interior volume by ridges 8028. The outer surface conforms to the shapes of interior flow channels 8024 to enhance the exterior surface area.

Figure 13:
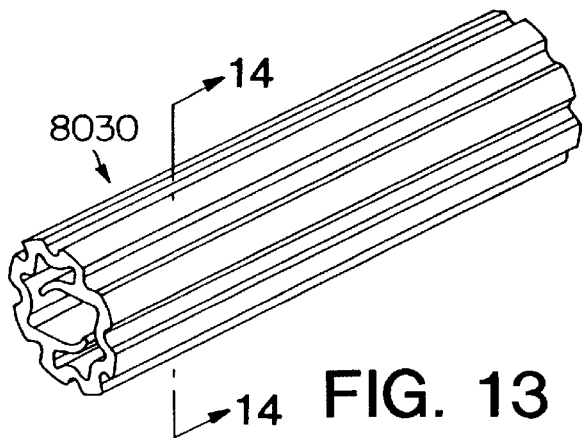
FIG. 13 is a perspective view of an alternative embodiment of a microreactor.
Figure 14:
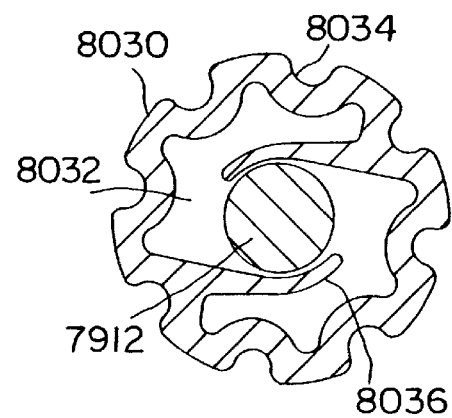
FIG. 14 is a cross-sectional view of the microreactor of FIG. 13 taken along line 14—14.

FIGS. 13 and 14 illustrate tube 8030, which has a pair of curved fins 8036 extending into the interior volume of the tube along with a scalloped cross-section to increase the interior surface area within two flow chambers 8032. The tube's exterior is corrugated to increase the exterior surface area. Fins 8036 are used to retain memory device 7912 within the interior of tube 8030.

Figure 15:
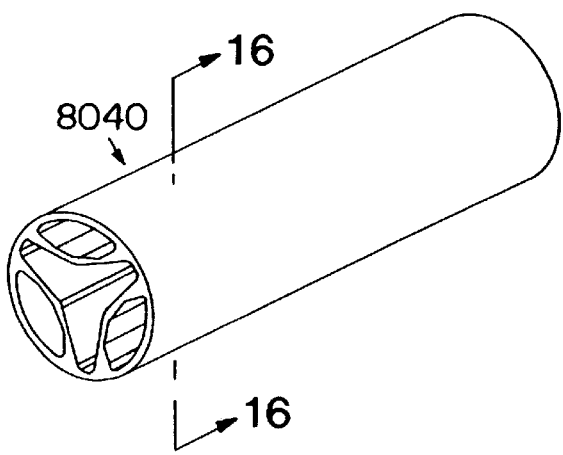
FIG. 15 is a perspective view of an alternative embodiment of a microreactor.
Figure 16:
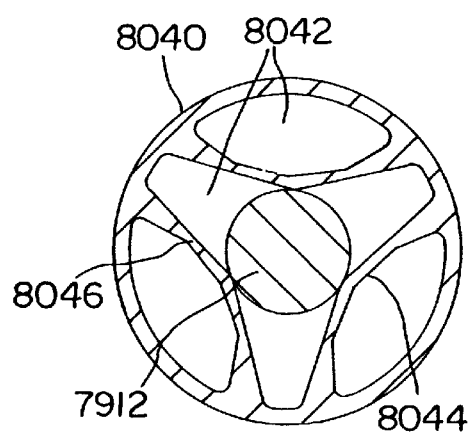
FIG. 16 is a cross-sectional view of the microreactor of FIG. 15 taken along line 16—16.
Figure 19:
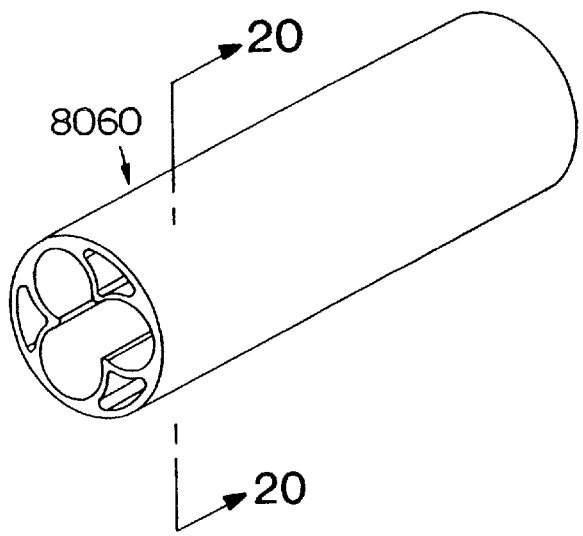
FIG. 19 is a perspective view of an alternative embodiment of a microreactor.
Figure 20:
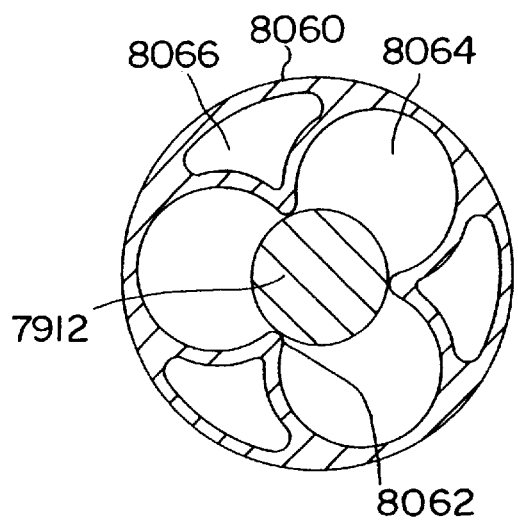
FIG. 20 is a cross-sectional view of the microreactor of FIG. 19 taken along line 20—20.

Tube 8040, illustrated in FIGS. 15 and 16, has a smooth exterior surface with enhanced interior surface areas 8044 provided by a three-sided primary flow channel and three secondary flow channels 8042. Memory device 7912 is retained by the sidewalls which divide the primary and secondary flow channels 8042. FIGS. 19 and 20 show tube 8060 which has a similar configuration to tube 8040, with a smooth exterior surface and primary 8064 and secondary 8066 flow channels. Ridges 8062, which are formed by the walls dividing primary and second flow channels, retain memory device 7912 between them.

Figure 18:
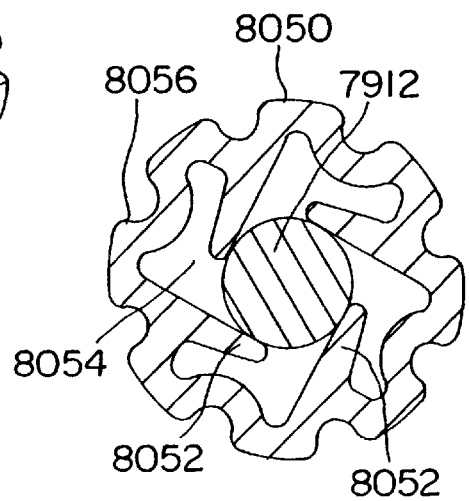
FIG. 18 is a cross-sectional view of the microreactor of FIG. 17 taken along line 18—18.

FIGS. 17 and 18 show tube 8050 which has four inwardly extending arms 8052 which help define four flow channels 8054 as well as retaining memory device 7912. The exterior surface 8056 is corrugated to further increase the total surface area.

As shown, the tubes may have any cross-sectional shape, and are not limited to a generally circular cross-section. Each of the tubes described above will have an outer diameter on the order of 7 mm, and is formed using polypropylene, copolymer, such as TEZFEL™, or similar pliable material which is transparent to the radiation used for reading and/or writing to the memory device. The tubes may be formed in short or long sections using a conventional extrusion process, which is well known in the art, such that they are economical to manufacture. Where long sections are used, a single long section with a number of memory devices may be exposed to a solution in one step of a procedure, then severed into a number of short sections, each with its own memory device, for distribution to different subsequent steps. The inner areas of the tubes which are adapted for retaining the memory device utilize the pliable nature of the tube material to retain the memory devices that are forcibly inserted into the designated interior spacing, producing an interference fit between the memory device and inwardly extending ridges or other features that define the spacing. The frictional retention of the memory device may be replaced or augmented by crimping the tube material, however, crimping will limit the use of the interior surfaces of the tube as reaction surfaces. The exterior surfaces and interior flow surfaces of the tubes may be enhanced by grafting a synthesis resin onto them, or by coating the surfaces with dielectric or polymeric films to provide a chemically functional substrate.

The inexpensive nature of the tubes, and the frictional retention of the memory device, allows the memory devices to be removed and the tube discarded after one use if necessary to avoid risk of contaminating a later procedure. The memory device can then be reused after a thorough cleaning. Alternative or additional identification means may be utilized with the tubes, including optical bar codes printed or otherwise formed on the exterior surfaces of the tubes. Where optical reading and/or writing to the exterior surfaces is used, it may be desirable to treat the exterior surface to minimize any discoloration or other surface degradation that might interfere with the ability to reliably read or write the optical code on the surface.

Such tubes may have snap on or screw lids or caps so that, in embodiments in which the memory device is a chip, the memory device or chip can be removed. For example, they may be conical tubes like Eppendorf tubes, with a snap on top, preferably a flat top. The tubes will be of a size to accommodate a memory device and thus may be as small as about slightly larger than about 2 mm×2 mm×0.1 mm to hold the small 2 mm×2 mm×0.1 mm device described herein. They will be fabricated from polypropylene or other suitable material and treated, such as by radiation grafting, preferably prior to introduction of the memory device, to render them able or suitable for use a solid supports for syntheses and assays.

The devices may also be formed from a ball with a screw cap [MICROBALLS®] or with other type of cap to permit access to the inside, or may be hollow and of such size or geometry to retain a memory inside or to include an optical memory. These types of memories with matrices are, for example, polypropylene or fluoropolymer tubes with a radiation grafted functionalized polystyrene surface that completely enclose a selected memory, such as an RF tag. The surface may also include an identifying symbology. Syntheses are performed on the functionalized polystyrene surface. These devices solid provide a means to phase chemistry without the need to load solid phase resins.

Other devices of interest, are polymeric supports, particularly polypropylene and fluoropolymer supports, generally about 5–10 mm in the largest dimension, and preferably a cube or other such shape, that are marked with a code, and tracked using a remote memory. These microvessels can be marked with a code, such as a bar code, alphanumeric code, the 2-D optical bar code provided herein, or other mark or include an optical memory, for identification, particularly in embodiments in which the memory is not in proximity to the matrix, but is remote therefrom and used to store information regarding each coded vessel.

Also contemplated for use in the systems herein is the Chiron "pin" technology [see, e.g., International PCT application No.WO 94/11388; Geysen et al. (1985) *Proc. Natl. Acad. Sci. U.S.A.* 82:178; Geysen et al. (1987) *J. Immunol. Meth.* 102:259–274; Maeji et al. (1994) *Reactive Polymers* 22:203–212], which relies on a support composed of annular synthesis components that have an active surface for synthesis of a modular polymer and an inert support rod that is positioned axially to the annular synthesis components. This pin technology was developed for the simultaneous synthesis of multiple peptides. In particular the peptides are synthesized on polyacrylic acid grafted on the tip of polyethylene pins, typically arranged in a microtiter format. Amino acid coupling is effected by immersing the pins in a microtiter plate. The resulting peptides remain bound to the pins and can be reused.

For purposes herein the "pins", without the annular support, are linked to a memory or recording device, preferably encasing the device, or each pin may be coded with the code and the identity of the associated linked molecule (s) being stored in a remote memory. As a result it is not be necessary to physically array the pins. Instead, the pins can be removed and mixed or sorted. The sorting and cleaving devices herein can be adapted for sorting the "pins".

(b) Optical Memories (i) Hollow or Solid Devices with Optical Bar Codes-OMDS

Figure 28:
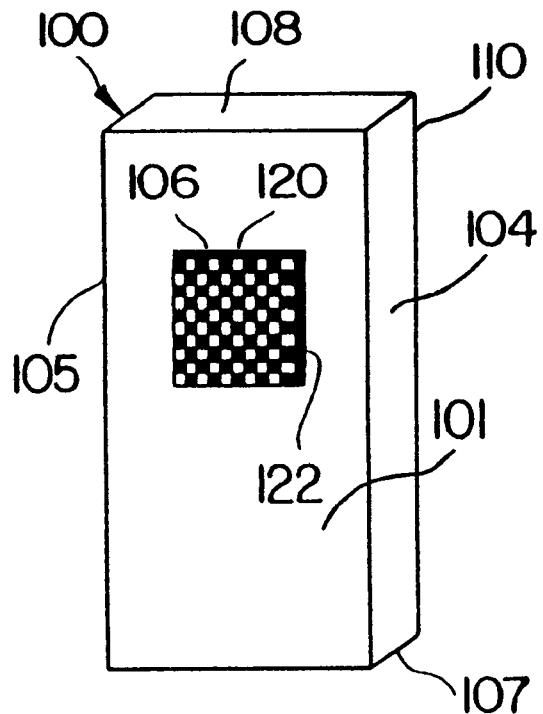
FIG. 28 is a perspective view of a first embodiment of an optical memory device.

In an exemplary embodiment, illustrated in FIG. 28, the optical memory device ["OMD"] 100 is a preferably a rectangular parallelepiped that provides a broad face upon which encoded information can be inscribed. The OMDS may be encoded with a pre-programmed identifying bar code, such as the 2-dimensional optical bar code, or they can be written to using an appropriate writing device during the process. Any geometry that is suitable for a particular application and that provides at least one surface for encoding information. The OMDs may also be containers used for chemical synthesis, such as microtiter plates, tubes, tubes adapted for use with microtiter-type plates. The two-dimensional bar code described herein is ideally suited for incorporation onto the outside surface of each well of a microtiter plate or on the outside of a small test tube or other such tube, particularly, tubes intended for use with a microplate frame, such as those available from NUNC and COSTAR. This two-dimensional bar code as well as the method for reading and writing may also be used to track and identify other laboratory equipment, such as chromatography tubes, test tubes, beakers, flasks and other such items.

The OMDs may also be fabricated as tubes, such as previously described. When used with such tubular devices, they will be engraved on the outer surface, preferably the top or bottom of the device. The material of which the OMDs are fabricated will depend upon the monitored processes. The materials that may be used include, but are not limited to, black, white or colored glass, TEFLON®, polyethylene, high density polyethylene, polypropylene, polystyrene, polyester, ceramic, such as alumina or zirconia, metal, or any composite of the above materials or any material that is physically or chemically structured to produce optical contrast as the result of exposure to the write process, which is described below. For use in the methods herein, these materials may be suitable or at least one surface there may have been treated to render them suitable for retaining molecules and biological particles for use as matrices as described herein.

For OMDs used as support matrices or other processes for which surfaces must be adapted for adsorption or absorption or any means of binding of molecules or biological particles, it may be desirable to separate the binding surfaces from the data storage surface 101. In this case, one or more of sides 104 and 105, bottom 107, top 108, and back 110 or portions thereof may be treated to enhance binding using radiation, mechanical or chemical abrasion, or other processes as appropriate.

Figure 29:
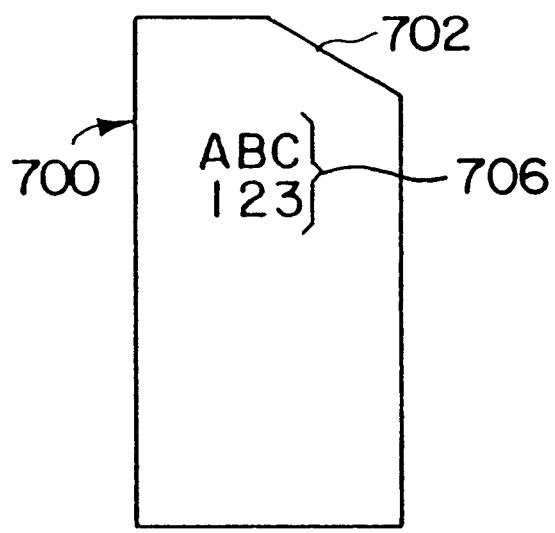
FIG. 29 is a front elevation of an alternate embodiment of the optical memory device.

In another embodiment, OMD 700, illustrated in FIG. 29, an orientation indicator is provided in the form of a notched or cut-corner 702. In this embodiment, the corner cut-out 702 will provide information as to the rotation and inversion of OMD 700, since, even if the OMD is face down, it will be apparent due to the unique outline of the face. The use of a physically detectable orientation indicator allows the handling equipment to readily detect improper positioning, for example, by placement of mechanical or optical edge detectors within the handling system. An improperly positioned OMD can be removed from the imaging position and placed back at the entry point into the reading handler, or mechanical means, such as a retractable blade, can be provided to flip the OMD over if it is presented face down within the field of view of the reader. An alternative symbology 706 is illustrated which is, in this case, an alphanumeric code, which can be read and decoded using known optical character recognition (OCR) techniques.

Other types of orientation indicators that can be used include chamfers, holes and protrusions. Several different and distinctive shapes can be included on a single OMD to assist in orientation, positioning and separation of the OMDs. For example, a group of OMDs can have a cut corner for orientation of each OMD, with some of those OMDs having a tab extending from one of its sides, so that those with tabs can be separated from those without tabs, which facilitates division of the group for diversion to different containers.

(ii) Other Optical Memories

Other optical memories, or optically encoded memories, such as memories that rely on changes in chemical or physical properties of particular molecules are contemplated for use in the matrix-with-memory combinations and drug discovery units provided herein.

These include optical memory systems are based on light-induced changes in the optical chemical or physical properties of materials; polymer-based photonic materials that can store 1 trillion bytes of date per cc have been developed [see, e.g., U.S. Pat. Nos. 5,268,862, 5,130,362, 5,325,324; see, also, Dvornikov et al. (1996) *Opt. Commun.* 128:205–210; Dvornikov et al. (1996) *Res. Chem. Intermed.* 22:115–28; Dvornikov et al. (1994) *Proc. SPIE-Int. Soc. Opt. Eng.* 2297:447–51; Dvornikov et al. (1994) *Mol. Cryst. Liq. Cryst. Sci. Technol., Sect. A* 246:379–88; Dvornikov et al. (1994) *J. Phys. Chem.* 98:6746–52; Ford et al. (1993) *Proc. SPIE-Int. Soc. Opt.* 2026:604–613; Ford et al. *Proc. SPIE-Int. Soc. Opt. Eng.* 1853:5–13; Malkin et al. *Res. Chem. Intermed.* 19:159–89; Dvornikov et al. (1993) *Proc. SPIE-Int. Soc. Opt. Eng.* 1852:243–52; Dvornikov et al. (1992) *Proc. SPIE-Int. Soc. Opt. Eng.* 1662:197–204; Prasad et al. (1996) *Mater. Res. Soc. Symp. Proc.* 413:203–213; and Dagani in *Chemical and Eng. News* Sep. 23, 1996, pp. 68–69]; memories based on photochromaic materials, such as 1-nitro-2-naphthaldehyde and the colorless base form of the laser dye rhodamine B, are also available [see, e.g., Dvornikov et al. (1996) *Res. Chem. Intermed.* 22:115–28]; optical memories that employ rhodopsins, particularly bacteriorhodopsin [BR], or other photochromic substances that change between two light absorbing states in response to light of each of two wavelengths [see, e.g., U.S. Pat. No. 5,346,789, 5,253,198 and 5,228,001; see, also Birge (1990) *Ann. Rev. Phys. Chem* 41:683–733]; and numerous other known to those of skill in this art.

(3) Containers

A container is typically of a size used in immunoassays or hybridization reactions, generally a liter or less, typically less than 100 ml, and often less than about 10 ml in volume, typically 100 $\mu$l–500 $\mu$l, particularly 200–250 $\mu$l. Alternatively, the container can be in the form of a plurality of wells, such as a microtiter plate, each well having about 1 to 1.5 ml or less in volume. When used with electromagnetic memories, the container is transmissive to the electromagnetic radiation, such as radio frequencies, infrared wavelengths, radar, ultraviolet wavelengths, microwave frequencies, visible wavelengths, X-rays or laser light, used to program the recording device.

The recording device will be in, on or embedded in the container. More than one recording device may be associated with a single container.

The container is typically for containing the solutions, but may also be adapted on a surface thereof for linking molecules or biological particles. As will become apparent, the containers with memories form a part of the drug discovery units provided herein.

The memory is part of the container that contains the sample or is part of the instrument. As a sample is moved, for example, from container to container or from instrument to container to a plate, the information from one memory is transferred by reading one memory and writing to the next so the identity of the contents is tracked as it is processed. Such movement and tracking can be automated.

The containers contemplated herein include test tubes, vials and microplates, such as 96 well or 384 well or higher density formats or other such microplates and microtiter plates. The matrices may contain one or more recording devices. For example, each well or selected wells in the microplate include a memory device in contact therewith or embedded therein. Automated robotic protocols will incorporate such plates for automated multiplexing [performing a series of coupled synthetic and processing steps, typically, though not necessarily on the same platform, i.e. coupling of the chemistry to the biology] including one or more of the following, synthesis, preferably accompanied by writing to the linked memories to identify linked compounds, screening, including using protocols with matrices with memories, and compound identification by querying the memories of matrices associated with the selected compounds.

Plates that include a bar code, particularly the two-dimensional optical bar code provided herein on the base of each well or elsewhere. The two-dimensional bar code or other such code is particularly suited for application to each well in a microplate, such as a microtiter plate, that contain 96, 384, 1536 or higher density formats. The bar code may also be used in combination with modules that are fitted into the frames of 96 wells, or higher density formats Separate containers or strips of containers are designed to fit into microplate frames. Each such container may be encoded with a bar code so that, upon removal from the strip, the container, and thereby, its contents or history, may be identified.

More than one data storage device, engraved coded, or combination thereof, may be in proximity to, or in contact with, one or more matrix particles. For example, microplates, such as microtiter plates or other such high density format [i.e., 96, 384, 1536, or more wells per plate, such as those available from Nunc, Naperville, Ill., Costar, Cambridge Mass., and Millipore, Bedford, Mass.] with the recording device containing the data storage unit embedded in each well, or vials, on the order of [typically with a] 1.5 ml or smaller capacity, with an embedded recording device may be manufactured.

3. Preparation of Matrix-with-Memory Combinations

The preparation of the matrices with memories is detailing in the co-pending and published applications enumerated above. For example, the recording device can cast in a selected matrix material during manufacture. Alternatively, the devices can be physically inserted into the matrix material, the deformable gel-like materials, or can be placed on the matrix material and attached by a connector, such as a plastic or wax or other such material. Alternatively, the device or device(s) may be included in an inert container in proximity to or in contact with matrix material.

The recording device with memory can be placed onto the inner or outer surface of a vessel, such as a microtiter plate or vial or tube in which the reaction steps are conducted, fractions collected or samples stored. Alternatively, the device can be incorporated into the vessel material, such into the a wall of each microtiter well or vial or tube in which the reaction is conducted. As long as the molecules or biological particles remain associated with the well, tube or vial, their identity can be tracked. The memory will be a programmable electronic memory or a bar code. These memories can also be associated with reagent containers.

In one embodiment, one or more recording devices with memory and matrix particles are sealed in a porous nonreactive material, such as polypropylene or TEFLON® net, with a pore size smaller than the particle size of the matrix and the device. Typically one device per about 1 to 50 mg, preferably 5 to 30, more preferably 5 to 20 mg of matrix material, or in some embodiments up to gram, generally 50 to 250 mg, preferably 150 mg to about 200 mg, and one device is sealed in a porous vessel a microvessel. The amount of matrix material is a function of the size of the device and the application in which the resulting matrix with memory is used, and, if necessary can be empirically determined. Generally, smaller sizes are desired, and the amount of material will depend upon the size of the selected recording device.

Figure 21:
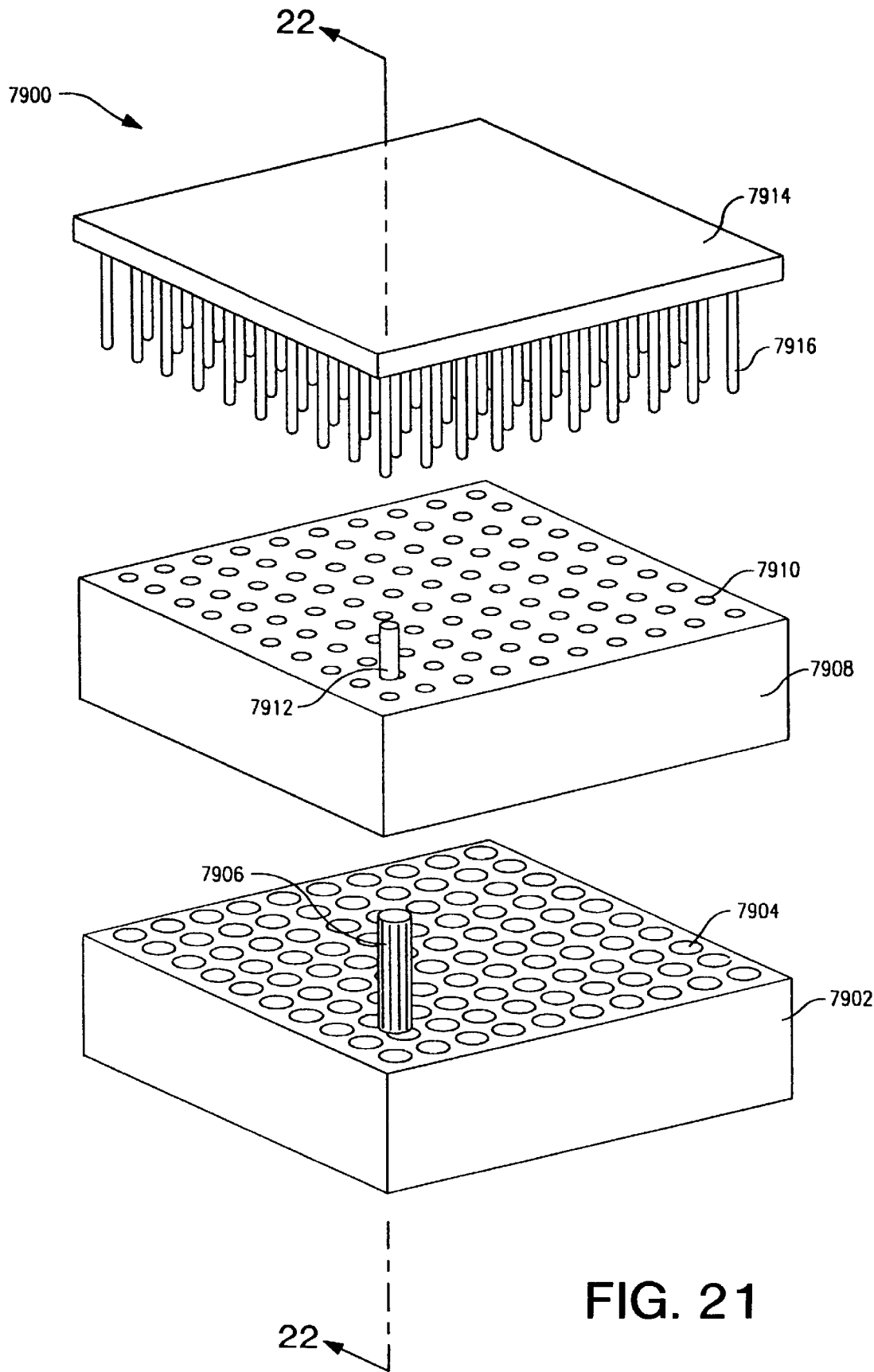
FIG. 21 is a perspective view of a microreactor assembly system showing the insertion of a microtag into a tubular microreactor.

An assembly system for preparation of the tubular microreactors illustrated in FIGS. 21–24. In FIG. 21, a microreactor assembly system 7900 is shown. System 7900 includes a microreactor loading block 7902, a microtag holding block 7908, and a plunger plate 7914. Microreactor loading block 7902 is formed with an array of bores 7904, each of which are sized to receive the tubular microreactor, with each bore being formed with a narrow ejection port 7928 to prevent the passage of the microreactor through the loading block 7902. The microtag holding block 7908 is formed with an array of bores 7910 which extend through the block 7908, and each of which are sized and formed to receive and retain a microtag 7912. The plunger plate 7914 includes an array of plungers 7916 which are aligned with the array pattern of bores 7910 and 7904 in the microtag holding block 7908 and microreactor loading block 7902, respectively.

Figure 22:
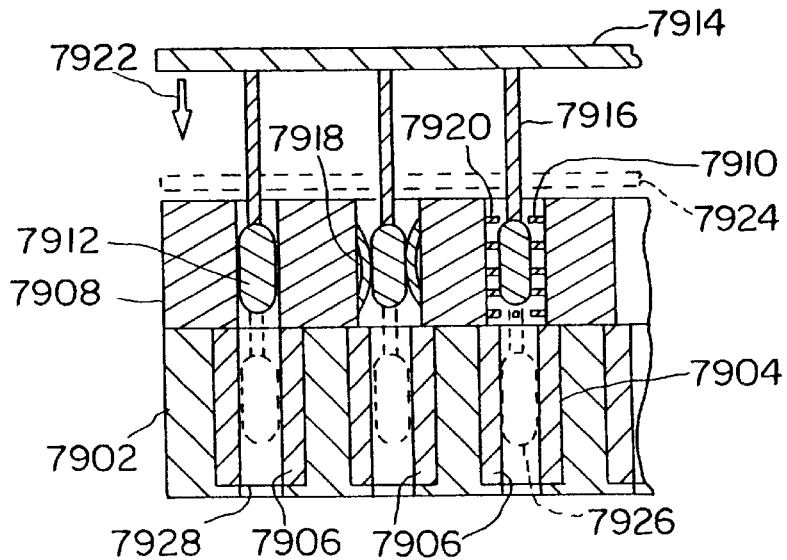
FIG. 22 is a cross-sectional view of the microreactor assembly system of FIG. 21 showing the insertion of the microtag into the microreactor.

FIG. 22 is a cross-sectional view of the system 7900 showing the insertion of microtags into a number of microreactors using microreactor loading block 7902. In the insertion configuration for this preferred embodiment, loading block 7902 is pre-loaded with a microreactor 7906 in each bore 7904. Immediately adjacent the top surface of loading block 7902 is holding block 7908 which is pre-loaded with microtag 7912 in each bore 7910. Each bore 7910 in holding block 7908 is closely aligned with corresponding bore 7904 in loading block 7902. Plunger plate 7914 is positioned with each of its plungers 7916 inside corresponding bore 7910 of holding block 7908. As shown, the plunger plate 7914 is moved in direction 7922 to second position 7924 such that each of the plungers 7916 simultaneously urges its respective microtag 7912 from the holding block 7908 into a second position 7926 within the loading block 7902. Following the insertion of the microtags 7912 into their respective microreactor 7906, the plunger plate 7914 and holding block 7908 are removed from loading block 7902. The microreactors may then be removed from the loading block, and used for solid phase synthesis and screening and the other applications, including as described elsewhere herein.

The holding block as shown in FIG. 22 has a number of bores 7910. Each of these bores are shown having a different retaining device to retain the microtag within the bore 7910. For example, the left-most bore 7910 is sized to retain microtag 7912 by friction generated between the microtag and the inside wall of the bore 7910. Additionally, the holding block may be manufactured from a pliable material which would be sufficiently resilient to allow the easy insertion and removal of the microtags while providing sufficient contact force to hold the microtag securely within the bore 7910. Such a material, for example, could include vinyl or teflon, or any other materials which exhibit similar strength and rigidity.

The center bore 7910 shown in FIG. 22 includes a pair of flexible members 7918 which are either pre-formed within the bore, or are inserted after manufacturing of the holding block. Alternatively, the right-most bore 7910 includes a number of pliable fingers 7920 which are positioned within the bore to allow easy insertion and removal of the microtag, while retaining the microtag in position during the assembly process. Other appropriate techniques may be used for holding the microtags in place pending insertion into the microreactors, or other vessels disclosed herein.

Figure 23:
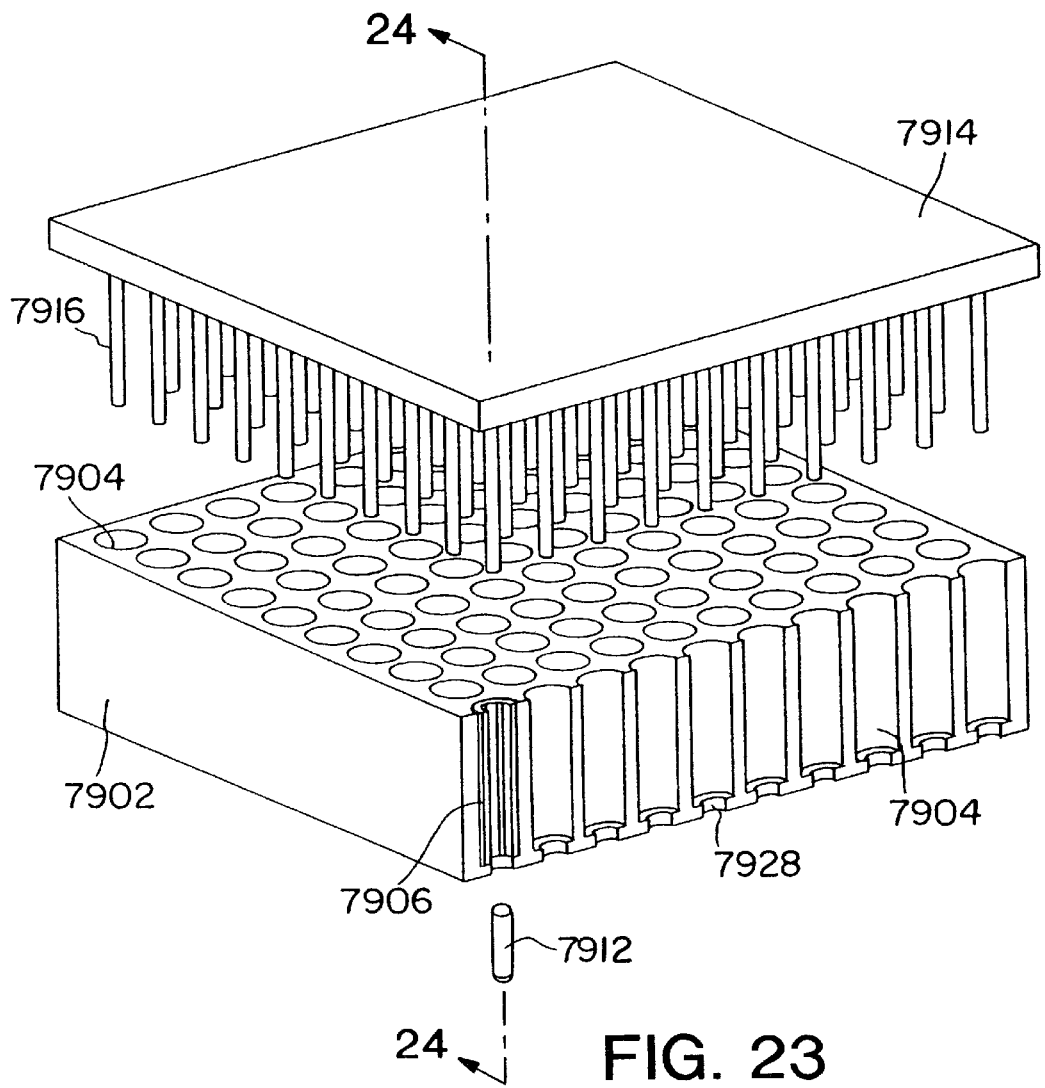
FIG. 23 is a cross-sectional view of the microreactor assembly system of FIG. 21, showing the removal of a microtag from a microreactor.

Referring now to FIG. 23, microreactor assembly system 7900 is shown in the ejection configuration with portions of the loading block 7902 cut away for clarity. Loading lock 7902 is shown having a microreactor 7906 installed in a bore 7904. Plunger plate 7914 is positioned above the loading block 7902 such that the plungers 7916 align with a corresponding bore 7904 and microreactor 7906.

Figure 24:
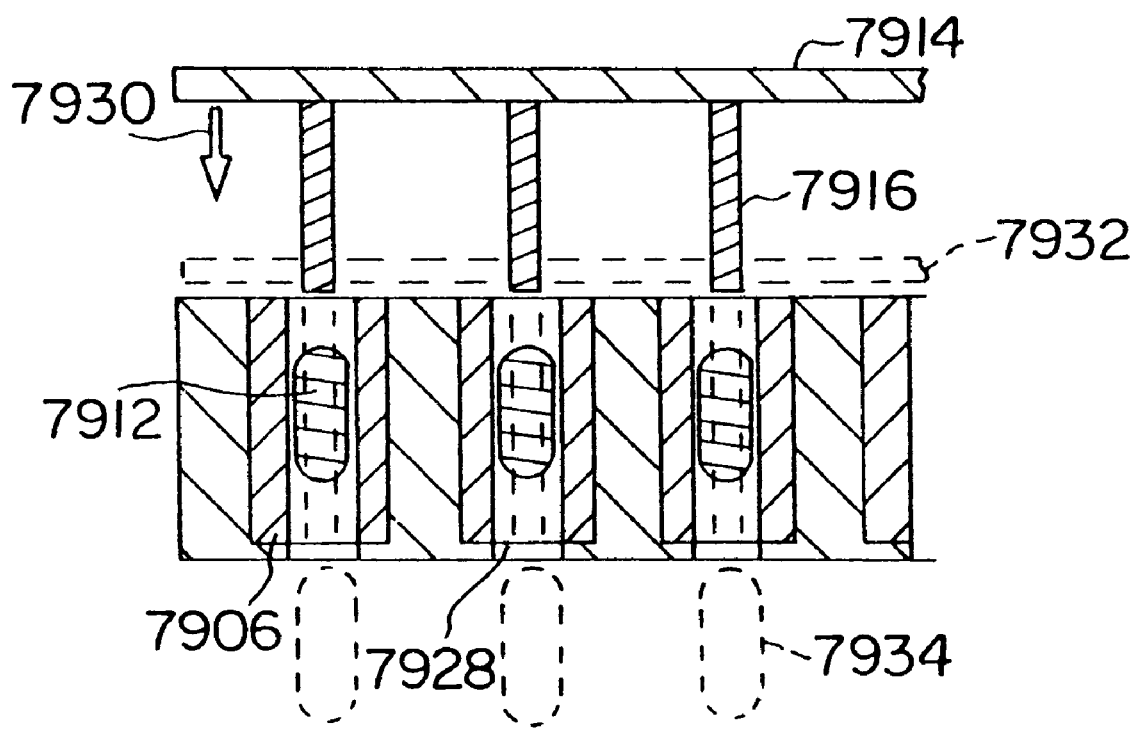
FIG. 24 is a cross-sectional view of the microreactor assembly system of FIG. 23, showing the removal process for removing a microtag from a microreactor.

FIG. 24 is a cross-sectional view of loading block 7902 and plunger plate 7914 which shows the positioning of plungers 7916 inside bore 7904 and microreactor 7906. As the plunger plate is advanced in direction 7930 towards the loading block to second position 7932, plungers 7916 enter microreactor 7906 and strike microtag 7912 which is forced from its position within the microreactor 7906, through ejection port 7928, and to ejected position 7934.

The pre-loading of holding block 7908 may be accomplished by manually inserting a microtag into each bore 7910, or the holding block may be provided from the manufacture pre-loaded with the microtags. Similarly, the loading block may be loaded with the microreactors manually, or may also be provided pre-loaded from the manufacturer.

The resulting microvessels are then encoded, reactions, such as synthetic reactions, performed, and read, and if desired used in desired assays or other methods.

In certain embodiments, combinations of matrices with memories and biological particle combinations are prepared. For example, libraries [e.g., bacteria or bacteriophage, or other virus particles or other particles that contain genetic coding information or other information] can be prepared on the matrices with memories, and stored as such for future use or antibodies can be linked to the matrices with memories and stored for future use.

Microplates containing a recording device in one or a plurality of wells can be prepared. The plates may further contain embedded scintillant or a coating of scintillant [such as FlashPlate™, available from DuPont NEN®, Cytostar-T plates from Amersham International plc, U.K., and plates available from Packard, Meriden, Conn.] FLASHPLATE™ is a 96 well microplate that is precoated with plastic scintillant for detection of β-emitting isotopes, such as $^{125}$I, $^{3}$H, $^{35}$S, $^{14}$C and $^{33}$P. A molecule is immobilized or synthesized in each well of the plate, each memory is programmed with the identify of each molecule in each well. The immobilized molecule on the surface of the well captures a radiolabeled ligand in solution results in detection of the bound radioactivity. These plates can be used for a variety of radioimmunoassays [RIAs], radioreceptor assays [RRAs], nucleic acid/ protein binding assays, enzymatic assays and cell-based assays, in which cells are grown on the plates.

4. Use of Matrices-With-Memories for Synthesis and Screening

When matrices-with memories are used for the synthesis of molecules, the memory of each particle is addressed and the identity of the added component is encoded in the memory at (before, during, or preferably after) each step in the synthesis (see, e.g., FIG. 1). At the end of the synthesis, the memory contains a retrievable record of all of the constituents of the resulting molecule, which can then be used, either linked to the support, or following cleavage from the support in an assay or for screening or other such application. If the molecule is cleaved from the support with memory, the memory must remain in proximity to the molecule or must in some manner be traceable [i.e., associated with] to the molecule. Such synthetic steps may be automated.

In preferred embodiments, the matrix-with-memory with linked molecules [or biological particles] are mixed and reacted with a sample according to a screening or assay protocol, and those that react are isolated. The identity of reacted molecules can then be ascertained by remotely retrieving the information stored in the memory and decoding it to identify the linked molecules. Such steps can be performed on a single platform or on a series of platforms in which with each transfer information from one memory is transferred to a subsequent memory that is in contact with the sample.

In using the matrix-with-memory combination, molecules, such as antigens, antibodies, ligands, proteins and nucleic acids, and biological particles, such as phage and viral particles and cells, that are associated with, such as in proximity to or in physical contact with the matrix combination or linked via information stored in a remote computer, can be electromagnetically tagged by programming the memory with data corresponding to identifying information or can be tagged by imprinting or encoding the matrix with identifying information. Programming and reading the memory is effected remotely, preferably using electromagnetic radiation, particularly radio frequency [RF] (and also including AM, FM, radar, infrared, UV, and microwave), or by reading the imprinted information.

The combinations of matrices-with-memories thus have a multiplicity of applications, including combinatorial chemistry, isolation and purification of target macromolecules, capture and detection of macromolecules for analytical purposes, high throughput screening, selective removal of contaminants, enzymatic catalysis, drug delivery, chemical modification, information collection and management and other uses. As a result, they can serve as a platform for all aspects of the drug discovery process. These combinations are particularly advantageous for use in multianalyte analyses, assays in which a electromagnetic signal is generated by the reactants or products in the assay, for use in homogeneous assays, and for use in multiplexed protocols. All are intended for use in the units and drug discovery protocols provided herein.

a. Tools

The matrix-with-memory and associated system as described herein is the basic tool that can be used in a multitude of applications, including any reaction that incorporates a functionally specific (i.e. in the reaction) interaction, such as receptor binding. This tool is then combined with existing technologies or can be modified to produce additional tools.

For example, the matrix-with-memory combination, can be designed as a single analyte test or as a multianalyte test and also as a multiplexed assay that is readily automated. The ability to add one or a mixture of matrices with memories, each with linked or proximate molecule or biological particle to a sample, provides that ability to simultaneously determine multiple analytes and to also avoid multiple pipetting steps. The ability to add a matrix with memory and linked molecules or particles with additional reagents, such as scintillants, provides the ability to multiplex assays.

As discussed herein, in one preferred embodiment the matrices are particulate and include adsorbed, absorbed, or otherwise linked or proximate, molecules, such as peptides or oligonucleotides, or biological particles, such as cells. Assays using such particulate memories with matrices may be conduced "on bead" or "off bead". On bead assays are suitable for multianalyte assays in which mixtures of matrices with linked molecules are used and screened against a labeled known. Off bead assays may also be performed; in these instances the identity of the linked molecule or biological particle must be known prior to cleavage or the molecule or biological particle must be in some manner associated with the memory.

In other embodiments the matrices with memories use matrices that are continuous, such as microplates, and include a plurality of memories, preferably one memory/well. Of particular interest herein are matrices, such as Flash Plates™ [NEN, Dupont], that are coated or impregnated with scintillant or fluophore or other luminescent moiety or combination thereof, modified by including a memory in each well. The resulting matrix with memory is herein referred to as a luminescing matrix with memory. Other formats of interest that can be modified by including a memory in a matrix include the Multiscreen Assay System [Millipore] and gel permeation technology. Luminescent moieties can be included in the particulate matrix materials, and the resulting combinations also can be used in scintillation proximity assays and fluorescence-based assays, such as HTRF and FRET assays.

Again it is noted that the memories may be replaced with or supplemented with engraved code, preferably at the base of each well [outer surface preferred] that is either precoded or added prior to or during use. The memory, in these instances, is then remote from the matrix. Among the preferred plates are those that contain a microplate type frame and removable wells or strips. Each well or strip can contain a memory and/or can be engraved with a code.

b. Synthesis

The combinations of matrices with memories are applicable to virtually any synthetic scheme and library preparation and screening protocol. These include, those discussed herein, and also methodologies and devices, such as the Chiron "pin" technology [see, e.g., International PCT application No.WO 94/11388; Geysen et al. (1985) *Proc. Natl. Acad. Sci. U.S.A.* 82:178; Geysen et al. (1987) *J. Immunol. Meth.* 102:259–274; Maeji et al. (1994) *Reactive Polymers* 22:203–212], which relies on a support composed of annular synthesis components that have an active surface for synthesis of a modular polymer and an inert support rod that is positioned axially to the annular synthesis components. This pin technology was developed for the simultaneous synthesis of multiple peptides. In particular the peptides are synthesized on polyacrylic acid grafted on the tip of polyethylene pins, typically arranged in a microtiter format. Amino acid coupling is effected by immersing the pins in a microtiter plate. The resulting peptides remain bound to the pins and can be reused.

As provided herein, "pins" may be linked to a memory or recording device, preferably encasing the device, or each pin may be coded and the code and the identity of the associated linked molecule(s) stored in a remote memory. As a result it will not be necessary to physically array the pins, rather the pins can be removed and mixed or sorted.

(1) Combinatorial Syntheses

By pooling and splitting matrix with memory microreactors [rather than individual solid phase resin beads] by a process known as "directed sorting", one discrete compound is synthesized in each matrix with memory reactor or microreactor (see, e.g., FIGS. 1 and 33C). Each microreactor contains a memory, such as an optical memory or electronic memory, that is a unique label or tag used to identify it during the sorting processes that occur between chemical synthesis steps.

The memory tag provides a unique ID for each matrix with memory reactor and therefore each compound. This unique ID allows each microreactor to be identified during the combinatorial directed sorting process.

(2) The "Directed Sorting™" Approach to Solid Phase Combinatorial Chemistry

The "directed sorting" approach to combinatorial chemistry is made possible by splitting and pooling matrix with memory microreactors rather than individual solid phase resin beads. During the first directed sorting step each microreactor is assigned to one specific compound. This assignment is maintained during all subsequent directed sorting and synthesis steps.

Tagging with a memory that is either engraved, imprinted or electronically encoded during processing, subsequent to or pre-encoded [with decoding information stored remotely and associated with identifying information] of microreactors provides positive identification of compounds for archival and storage purposes. Such tagging permits the microreactors to be sorted between the individual steps in the synthesis.

Traditional split-and-pool methodology relies on a statistical distribution of resin beads between each step in the chemical synthesis. Typically, a large number of resin beads are used for each compound being synthesized to ensure an adequate statistical distribution of compounds. A consequence of this approach is that individual compounds are synthesized on multiple solid phase resin beads. These multiple copies of each compound are mixed together with multiple copies of all the other compounds. These mixtures need to be deconvoluted during screening. In contrast, the directed sorting approach ensures that: every compound is synthesized; only one copy of each compound is synthesized, and all compounds are present as discrete entities (no mixtures).

c. Screening

The activity of molecules synthesized on the surface of the microreactors may be evaluated in a variety of solid based assay formats. Scintillation proximity assays [SPA], FP [fluorescence polarization] assays, FET [fluorescent energy transfer] assays, FRET [fluorescent resonance energy transfer] assays and HTRF [homogeneous time-resolved fluorescence] assays may be performed using matrices-with-memories that are be coated with, embedded with or otherwise combined with or in contact with assay material, such as scintillant, fluophore or other fluorescent label. The resulting combinations are called luminescing memories with matrices. When used in SPA formats they are referred to as scintillating matrices with memories and when used in non-radioactive energy transfer formats [such as HTRF] they are referred to as fluorescing memories with matrices.

Thus, the assays include, but are not limited to, receptor assays, cell-based assays, immunoassays, non-radioactive energy transfer reactions, such as FET or FRET, FP and HTRF assays (see, e.g., Cardullo et al. (1988) *Proc. Natl. Acad. Sci. U.S.A.* 85:8790–8794; Peerce et al. (1986) *Proc. Natl. Acad. Sci. U.S.A.* 83:8092–8096; U.S. Pat. No. 4,777,128; U.S. Pat. No. 5,162,508; U.S. Pat. No. 4,927,923; U.S. Pat. No. 5,279,943; and International PCT Application No. WO 92/01225), scintillation proximity assays, and any other assay of interest.

Any assays and reactions known to those of skill can be performed with the matrix-with-memory microreactor or with a container with a memory (see, e.g., the co-owned copending and allowed U.S. patent applications and International PCT applications enumerated above).

a. SPA Assay and Other Non-Radioactive Energy Transfer Assays

The biological activity of small molecules synthesized on the surface of the matrices with memories with scintillant may be evaluated in a variety of scintillation proximity assay formats as described herein. For example, biotin and its derivative (2-imidazolidone-4-carboxylic acid) were synthesized on the tube and the binding characteristics of the synthesized molecules on the solid support to 125I-streptavidin in scintillation proximity assay were evaluated. The results demonstrated that biotin derivative (2-imidazolidone-4-carboxylic acid) that has much lower affinity for streptavidin exhibited a lower signal.

Similarly, other non-radioactive assays that rely on non-radioactive energy transfer reaction, such as HTRF, FRET and FET assays may be performed using luminescing matrices-with-memories.

b. ELISA Type Assay and Other Immunoassays

Immunoassays may be performed using memories with matrices. For example, ELISAs can be performed using antibodies to small molecules, such as a peptide. For example metenkephalin was synthesized on the MICRO-TUBE microvessel, and anti-metenkephalin antibody was used. As an example of nonpeptide small molecule biotin was synthesized and an anti-biotin antibody labeled with alkaline phosphatase was used to detect by calorimetric, fluorometric or luminescent means.

c. Radioimmunoassay

Using radio-labeled antibody or receptor, a variety of radioimmunoassays may be designed using the microvessels, such as the MICROTUBE microreactors.

d. Detection of the Oligonucleotides

A variety of the labeled probes (e.g., fluorescence and radiolabels) may be used to detect the identity of a synthesized oligonucleotide on the surface of the polymer, which has been radiation grafted [see, below] on the MICROTUBE microvessel (or on a particle in a MICROKAN microreactor]. Oligonucleotides may be also characterized using a labeled complementary DNA or RNA in a hybridization assay.

d. Multiplexed or Coupled Protocols in Which the Synthesis Steps (the Chemistry) is Coupled to Subsequent Uses of the Synthesized Molecules Multiplexed or multiple step processes in which compounds are synthesized and then assayed without any intermediate identification steps are provided herein. Since the memories with matrices permit identification of linked or proximate or associated molecules or biological particles, there is no need to identify such molecules or biological particles during any preparative and subsequent assaying steps or processing steps. Thus, the chemistry [synthesis] can be directly coupled to the biology [assaying, screening or any other application disclosed herein]. For purposes herein this coupling is referred to as multiplexing. Thus, high speed synthesis can be coupled to high throughput screening protocols.

As described elsewhere herein, automated and tagged laboratories are also provided. Memories (tags) are combined with containers, tubes and instruments used in processing the products; as a product is moved from one container to another the identifying information and/or other associated information becomes associated with or written to a tag combined with the next vessel used in the process. As a result the information remains associated with the products. Ultimately, the tag is associated with the product when and if it is stored for later use.

Figure 25:
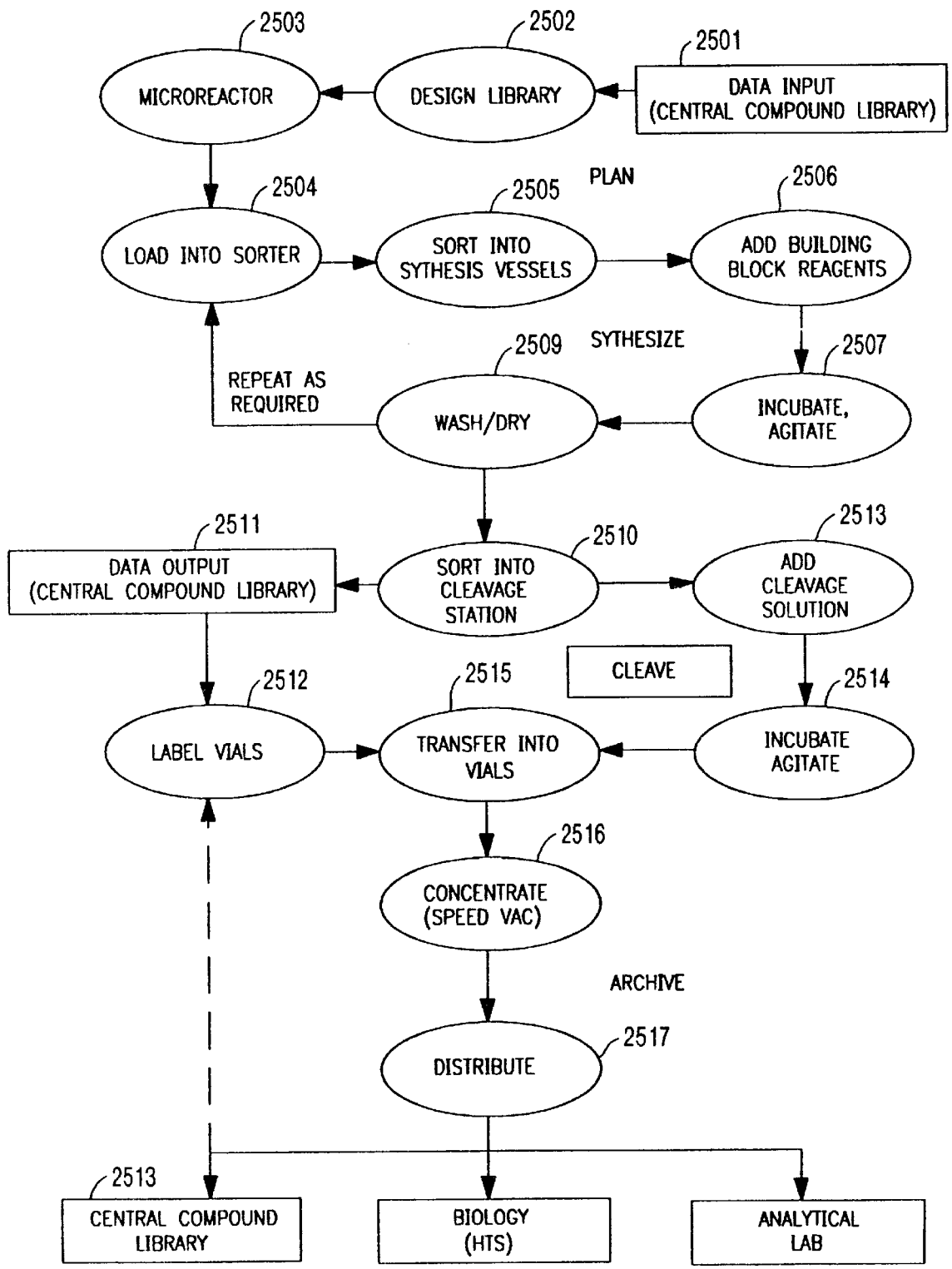
FIG. 25 depicts a process flow in an exemplary automated drug discovery (ADD) unit.

C. Units for Drug Discovery, the Automated Drug Discovery (ADD) System, Including Manual and Automated Systems for Combinatorial Syntheses, Other Synthetic Protocols and Screening Illustrated in FIG. 25 is a diagram of the process steps for operation of an exemplary automated drug discovery unit, which provides a means for seamless data tracking between and among the components of the units in which all critical components, including instrumentation and vials include memories for seamless transfer information to other memories in a unit. The process steps are initiated by entry of data into the host computer (step 2501). In the illustrated example, the data comprises information from a central compound library. The central compound library refers to compounds as sorted in racks, vials, microtiter plates, and other such vessels, using the memories for tracking. A second library is then accessed with the procedures for operating the desired test sequence (step 2502). Microreactors, such as those described previously, are identified (step 2503) and loaded into the sorter (step 2504), so that a record can be initiated in the host computer for each microreactor. The preferred microreactors are resin-loaded microvessels and tube microreactors.) The sorter, which may be an automated or manual sorter, is used to distribute the microreactors into the appropriate microvessels. Depending on whether the sorter is automatic or manual, steps 2503 and 2504 may be interchanged since, in an automatic sorter, the identification procedure is conducted during the sorting process. The microreactors are then sorted into the synthesis vessels (step 2505) and the building block reagents are added to the vessels (step 2506). The vessels are incubated and agitated to optimize exposure of the matrices within the microreactors to the reagents (step 2507). The microreactors are then washed and dried to remove excess reagent (step 2508), then may either be resorted for additional exposure to reagents (beginning at step 2504), or proceed to be sorted into a cleavage station (step 2509). As the microreactors are sorted for loading in the cleavage station, the memory devices within the microreactors are interrogated to determine their identities and any other information contained therein (step 2511). The data is used to label vials into which the cleaved solution from the microreactors is to be deposited (step 2512), which data is communicated to the central compound library for storage (step 2513).

The sorted microreactors are now located in an array of microreactor carriers that are positioned within trays for cleavage (step 2510). Cleavage solution is added to the carriers (step 2514) and the carriers (within the cleavage station) are incubated to assist in the cleaving process (step 2515). The cleaved solutions are transferred into the vials, which are located within the vacuum chamber of the cleaving station (step 2516), concentrated (step 2517), then distributed to various analytical facilities (step 2517).

As will be described in more detail later with regard to several embodiments of the ADD system, the system includes a host computer with memory, a manual or automatic sorter, an automated or semi-automated synthesizer, a microreactor washer/dryer, a manual or automated cleaver for removing compounds from the matrix with memory microvessels, and the associated software. In addition to memories with matrices upon which synthesis is performed, all instrumentation, vials, plates, sorters, robots, and other components, will also include memories. Information from one memory will be transferred to another as a protocol proceeds.

Figure 26:
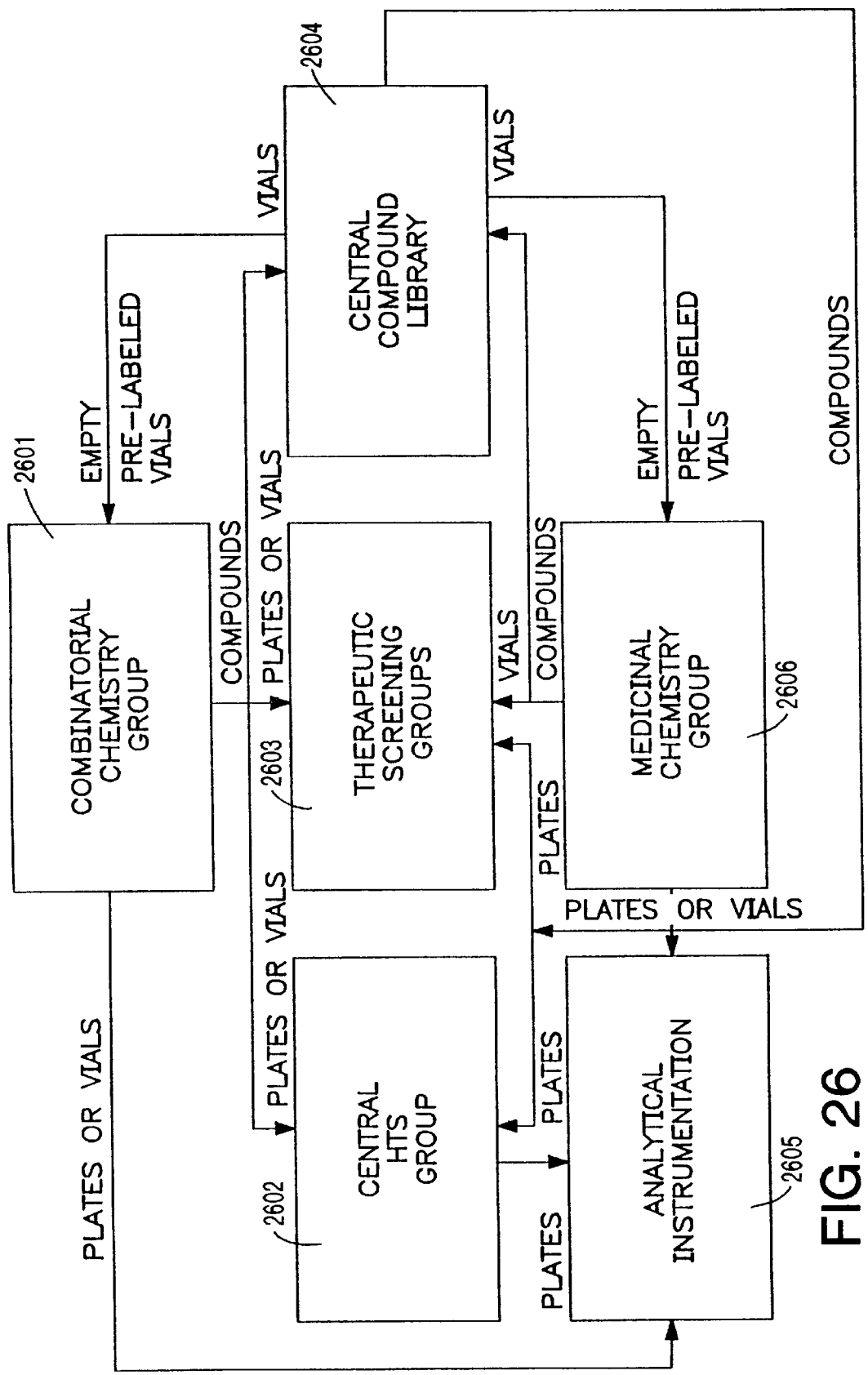
FIG. 26 is a flow chart of the automated drug discovery laboratory provided herein.

FIG. 26 is a chart of the inter-relationship within an automated drug discovery laboratory provided herein, including analytical instruments and workflow between research and support groups, in which the entire process is based on a single platform: the matrices-with-memories provided herein. The libraries on synthesized and stored on the matrices-with-memories, which can then be used for a variety of applications. In addition to matrices-with-memories upon which synthesis is performed, all instrumentation, vials, plates, sorters, robots, and other components, will include memories. Information from one memory will be transferred to another as a protocol proceeds.

Using the group inter-relationships and a central host computer and data base, i.e., the central compound library, each of the research groups can call upon the other groups' research. The matrices-with-memories can also be exchanged or circulated between the groups for further research, with the identifying information being readily accessible via the host computer.

Figure 27:
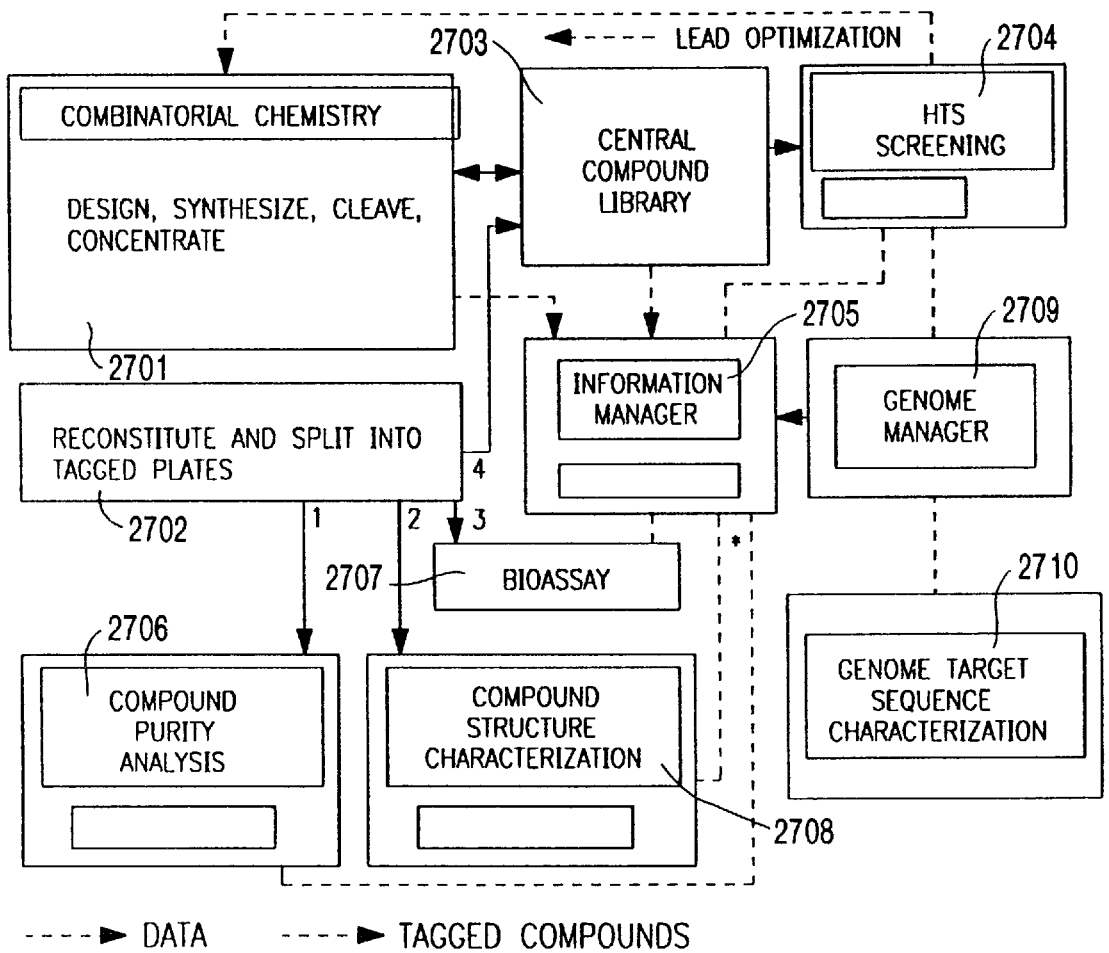
FIG. 27 is a block diagram showing the linkage between the drug discovery process and matrix-with-memory platform.

FIG. 27 shows how the entire drug discovery process is linked by the matrix-with-memory matrix platform. The compounds are synthesized on the matrix, sorted, cleaved and concentrated as described herein. The compounds can then be assayed, characterized, analyzed, used for high throughput screening and tracked throughout using the memories for identification. The resulting information will be accumulated in databases. The box designated combinatorial chemistry refers to hardware, software, and consumables using the micromemory (electronic tags, optical memories, etc., or combinations thereof) technology provided herein for synthesis, cleavage, concentration and design of libraries of molecules and biological particles. The final product is a library of discrete multimilligram quantities of compounds ready for further processing, including screening and other analyses, that can remain linked to the matrix with memory or can be cleaved. The micromemories and associated software will provide the means to transfer information as the compounds are processed and moved from location to location. High throughput screening (HTS) refers to on bead or off bead screening, while the memories and databases relate back to the compound/library/synthesis/ analysis data. Information on targets can come from genomics databases and other such sources. Genome manager software refers to software, databases and drivers that deal with genomic information. This can be linked to the software provided herein, such as the Synthesis Manager software, and the Information manager software. Information Manager software is a software platform that runs the entire drug discovery process by providing multiple links to HTS, genomics databases, combinatorial chemistry and analysis, and that relies on the micromemory technology to track the information. Compound analysis and structural information, includes results of structural and physical analyses, including HPLC results, mass spectrometry results, NMR and any other analytical procedure. This database is linked to synthesis manager, assay manager (HTS) software via the information manager software.

Of particular interest herein, are automated protocols, or partially automated protocols, in which the matrices-with-memories serve as the platform on which all manipulations are performed or that serve as the repository of information that is transferred to other memories as the synthesized compounds are processed and screened [see, e.g., FIGS. 25–27]. Thus, an automated drug discovery (ADD) unit provides a means for "seamless" data tracking between and among the components of the units in which all critical components include memories instrumentation and vials. The seamless nature of the data tracking, i.e., the continous and uninterrupted progression from each step to the next, is enabled by including memory devices in the instrumentation and vials, and a host computer which transfers information between the various memory devices. The ADD units include some or all of the following: an automated or manual sorter, microvessels, which contain memories, an automated or semi-automated synthesizer, a microvessel washer/dryer, a manual or automated cleaver for removing compounds from the matrix-with-memory microvessels, and associated software to direct the instrumentation as well as the user.

The memories used in conjunction with the ADD units may be any of any type, including electromagnetically encodable memories and optical memories, or combinations thereof. The memories may be pre-encoded or may be encodable during, after or before processing. Remotely encodable memories are presently preferred, however, in some embodiments, memories associated with certain of the components, such as instrumentation or vials used therewith, for convenience and ease of reuse, may be pre-encoded.

The units may optionally include a carousel (such as those sold by Hewlett Packard) equipped with a reader and linked to a computer with software is also provided. The carousel houses a plurality of vials or vessels, which are each equipped with a memory device. Preferably the memory device, preferably a small monolithic tag, is attached to or encased in a sleeve that is removably fitted to the outside of each vial or is embedded in the vial. The carousel is mounted on a rotating seat that is designed to be rotated either manually, or by electrical, mechanical or other suitable control. This seat is mounted to a housing and is positioned such that the carousel rotates with the memory device [i.e., a read/write device] coming in proximity to a read/write controller. This read/write controller is located within the housing and positioned such that a detector head for the read/write controller is adjacent to the read/write device as held in the carousel. In order to assist the accurate positioning of the carousel, a plunger is oriented on the surface of the housing to strike the carousel at the location of the vial which helps to prevent further rotation of the carousel while the read/write device is communicating with the read/write controller. The read/write controller is a micro-controller based instrument that generates a selected frequency, such as 125 kHz radio frequency (RF) signal, when RF devices are used, which is transmitted to the read/write controller head which includes an antenna element that is designed to transmit the particular RF signal. It will be appreciated that other electromagnetic frequencies, such as microwave, radar, x-ray, UV, and IR may be used.

It is intended that other instruments, as desired and described herein, will also be included in the drug discovery unit as needed or desired. Information, preferably will be transferred from memory-to-memory, and can be under the control of integrating software.

1. Units for Drug Discovery Using Matrices-with-Memories as the Platform: Single Platform Automated Drug Discovery A completely automated synthesis process [see, e.g., FIGS. 25–27] may be accomplished by using the apparatus described herein. For example, matrices-with-memories microreactors, can be fed to an automated sorting device, which sorts the microreactors into their respective microreactor carriers in a microreactor carrier tray, keeping records as to the location of each matrix within the microreactor carrier tray. The microreactor carrier tray may then be placed on a cleaving assembly where a cleaving agent is added to each microreactor carrier within the microreactor carrier tray, thereby initiating the cleaving process which is accelerated by placing the cleaving assembly onto a shaker. Alternatively, a shaker can be integrated into the cleaving assembly. Once the initial cleaving process is complete, the cleaving assembly is placed so that it abuts and seals a vacuum chamber with the assembly in a pre-determined orientation to ensure that the location of each matrix and its associated cleaved compound is known. Then, by activating the vacuum within the vacuum chamber, the cleaved compounds are drawn from each microreactor carrier into a corresponding vial located within each vial rack in the vacuum chamber. Because the orientation and position of each vial rack within the vacuum chamber is known, and the mapping configuration from each microreactor carrier in the microreactor carrier tray to each vial location is also known, the compound within each vial in a vial rack is identifiable, such as by accessing an identification tag embedded therein or attached thereon.

a. Synthesis and/or Linkage of Compounds (Molecules) or Biological Particles to Matrices with Memories Synthesis on the solid phase matrices-with-memories will be performed in reaction vessels, made of glass or other suitable material. A reaction vessel may include internal fins that will tumble the microvessels, while minimizing the amount of synthesis, i.e., building block, solution required. Each reaction vessel preferably has a capacity of about 250 to 500 or more microvessels.

Within the vessels, pre-synthesized molecules or other molecules or biological particles are linked. At each step in the synthesis, and where needed thereafter, the microvessels may be sorted using either a manual, or preferably automated, sorter. In the automated sorter microvessels, are automatically sorted into output reservoirs. The reservoirs preferably have a capacity of up to 10,000 [or more] microvessels, with throughput rate of, for example, 1000 microvessels per hour. The sorter includes output reservoirs capable of holding up to 1000 microvessels each. The sorter may have on the order of 50 or 100 output reservoirs. Exemplary embodiments of the sorter are provided in the EXAMPLES and FIGURES.

A semi- or fully- automated synthesizer includes components comprising reaction vessels containing the microvessels modules for holding the reaction vessels, heating and cooling elements, and reagent adding means. Each of the components can be run manually or automatically under control of a computer with appropriate software [see Appendices].

Sorted microvessels are loaded, either manually or robotically, into reaction vessels containing a stir bar. The stir bar preferably has a memory. The reaction vessels can be heated, cooled, and agitated per computer controlled methods. Each module will hold a selected number of reaction vessels configured to hold up to 500 microvessels. Each module will hold six reaction vessels, each of which can hold, preferably at least 250 microvessels so that there will be, for example, 1500 microvessels per module. The synthesizer includes computer controllable heating and cooling means with a temperature range about −80° C. up to at least 120° C. and timing means for each reaction vessel, each of can be separately heated and timed. The materials of which each of components is formed should withstand temperatures from about −80° C. up to at least 120° C. Such materials include TEFLON® and glass.

Following synthesis, and between steps, the microvessels are washed, rinsed, and, if desired, dried in a microvessel washer/dryer. The washer/dryer is preferably fabricated from TEFLON™ and glass and has a capacity of up to, for example, 10,000 microvessels or memories with matrices in other formats.

Figure 39:
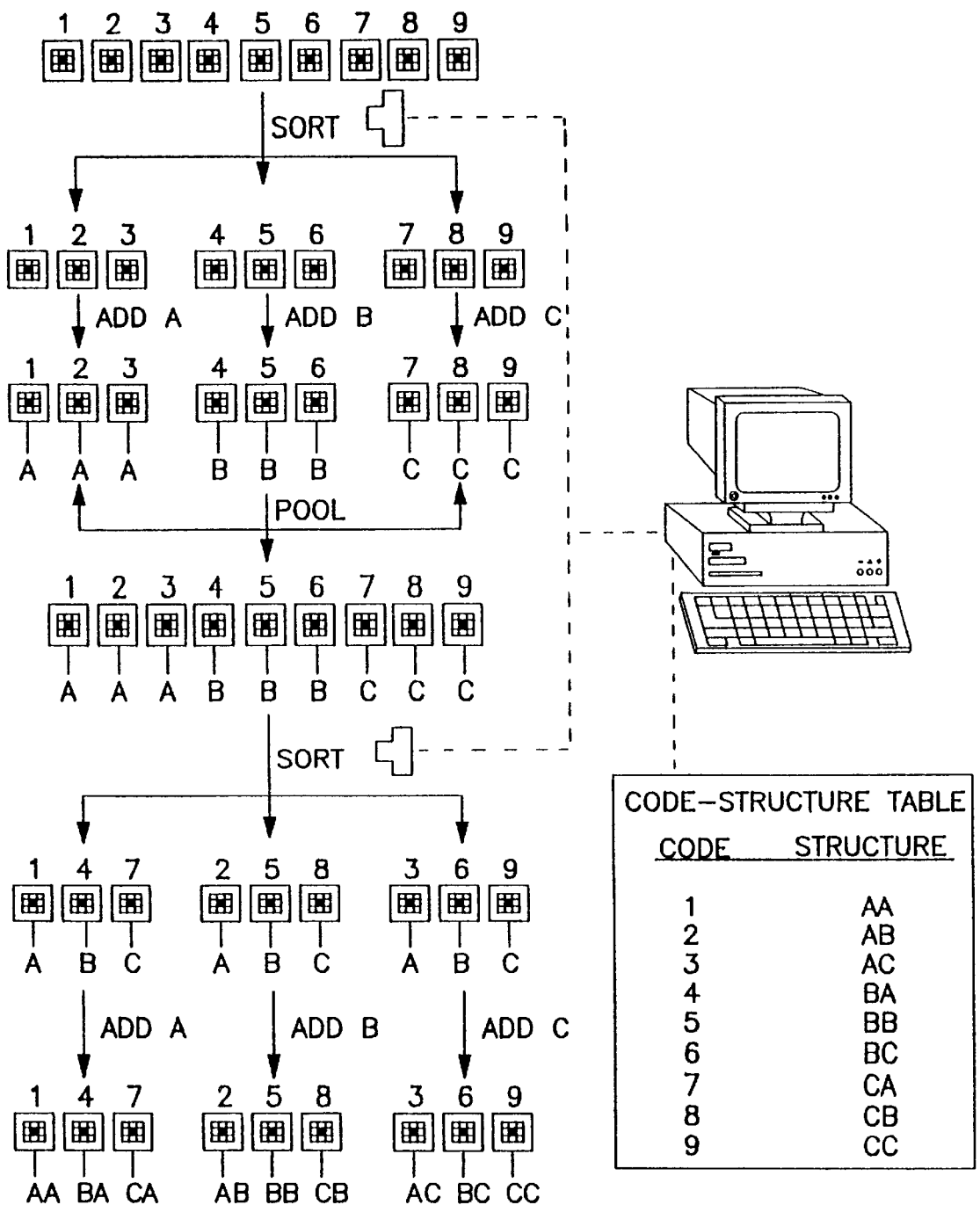
FIG. 39 depicts a split and pool combinatorial synthesis protocol using the OMDs and directed sorting. A, B and C represent building blocks, and the numbers above each OMD represent a 2-D optical bar code (single digits are used merely for exemplification). Other matrix-with-memory microreactors can be substituted for the OMDs.

An improved washing protocol for washing memory-with-matrix microreactors, microvessels, and other solid supports following synthesis and prior to any assays involves washing with buffer (pH about 7 to 7.5, preferably 7.2) containing about 0.75% (0.5% to 0.1%) SDS for about 2 days. The buffer, preferably PBS (pH 7.2) may also contain about 25–50% charcoal (preferably about 35%).

b. Synthesis and/or Linkage of Compounds (Molecules) or Biological Particles on OMDs A directed sorting strategy [instead of statistical pool and splitting] was used in the construction of combinatorial libraries with zero redundancy [i.e., the number of OMDs is equal to the number of the library members]. In an example of a 3×3 directed sorting synthesis [FIGURE 39], nine OMDs are first scanned optically using a small camera [i.e., such as the QuickCam™]linked to the pattern recognition software [see, Appendix IV] on a computer, and each device [with a unique 2-D bar-code], i.e., 1–9, for exemplification, is assigned to one of the nine members in the library [a Code-Structure Table] by the software that directs the synthesis, such as the Synthesis Manager software, [see Appendix I and description above and in the EXAMPLES]. The OMDs are then split [sorted], using software for synthesis and for decoding the 2-D code pattern [see Appendix IV and description herein] into three groups according to the first building block (A, B, or C) for each structure as pre-assigned in the Code-Structure Table. A reaction with building block A, B, or C is then performed on each specific group. The OMDs are then pooled, washed, subjected to common reactions, scanned and re-sorted into three new groups according to the second building block (A, B, or C). A second reaction with building block A, B, or C is then performed with each group of OMDs. The OMDs can then be pooled again, subjected to common manipulations, and sorted. The process is repeated until the synthesis is completed. The structure of the compound synthesized on each OMD can then be decoded by optically reading the 2-D image with synthesis software via the camera and the decoding software and correlating the bar code with the structures in the Code-Structure Table.

The same protocol can be used when the memories-with-matrices are electronically encoded or encodable, rather than optically encoded.

c. Cleavage and Cleaver Therefor

When desired, the compounds (molecules) or biological particles are cleaved from the microvessels. Typically, when cleaved, they will be introduced into a microplate well or vial, each including memories. Information from the microvessel memory will be written to or associated with the memories in the microplate wells, vials or other vessels [i.e., cleavage vessels].

(i) Manual Cleaver

Matrix-with-memory microvessels with synthesized compounds or linked biological particles are manually sorted into individual cleavage vessels that are organized into microplate-size modules: cleavage solution is added: heating, cooling, and agitation is manually performed, cleavage effluent is collected in individually identified vials or microplates, each vial and microplate including a memory or plurality of memories, preferably remotely programmable and preferably electronically, such as RF.

Each cleavage station will handle one microplate containing twenty-four, forty-eight or ninety-six wells, or other density of wells. Output reservoirs are preferably vials or deep well microplates. Each output reservoir will preferably include a memory or a plurality of memories to which information regarding the cleaved compounds is read or associated [in the case of pre-encoded memories] within a remote memory device, such as in a computer. An exemplary manual cleaver is described in the EXAMPLES and set forth in FIGS. 40–43.

(ii) Automated Cleaver

Matrices with memory microvessels with synthesized compounds or linked biological particles are automatically or manually sorted into individual cleavage vessels that are organized into microplate size modules; cleavage solution is added; heating, cooling and agitation is programmable, preferably as a batch; cleavage effluent is collected in individually identified vials or microplates. The capacity is, for example, u to 50 microplates containing 24 or 46 cleavage wells each [i.e., 1200 or 2400 microvessels]. The throughput is high, typically 4 hours for 1200 or 2400 microvessels. Output reservoirs are individual vials or microplates; again, each vial or microplate contains a memory or plurality of memories. FIGS. 68–75 and the Examples provide an exemplary automated cleaving station.

d. Software

Software, such as that provided herein, (see, e.g., Appendices I–V and the description herein) seamlessly ties all processing and analytical steps together. Exemplary software for aiding in the steps of combinatorial synthesis and screening may be used in combination with the ADD system. The code for such software is provided in the Appendices I, however, appropriate software could readily be developed by those of skill in the art by using the description provided herein. The exemplary software is commercially available (from IRORI, La Jolla, Calif.) under the name ACCUTAG™ SYNTHESIS MANAGER Software as a part of the AccuTag™-100 Combinatorial Chemistry System [e.g., an embodiment of the system provided herein]. These systems exemplified with the device of FIG. 34 [e.g., sold under the name ACCUTAG™], computer-based hardware, and the matrices-with-memories used therewith.

The software is organized into the following sections. These sections represent the normal sequence of activities that go into building library with the system provided herein.

Figure 30:
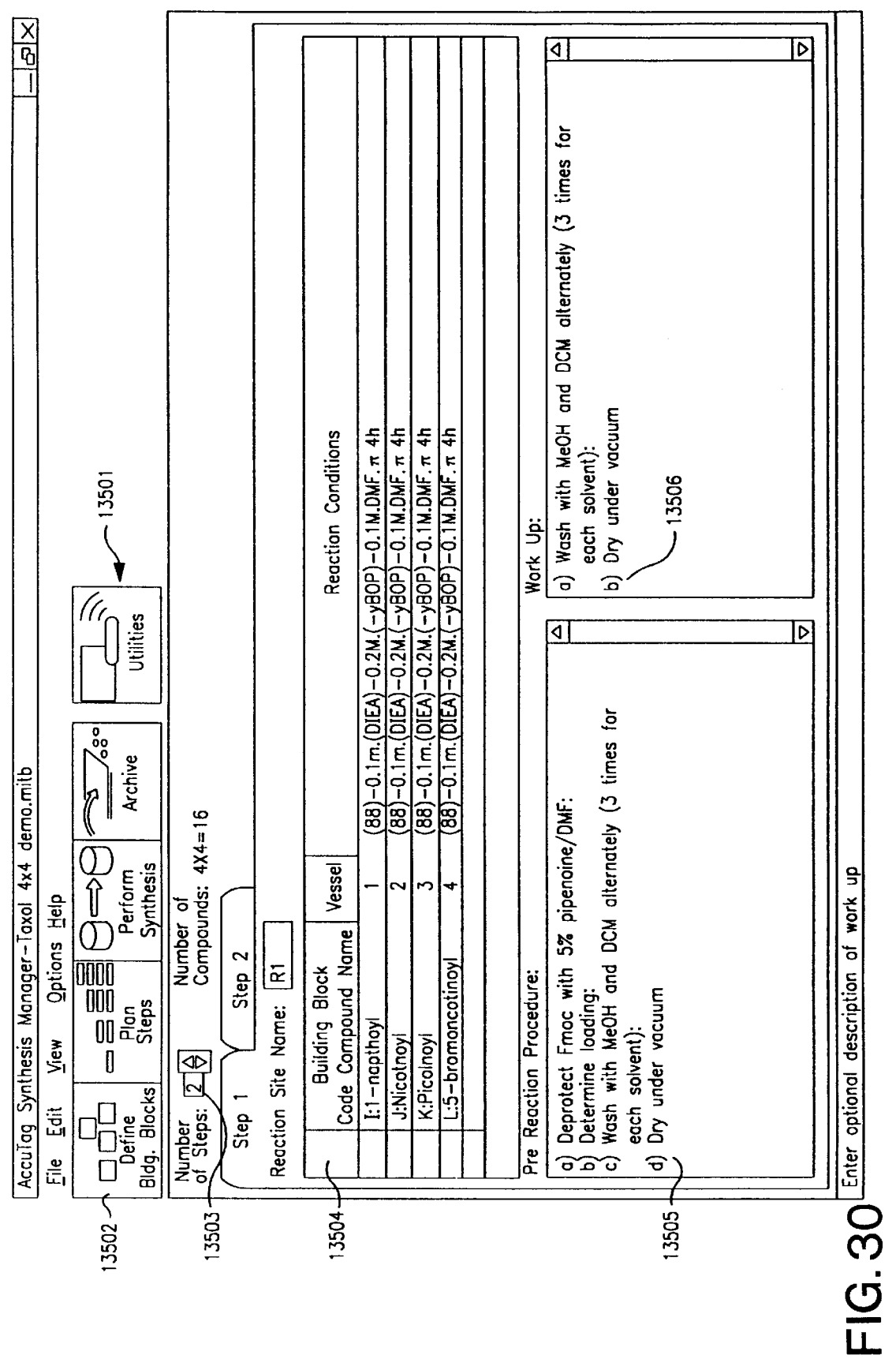

1. Define Building Blocks. The user enters the names of the chemical building blocks to be used. For brevity of reference, a code letter is assigned to each building block. An example of a screen that will be generated by the software and displayed in a Microsoft WINDOWS™ format is provided in FIG. 30, showing the button bar 13501 with the button for selecting the first step "Define Building Blocks" 13502, with the user selecting the step using a mouse or the keyboard.

2. Plan Steps.

a. Number of Steps. The user specifies the number of steps 13503 as shown in the upper left portion of the screen. In a given step, a building block, such as a monomer, amino acid, nucleotide, will be chemically added to each compound that is being synthesized.

b. Building Blocks To Use. The user specifies which of the defined building blocks 13504 will be used in each step.

Multiple building blocks may be selected, each of which will create a reaction within the step. The user may use a conventional Windows™ clipboard graphical interface to copy, cut and paste building block data.

If, for example, there are 3 steps and the user specifies building blocks A, B, C in step 1, building blocks D, and number in step 2, and building blocks F, G, H, I in step 3, then the resulting library will contain 24 unique compounds because there are 3×2×4=24 combinations of building blocks. Pre-reaction procedure 13505, and work-up procedures 13506 are also stored for each step.

Figure 31:
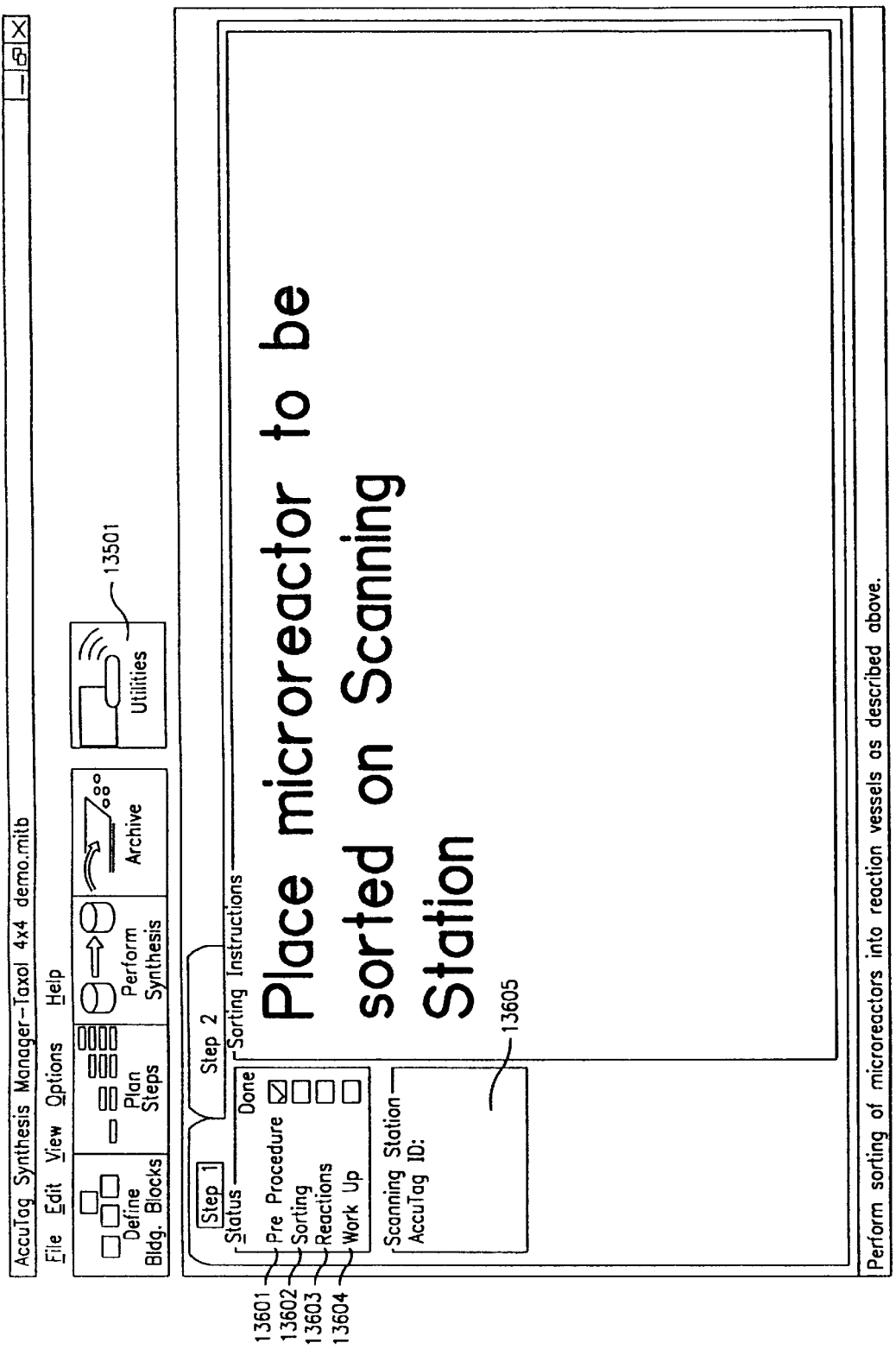
FIG. 31 is a diagram of an exemplary view screen produced by the SYNTHESIS MANAGER™ software for the step of performing synthesis operations.

Several database fields are defined in tabular form for creating the building block definitions. Under the database field "tblBldgBlocks.Name", the textual name of the building block or core compound is provided. Under "tblBldgBlocks.Abbrev", the code or abbreviation for a brief representation of the compound is entered. The database "tblBldgBlocks.DiagramFile" is a file which contains descriptions of the compound structure. Files can be either BMP or WMF. Finally, the user can enter comments about the compound in the database designated as "tblBldgBlocks.Notes."

c. Procedural information. The user optionally enters "recipe" information such as reaction times, temperatures, molarities, and reagents to use for each building block's reactions as well as procedures common to all building blocks. At the appropriate times during the "Perform Synthesis" section of the program, which is shown in FIG. 31, the pre-procedure information is "played back" to the user.

3. Perform Synthesis. Using a virtual library database of all the involved building blocks, reactions, process and compound tracking data, the software facilitates the step-by-step synthesis of the chemical library using memories with matrices, such as a MICROKAN™ OR MICROTUBE™ microreactor. For each step specified in Plan Steps (above) the following four tasks are performed.

a. Pre-Procedure 13601. Any preliminary procedures that the user entered are displayed. Typically these will involve chemical "deprotection" of the reaction site associated with this step.

b. Sorting 13602. The "directed sorting" process for the current step is administered by the software. The user is prompted to place a matrix-with-memory on the scanning station 13605 [see, e.g., FIG. 34], which is connected to a computer. For automated systems, the sorter will be directed to advance the matrix-with-memory to the scanning position. The memory in the matrix, i.e., the tags, identification [ID] is read. The software does a database look up, seeking this unique ID.

On the first step, the tag's ID is not found in the data base, so the software assigns it to the first compound in the library, which has not yet been associated with a tag. The user is instructed to place the device into the reaction vessel for the appropriate building block. If the tag that is read is not assigned to the database (a "bad tag"), a message is displayed that the matrix-with-memory device does not belong. From this point on, when this tag is read, the user is instructed to put the device into the reaction that will add the building block planned for this step for this specific compound.

c. Reactions 13603. Through directed sorting, all the devices in the library are now in reaction vessels. There is one vessel provided for each building block in the current step. When a reaction record is created, if the vessel field is empty, the program will automatically assign the lowest available integer that is not in use for any other vessel field in the step. The user is now prompted to perform the synthetic chemistry that will add each vessel's building block to the compounds it contains. The software displays any procedure information pertaining to reaction conditions that the user entered in Plan Steps. The number of reactions for each step and their product, and the overall number of combinations are continuously displayed.

d. Work Up 13604. The user is prompted to perform the "work up" [follow-up] task. Any work-up procedures the user entered in Plan Steps are displayed. Typically these involve rinsing and drying the reactor devices.

Figure 32:
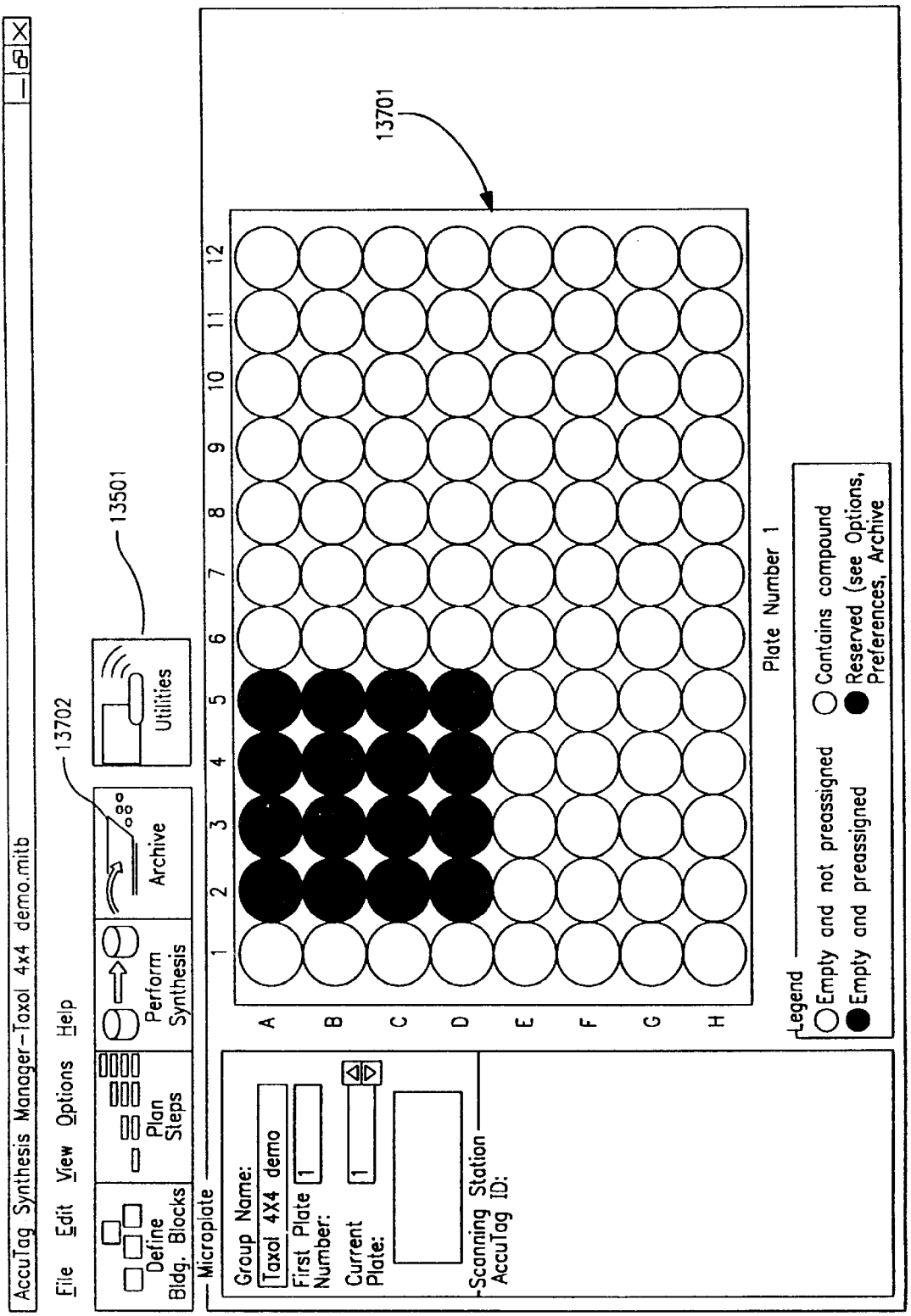
FIG. 32 is a diagram of an exemplary view screen produced by the SYNTHESIS MANAGER™ software for the step of producing a map and archiving information relative to specific compounds in an array of containers.

4. Archive. Archive refers to the process of transferring the completely synthesized compound from matrices-with-memories to a storage medium, such as a ninety-six well microplate or vials of any shape or size. This works as follows.

a. User chooses either vials or microplates [or other container]. These containers or vials may include memories into which identifying information can be entered, such as by scanning the first memory and then entering the scanned information into the memory in the matrix [container] into which the compounds are transferred. Using a template function appropriate for the containers to be used, a map 13701 can be generated and displayed by pressing button 13702 in button bar 13501, as shown in FIG. 32. Here, a ninety-six well template is used. Specific columns, designated 1–12, rows, designated A–H, or individual wells within the plate can be protected or pre-assigned to accommodate the need for standards and controls.

b. User places device on matrix-with-memory reader, a scanning station [see, e.g., FIG. 34]. (Note that in the automated sorter systems, user the "user" is the computer-controlled sorter.)

c. User selects a placement location: a well in a plate or a specific vial number.

d. User affirms placement location and the database is updated to document this. Chemically, the user typically cleaves the compound from the solid phase support and deposits only the synthesized compound in the storage media, while salvaging the reusable tag device for reuse on a another library.

e. The software automatically selects the next available storage location. The user may override this, and make another selection.

While not required part of the process, additional functions, such as the following functions are provided.

Figure 33:
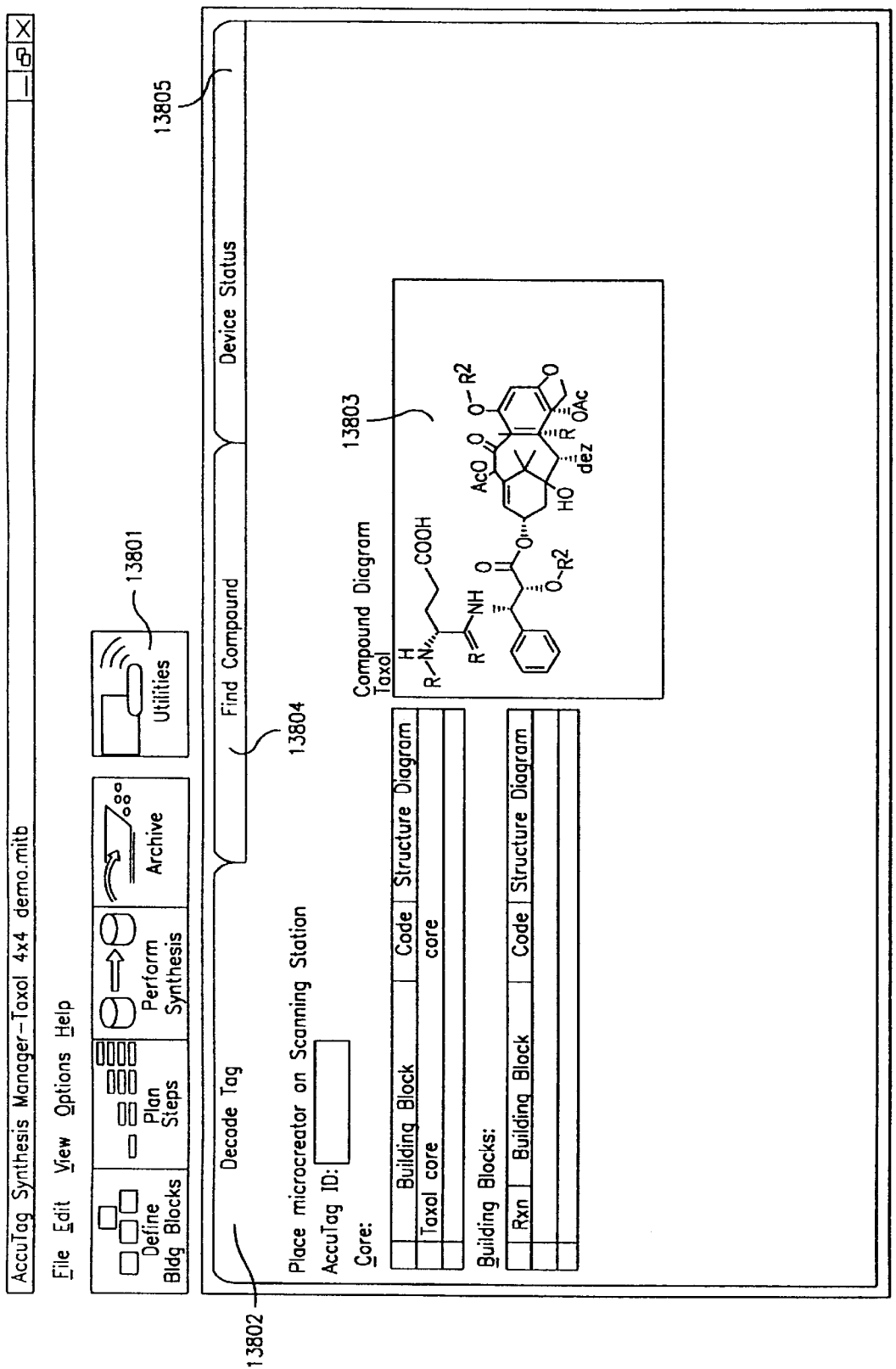
FIG. 33 is a diagram of an exemplary view screen produced by the SYNTHESIS MANAGER™ software for the utility function of decoding information stored on a memory device and displaying the associated compound.

1. Utility Functions.

a. Decode Tags. Using this function, at any time, the user can place a tag on the Scanning Station. If the tag has been assigned to a compound in the library, then information about that compound 13803 is displayed, as shown in FIG. 33. To select this utility, the user first selects button 13801 on the button bar, the selects folder 13802 for "Decode Tag".

b. Find Compound. The user can specify a combination of building blocks by selecting folder 13804 for "Find Compound." The software looks up this combination, and if it exists, it displays information about the compound and its tag.

c. Status. Spreadsheets showing all devices, their building block assignments and process status (which steps have been sorted) may be displayed by selecting folder 13805 for "Device Status".

2. Printing. The user can print out report describing:
 a. Building Blocks
 b. Steps planned.
 c. List of All Compounds.

3. On Line Help. The user can get context-sensitive assistance and a hypertext version of the System's User's Guide.

This system and software can be used in combination with a sorting system that provides the user with destinations for each matrix-with-memory during synthesis, screening or other protocols. FIGS. 36–38 set forth an exemplary embodiment of a manual sorting system.

Also provided is a wedge program [see, e.g., Appendix V] intended to be used to receive tags, particularly read-only tags, and perform in a manner similar to the SYNTHESIS MANAGER™ program in Appendix I. This program, referred to as TAGGER, is a "keyboard wedge" program. It receives data via a communications port from a scanning station or other form reader and operates on the received data in the same manner as SYNTHESIS MANAGER. TAGGER sends the data to whatever program is active. The data appears as keystrokes to the receiving program. The receiving program cannot distinguish between human-generated keystrokes and the synthesized "keystrokes", thereby providing a "wedge" function. For example, a bioassay program could be the active program. The user will select a field in the program into which an ID code, for example for a microplate, can be typed. Instead of typing in the information, an tag is scanned. Tagger sends this information as keystrokes to the program. Thus, the ID of the plate is deftly scanned right into the bioassay program. TAGGER also provides a find function. The user specifies a tag ID that is sought and scans the tags. When the tag with the sought for ID is scanned, TAGGER generates a visual and audible annunciation.

e. Assays

Following cleavage, compounds are assayed as described elsewhere (see, e.g., International PCT application No. WO 96/36436, and the other applications enumerated above, and briefly elsewhere herein). Alternatively, assays can be performed, where appropriate, without cleaving the compounds or biological particles from the matrix. In addition, following synthesis the compounds or biological particles may be stored on the matrix-with-memory support for subsequent assays. The larger microvessels, such as the tubular microreactors that are designed to be chopped into pieces, may be used for storage and as a repository for the synthesized compounds and linked biological molecules, to provide, for example, libraries of compounds.

2. Matrix-with-memory device to matrix-with-memory device communication and programming-the automated laboratory In accordance with the methods provided herein, communication among multiple matrices with memories is contemplated. In particular, matrices-with- memories can be programmed to interrogate neighboring matrix-with-memory devices and effectively communicate and program that neighboring device. The matrix-with-memory device which is programmed to reprogram other devices, called a master memory, is placed within an electromagnetic field, whereby its operating power can be derived, for example, as discussed above with respect to the event-detecting embodiment. Once powered, the master memory can emit an interrogation signal to which other matrix-with-memory devices or memory devices receiving the interrogation signal can respond with their identify. In the case where the responding identity is one of a class that is to be programmed, the master memory can send a programming signal to the neighboring matrix-with-memory device to write information into the neighboring matrix-with-memory device. In this manner, a number of matrix-with-memory devices can be programmed serially by programming a master matrix-with-memory device, and placing the master matrix-with-memory device in close proximity to other matrix-with-memory devices, while all of the memories are within an electromagnetic field, such as an F field. Other methods for powering the devices to permit communication among and between devices can be effected are also contemplated herein.

3. Manual and automated sorting devices and methods using these devices are provided herein.

a. Manual sorting

The manual system includes matrices-with-memories, a device for reading from and writing thereto, including a controller, and software for controlling the read/write function. Such a system also includes an apparatus and associated means, which may include software, processor(s) for running the software, and a user-interface/display, for assisting the user in identifying a particular matrix-with-memory and for identifying the destination of a given matrix, providing means for simplifying, expediting, and increasing the accuracy of the transferring procedure.

Figure 34:
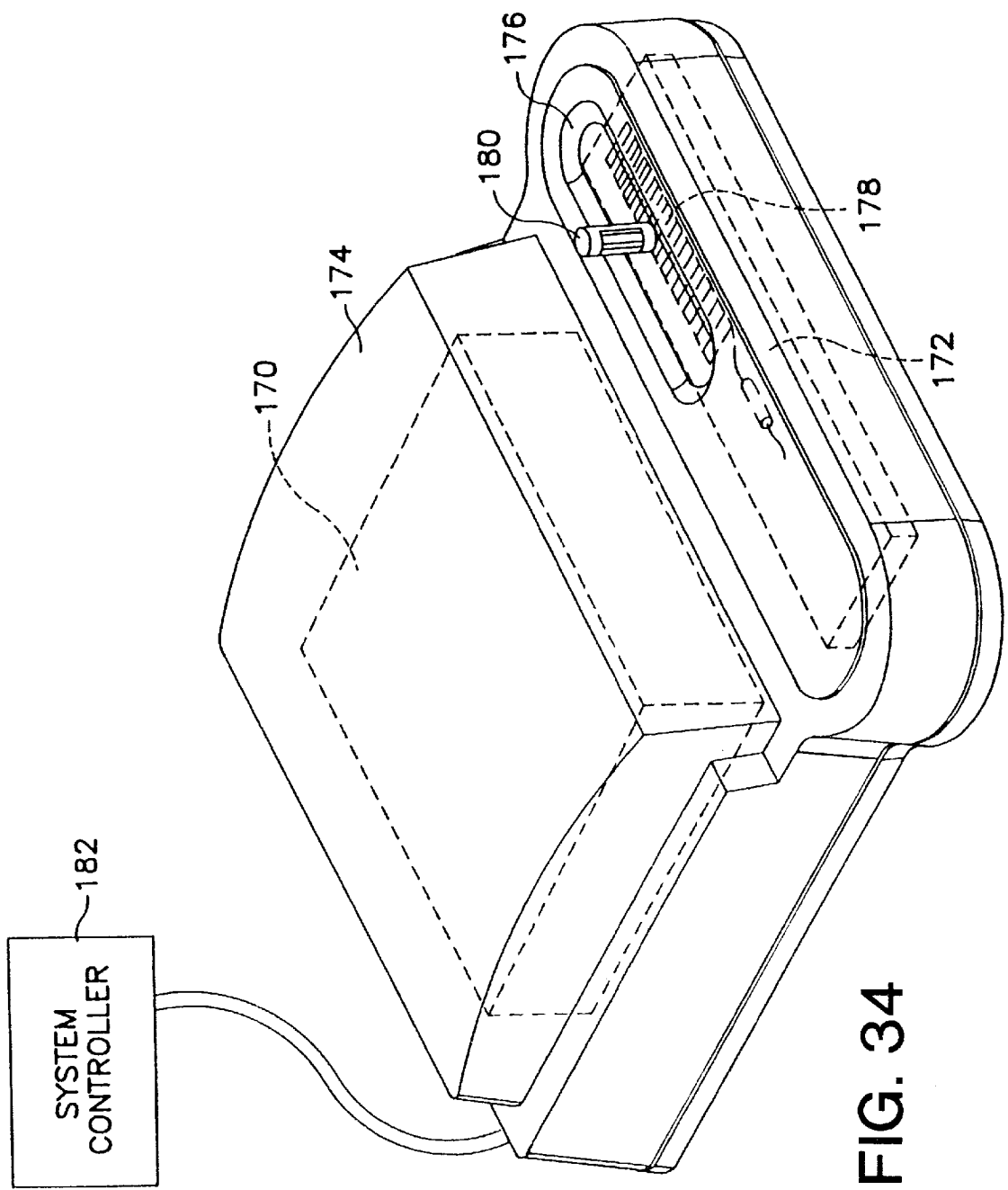
FIG. 34 is a perspective view of an exemplary write/read station.

A first embodiment of the manual system in which the matrices-with-memories have electromagnetically programmable memories, includes a transponder, particularly the BMDS transponder described below, an IDTAG™ transponder, an integrated antenna and memory device as described above, or any suitable read or read/write memory device. An example of the reading and writing device is illustrated in FIG. 34. The process flow for use of the writing and reading device of FIG. 34 is provided in FIG. 35. Briefly, the user manually places a microvessel 180 with memory within recessed area 176 so that the interrogation signal 185 provides a response to the controllers indicating the presence of the microvessel, and information is read from or written to the transponder. Similar methods may be employed with the optically-encoded matrices-with-memories.

The manual system is intended for usage with all types of microvessels previously described, and variations thereon, including the tube microreactors and the container. The read/write hardware [such as that available from BMDS or IDTAG™] is connected to a personal computer (PC) and software running on the PC which performs a user interface and system control function. The software is designed to facilitate a number of aspects of synthetic combinatorial chemistry libraries, including: organization, planning and design, synthesis compound formula determination, molecular weight computation, reporting of plans, status and results.

The system software creates a data base filed for each chemical library or group of matrices-with-memories or each matrix-with-memory. The data base file contains all of the information pertinent to the library, including chemical building blocks to be used, the design of the library in terms of steps and splits, and what synthesis has been performed. This file-oriented approach allows a number of different chemical library projects to be conducted simultaneously. The software allows the user to specify what chemical building blocks are to be used and their molecular weights. The user specifies the number of steps, the number of "splits" at each step, and what chemical building blocks are to be used at each split. The user may also enter the name of the pharmacophore and its molecular weight. Additionally, the user may specify graphical chemical diagrams for the building blocks and the pharmacophore, which information may be useful in displaying resulting compounds. The software directs all of the above "design" information to be stored in memory. The software includes algorithms for computing and displaying the size of the library. It may also include operations for predicting the range of molecular weights of the resulting compounds.

For example, the user may specify that there will be eight chemical building blocks. The names of the eight selected chemical building blocks are entered into the system controller via the user interface, and the user enters a unique letter codes for each: A, B, C, D, E, F, G and H. The user then specifies the number of steps which, in the present example, is specified as three steps. Step one will have four splits, appending the A, B, C and D building blocks. Step two will also have four splits, adding the B, D, E and H building blocks. Step three will have six splits, adding the B, C, D, E, F and G building blocks. Using a library size algorithm, the software computes the number of compounds that the library will contain, which in this case is 96 (4×6×5=96) unique compounds. Once the planning and design are completed, the software generates an output for guiding the user in performing the synthesis steps. The user-guidance function is done in concert with the read/write hardware [transceiver or a scanner, such as the BMDS - DAS 5003] or a similar device available form IDTAG Ltd [Bracknell, Berks RG12 3XQ, UK] and devices, such as a MICRO-KAN™ or MICROTUBE™ microvessel with memory devices. Before the synthesis begins, the microvessels are filled with polymer resin. The microvessel devices are placed upon the scanner one at a time so that the reading/writing device and its associated software can read the contents of data encoded in the recording device/transponder, such as the BMDS tag or the IDTAG™ tag, contained in each microvessel. The software includes algorithms for selecting which building block is to be added to the compound contained in each microvessel. The software directs the transceiver of the reading/writing device to write encoded data to the transponder which includes the designation of the selected building block. The software causes a message to be displayed for directing the user to place the microvessel in the appropriate reaction vessel so that the chosen building block will be added. This process is repeated a plurality of times with each microvessel and for each synthetic step in the preparation of the library.

The software directs the read/write scanner to read a tag and receive its encoded information. Using the user-entered compound names stored in the library's data base, the software translates the encoded information into the names of the chemical building blocks. The software can also produce a graphic display of compounds, using graphical information specified by the user. The software may include algorithms for calculating the molecular weight of compounds from the data provided for the pharmacophore and building blocks.

The use of software within the sorting devices facilitates creation of a record of progress through the above process. The software provides for generation of displays and reports for illustrating steps of the process as well as providing means for displaying and/or reporting the planning, design, compound data, and graphical representations of compounds. An example of the software, commercialized under the name SYNTHESIS MANAGER™ (IRORI, La Jolla, Calif.) and use thereof, is set forth in Appendix I and in the Examples below. Using the description of the functions that is provided herein, software for performing similar functions can readily be developed by one skilled in the art.

Briefly, in the first step in building a library, the individual building blocks [i.e., the monomers, nucleotides or amino acids or other small molecules] and the steps in which they will be used are defined. The software then performs operations for automatically creating a data base record for each compound to be synthesized. Pre-reaction procedures, reaction conditions, and work-up procedures are stored for each step. When the synthesis begins, the step "Perform Synthesis" is selected. The software generates a display of the procedure for review by the user, then reads each of the memories in each microreactor and sorts them for the next reaction step. When the sorting is complete, the reaction condition information and work-up procedure are also displayed to the user.

When the chemical synthesis is complete, compounds are cleaved from the microreactors and archived. The software provides archival capability for either individual vials or a 96-well format, or may be adapted for other formats. Specific columns, rows, or individual wells can be protected to accommodate the need for standards and controls in virtually any screening format.

The software provides several utilities that permit one tag to be read at any time, displaying the corresponding building block names and structures, and the current synthesis status of that compound. A search may be conducted for a specific compound or compounds that contain certain building blocks. For compounds that have already been archived, the archive location [i.e., microplate group name, number, and well] will be displayed.

Also provided are manual system and automated systems for directing synthesis, screening and other protocols. In particular, apparatus are provided that, with associated software [including that provided herein or that may be generated based upon the disclosure herein] provide protocols and implement the protocols by directing each matrix-with-memory to a particular reaction vessel. These apparatus and software are used in conjunction with manual and automated systems.

For example, a manual sorting system [see Examples] may include a device for reading and, in instances in which the memories are encodable, writing to the memories, a computer, including a user interface, for storing a database with identifying information and for containing and implementing the software, and a sorter, which may be manual or automatic. A manual sorter may include, for example, an apparatus that assists the user in identifying a particular matrix-with-memory, such as the MICROKAN™ microreactors and MICROTUBE™ microreactors, identifying the destination of that matrix, and providing an indication, such as a visual or audio cue that identifies the destination as a means simplify, expedite, and increase the accuracy of the synthetic and screening protocols.

A manual system provided herein, for example, includes the identification station [such as that discussed above] that identifies a particular matrix-with-memory, a computer having a database that stores identifying information and software for directing the protocol. Such information includes the source of the particular matrix-with-memory, the identity of linked molecules or biological particles, any desired historical information about the matrix-with-memory, such as batch number, and the destination of that matrix-with-memory. Once the destination of the matrix-with-memory has been determined, the computer system provides the user with a cue, such as an audio cue, visual cue, a combination of the two, or other cue, that identifies the destination of the matrix-with-memory. In a particular embodiment [see, e.g., FIGS. 36–38], the visual cue is created by identifying one in a number of light emitting diodes (LEDs) that are physically attached to a series of containers, such as beakers containing a particular solution. The attachment of the LEDs to the containers is accomplished using an inverted U-shaped bracket with a LED mounted so that it is observable by the user. The bracket is sufficiently heavy that, once the bracket is placed on the rim of the beaker, the weight of the bracket will hold itself in place. In use, the matrix-with-memory is presented to the identification station which accesses the memory of the matrix and, by decoding the identification information provided by the matrix memory, identifies the matrix-with-memory. Once identified, the computer accesses the data base and determines the relevant information pertaining to the particular matrix-with-memory, and the destination of that matrix-with-memory. Once the matrix-with-memory destination has been determined, the computer generates a visual cue over the proper beaker by illuminating the LED attached to that beaker. Once the beaker is identified, the user can look for the visual cue, and place the matrix-with-memory in the identified beaker. Audio cues could be used instead of, or in addition to, the visual cues.

The methods for sorting matrices-with-memories using the manual system [or automated system] include the steps of programming the memories, either at the time of sorting, or at an earlier time, with the information required for tracking and identifying the source and destination of the memory device. A library is created to define each of the matrices-with-memory, microreactors, or other suitable vessel or container, with the compounds which will be synthesized therein. This library will most preferably reside in the data base which can then be used to coordinate the movement of all, or part of, the matrices-with-memories in a particular laboratory. Once the library is created, the data base will be capable of identifying the particular memory device, the particular matrix-with-memory associated with the memory device, and will be capable of indicating where the matrix-with-memory should be placed to continue the necessary process steps for synthesis.

In order to simplify the assignment of a particular visual or audio indicator to a particular container, it is possible to have the computer dynamically assign any indicator to the container. This is accomplished by instructing the computer to assign an indicator to a beaker containing a compound XYZ, for example. The computer, in response, will search its data base for the unused or unassigned indicators, and selecting one, will begin flashing or beeping the particular indicator so that the user can grab the activated indicator and place it on the appropriate beaker, thus minimizing the required setup procedure for the automatic sorter. Risk of error is greatly reduced by using the computer to direct the entire sorting process—from assignment of the indicators to certain containers to the placement of the various memory devices into each of those containers.

Once the library has been created and the computer data base is enabled to coordinate the movement of the matrices with memory, the manual sorter may be utilized. The manual sorting process begins with the passing of the memory device within the field of detection of the identification station. Specifically, if the identification station is an optical bar code reading station, the matrix-with-memory must be passed within its field of view of the scanning laser, or other optical scanning device. If the identification station is an RF communicating identification station, such as for the IDTAG™ memory device, the memory device must be passed through the electromagnetic field to induce an energy level sufficient to excite the RF device and to solicit a response from the device.

Once the memory device is accessed, the device transmits back to the identification station, by either RF transmission, RF or optical reflection, or any other manner of communication discussed herein, the particular identification number, and any other relevant information stored in the memory system. This information is then modified to fit a standard serial data format by the controller 6703 of the identification station, and provided to the computer system with cable 6712. The computer receives the serial data and matches that information to the data library contained within the data base. The specific characteristics of the matrix-with-memory associated with the memory are then determined by indexing the data base to find the identification number corresponding to the particular memory device. Once the memory device record is identified, the computer may determine the proper next step for the synthesis on the matrix-with-memory, and corresponding destination. Once the destination is determined, the computer activates the proper indicator device corresponding to the destination of that memory device. Once the destination indicator device is activated, the user can look for the LED indicator which is activated, and deposit the matrix-with-memory inside. This step may be repeated until all of the matrices with memory have been properly distributed to their respective destinations.

In light of the disclosure herein, it will be apparent to those skilled in the art that numerous alternative means are available which may be used to identify a particular destination for the matrix-with-memory. Such other indicators may include, for example, an audible tone, a light source, a mechanical pointing device, an electromechanical indicator, such as a flag or solenoid, or any other indicator known in the art, or any combination of one or more or such indicators, such as audio and visual indicators. The identification station discussed above and described in detail for the electronic memory device, such as RF tag, is exemplary only. Generally, any combination of readable memory device and memory identifying station may be used in conjunction with the manual sorting device as provided herein.

b. Automated sorting

In addition to the manual sorting device discussed above, an automated sorting device is contemplated. Such device will combine a means for conveying the memory devices past the identification station, with a means for distributing the memory devices to various destinations.

Automated sorting devices, systems incorporating such devices and methods of sorting are provided. For example, an automated sorting device which includes a lower frame with a drawer having a number of addressable container positions may be used. Positioned above the drawer is an X-Y positioning device that can move in two directions, effectively covering the entire area above the drawer. Mounted to the lower frame is an upper frame which supports a matrix-with-memory device feeder. The feeder holds a large number of matrix-with-memory devices, feeding one of the matrix-with-memory devices at a time to a supply tube. The supply tube, which is oriented in a generally vertical configuration, leads downward to a turnstile that is formed with at least one slot having dimensions for receiving a single matrix-with-memory device. Once a matrix-with-memory device is captured in the slot, the turnstile rotates to dispense the matrix-with-memory device to a positioning tube. The positioning tube is equipped with a stopping solenoid for temporarily retaining the gravity-fed matrix-with-memory device in a position adjacent to an antenna coil of a read/write. Once the memory device is in position, the antenna is activated to access the matrix-with-memory device to be read and identified, and, if appropriate, write to the device. Once the matrix-with-memory is identified, a host computer determines the proper container into which the matrix-with-memory device should be released after which the positioning device is moved to the position of the specified container. The stopping solenoid is opened to permit the matrix-with-memory device to slide down the positioning tube and drop into the appropriate container. A proximity sensor located near the solenoid tests for the presence of the matrix-with-memory device to confirm that the matrix-with-memory device has dropped. After placement of a first matrix-with-memory device, the turnstile is rotated to allow the next matrix-with-memory device waiting in the supply tube to be accessed and identified, written to as necessary, and placed in the proper container. This process can be repeated in rapid succession, with a positioning time of less than one second for a drawer which has dimensions of approximately thirty inches by fifty inches and contains fifty separate containers.

The automated sorting device can place matrix-with-memory devices into a variety of containers, including various sized beakers, fleakers, vials, tubes or other containing devices. The X-Y positioning device is accurate to within 0.1 inch, resulting in a device capable of placing matrix-with-memory devices in a dense arrangement of containers, with the quantity of containers being limited only by the size of the drawer and the range of travel of the positioning device in both the X and Y directions. The automated sorting device is controlled by a host computer that communicates with a Programmable Logic Controller (PLC), which has all the necessary digital and analog control lines for the control of the positioning device, the turnstile, and read/write station. An exemplary device and use thereof is set forth in FIGS. 40–44 and described in the Examples.

4. Combination of the sorter and cleaver devices for seamless data tracking

FIGS. 60–65 illustrate the seamless nature of the data tracking provided by the units herein. FIGS. 60–65 depict an automated sorting and cleaving process, the requisite apparatus and linkage between the processes, incorporating an automated sorting device and an automated cleaving station. For example, in FIG. 60, an automated sorting device is shown and generally designated 11000. Sorting device 11000, which includes a hopper 11002, is attached to a computer 11004 which, in accordance with the description of the automated sorting devices herein, sorts matrices-with-memories into the appropriate microreactor carriers 11014 in the microreactor carrier tray 11012. In a preferred embodiment, after synthesis, the tagged microreactors are sorted, preferably using the automatic sorter provided herein. In embodiments in which capped microreactors, such as the embodiment of FIGS. 2–4 are used, they are decapped prior to cleavage. The sorter holds twelve carriers of ninety-six tagged microreactors (1152 total). Higher density carriers (and larger sorters) may be used.

Figure 61:
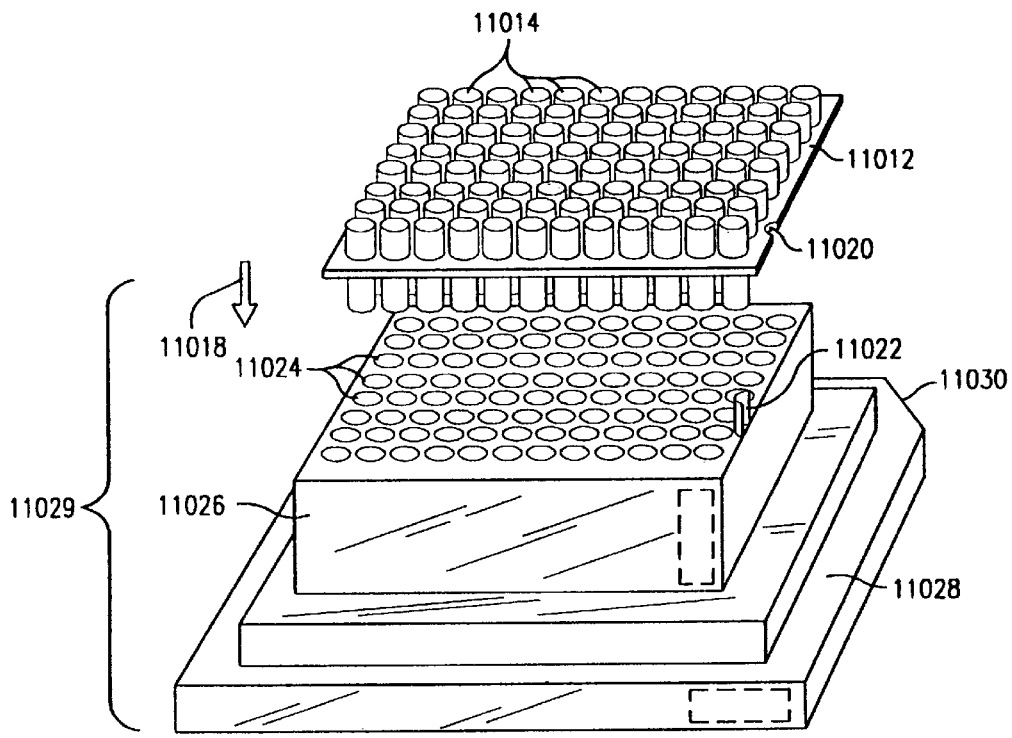
FIG. 61 is a perspective view of a microreactor carrier tray being installed in a cleaving block having an integral nozzle array interface.

Referring to FIG. 61, carriers 11014 are placed in a carrying tray 11012 which is disposed on cleaving block 11026, which is part of cleaving assembly 11029. First, a reagent such as TFA is added. Using the cleaving assembly 11029, solutions are drawn into racks of vials within a vacuum chamber. Each rack includes means for physically distinguishing it from other racks and is designed to fit into a single pre-determined location within the cleaving assembly. Also, each rack preferably includes one or more memory means, such as an electronic tag or an optically-readable code. After cleavage, the carriers and racks are scanned, their identities stored, and the contents of the tubes in the vials or tubes in the racks concentrated or lyophilized for storage. The memory means on each carrier (or each position in the rack) can be scanned to readily identify the contents for further processing, such as screening and analysis, following reconstitution.

Figure 60:
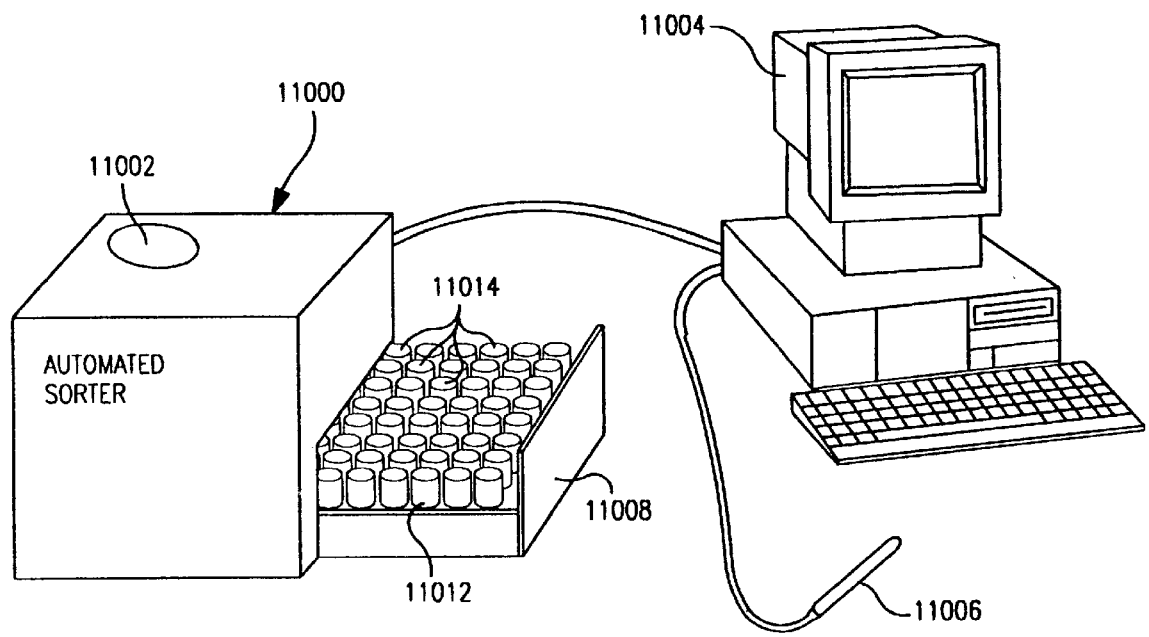
FIG. 60 is a perspective view of an automated sorting device and its associated computer and RF or microwave wand, where the microreactor carrier tray is partially inserted into the automated sorting device.

Referring to FIG. 60, the automated sorting device may have a removable portion 11008, such as a drawer, sliding tray or shelf, or an autoloader, which facilitates the insertion and removal of the microreactor carrier tray 11012. As described above in conjunction with FIGS. 36 and 44–51, each microreactor in the microreactor carrier is loaded with a matrix-with-memory, allowing the unique identification of the matrix, microreactor, and microreactor carrier 11014. The automated sorting device 11000 places one or more matrices-with-memory into each of the microreactor carriers 11014 which are oriented in an array, such as an 8 by 12 array for a 96 position microreactor carrier tray, e.g., tray 11012, allowing the automated sorting device 11000 to maintain records of the location of a specific matrix within a microreactor carrier tray. These records would typically be maintained digitally within a memory associated with computer 11004, however it may also be desirable maintain supplemental records in a tangible format, such as printed records, and to maintain back-up or permanent records on conventional data storage media such as floppy disks, CD/ROM, or data tapes.

Each microreactor carrier tray 11012 may be equipped with an identification tag, such as an RF tag, a microwave tag, or an optical tag, to facilitate the tracking and maintenance of the group of individual microreactors. For example, when an individual microreactor is placed in a microreactor carrier 11014 in a first position of the microreactor carrier tray 11012 and is loaded with a matrix having an RF or microwave tag, the individual matrix may be identified by its position within the carrier tray 11012 as well as by accessing the individual memory associated with the microreactor. Once the matrices-with-memory have been placed in their respective microreactor carriers 11014 at a known position within a microreactor carrier tray 11012, the individual microreactors may be located simply by identifying the microreactor carrier tray.

Computer 11004 may be equipped with an hand-held identification wand 11006 which is capable of reading and identifying individual matrices-with-memories and other items identified by the methods described herein. For example, the identification wand 11006 may be an RF or microwave wand, an optical scanning wand, or any other suitable identification apparatus. By moving the identification wand 11006 to a position within the detection range of the selected scanning technique, the individual matrix-with-memory may be identified. The ability to move a scanning device to the object to be scanned is permits ready access to identification tags which are associated with larger or heavier objects, such as the microreactor carrier trays 11012, cleaving blocks 11026, vial collection racks, microplates, or other objects within the laboratory environment that have a size or weight, or contain materials which should not be moved, which would make movement to an identification station impractical.

Referring to FIG. 60, once the matrices with memory have been positioned within the microreactor carriers 11014 in the microreactor carrier tray 11012, the microreactor carrier tray 11012 is removed from the automated sorting device 11000, and placed on a cleaving block 11026, as shown in FIG. 61.

In FIG. 61, microreactor carrier tray 11012 is shown positioned over cleaving block 11026, so that alignment pin 11022 is aligned with alignment hole, notch or groove 11020 in carrier tray 11012. Alignment pin 11022, which is shown extending upward from cleaving block 11026, mates with alignment notch 11020 in only one orientation to ensure correct orientation of the microreactor carrier tray 11012 on cleaving block 11026. The ability to limit the relative positions of the tray 11012 and cleaving block 11026 to only one possible position eliminates the need to separately identify each of the matrices-with-memory within the tray. Thereafter, each matrix may be identified simply by identifying microreactor carrier tray 11012, and accessing the record associated with carrier tray 11012 to identify a matrix within a particular location within the carrier tray 11012. Once positioned above the cleaving block 11026, the microreactor carrier tray 11012 may be lowered in direction 11018 onto the cleaving block 11026 so that microreactor carriers 11014 are inserted into bores 11024.

Figure 62:
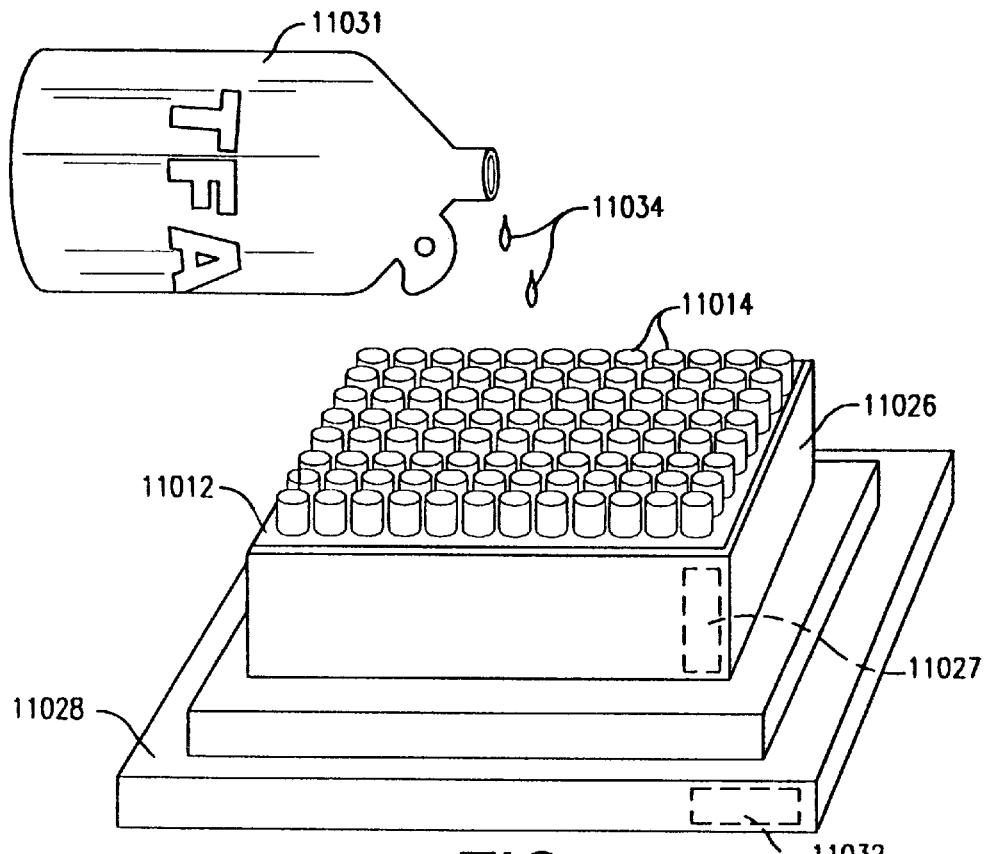
FIG. 62 is a perspective view of the nozzle array interface with the microreactor carrier tray installed, and the addition of TFA to the microreactor carriers.
Figure 63:
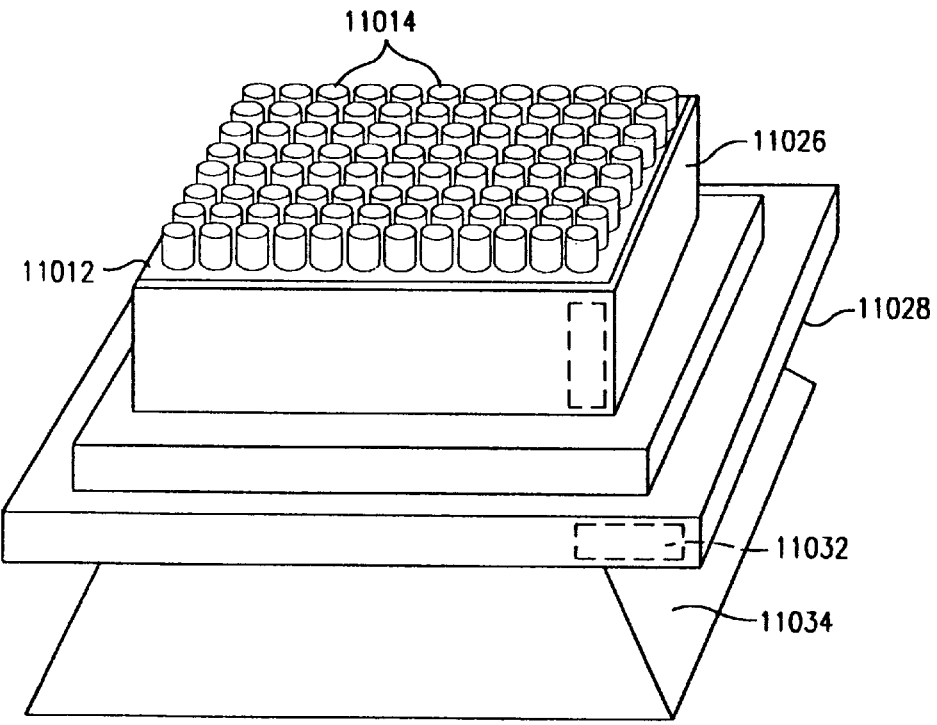
FIG. 63 is a perspective view of the microreactor carrier tray on the cleaving assembly and positioned on a shaking table to facilitate the cleaving process.

In addition to the identification of each microreactor carrier tray 11012 with its own identification tag, cleaving block 11026 may also have a dedicated identification tag 11027, as shown in FIG. 62, which facilitates tracking and maintenance of cleaving block 11026 and microreactor carrier tray 11012. The cleaving block 11026 may also have an integral nozzle array interface, or manifold, 11028. While the cleaving block 11026 and nozzle array interface 11028 have previously been discussed as separate components of an automated cleaving station, it will be apparent that such components may be combined, and collectively referred to as cleaving assembly 11029. The combination of these components reduces the need for addition of new components after the cleaving or synthesis process has begun. The nozzle array interface 11028 may also be optionally identified with an identification tag 11032. To facilitate the proper orientation of the cleaving assembly 11029, the nozzle array interface 11028 may be formed with an orientation key 11030 which will allow the cleaving assembly to be uniquely positioned for further processing in the cleaving and synthesis operation. Here, orientation key 11030 is shown as a notch in one corner of the interface, however, as will be apparent, any of a number of orientation indicators may be used to limit the relative positioning options to one.

Figure 64:
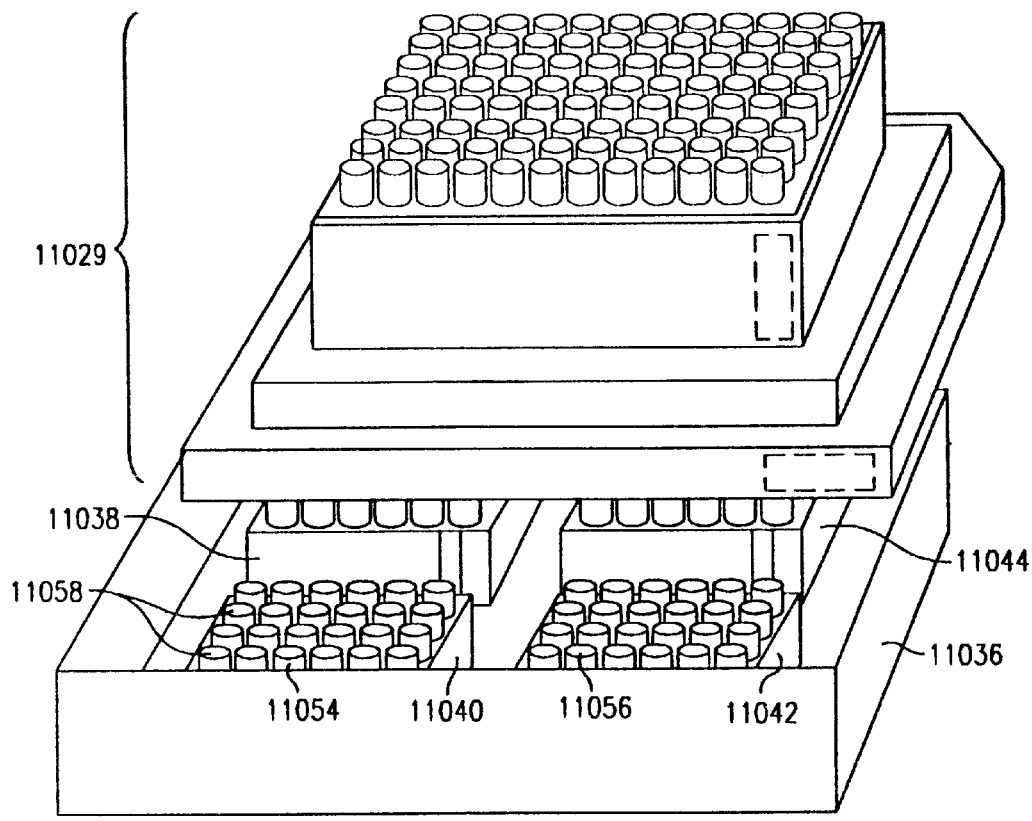
FIG. 64 is a perspective view of the nozzle array assembly positioned on a vacuum chamber with portions cut away for clarity, showing a collection rack having four 24 vessel vial racks.

Referring still to FIG. 62, cleaving assembly 11029 is shown with microreactor carrier tray 11012 in position on cleaving block 11026. Each microreactor carrier is filled with a cleavage reagent 11034, such as TFA 11031, to facilitate the cleaving of molecules (compounds) or biological particles from the matrices within the microreactors. To expedite the cleaving process, the cleaving assembly 11029 may be placed on a shaker 11034 of the type well known in the art, and shown generally in FIG. 63. Following agitation by shaker 11034, the cleaving assembly 11029 is positioned over a vacuum chamber 11036, as shown in FIG. 64, so that vacuum chamber 11036 is fully closed with a sufficient seal to retain a vacuum. Vacuum chamber 11036 is equipped with a keying mechanism which accepts the cleaving assembly only when the orientation key 11030 of the nozzle array interface is properly positioned. In the case of key 11030, which is a cut-off corner, the corresponding keying mechanism could be one or more pins projecting upward from the back, right corner of the top of vacuum chamber 11036, or it could be a solid raised area on the top of vacuum chamber 11036 which completes the missing area corner 11030. Such keying permits only one orientation of the cleaving assembly 11029 on top of vacuum chamber 11036.

Figure 73:
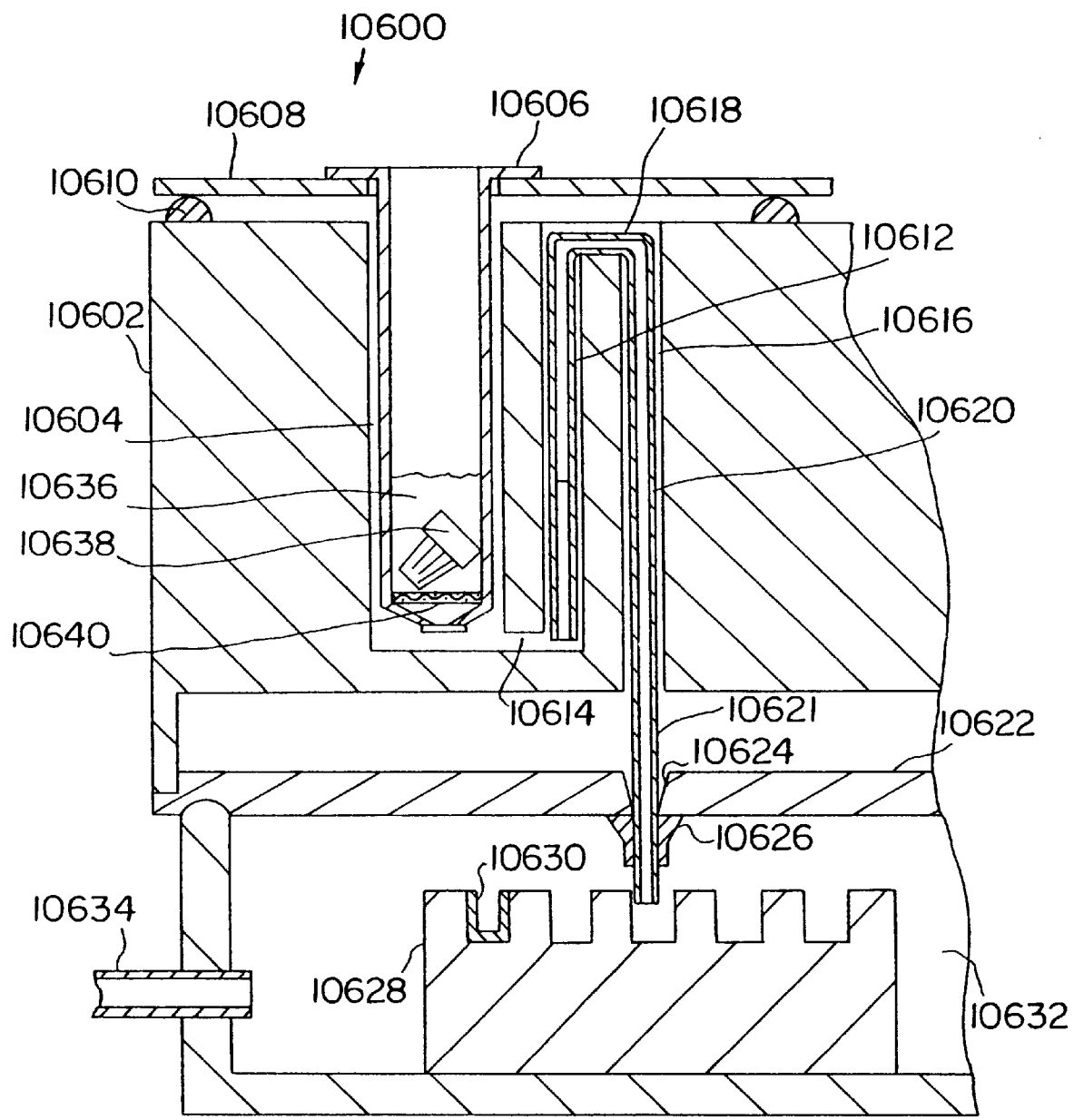
FIG. 73 is a cross-sectional view of another alternative embodiment of the automated cleaving station, showing a pre-formed U-tube which is inserted into a pair of bores within the cleaving block.

Still referring to FIG. 64, within the vacuum chamber 11036 are vial racks 11038, 11040, 11042 and 11040. As illustrated, each vial rack holds a 4-by-6 array of collection vials 11058, however, such an arrangement and quantity is exemplary only, and other arrangements of vials may be used. For example, the cleaving block 11026 may be formed with any number of bores 11024, and the location and quantity of vials and/or vial racks will be selected to correspond with the cleaving block and the number of samples to be created. Referring briefly back to FIG. 73, cleaving block 10602 is shown to be in fluid communication with collection rack 10628 via U-tube 10621. This U-tube configuration may also used in conjunction with the embodiment shown in FIG. 64, allowing the transfer of the cleaved compounds or biological particles from the microreactor carriers to the vials 11058.

Figure 66:
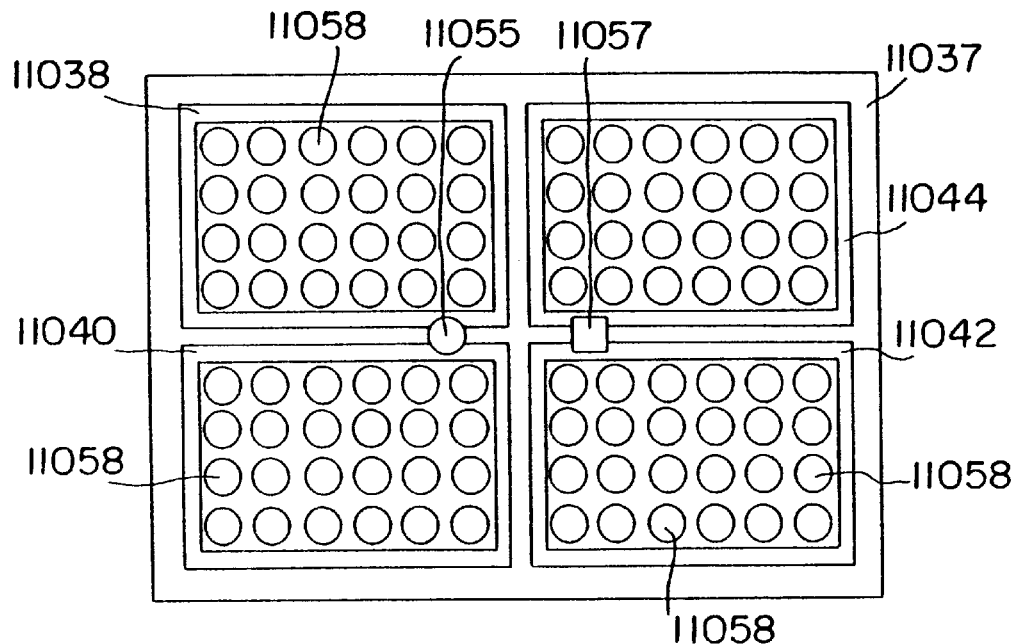
FIG. 66 is a top view of a typical collection rack showing the positioning and keying of the individual vial racks.

Each vial rack 11038, 11040, 11042, 11044 is equipped with a keyway for orienting and positioning the racks within vacuum chamber 11036. As illustrated in FIG. 64, keyways 11054 and 11056 are visible in vial racks 11038 and 11044. Keyways 11054, 11056 are shown in more detail in FIGS. 66 and 67, in which the vial racks are viewed from above. Collection rack locator tray 11037 is formed with four quadrants which are sized to receive vial racks 11038, 11040, 11042, and 11044. Locator tray 11037 will have raised ridges or some other form of demarcation to indicate the footprint of the vial racks for general guidance as to where the vial racks are to be placed. Each vial rack is formed with a keyway to restrict the position of the rack to only one location within the collection rack locator tray 11037. As shown, keyways 11053, 11054, 11056 and 11059 are grooves or channels formed in the center-facing side of each vial rack. Each keyway mates with only one key in rack locator tray 11037, and only when the vial rack is correctly oriented. In FIG. 66, keys 11055 and 11057 are a round peg and a square peg, respectively. Thus, in order to fit in locator tray 11037, keyways 11054 and 11059 are formed as rounded channels, while keyways 11053 and 11056 are formed as squared channels.

Referring to FIG. 67 for a more detailed view, vial rack 11038 is formed with a keyway 11054 sized and positioned to receive key 11055. This ensures that vial rack 11038 will only be able to be positioned within the locator place 11037 in one location and in one orientation. Similarly, vial rack 11040 is formed with keyway 11059 which is also sized and positioned to receive key 11055, yet maintaining a distinction between vial rack 11038 and vial rack 11040. Such distinction may be accomplished by offsetting the keyways such that even if the vial rack was rotated or orientated in a different position, it would not be possible to position the vial rack in the wrong position within the locator tray 11037. It should be noted that the keying shown and described herein is merely exemplary, and that other methods of uniquely orienting and positioning the vial racks within the vacuum chamber may be used.

Referring again to FIG. 64, vial racks 11038, 11040, 11042 and 11044 are shown having identification tags 11046, 11048, 11050 and 11052, respectively. The identification tags allow for the unique identification of each vial rack. In combination with the specific orientation of the vial rack within the vacuum chamber, the identification tags in the vial racks permit the unique identification of each vial 11058 within the vial rack. The vials may be identified either by tracking their physical position, by including a memory at each location, or combinations thereof.

To facilitate such identification, a vacuum chamber may be equipped with an identification station in close proximity to each vial rack position within the vacuum chamber. Using the identification station, each vial rack can be identified as it is placed into the vacuum chamber, further facilitating the tracking of the compounds from the microreactor carriers by eliminating the need for manual tracking of the vial racks within the vacuum chamber.

The unique identification and orientation of each vial rack ensures that each individual matrix-with-memory and the respective cleaved compound may be effectively tracked from the microreactor in the automated sorting device to its microreactor carrier in the microreactor carrier tray, through the cleaving assembly, and eventually to the vial rack after the sorting process.

Referring still to FIG. 64, once the vial racks 11038, 11040, 11042, and 11044 are in position within the vacuum chamber 11036, a vacuum is created in the vacuum chamber to draw the cleaved compound from each microreactor carrier, through its corresponding U-tube, and into its respective vial 11058 within a vial rack. It is not necessary for a direct mapping from microreactor carrier to vial to occur within the nozzle array interface tray, and such mapping may have virtually any configuration. For example, it is possible for a mapping configuration to allow for the transfer of a compound from a single microreactor carrier to be divided and mapped to more than one vial. Alternatively, it may be possible to map the compounds from more than one microreactor carrier into a single vial, such as for combining the compounds following the cleaving process.

Figure 65:
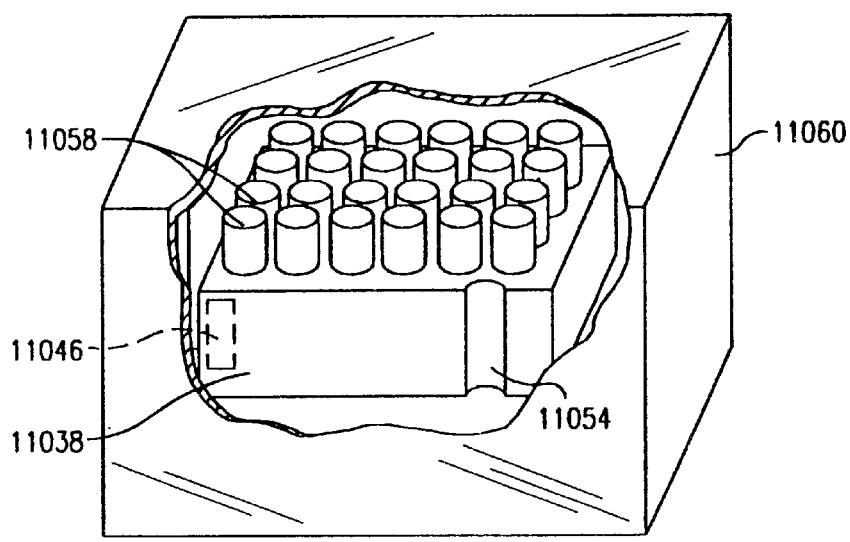
FIG. 65 is a perspective view of a speed-vacuum chamber with portions cut away for clarity, where the individual vial racks are speed-vacuumed.

Once the compounds have been drawn from the microreactor carriers in the cleaving assembly 11029 into the vial racks, each vial rack is typically placed in a speed-vacuum 11060, as shown in FIG. 65. The speed-vacuum, or speed-vac, facilitates the evaporation of a cleaving agent, such as TFA, leaving only the cleaved compound in the vials 11058. Speed-vacuums are well known in the art, and will not be discussed in detail here.

The following examples are included for illustrative purposes only and are not intended to limit the scope of the invention.

EXAMPLE 1

Manual systems for synthesis, screening, sorting and cleaving

Synthesis is performed on matrices-with-memories. The synthesis is guided by the software provided herein, which directs the synthesis and screening protocols.

A. Read/Write station for synthesis

Illustrated in FIG. 34 is a program/read station for writing to and reading from the memory devices in the microvessel. The electronic components are commercially available, typically from the supplier of the memory devices, e.g., BMDS or ID TAG or the monolithic memory provided herein [Bracknell Berks RG12 3XQ, UK], so that the basic operations and frequency are compatible. The basic controller 170 and the transceiver 172 are disposed within a housing 174 which has a recessed area 176 positioned within the transmission range of coil 178. The microvessel 180 may be placed anywhere within recessed area 176, in any orientation, for programming and reading functions. Basic controller 170 is connected to the system controller 182, illustrated here as a functional block, which provides the commands and encoded data for writing to the memory device in the microvessel and which receives and decodes data from the memory device during the read function. System controller 182 is typically a PC or lap top computer which has been programmed with control software 184 for the various write and read functions.

Figure 35:
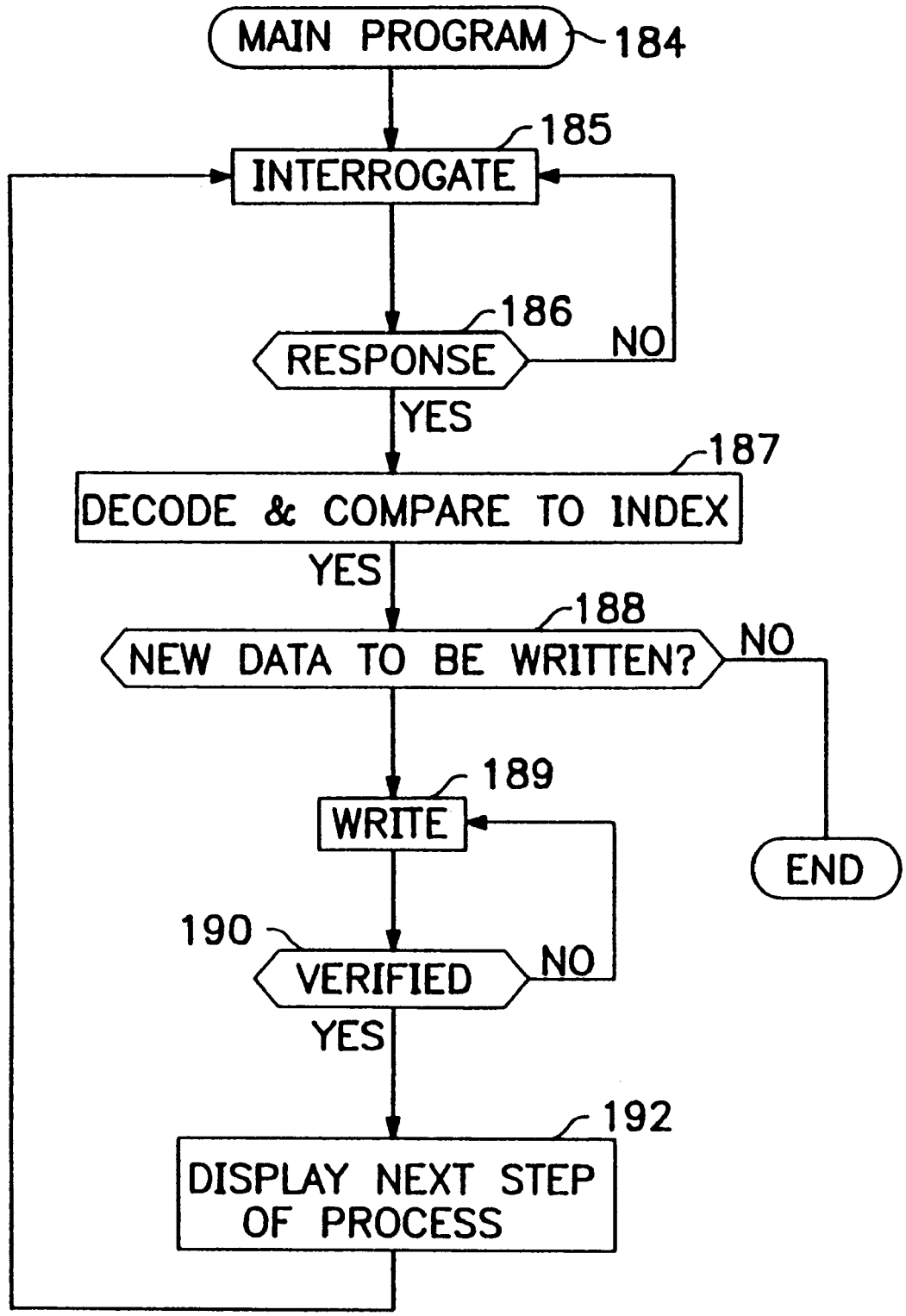
FIG. 35 is a flow diagram of the operation of the system of FIG. 34.

An example of the operation of the system of FIG. 34 is illustrated in FIG. 35. When power is supplied to the system, transceiver 172 emits an interrogation signal 185 to test for the presence of a memory device, i.e., a responder, within its detection range. The interrogation signal 185 is essentially a read signal that is continuously transmitted until a response 186 is received. The user manually places a microvessel 180 within the recessed area 176 so that the interrogation signal 185 provides a response to the controllers indicating the presence on the microvessel. The system receives the interrogation signal and performs a decode operation 187 to determine the data on the memory device within the microvessel, which data may include identification of the device and data concerning prior operations to which the microvessel has been exposed. Based upon the data obtained, the system makes a determination 188 of whether additional information is to be written. The system then performs a write operation 189 to record the immediately preceding operation. The write operation 189 involves modulating the transmitted signal as a series of "0's" and "1's", which are recorded on the memory chip, which typically has a 128 bit capacity. After completion of the programming step 189, an error check 190 is performed wherein a second read signal is emitted to verify the data that was written for integrity and correct content. If the correct data is not verified, the system may attempt to perform the write operation 189 again. After verification of the correct data, if the microvessel is one that should proceed to another operation, the system controller 182 will display instructions 192 for direction of the microvessel to the next process step.

The read operation is the same as the beginning of the write operation, with the interrogation signal being continuously transmitted, or transmitted at regular intervals, until a response is received. The response signal from the memory device in the microvessel 180 is conducted to system controller 182 for decoding and output of the data that is stored on the memory device. Software within the system controller 182 includes a data base mapping function which provides an index for identifying the process step associated with data written at one or more locations in the memory device. The system memory within the system controller 182 will retain the identification and process steps for each microvessel, and an output display of the information relating to each microvessel can indicate where the microvessel has been, and where it should go in subsequent steps, if any. After the data stored within the microvessel has been read, it is removed from the interrogation field and advanced to its next process step.

B. Manual sorter

Referring to FIG. 36, a manual sorting device is shown and generally designated 6700. As shown, the manual sorting device contains an identification station 6702, a computer system 6706, a number of visual cue devices 6740 mounted on an equal number of destination beakers 6720.

The identification station 6702 is a memory-reading and/or writing device which is capable of accessing the memory within the matrix-with-memory. The identification station is similar to or is the read/write station identified and discussed in conjunction with FIG. 34. As will be apparent to those skilled in the art, any variety of optical or RF reading and or writing devices may be used as long as the identification station had a data output channel. This channel is represented by the cable 6712 which passes between the identification station 6702 and the computer system 6706. The cable 6712, in addition to carrying the data to and from the identification station, provides any necessary power that the identification station should require.

In embodiments in which the memory in the matrix-with-memory is an optical bar code, the identification station 6702 includes a light emitter and detector capable of transmitting light away from the station, and receiving reflected light from the bar code or similar marking, on the memory device. Thus, by passing the memory device over the sensor portion of the identification station, the identifying marking is illuminated and reflected back onto the identification station. Then, by receiving and decoding the markings, the identification station provides information from the memory device to the computer system.

In embodiments in which the memory in the matrix-with-memory is an electronic memory, such as an RF tag, the identification station 6702 includes a RF emitter and detector 6705. This emitter and detector operates in the same manner as those described herein. For example, when the tag is an RF tag, the identification station emits an RF signal in about the 125 KHz range that creates an electromagnetic field in a region surrounding the station. When the matrix-with-memory with memory 6704 is passed in proximity of the station, the electromagnetic energy from the station excites a coil which is either part of, or attached to, the memory device. Upon excitation a voltage is induced in the coil which, when rectified within the memory, powers the memory device. Once powered, and in response to the electromagnetic field, the memory device, of the RF tag or other type described in this application, transmits a data signal back to the identification station. This data signal can include many pieces of information. For instance, each memory device has its own identification code, or serial number. In association with that identification code, a variety of other information may be associated. This other information can include the source of the memory device, the characteristics of any molecules or biological particles linked to or associated with the memory device, other information, including the destination of the memory device [which, however, will generally be provided by the software that directs the protocol], or any other information relevant to the procedure or test in progress.

The identification station 6702 is attached to the computer system 6706 via cable 6712. This cable is typically a serial data channel that provides serial communication between the identification station and the computer, where the identification number, serial number, and any other information can be communicated to the computer system. As a result of this information transfer, the computer system may use a large data base which accumulates information about all of the matrices-with-memories, and can monitor the location of the various matrices-with-memories and otherwise coordinate their movement. For instance, the matrices-with-memories can be accessed and programmed in accord with the procedures set forth elsewhere herein, and can be identified using a serial number that was either programmed, or pre-programmed during the manufacturing process of the memory. In any case, once accessed, the memory device, whether attached to a matrix-with-memory, a container, or completely unattached, can be identified and tracked by updating the information in the computer data base entry that corresponds to the particular memory device.

The computer system 6706 has a video display 6710 which is capable of displaying the identification number of the memory device, the destination of the memory device, the source of the memory device, and various other features of the device, such as the contents of the matrix-with-memory, or the contents of a vial, or other vessel attached to the memory device. Data fields 6711 can be used to display the data fields discussed above. The ability to create an appropriate data base is generally within the level of skill in the programming art. The data base for monitoring and directing the locations of memories could include a virtually unlimited number of data fields, and could correspondingly maintain a data field for a virtually unlimited number of memory devices. For example, a numeric serial number having six characters would accommodate $10^6$ memory devices, ranging from number 000000 to 999999. Using conventional computing capabilities, an almost unlimited number of matrices-with-memories could be simultaneously monitored and tracked throughout a protocol or series of protocols.

In accordance with the tracking and location functions of the data base and computer system, it is advantageous to provide the ability to direct the placement of a matrix-with-memory to a particular location or destination. For example, when testing a number of assays with a particular series of matrices-with-memories, it may be useful to coordinate the movement of the matrices throughout the laboratory. When handling large quantities of matrices-with-memories, the likelihood of error or failure increases. To minimize the chance of error, the computer system and database can be used to assist and/or direct the user in the placement of the various matrices-with-memories in solutions for the various reaction vessels or vessels containing reagents for screening. With such a system, it would be possible to coordinate the movement of virtually any objects with the assistance of the computer and data base.

The computer-aided direction can be achieved using a variety of humanly perceptible cues which can be generated to direct the placement of the matrices-with-memories. Such cues may include displaying the destination location on the computer graphic display screen 6710, such as in a location 6711. As another example, a speech synthesizer could be connected to the computer for generating human-sounding voice patterns to verbally instruct the user to place a given memory device in a particular destination, such as a beaker, container, or other location suitable for testing purposes. A voice message could provide an instruction such as: "Memory Identification Number 123456, place in beaker number 23." Alternatively, the voice message may simply say "23". In either case, the user would know to place the memory device in beaker number 23. The spoken verbal assistance could minimize errors resulting from misreading the displayed location 6711.

Other audible signals, such as those from a simple audio generator, could be used for guiding the user to the correct destination for placement of a given memory device by using patterns of audible signals. Piezoelectric transducers which generate audible tones could be placed on or near each of a group of containers into which the memory devices are to be placed. In operation, the memory device would be read using the identification station and the computer to determine its identification information, then, the computer would activate the audio transducer located on the correct container.

An optical guidance device could be integrated with the computer system 6706 and used alone or in combination with an audible system. A optical system could include a separate alphanumeric indicator, independent of a graphic display on the computer monitor. For example, a conventional digital LED alphanumeric display could display "BEAKER 23" to indicate the correct destination beaker. However, since the need to read the display can lead to error, an alternative or supplementary optical guidance device consisting of a number of independent LEDs could be used, with at least one LED corresponding to each destination option. Using the second optical guidance device in an array of destination options, a memory device would be identified as above, then the computer would determine the proper destination for the memory device and cause an LED corresponding to the proper destination, e.g., beaker #23, to be activated, thus guiding the user to the proper destination.

Continuing the description of the exemplary embodiment of a manual sorter as illustrated in FIG. 36. A cable 6716 extends from an output of computer 6708 for providing the electrical signals to the visual indicators 6740. As illustrated, the cable 6716 includes eight individual lead wires 6718, and a common ground wire. The interface for connecting cable 6716 to computer 6708 may be provided using a digital input/output (I/O) card [not shown]. The particular card selected for this embodiment was manufactured by COMPUTER BOARDS, of 125 High Street, Mansfield Mass. 02048, and was model number C10/D10 48H. The selected I/O card is capable of driving forty-eight different electrical output lines, each of which can be switched between about a 5 volt level and a 0 volt level, and have the capability to drive the LEDs without any interface driving buffers. (It should be noted that the system is illustrated with one cable 6716 with eight lead wires 6718 for simplicity only, and that the I/O card is capable of supporting forty-eight signal wires.) Each lead wire 6718 consists of a signal wire and a ground wire, which may be in the form of a twisted pair. Connected at the end of each lead wire 6718 is a visual indicator 6740. This visual indicator is configured for placement on the rim of a beaker 6720.

Shown in greater detail in FIGS. 37 and 38, visual indicator 6740 comprises an inverted U-shaped bracket 6742 and a light emitting diode (LED) 6752. LED 6752 is disposed at an upper portion of the bracket so that it is visible from the front of the bracket. The bracket is formed with a slanted portion 6750 which causes LED 6752 to be directed slightly upwards at an angle from the bracket to optimize its visibility to the user, who will typically be viewing the system from in front of and above the set-up.

Inverted U-shaped bracket 6742 has a first leg 6744 and a second leg 6746, with a gap 6748 being formed between them. As shown in FIG. 36, bracket 6742 is hung over the rim of a beaker 6720 so that the bracket is held in place by gravity and/or friction between the inner surfaces of legs 6744 and 6746 and the beaker wall, making positioning and removal of the bracket from the beaker simple and quick, requiring only minimal time to set up the manual sorter.

Referring now to FIG. 37, visual indicator 6740 is shown in cross-section. This view shows the relative position of the LED 6752 within a bore 6758 formed in the bracket. LED 6752 may extend slightly beyond the face of slanted portion 6750 so that it may be more readily seen from oblique angles as well as from directly in the front of the bracket. Epoxy or silicone 6760 may be used to secure the LED within the bore, however, by forming the bore with the appropriate inner diameter relative to the LED outer diameter, the LED may be retained frictionally using a slight interference fit. Lead 6756 extends out the back of bracket 6740 for attachment to lead 6718. In the instant embodiment of indicator, LED 6752 is available from Chicago Lamp Company as part number CMD531D-5V, and is powered with 5 volts at 12 mA, and generates 40 micro-candela ($\mu$Cd). An LED with these operating parameters can be connected directly to the output of the I/O card without the need for current-limiting resistors. Other LEDs may be used with appropriate current compensation.

Leads 6718 and cable 6716 may be wrapped in shrink tubing and can also be shielded against electromagnetic interference. The electrical shielding can be a wire braid, or a full or partial foil, terminated to the computer chassis via cable 6716. Electromagnetic radiation-inhibiting ferrite beads may also be used. Such shielding will minimize interference caused by electromagnetic radiation emitted from the manual sorting system 6702 that may be located in relatively close proximity to the leads 6718 and cables 6716.

C. Manual Cleaving Station

Referring now to FIG. 40, a manual cleaving station is shown and generally designated 9700. Manual cleaving station 9700 includes a cleaving block 9702 formed with an array of bores 9704 and having a number of standoffs 9706 and sleeves 9708. Manual cleaving station 9700 also includes a top plate, or tray, 9710 which is formed with four mounting holes 9712 aligned with the standoff pegs 9706, and an array of holes 9714 aligned with bores 9704. As shown, microreactor carrier, such as a syringe body or similar funnel-ended cylindrical tube 9716 and 9718 are removably inserted into holes 9714.

FIG. 41 illustrates a section of the manual cleaving station 9700 in cross-section with the top plate 9710 mounted on standoff pegs 9706 with removable sleeves 9708 suspending the top plate 9710, with microreactor carrier 9716, above one of the bores 9704. Microreactor carrier 9716 preferably includes a filter or frit 9720 at its lower end to prevent particles from microreactor 9722 from exiting through the opening in the lower end and passing into the cleaved solution. Frit 9720 is preferably made from polyethylene or polypropylene, and has filtering properties for particles sized above 10–20 microns.

Details of standoff pegs 9706 and sleeves 9708 are illustrated in FIG. 42. Sleeve 9708 is formed from a flexible, resilient material and is adapted to be press fit over standoff peg 9706. Sleeve 9708 is placed of peg 9706 by pressing sleeve gap 9728 against peg 9706 in a direction perpendicular to peg 9706, causing sleeve gap 9728 to expand until it snaps into position as indicated by dashed lines 9732. Sleeve 9708 is removable from peg 9706 pressing the edges of sleeve gap 9728 in a perpendicular direction away from the peg, causing sleeve gap 9728 to expand until it clears peg 9706. Referring back to FIG. 41, the top plate 9710 may be lowered in direction 9724 against the cleaving block 9702 by removing sleeve 9708.

Referring now to FIG. 43, top plate 9710 is shown resting on the upper surface of the cleaving block 9702, with microreactor carrier 9716 extending fully into the bore 9704. In this position, the microreactor 9722 is typically bathed in a cleaving reagent such as TFA solution 9726, and the entire cleaving station may be agitated using a standard chemistry lab agitator to enhance the cleaving process. After the cleaving is completed, the top plate 9710 is lifted to its original position and sleeves 9708 are installed over standoffs 9706. In the raised position, microreactor carrier 9716 and microreactor 9722 are suspended above the level of solution 9726 to drain. If desired, the cleaving process may be repeated as needed by again removing sleeves 9708 to lower top plate 9710, washing the microreactor with a solution of TFA, raising the top plate and re-installing the sleeves 9708 to allow the microreactor and microreactor carrier to drain. Once the microreactor and microreactor carrier have been sufficiently cleaved and drained, the solution 9726 within the bore 9704 is then removed with a pipet for placement on a standard microtiter plate for drying and further processing.

Cleaving block 9702 is typically manufactured from polypropylene or TEFLON™, however, other materials may be used provided they are non-porous, washable to remove all residues, and can withstand exposure to the chemicals used in the cleaving process. Such other materials could include various glasses, for example. As shown, manual cleaving station 9700 has an array of 3×9 bores, however, a cleaving block may be formed having any number of bores in any variety of arrays. For use with an automated sorter, the cleaving block should be compatible with the configuration of the sorter tray.

EXAMPLE 2

Automated system

A. Sorter (1) A first embodiment

Figure 44:
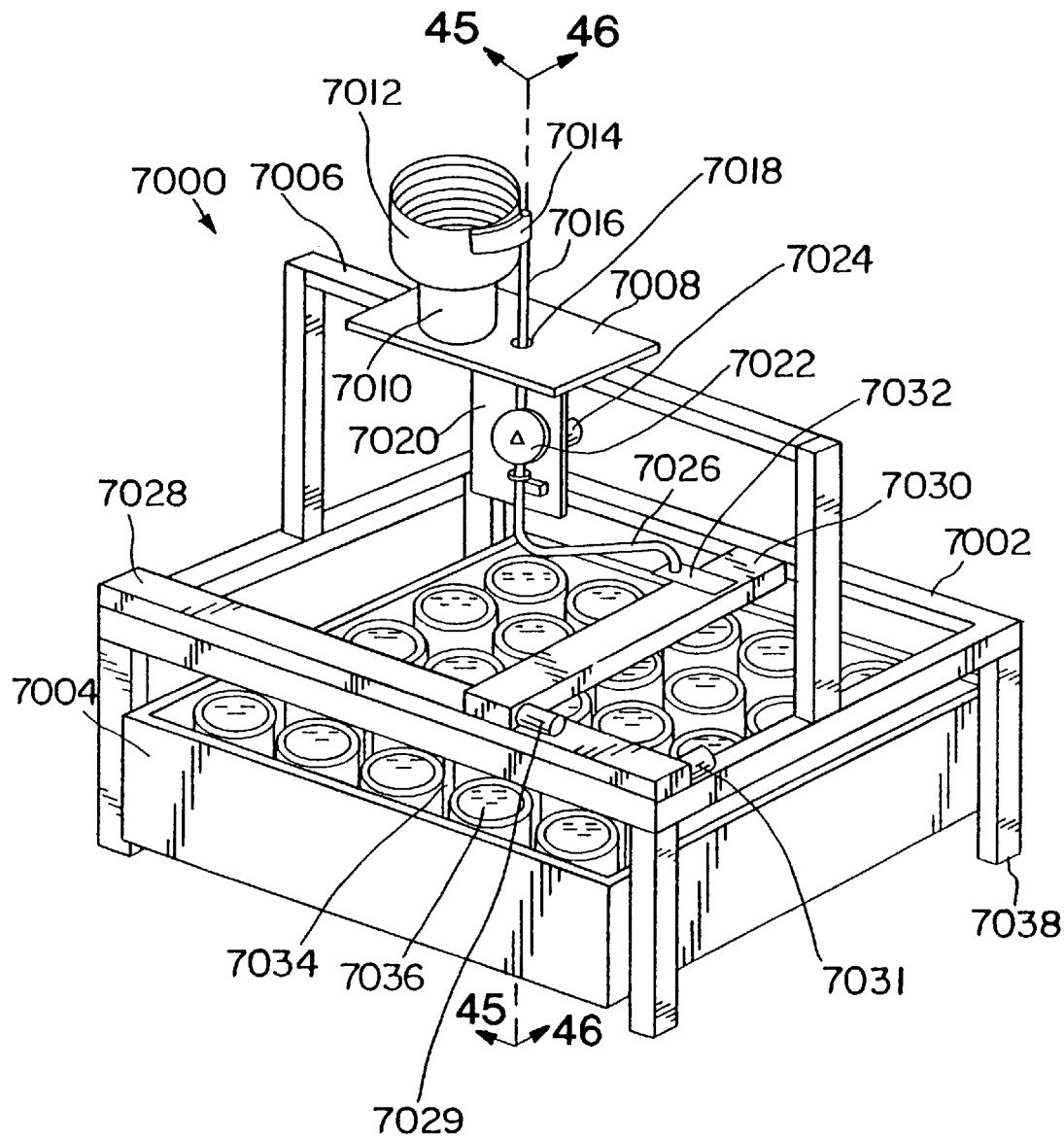
FIG. 44 is a perspective view of an automated sorting device showing the vibratory feeder, turnstile, positioning means, and a drawer holding a number of containers.

Referring first to FIG. 44, one exemplary automated sorting device is shown and generally designated 7000. Automated sorting device 7000 includes a frame 7002 that is supported by legs 7038 to provide an area for a drawer 7004 to slide in and out from beneath the frame 7002. Drawer 7004 is shown having a number of containers 7034, in this case, beakers, which are distributed evenly within the drawer. The actual number and distribution of the containers will depend on the sizes of the containers and the drawer and, thus, may vary from the arrangement illustrated. Depending upon the nature of the container used, appropriate supporting means, such as a rack or tray, will be required if the container is not free-standing and/or is likely to shift when the drawer is moved.

Extending upwards from the frame 7002 is an upper frame 7006 that attaches to two opposite sides of the frame 7002 to span the width of the frame. Attached to upper frame 7006 is supporting table 7008, which supports vibratory feeder 7010. Vibratory feeder 7010 is equipped with a sorting bowl 7012 that has a spiral ramp on its inside surface, which is described below with reference to FIG. 45. Vibratory feeders are well known in the art and are commercially available from manufacturers including Automation Devices, Inc., and Hoppmann Corporation of Chantilly, Va. In the present application, feeder 7010 is selected to minimize the vibration experienced by the matrix-with-memory devices that will pass through the sorter. The preferred feeder, from Automation Devices, moves the parts within the bowl 7012 using a sawtooth-type oscillation which gradually lifts and advances the devices within the feeder, thus minimizing exposure of the matrix-with-memory devices to extreme vibrations.

Figure 45:
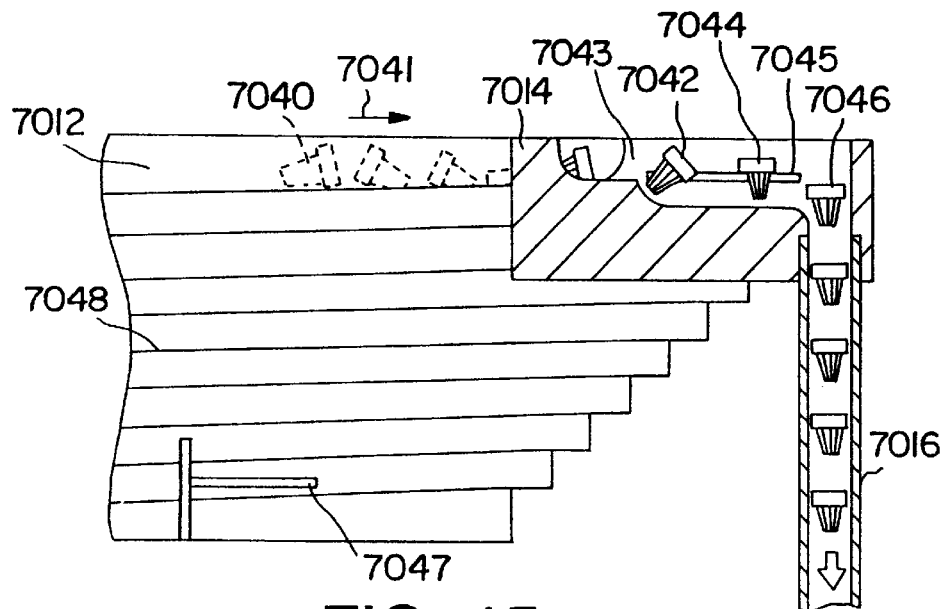
FIG. 45 is a cross-sectional view of the vibratory feeder taken along line 45—45 of FIG. 44 showing the circular ramp and delivery bracket, with devices in transit to the supply tube.

Delivery from vibratory feeder 7010 to supply tube 7016 is achieved via delivery bracket 7014. Referring to FIG. 45, delivery bracket 7016 is shown in detail using a cross-section of a portion of vibratory feeder 7010. The inner surface of bowl 7012 is formed as a spiral ramp 7048. When bowl 7012 is oscillated, microvessels 7040 "climb" up the ramp 7048, eventually reaching bracket 7014. At this point, as the microvessels 7040 proceed in direction 7041, they are not oriented any particular direction. Bracket 7014, which has a width just slightly larger that the diameter of the upper portion of the memory devices is formed with a chute 7043 that provides enough room for the device to orient itself so that the larger, upper portion of the microvessel 7040 is facing upwards. Orientation is achieved as the microvessel 7040 advances into the bracket 7014, so that its upper portion strikes ridge 7045. Note that there are preferably two ridges 7045, one on each side of chute 7043. Ridge 7045 extends inwardly to decrease the inside width of bracket 7014, thus preventing the microvessel 7040 from moving further down into the chute 7043 if it is not properly oriented. Now looking at microvessel 7042, which has partially progressed into chute 7043, it begins to rotate counter-clockwise so that its upper portion is in contact with the upper edge of ridge 7045, and gravity pulls its lower end downward. Further along the pathway, looking now at microvessel 7044, it is oriented vertically, with the larger portion facing upwards. As the microvessel continues to advance to the end of bracket 7014, microvessel 7046 passes the end of ridge 7045 and falls downwards into supply tube 7016.

In addition to the sawtooth vibration of the bowl 7012, an arm 7047 is located at the center of the bowl to prevent the microvessels from sinking to the center of the bowl so that they remain within the bowl. The positioning of arm 7047 within bowl 7012 is not critical as long as the arm extends through the center to prevent a device from achieving equilibrium within the bowl 7012.

Supply tube 7016 is a hollow tube having approximately a one half inch internal diameter. Tube 7016 may be formed from polyvinyl chloride (PVC), or a variety of other plastics or polymers, such as Tygon™, or may be metal or metal-coated tubing. In some cases, a metallic material could assist in protecting the memory devices within the microvessels against stray electromagnetic radiation. Supply tube 7016 is preferably at least partially clear, which may include metal tubing with a clear window, to permit visual inspection of the tube and observation of the flow of microvessels through it without requiring disassembly.

Figure 46:
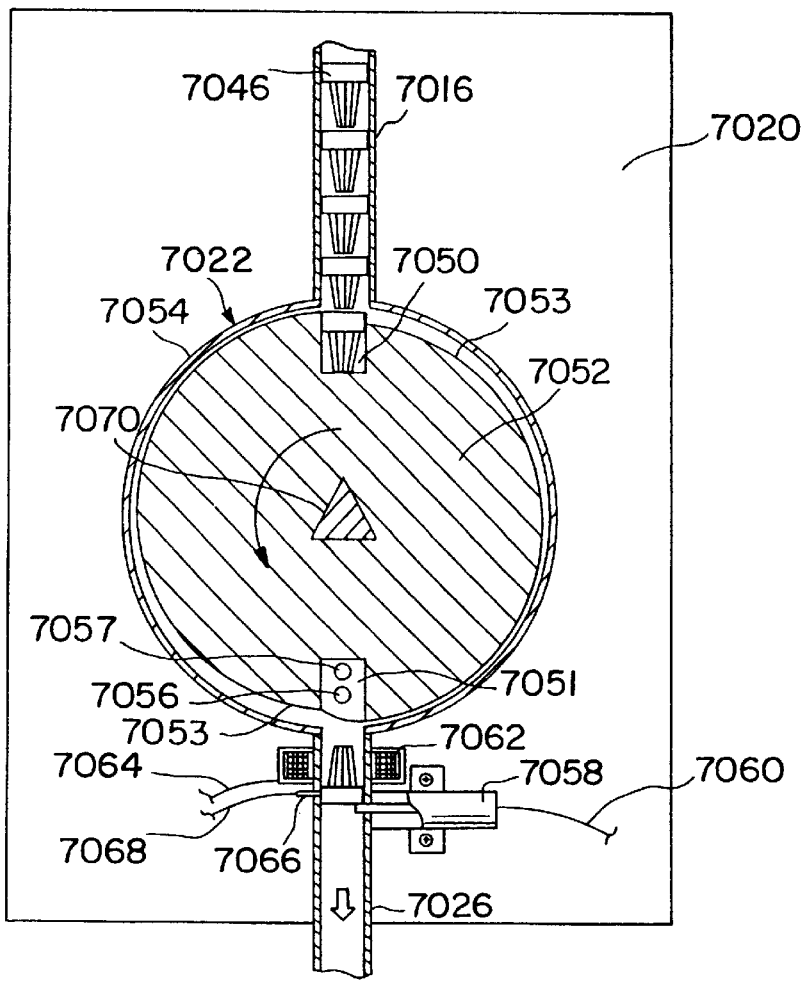
FIG. 46 is a cross-sectional view of the turnstile taken along line 46—46 of FIG. 44 showing the rotating hub, optical sensors, stopping solenoid, and antenna coil.

Referring again to FIG. 44, supply tube 7016 passes through an opening 7018 formed in supporting table 7008. Mounted on upper frame 7006 and extending downward from supporting table 7016, is mounting plate 7020. Mounting plate 7020 includes mounting means, such as a plurality of mounting holes (not shown) for receiving screws or bolts (not shown), for attachment of the turnstile 7022, solenoid 7058, and antenna 7062. FIG. 46 provides a more detailed view of this assembly.

As shown in FIG. 46, supply tube 7016, with a number of microvessels 7046 stacked within it, terminates at turnstile 7020. This cross-sectional view shows that the turnstile 7020 includes a hub 7052 and a housing 7054. The hub is formed with a pair of slots 7050, 7051 that are sized to receive the sorted microvessel. The hub is formed with a triangular hole for positioning over the shaft 7070 of motor 7024 (shown in FIG. 44). Such a configuration allows the hub to be changed easily in order to install a hub having either more slots, or a different size slot, or a combination of a different quantity of either larger or smaller sized slots. Thus, by replacing the turnstile hub 7052, a microvessel or other matrix-with-memory device of virtually any size could be sorted.

The hub 7052 is substantially circular shaped, except for the slight arcuate portions 7053 adjacent to each slot. This arcuate portion 7053 is shaped to minimize the likelihood of damaging the microvessel as the hub is turned. Since, otherwise, it would be possible for the next microvessel to become caught in the same slot as the hub turned. Arc 7053 is configured such that there will not be any trailing edge of the slot to catch the next microvessel. As the hub continues to rotate, the microvessel will be pushed upwards back into the supply tube slightly until the next slot is in position under the supply tube 7016 to catch to the microvessel. At that time, the raised microvessel falls into the slot 7050 in the hub.

In order to determine whether a microvessel is positioned in the slot, the hub 7052 can be formed with at least one optical detector hole 7056, 7057 in each slot. As shown in FIG. 46, the hole 7056 is adjacent to a device such that the optical detector could sense whether there is a microvessel within the slot. If there are no devices in the supply tube 7016, the sensors located near the higher portion of the hub would sense the absence of a microvessel in the slot 7050, and the hub would not receive a rotate signal. Similarly, when it is time for the hub to drop a microvessel, sensors located towards the lower portion of the hub verify that the microvessel was released prior to rotational movement of the hub 7052.

Once a microvessel falls from the turnstile and into the positioning tube 7026, it is stopped by gating solenoid 7058 that is positioned such that the plunger of the solenoid extends into the positioning tube 7026. Antenna 7062 is positioned around the positioning tube 7026 so that the device is within the electromagnetic field generated by the antenna. In this particular embodiment, the antenna 7062 is made from approximately 75 turns of 28 gauge epoxy coated wire on a bobbin having an internal diameter of one half inch, yielding an antenna having about 87 micro Henries of inductance at a resonant frequency of approximately 125 kilohertz. Antenna 7062 is attached via wire 7064 to a read/write station as discussed above in this application. As the device is being held, the matrix-with-memory device is accessed using the antenna 7062.

While the device is being retained by the solenoid, an additional optical sensor may be used to confirm that the device is present. Optical sensor 7066, such as part number E32D32, from Omron, which is electrically attached to a controller module E3XNM11, is positioned to sense the presence of a device when solenoid 7058 is closed. Solenoid 7058 is a linear solenoid, part number F13038L.9224, and is available from Shindengen America, Inc., located at 2985 E. Hillcrest Drive, Westlake Village, Calif. 91362. This solenoid is activated by 24 volts used to draw the plunger into the solenoid. Because the solenoid is at rest with the plunger extended, i.e., normally closed, little power is required to control the solenoid.

Referring to FIG. 44, the positioning tube 7026 extends downwards and is attached to a clamping plate 7032 that, in turn, is attached to the frame by a pair of arms configured in an X-Y axis. Arm 7028 attaches to the frame 7002 to provide linear movement of a platform along the X axis. Attached to the arm 7028 is arm 7030, for providing linear movement along the Y axis. The range of X-Y motion should be such that it covers the entire area of drawer 7004. Motors 7031 and 7029, respectively, can be activated either independently or together to provide X, Y or combined X-Y movement within the frame 7002. Selection of appropriate motors is well within the level of skill in the art. In the exemplary embodiment, x-axis motor 7031 is available from Mycom as part number PS4913M-02A, which is a high resolution size 34 frame size, triple stack stepper motor. Motor 7029 is part number Y PS499M-02, which is a two stack high resolution stepper motor. The motors are driven by a SD-45-230 motor driver also available from Mycom. Using the X-Y translation, any location within the frame can be accessed quickly and repeatably, by designating a particular X and Y coordinate.

Motors 7029 and 7031 are capable of precisely moving the plate 7030 within the frame to a coordinate with a preferred tolerance of less than 0.10 inches. This level of control permits a wide variety of container sizes to be used within the drawer 7004. One way to adapt the automated sorting device to a variety of containers is to create a container and drawer size library that will effectively map the coordinates of each container within the drawer. Such a mapping would expedite the loading of a different size container because the device would effectively know the location of each container without having to calculate it, or have the user of the system specify the location. In any event, having a coordinate mapping scheme increases the efficiency and throughput of the sorting device.

In the exemplary embodiment, 7028 and 7030 are available from THK America, Inc., 200 E. Commerce Drive, Schaumberg, Ill., 60173 as part numbers GL15B-500L for the Y axis, and GL20B-1000L for the X-axis.

Once the matrix-with-memory device, e.g., microvessel or microreactor, is accessed and identified, the X and Y destination coordinates are determined either from calculation or from accessing a look-up table or database, and the positioning tube 7027 is positioned over the designated container, gating the solenoid 7058 is activated to open, thereby releasing the device to fall downwards through the positioning tube into the appropriate container.

As noted above, in order for the automated sorting device to automatically determine the proper container or location in X-Y coordinates to position the arms and drop the device, the library of container locations within a given drawer 7004 may be created and entered into the computer's memory. Alternatively, a standard configuration for a particular automated sorting device may be adopted. A memory device, such as an RF tag or bar code, may be placed on the drawer 7004 and programmed with information regarding the drawer and/or its contents, so a record can be created for each drawer. For example, for a five by five array of beakers in the drawer, the associated memory device can be encoded with positioning information for each beaker, or the memory device could include a precoded identification number that would identify the drawer associated with a particular beaker configuration. With the ability to individually identify each drawer, numerous different testing configurations could be set up in multiple drawers to permit a large number of tests to be performed in rapid succession. With a positional accuracy of within 0.10 inches, the X-Y translator enables the loading and recording of information for a drawer containing a very high density of containers.

In addition to the various sensors and solenoids discussed above in connection with FIGS. 44–46, there are also numerous interlock and safety devices that are not depicted, but which are contemplated for inclusion in a commercial system. For example, there is preferably at least one emergency disable switch that will instantaneously halt the operation of the system. The emergency disable can be activated either by entering a command via the host computer, or by a safety switch located on the automated sorting device frame. Such switches should be readily accessible while the system is in operation.

Interlock switches may also be used to ensure the proper sequence of events occur prior to, or during, a sorting procedure. For example, the drawer can be equipped with a microswitch or other position-sensitive switch to prevent operation of the sorter if the drawer is not properly seated within the frame. Such an interlock avoids any offsets or inaccuracies that might occur if the drawer is offset from its correct position. Incorporation of emergency disable and interlock switches is well within the level of ordinary skill in the art.

Figure 47:
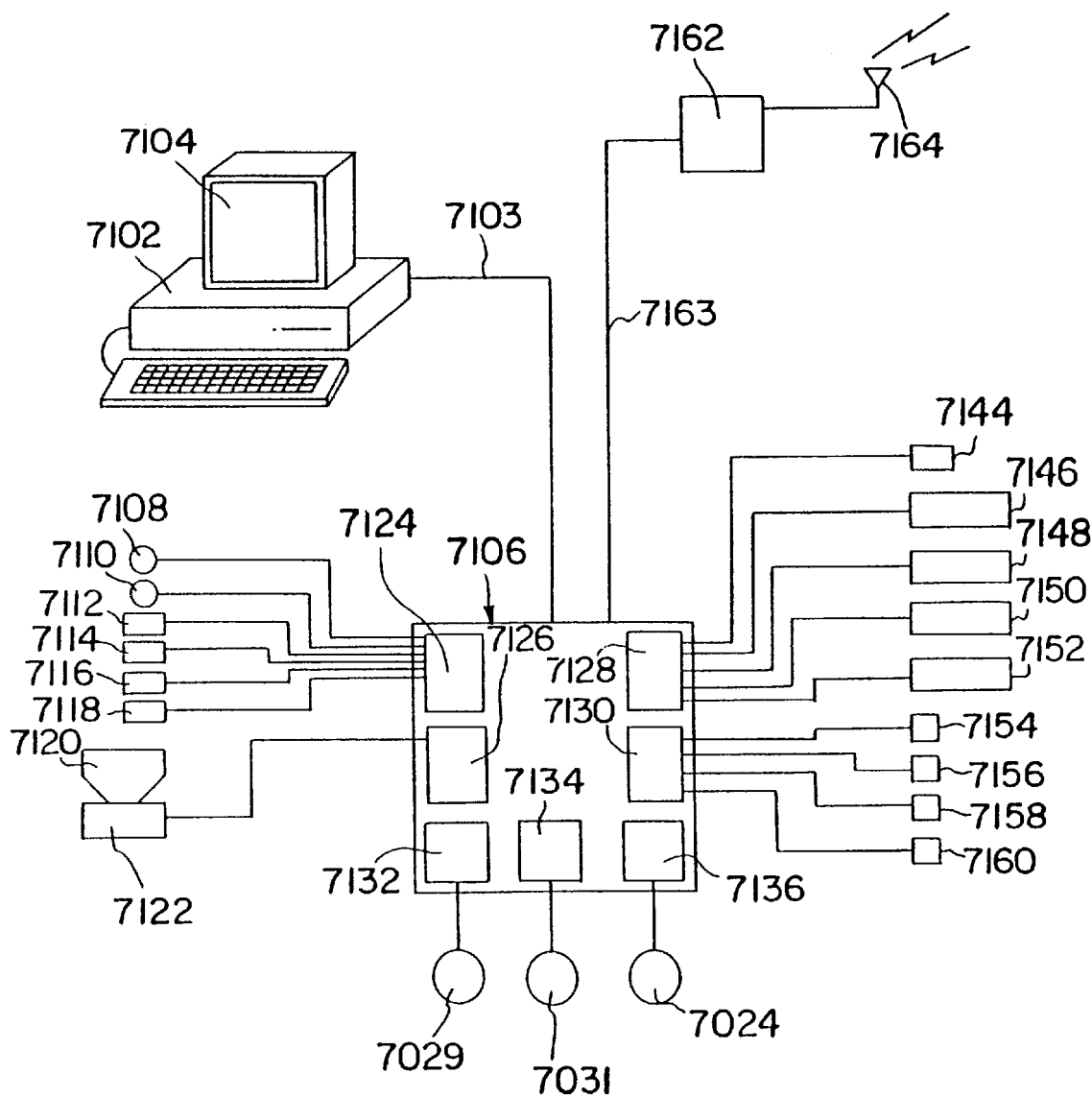
FIG. 47 is a block diagram of an automated sorting device showing the host computer, Programmable Logic Controller (PLC), and other electronic sensors and devices used in the sorting device.

Referring now to FIG. 47, a block diagram of the automatic sorting device 7000 of FIG. 44 is shown. A host computer 7102 contains the database and other controlling software [see, e.g., Appendices II and Ill]. This software controls all aspects of the operation of the automated sorting device, with the exception of embedded software that may be housed within the PLC 7106. Host computer 7012 is connected to PLC 7106 via serial communication link 7103 for communication and data exchange between computer 7102 and PLC 7106. In order for the user of the automated sorting device to properly operate the device, a display 7104 is provided to instruct the user in the proper placement of the various containers within the drawer, to indicate the particular batch of devices to place in the vibratory feeder, such as feeder 7012 in FIG. 44, or to provide other helpful or troubleshooting information to assist the user in performance of the sorting process. Alternatively, as noted above, placement may be preprogrammed and each drawer prepared prior to use.

The PLC 7106 contains a variety of digital and analog motion control communication modules, such as part numbers ID21 6 and OD 218 available from Omron, Inc., connected to a controller module (CPU), such as part number C200HS also from Omron. Beginning with the digital input sensors, a digital input module 7124 is used to interconnect the panic switches 7108, 7110 to PLC 7106 and computer 7102. Additionally, a number of limit switches 7112, 7114, 7116, and 7118 are positioned around the automated sorter and electrically connected to PLC 7106 via digital input module 7124. Analog output module 7126 is used to control the vibratory feeder in order to turn the feeder on and off, depending on the number of devices used in a particular sorting task. Analog output 7126 module accepts the information from PLC 7106 and computer 7012, and with either a relay or other switching device, turns the feeder on or off, depending on the current need for more devices.

Motor 7029 for X-axis arm 7028, motor 7031 for Y-axis arm 7030, and motor 7024 for turnstile 7022 are controlled by motor controllers 7132, 7134, and 7136. These motor controllers activate the stepper motors in small increments, and at a variety of speeds. As a result, the rate of response of the X-axis and Y-axis arms is sufficient for the arms to be moved from one corner of the drawer to the opposite corner of the drawer within one second, thus providing quick and accurate sorting of the matrices-with-memories with the automated sorting device.

To identify the matrix-with-memory device on the sorter, read/write station 7162 is attached to PLC 7106 via serial link 7163. Serial link 7163 allows the identification information received by antenna 7164 to be communicated to PLC 7106 and back to host computer 7102. This communication allows the read/write station to be activated only when there is a device in place near the antenna.

One or more optical sensors can be attached to analog input module 7130 for monitoring of the sorter operation. By polling module 7130, PLC 7106 can verify the presence of devices at various stages within the automated sorting device. When the sensors indicate that a step has been missed, the PLC can repeat the missed step, thus providing for the continued operation of the sorter without human intervention. To provide an example, optical sensors could be placed in the turnstile to confirm the presence of the microreactors within the turnstile prior to its rotation. An optical sensor can also be installed close to the antenna in the positioning tube to trigger activation of the read/write station. Additional optical sensors could be used at various locations throughout the sorter for virtually error-free sorting. Implementation of such additional sensors is within the level of skill in the art.

In addition to the optical sensors, a number of other types of sensors could be used. For example, a Hall-effect sensor 7144 can be used to detect the presence of a device or container. Additionally, limit switches 7146, 7148, 7150, and 7152 can be used to effectively monitor the accuracy of the X and Y arms. For example, upon start-up of the sorting device, the X and Y arms can be operated to their limits, tripping the limit switches at either end of the travel so that the full range of travel of the arms can be verified and the system calibration accordingly, if necessary.

The software for controlling the operation of this sorting device includes a high-level language which implements "ladder-logic" [see, Appendices I–III and III, especially pages 1, 2 and 3]. The ladder logic is a Boolean representation of a state machine which allows the programmer to graphically implement a variety of control parameters. The development tool "Syswin" is available from Omron and is used to implement the particular logic and control parameters necessary to control the sorting device using the PLC. These control parameters are defined and ordered on pages 4 and 5 of the Appendix and represent hardware addresses in the PLC, or other memory locations. The sorting process is controlled by the statements contained within and defined by the ladder logic. This process, as discussed below, controls and monitors the various electronic and mechanical parts of the sorting device.

Figure 48A:
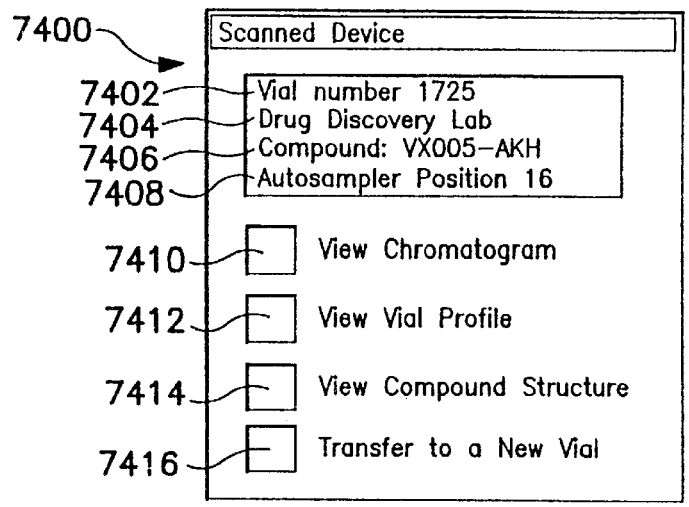
FIG. 48(a–c) depicts exemplary images displayed on the host computer that assist the user in selecting the various locations, containers, or devices, and viewing the contents thereof.

Referring now to FIG. 48a, a typical display is shown and generally designated 7400. This display is a computer generated display and is shown in the monitor 7104 of the host computer 7102 as discussed above with reference to FIG. 47. Display 7400 includes several fields which are visible to the user. Generally, this format of display may be used in conjunction with any of the sorting devices or other identification devices discussed in this application, and will be discussed here only as an example. Display 7400 could also contain a variety of other fields which include information about the date of last access, the source of the contents of the vessel, or other pertinent information. FIG. 48a shows the vial identification number 7402, the particular location 7404 of the scanned device, shown here as the "Drug Discovery Lab", the contents 7406 of the scanned device, shown here as "Compound VX005-AKH" (which can either be an actual compound name, an identification code, or other identifying information), and the position within the auto-sampler 7408, shown here as "Position 16". The position number could represent a position with a drawer, or any other location within the laboratory environment.

In addition to the identification information shown in portions 7402, 7404, 7406, and 7408, other options can be provided. For example, option 7410 allows the user to view the chromatogram of the contents of the scanned device, option 7412 allows the user to view the vial profile, option 7414 allows the user to view the compound structure, and option 7416 allows the user the option of transferring the contents of the vial to a new vial.

Figure 48B:
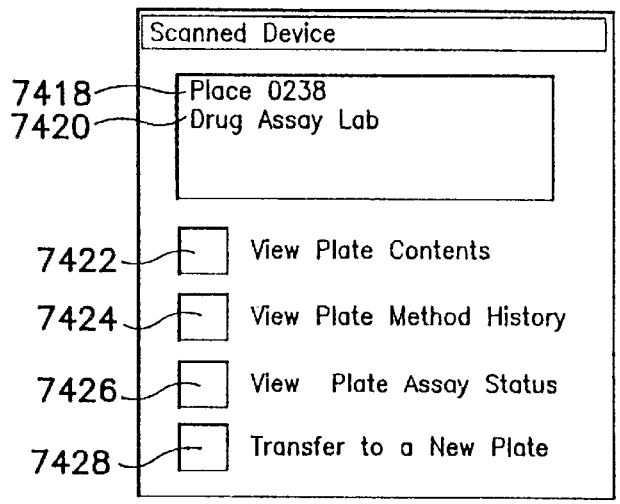

FIG. 48b shows a similar display having an identification code 7418 which indicates that this is a plate number "0238". Such an identification code would most likely be used in conjunction with a Microplate, but could be used with other, less widely known plate configurations. The location field 7420 of the display shows that the microplate is located in the "Drug Assay Lab". As with the display of FIG. 48a, this display includes different options that are consistent with the type of device. In this case, the options include the ability to view the plate contents 7422, view the plate method history 7424, view the plate assay status 7426, and transfer the contents to a new plate 7428.

Figure 48C:
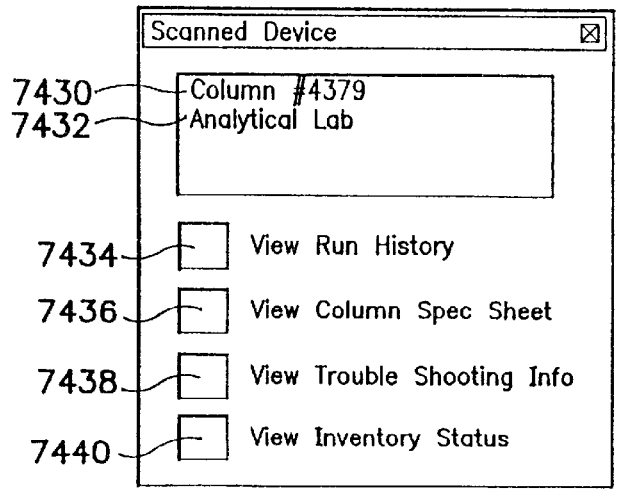

FIG. 48c shows another exemplary display applicable for identification and tracking of a GC Column. This display has an identification code 7430 showing "Column #4379", with a location code 7432 designated as the "Analytical Lab". Available options in this display allow the user to view the run history 7434, view the column specification sheet 7436, view trouble-shooting information pertinent to that column 7438, and to view the inventory status 7440.

Referring again to FIG. 44, operation of the automated sorting device begins with the loading of the drawer 7004 with a collection of containers. As described above, virtually any number or size of container could be placed in the drawer, or the drawer itself could have integrated containers. For example, the drawer could have be formed with a number of wells, or other fluid-tight containers so that the drawers could be used instead of having to place a number of containers within the drawer. Once the containers or wells are positioned within the drawer, the drawer slides under the X and Y arms within the frame 7002. The user places a quantity of matrix-with-memory devices, such as microreactors or microvessels, in the vibratory feeder bowl 7012 and the host computer is engaged to control the operation and sorting of the devices to different locations within the drawer.

As the microvessels are fed from the vibratory bowl 7012 to the supply tube 7016, they fall into position above the turnstile 7022. As turnstile 7022 rotates, a single microvessel is passed through the turnstile and downward into the positioning tube 7026. As the microvessel drops, the piston from the solenoid 7058 stops its fall and holds the microvessel in position until the antenna is activated and the microvessel's memory device is accessed. Once accessed and identified, the memory device can be written to or its identify recorded in the computer database which is maintained within host computer 7102. After identification and writing, if appropriate, the X-axis arm 7028 and Y-axis arm 7030 are moved into position where the microvessel is to be placed, preferably over a container 7036 in the drawer 7004 identified by host computer. Gating solenoid 7058 is opened to drop the device through positioning tube 7026 and into the appropriate container 7036.

When using microvessels having a lighter weight or low weight-to-size ratio, it may be necessary to apply additional force to assist the microvessel's passage through the various tubes. In some cases, compressed air can be used, however, the introduction of compressed air into a laboratory environment is sometimes not desirable. In those instances, it is possible to utilize a conveyor belt, or other means for advancing the devices, into the various containers. A person skilled in the art would be able to identify and implement alternatives to the supply tube and positioning tube described above. Once the microvessel has been placed within the proper container, the process can be repeated. Vibratory bowl 7012 has a capacity for holding several hundred microvessels, allowing the automated sorting device to be used to sort hundreds of microvessels into the various containers 7036. Vibratory bowl 7012 can be further equipped with a hopper which would effectively increase the quantity of microvessels into thousands that can be sorted without human intervention.

Drawer 7004 could be replaced with a conveyor belt having a replaceable number of containers that would be passed under the X and Y positioning arms. In this embodiment, the containers could be either manually or automatically placed on the conveyor belt which, when passed under the frame 7002, would be available for placement of microvessels by the automated sorting device.

The automated directed sorting process can also be used to monitor and control the movement of various microvessels between containers, as well as other machines or equipment typically found in a laboratory environment. Such a sorting and inventory maintenance system could include a number of RF decoding stations, or read/write stations, a number of auto samplers, fraction collectors, plate readers, reagent carriers, microplates, collection vials, auto sampler carousels, GC columns, and CE columns. It will be apparent that virtually any device, machine, reagent source, or other device can be identified, tagged with a matrix-with-memory device, and used in an automated sorting system. Such universal tagging of all relevant devices and machines within a laboratory can provide a nearly fully automated laboratory, removing much, if not all, human interaction required for testing and synthesis operations.

(2) A second embodiment

Figure 49:
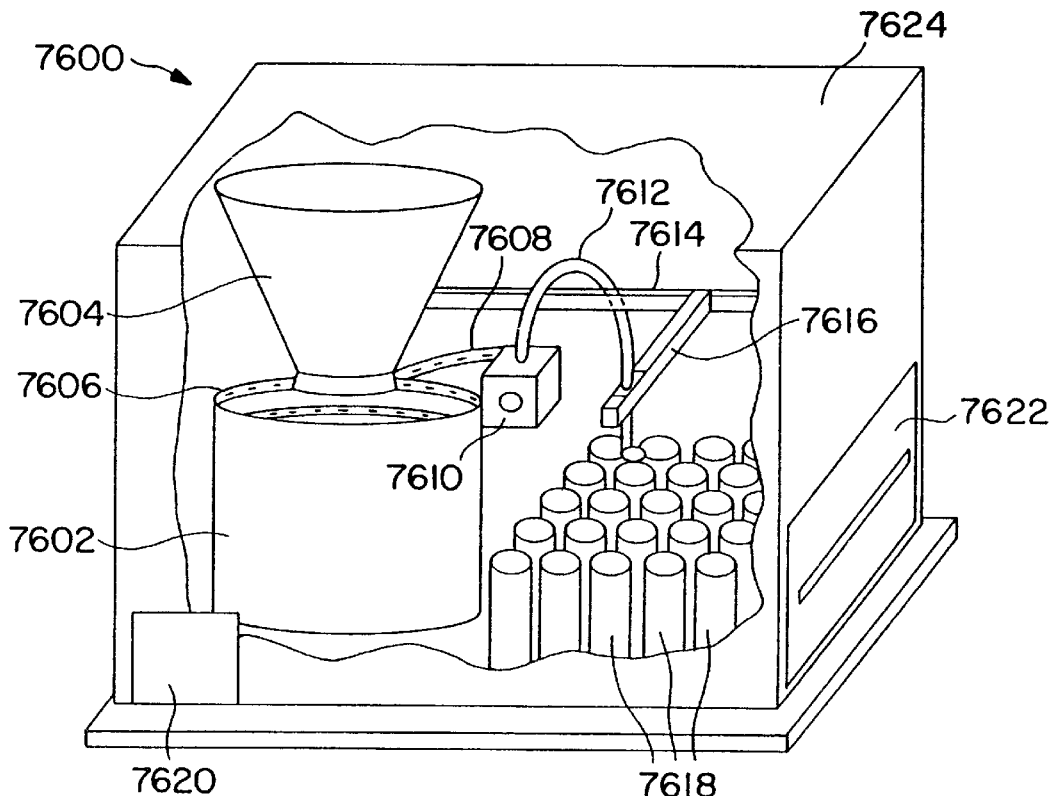
FIG. 49 is a perspective view of an alternative embodiment of an automated sorting device, with portions cut away for clarity.

Referring initially to FIG. 49, an alternative embodiment of an automated sorting device is shown and generally designated 7600. Sorting device 7600 includes a vibratory feeder 7602 which has a hopper 7604 for holding a large quantity of microreactors. Typically, the hopper can hold in excess of 10,000 microreactors. The microreactors are advanced through feeder 7602 to supply tube 7608 and to the singulator 7610. The singulator 7610 isolates a single microreactor from the stream of microreactors 7606 for identification of the microreactor which is positioned within delivery tube 7612. Once the microreactor is within the delivery tube 7612, it is identified by control electronics 7620, and the x-axis robotic arm 7614 and the y-axis robotic arm 7616 are activated to position delivery tube 7612 immediately above the appropriate container 7618. Container 7618 is typically a synthesis vessel, or can be a cleavage well, or any other vessel described herein. In order to facilitate the positioning and removal of the containers 7618, a drawer 7622 is provided. Also, cover 7624 may be used to prevent the introduction of contaminates into the containers, as well as to protect the sorting device 7600 from damage. Additionally, the cover 7624 may be formed with an opening on its top surface (not shown) such that microreactors may be added to the hopper 7604 without the need for removing the cover.

(3) A third embodiment

Figure 50:
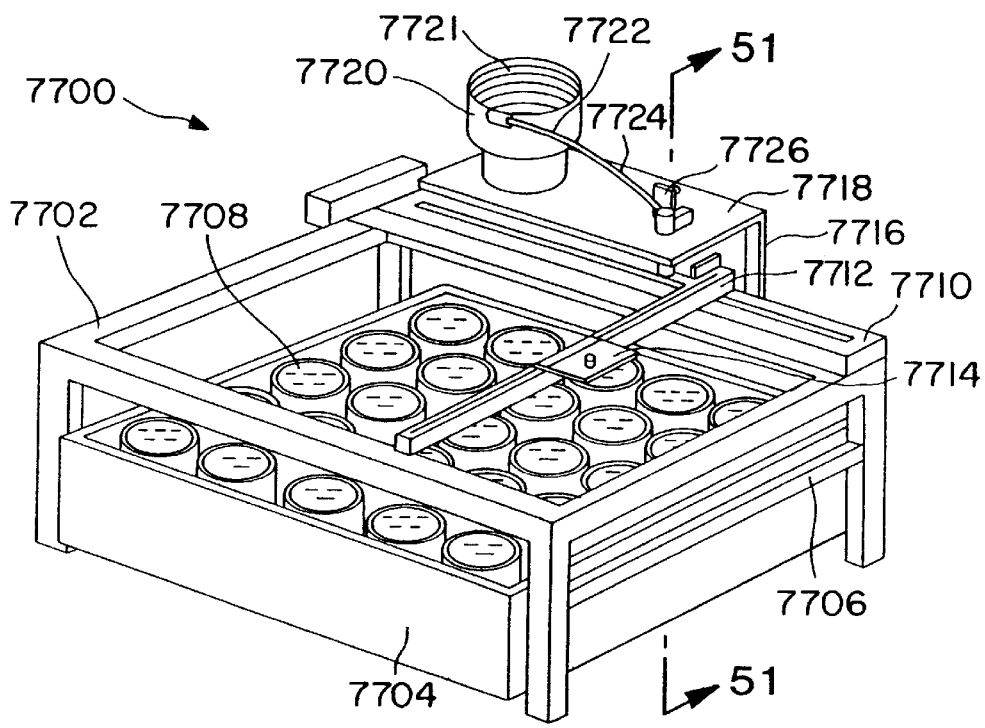
FIG. 50 is a perspective view of yet another alternative embodiment of an automated sorting device.

Referring now to FIG. 50, another alternative embodiment of an automated sorting device 7700 is illustrated. Sorting device 7700 includes frame 7702 which is equipped with drawer 7704 that is slidable outwards from frame on slides 7706. Drawer 7704 is sized to receive a number of containers 7708 which are typically filled with a solution. In general, the number of containers 7708 within drawer 7704 may be varied, and be as few as one or two containers, a ninety-six or 384 well titer plate, or any other container or array of containers described herein.

Base frame 7702 is equipped with an X-axis translator 7710, and a Y-axis translator 7712. X-axis translator 7710 is attached directly to the surface of the base frame 7702, while the Y-axis translator 7712 is attached to the surface of the X-axis translator 7710. By combining the movement of the X- and Y-axis translator 7710 and 7712, any location within the range of the X- and Y- axis may be accessed with dynamic dropper 7714. An example of an appropriate axis slide is a member of the FS series of timing belt actuators available from Intelligent Actuator, Inc. of 3302 South New Hope Rd. # 200F, Gastonia, N.C. 28056. This family of actuators is capable of linear positioning to within 0.003 inches. Such accuracy is particularly important when sorting microreactors to containers which have a relatively high density, or which have small openings.

Frame 7716 extends upward from base frame 7702 and supports a platform 7718. Platform 7718 is sized to accommodate placement of a vibratory feeder 7720, which receives and advances microreactors 7721, and a singulation device 7726. The microreactors 7721 are advanced from vibratory feeder 7720 along orientator 7722 to delivery slide 7724, microreactors 7721 until singulator 7726 identifies and advances the microreactors individually for dropping into dynamic dropper 7714. Dynamic dropper 7714 is then moved along the X- and Y-axis so that dynamic dropper 7714 and the corresponding microreactor are positioned above container 7708. Once in position, dynamic dropper 7714 releases the microreactor into container 7708, then returns to the initialization location immediately under the platform 7718 and singulation device 7726.

Figure 51:
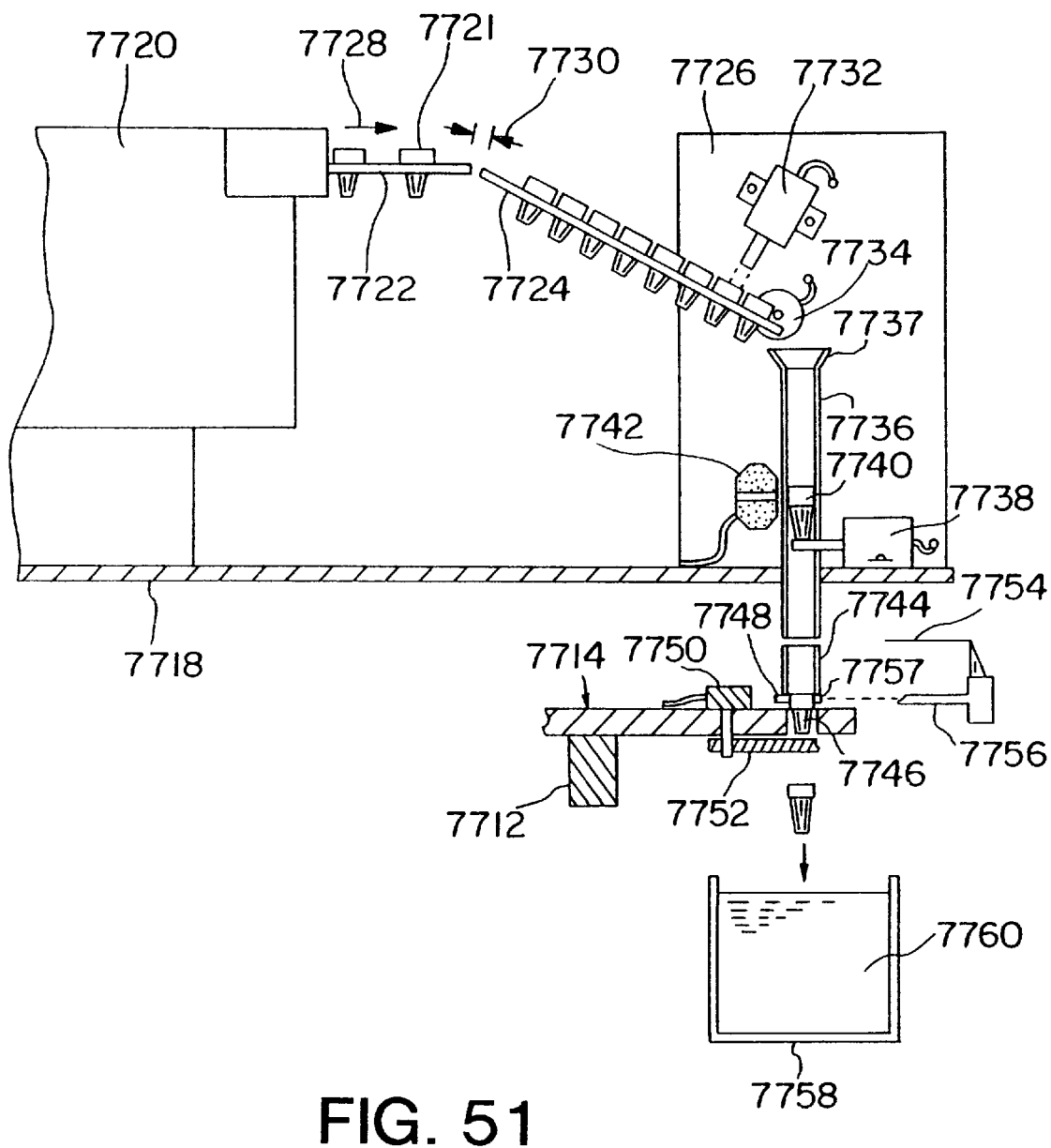
FIG. 51 is a cross-sectional view of the automated sorting device of FIG. 50 taken along line 51—51.

Referring to FIG. 51, portions of the automated sorting device 7700 are illustrated in cross-section. As shown, vibratory feeder 7720 is mounted on platform 7718 with orientator 7722 extending from feeder 7720. Microreactors are advanced in direction 7728 such that when they reach the orientator 7722, the microreactors are properly oriented. Orientator 7722 comprises two parallel supports which are spaced apart a distance slightly larger than the diameter of the lower portion of the microreactor, and less than the diameter of the upper portion of the microreactor. As the microreactor is advanced in direction 7728, gravity pulls the lower portion of the microreactor downward between the two parallel supports, so that the upper portion of the microreactor is supported on the upper surface of the parallel supports. Thus, the microreactor will be oriented upright, regardless of the orientation with which the microreactor is advanced from vibratory feeder 7720.

Delivery slide 7724 is positioned adjacent the end of orientator 7722 and also comprises a pair of parallel supports. Delivery slide 7724 and orientator 7722 are separated by gap 7730 which prevents the propagation of the vibrations generated by vibratory feeder 7720 into the remainder of automated sorting device 7700. Typically, gap 7730 is on the order of 2 to 3 millimeters, but any gap distance would suffice so long as the orientator 7722 and the delivery slide 7724 do not abut each other.

Delivery slide 7724 is at an incline from the orientator 7722. The inclined configuration eliminates the need for a supply tube such as that shown in FIGS. 45 and 46, thus minimizing the overall height of sorting system 7700. As the microreactors advance downwards along delivery slide 7724, a pair of singulation solenoids 7732 and 7734 prevent the continued downward movement of the microreactors. First, singulation solenoid 7732 is a linearly actuated solenoid which is positioned on mounting plate 7726 such that the solenoid, when activated, strikes the upper surface of a microreactor, trapping it against the upper surface of delivery slide 7724. Second, singulation solenoid 7734 is positioned to prevent the advancement of a microreactor beyond the end of the delivery slide 7724 by extending a pin or bar into its path. In operation of the singulator, a number of microreactors 7721 are positioned on the delivery slide 7724. Singulation solenoid 7734 is activated to prevent the lower-most microreactor from falling from the end of the delivery slide. When a single microreactor is to be released, first singulation solenoid 7732 is activated to prevent the microreactor adjacent to the lower-most reactor from moving. Second singulation solenoid 7734 is then operated to retract the bar allowing the lower-most microreactor to slide down delivery slide 7724 and drop into tube 7736. Tube 7736 may be formed with a funnel portion 7737 to receive and position the microreactor within the tube even if it does not drop in perfect axial alignment with tube 7736. Once the lower-most microreactor has been delivered, second singulation solenoid 7734 is again activated to extend the bar and first singulation solenoid 7732 is de-activated to allow the next microreactor to slide down the delivery slide until striking the singulation solenoid 7734.

Once the microreactor has been singulated into the tube 7736, the microreactor is held in position by a stopping solenoid 7738. Stopping solenoid 7738 is positioned on platform 7718 to that when activated, the solenoid shaft extends a plunger or pin into a hole in tube 7736 to prevent the passage of the microreactor through the tube and into dynamic dropper 7714. Alternatively, stopping solenoid 7738 may be a rotating solenoid which rotates a stopping door (not shown) into and out of the tube 7736. While the microreactor is being held in position by the solenoid 7738, antenna 7742 accesses the memory device within the microreactor to identify the memory device and read any additional information related to the device, as described elsewhere herein. Antenna 7742 may be orientated in a number of different directions with little effect on the operation of the antenna. As shown, antenna 7742 is oriented perpendicularly to tube 7736, such that the microreactor will lie within the electromagnet field generated by the antenna. Although depicted in a perpendicular orientation for purposes of illustration, it may be preferable to orient antenna 7742 at an angle other than perpendicular to the tag due to the interaction between perpendicular E–M fields. For example, antenna 7742 may be oriented at about a 45° angle with respect to the tag to ensure that the radiation pattern surrounding the microreactor is sufficiently powerful to excite the coil in the tag.

The antenna may be positioned near tube 7736, instead of actually encircling the tube as in FIG. 46, so that the same antenna can be used regardless of the tube size and material. This permits the diameter of tube 7736 to be changed to accommodate microreactors of different sizes.

Once the memory device within the microreactor has been identified, and dynamic dropper 7714 is in its original starting position under tube 7736, the microreactor is released by solenoid 7738 so that it drops into dynamic dropper 7714. The microreactor drops from tube 7736 into the drop tube 7744 where it is retained by rotating door 7752. Rotating door 7752 is operated by rotating solenoid 7750 which, when de-activated, holds the door to cover the exit to drop tube 7744. When solenoid 7750 is activated, rotating door 7752 is rotated out of the path of the microreactor which then drops out of the drop tube 7744. Rotating door 7752 can accommodate microreactors of a variety of sizes.

Dynamic dropper 7714 can be equipped with at least one optical sensor 7748 which is positioned to provide a signal to indicate the presence of a microreactor within drop tube 7744. Sensor 7748 provides feedback to the host computer, such as shown and described in conjunction with FIG. 47. After optical sensor 7748 detects the presence of the microreactor within the drop tube 7744, the X, Y, translators 7710, 7712 are controlled to position dynamic dropper 7714 directly above the proper container 7758. Once in position, solenoid 7750 is activated to open door 7752, thereby allowing the microreactor 7746 to fall into container 7758 and its corresponding solution 7760.

The lid to the microreactor may be removed to improve the exposure of the matrix material to the solution. Removal of the lid is particularly helpful in applications involving cleaving steps because the contents of the microreactor are more easily agitated when outside the microreactor. Removal of the lid is achieved by providing punch 7756 which projects into drop tube 7744 to strike the microreactor lid. Punch 7756 is mounted on frame 7702 at a location that allows dynamic dropper 7714 to be positioned to align aperture 7757 in drop tube 7744 with punch 7756. Dynamic dropper 7714, which contains microreactor 7746, is moved so that drop tube 7744 is forced against punch 7756 with aperture 7757 align with punch 7756, the lid is removed from the microreactor. Because the lid removal process can require that the microreactor strike the punch with considerable force, a protective cover 7754 is provided to prevent the upward ejection of the lid from drop tube 7744. This eliminates a safety hazard and prevents cross-contamination between containers which could be caused by introducing the lid of one microreactor into a solution containing another microreactor. Following lid removal, dynamic dropper 7714 is positioned over a designated container as previously described.

The automated sorting device 7700 as shown in FIGS. 50 and 51 is representative of a preferred embodiment. System 7700 also includes a host computer, such as the host computer 7102 shown and described in conjunction with FIG. 47.

In addition to the height savings provided by the embodiment of FIGS. 50 and 51 as compared to the embodiment of FIG. 44, because the path of the microreactor from the vibratory feeder to the placement within the container is significantly shorter in device 7700 than in device 7000, the microreactors may be sorted more rapidly. Device 7700 is capable of sorting over one thousand microreactors per hour, depending on the size of the drawer, since the longer the potential travel distance for the x-axis and y-axis, the more time it will take to reposition the dynamic dropper. The positioning actuators provided by Intelligent Actuator are capable of traversing approximately a five foot distance within one second. Thus, the positioning of the dynamic dropper within a drawer having dimensions of three feet square, could take less than one second, providing for a sorting rate of approximately thirty microreactors per minute, when taking into account the longest possible positioning and return paths.

The travel time for placement of the microreactors can be minimized by locating the initialization point for dynamic dropper 7714 adjacent punch 7756. This would eliminate the need to repeatedly move dynamic dropper 7714 to the punch location.

(a) Orientator embodiments

Figure 53:
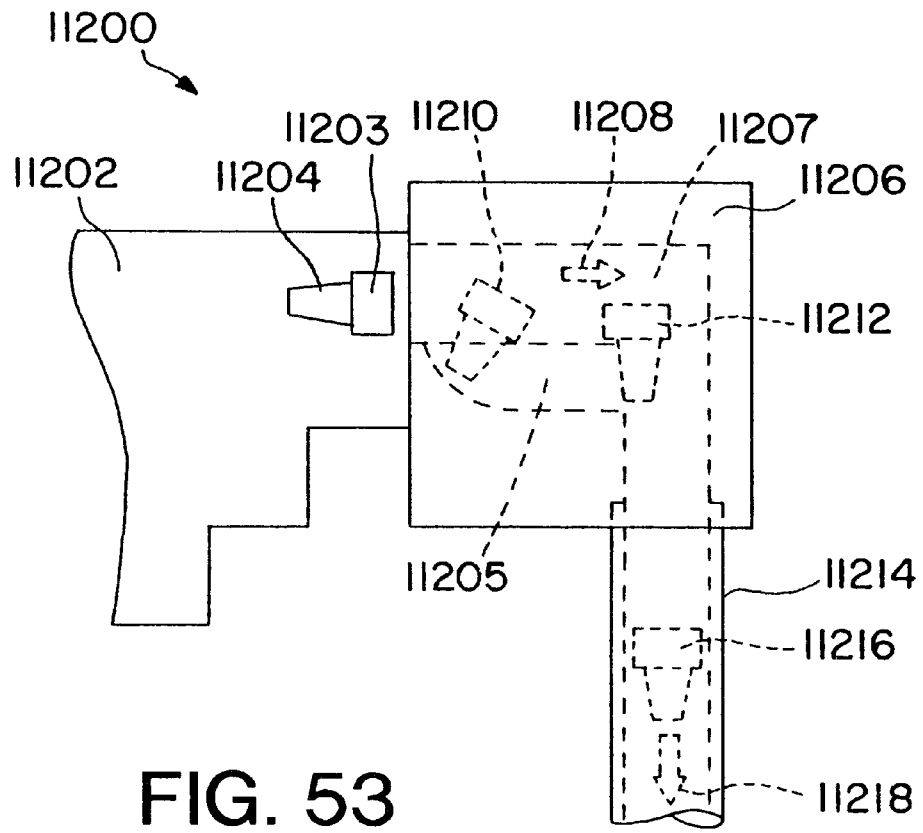
FIG. 53 is a side view of an alternative embodiment of an orientator within the automated sorting device which is intended for use with single-bodied microreactors.
Figure 54:
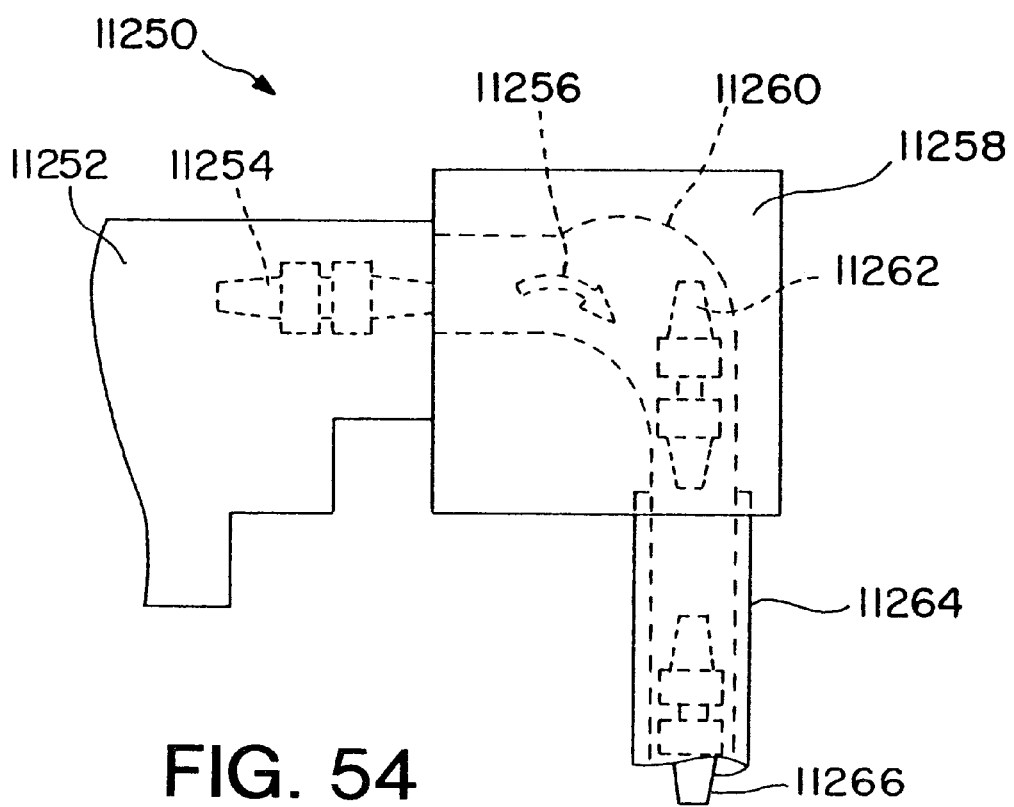
FIG. 54 is a side view of another alternative embodiment of an orientator for use with the double-bodied microreactors.

Orientator 7014 of FIG. 45, and orientator 7722 of FIG. 50 provide alternative embodiments of a structure for assisting in the proper alignment and orientation of matrices-with-memories, such as microvessels or microreactors. Another embodiment of an orientator is shown in FIGS. 53 and 54. The embodiments of FIGS. 53 and 54 are interchangeable so that the automated sorting device may be used for virtually any embodiment of matrix-with-memory.

Referring to FIG. 53, orientator 11206 is shown attached to a vibratory feeder 11202 which causes a single-bodied microreactor 11204 to advance in direction 11208 from feeder 11202 to orientator 11206. Orientator 11206 orientates microreactor 11204 in a vertical orientation using a principle similar to that described with reference to the embodiment of FIG. 45. A channel within orientator 11206 is divided into an upper area 11207 and a lower area 11205 by ridges 11203 which extend into the channel. (Although only one ridge 11203 can be seen as illustrated, two ridges are actually provided, with one on either side of the channel.) Ridges 11203 are spaced apart at a distance smaller than the diameter of the top portion of microreactor 11204. As microreactor 11204 progresses through the channel its top portion is pushed against ridges 11203 which prevent the top portion of microreactor from proceeding unless it aligns itself to pass through the larger spacing of the upper area 11207. Lower area 11205 has a smaller spacing that will allow only the smaller diameter lower portion of microreactor 11204 to pass. Once the microreactor reaches position 11212, it drops downward in direction 11218 into feeder tube 11214, as shown by microreactor 11216.

As illustrated in FIG. 54, in an alternative embodiment, orientator 11258 is used for vertically orienting a microreactor which has end-to-end symmetry and, thus, does not require any particular side to be up or down. Here, the example of a double-bodied microreactor is used. As microreactor 11256 advances from vibratory feeder 11252, it rotates in direction 11256 within enlarged curved spacing 11264. The reduction of the opening size at the lower portion of the curved spacing 11264 forces the microreactor to orient itself vertically, as indicated by microreactor 11262. Using gravity, the microreactor then proceeds into feeder tube 11264, as shown by microreactor 11266. Generally, orientator 11258 can be used for a variety of matrices-with-memories, such as double-bodied microreactors, and any other embodiment, particularly those that do not require a particular orientation other than a vertical orientation.

(b) Feeder hopper embodiments

Figure 52:
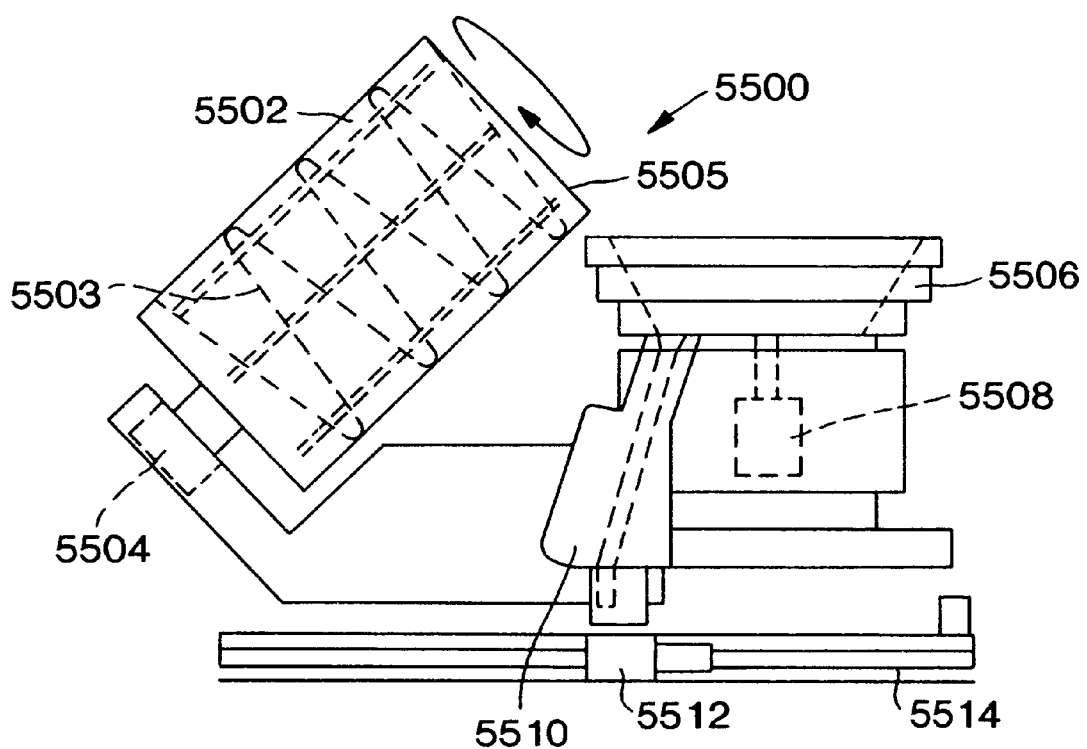
FIG. 52 is a diagrammatic view of a rotating feeder for use in an automated sorting device.

In addition to the vibratory feeders 7012, 7602, and 7720 of FIGS. 44, 49 and 50, respectively, an alternative rotating feeder may be used, as illustrated in FIG. 52. In sorter assembly 5500, rotating feeder 5502 comprises a substantially cylindrical bowl which has a helical ramp 5503 running from the bottom of the bowl to the top, operating much like a cement-mixer. As the bowl is rotated by drive motor 5504, microreactors or other similar devices are walked up ramp 5503 until they are pushed over top edge 5505. The microreactors then fall into tapered bowl 5506 which is attached to rotating drive motor 5508. Alternatively, bowl 5506 can be stationary, and ramps can be provided leading to the entrance to singulator 5510. Bowl 5506 has at least one opening in its bottom which aligns with the entrance opening to singulator 5510 at a point in the rotation of bowl 5506. Operation of singulator 5510 is the same as other singulators described herein, so that the microreactor is dropped into positioning block 5512 and translated on X-Y translator 5514 to the appropriate container within the sorter tray.

(4) A fourth embodiment

In a fourth embodiment, movement of matrices-with-memories, including OMDs, microreactors or microvessels, which are encoded with optical bar codes or other optical memories can be achieved by one or more sets of conveyor belts, chutes or guide rollers, each of which can be fed by a commercial-type centrifugal feeder, such as those available from Hoppmann Corporation of Chantilly, Va. and Kirchlintein, Germany. Feeders of this type are known in industry for mass handling of parts and products, including foods, pharmaceuticals, containers and hardware. Linear and vibratory feeders are also known and may be used for handling the microreactor. An exemplary handling system is illustrated in FIG. 55 and will be discussed in more detail below.

Figure 55:
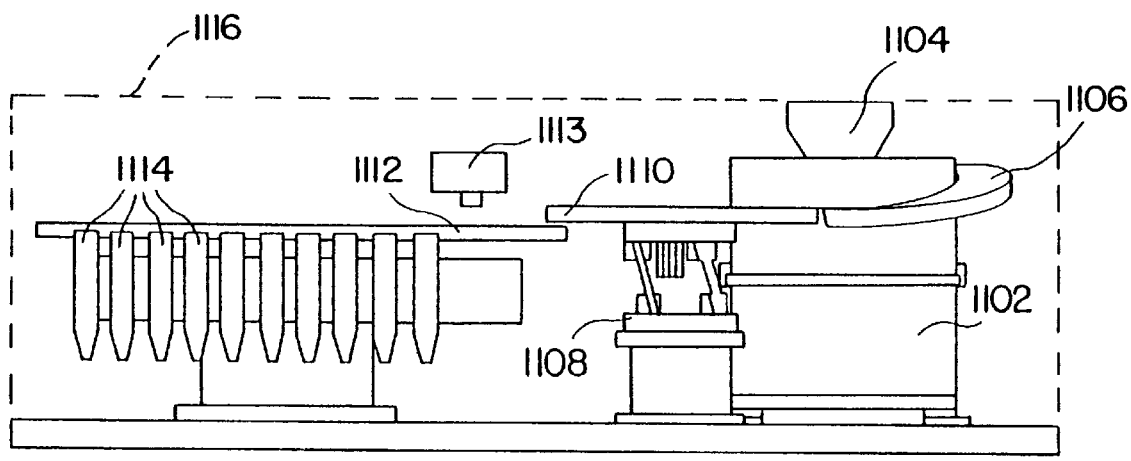
FIG. 55 is a diagrammatic view of an alternative embodiment of an automated sorter for use with optically-readable microreactors.

FIG. 55 provides a diagram of an exemplary handling system for separating and reading and/or writing to a microreactor, particularly those in the shape of a parallelopiped. Such handlers, such as vibratory feeders, are commercially available [e.g., from Hoppmann Corporation, Chantilly, Va., see, U.S. Pat. Nos. 5,333,716, 5,236,077, 5,145,051, 4,848,559 4,828,100, 4,821,920, 4,723,661 and 4,305,496]. The microreactors are placed in vibratory feeder 1102 by way of supply hopper 1104. Vibratory feeder 1102 includes rings and ramps [not shown] which support the microreactors as they move within the feeder, driven by the feeder's vibration in a direction toward exit chute 1106. An orientation rim, bar, or other feature [not shown] may be included in the internal ramps or exit chute to rotate the microreactors when a physical orientation indicator, such as the cut corner OMD of FIG. 29, is provided. Exit chute 1106 feeds the OMDs to ramp 1110 of linear feeder 1108. The reciprocating motion of the ramp 1110 causes the microreactor to move forward [to the left in the figure] toward walking beam 1112 and within the field of view of camera 1114. [Where a write operation is to be performed, the write laser and optics can be positioned in place of or nearby the camera.] Movement of the walking beam 1112 is stepped so as to pause advance motion of the microreactor to allow writing and/or reading of the appropriate information.

After completion of the writing or reading step, the microreactor is advanced along the walking beam 1112 toward one or more vials or flasks 1114 containing chemical or biological solutions. Ramps [not shown] leading from the walking beam to the vials or flasks 1114 can be selected by opening gates, or by tilting the walking beam 1112 in front of the selected vial, thus feeding the microreactor into the desired vial for the next process step. The vials or flasks 1114 can be fixed within a tray or rack that allows it to be removed after the processing has finished so that the microreactors can be dumped into the hopper of the same or another feeder to repeat the above steps for handling, writing, reading, and distributing the microreactors to the next process step.

It may be desirable to include a protective enclosure 1116, such as a polycarbonate and polyphenylene oxide resins, preferably the polycarbonate resin sold under the name LEXAN™ [the well known polycarbonate resin commercially available from General Electric Corp, Waterford, N.Y., or MERLON™ made by Mobey Chemical Co., Pittsburg, Pa.] or the resin sold under the tradename NORYL [from General Electric Corp] other such polymer such as polyethylene, lucite, bakelite and other such resins that have high tensile and impact strength over a broad temperature range, are virtually shatter-proof and are extrudable as transparent sheets, over the handling system to prevent contamination of the OMDs and solutions as well as for the safety of the system operator.

(5) A fifth embodiment

Figure 57:
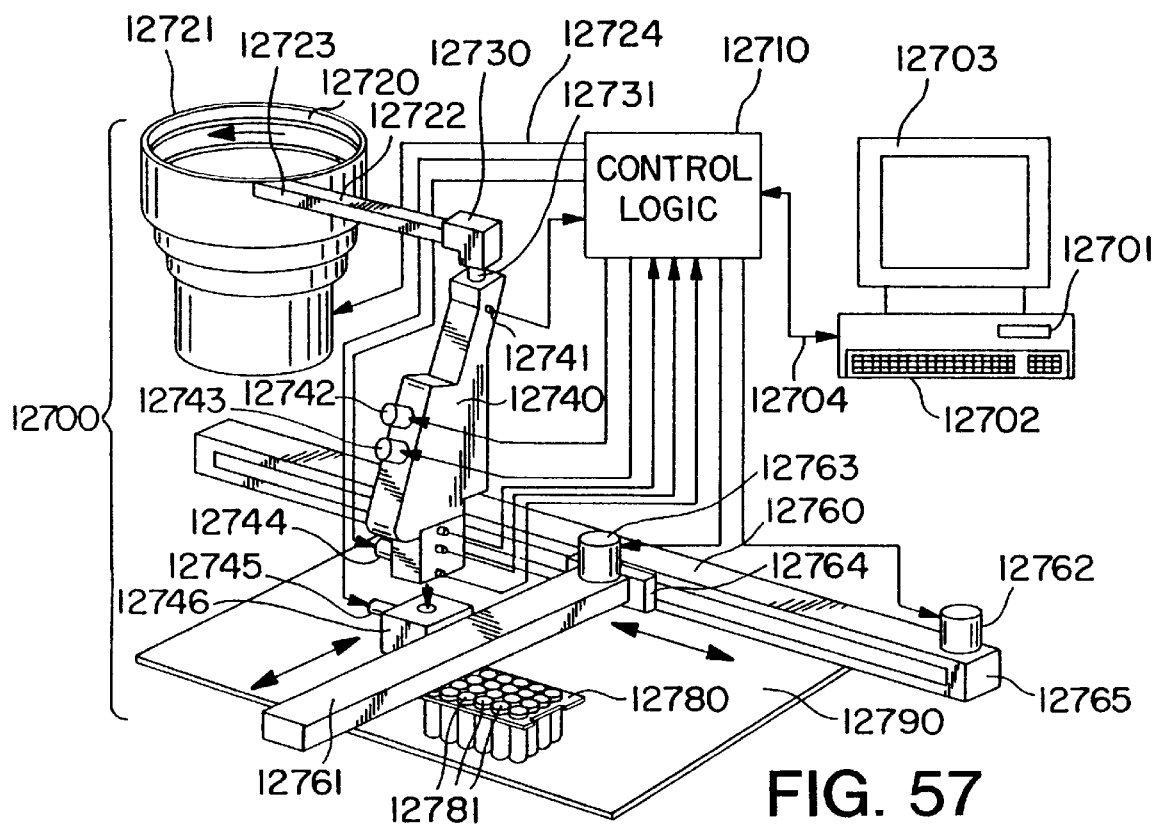
FIG. 57 is a schematic view of a fifth embodiment of the automated sorting system.

A fifth embodiment of the automated sorting system 12700 is illustrated in FIG. 57. As in the previous embodiments of automated sorters, the basic components of the system 12700 are a host controller 12701 which interacts with control logic 12710, a feeder 12720, an orientator 12730, a metering device 12740, an X-Y translation system 12760, and a container tray 12780. As previously noted, feeder 12720 may be either a vibratory feeder or a rotating feeder. Container tray 12780 may be supported by a frame, as in previously-described sorter embodiments, or may be placed on deck 12790, i.e., the bottom of the sorter.

Host controller 12701 is an IBM-type PC with processor such as a Pentium® (Intel Corporation) processor which has a speed of 100 MHZ or faster. The preferred PC is the Vectra Pentium® PC from Hewlitt-Packard Corporation. The PC should be equipped with 16 MB or higher RAM (random-access memory), a 1 GB or higher hard drive, a CD/ROM and/or disk drive, and should run on the Windows 95™ operating system from Microsoft Corporation. User interfaces include a mouse or similar pointer (not shown), a keyboard 12702, and parallel and serial ports, including two RS-232 high speed UART (universal asynchronous receiver/ transmitter) links 12704. Fixed communication parameters for the system include 9600 baud rate, eight bit words, no parity and no flow control. The user can select the COM port from COM1, COM2, COM3 and COM4, with COM1 being the factory default. Monitor 12703 provides means for displaying instructions and information to the user.

Figure 58:
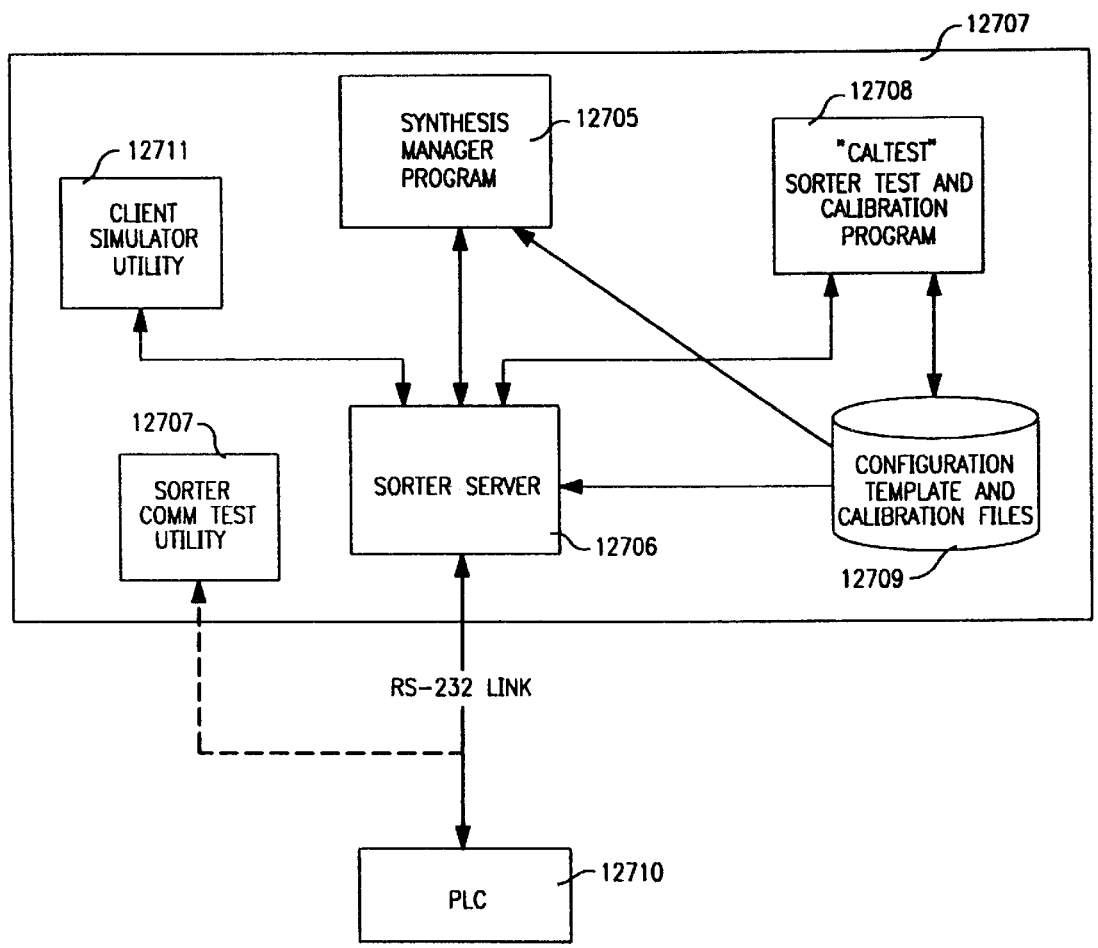
FIG. 58 is a block diagram of the software architecture for the automated sorter system.

The basic architecture for the software that is run in host controller 12701 is illustrated in FIG. 58. The source code for the following programs is filed herewith as Appendices I–III. The SYNTHESIS MANAGER™ program 12705, which has been described herein, reads the sorter files and uses the information to present sorting options to the user, and facilitates the overall synthesis and cleavage processes. The analytical operations performed and the graphical displays provided by the SYNTHESIS MANAGER™ software in the present automated sorting system are the same as those used in the other sorting systems, both manual and automated, see, e.g., FIGS. 30–33 and the description therefor. The primary difference is that interface capabilities are provided for allowing interaction between the SYNTHESIS MANAGER™ (Appendix I) software and operation and control of the sorter.

Sorter server 12706, using the combined source code listed in Appendix II ("Sorter Server") and Appendix III (Sorter operation code ("Sorter.ocx"), designated sorter support) provides communication services to and from the sorter, sending commands, including operational commands and status inquiries, to logic controller 12710 and communications with the SYNTHESIS MANAGER™ program 12705. Sorter server 12706 operates on a separate thread from applications software so that it can operate independently, without being interrupted by input or other operations within an application.

Figure 56:
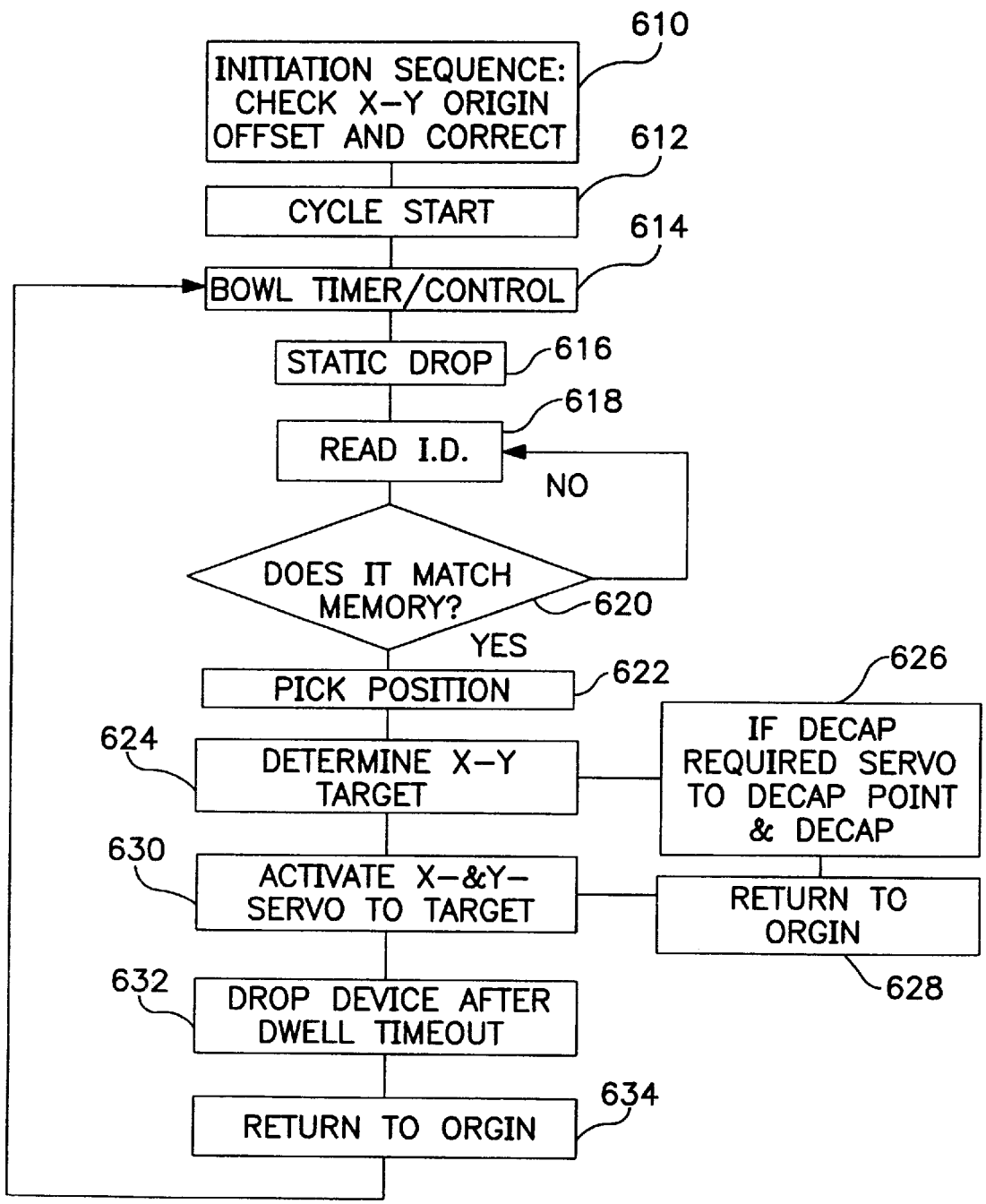
FIG. 56 is a flow diagram of the automated sorter operation.

FIG. 56 provides a flow chart of the operation of the softer software as controlled by PLC 12710 for one step in a loading sequence. In step 610 the process is initiated by turning in the sorter, at which time the sorter automatically checks the X- and Y-axis origins and offsets and provides corrections if needed. In step 612, the microreactors are loaded into the feeder bowl and the cycle is started. The PLC provides timing and control signals to the feeder bowl in step 614, causing the feeder to begin feeding the microreactors out of the bowl and toward the singulator. Step 616 covers the travel of the microreactor through the singulator under the force of gravity, with the various gating solenoids being activated to position the microreactor within the singulator. The microreactor is stopped in close proximity to the RF reader and the reading operation is performed to identify the particular microreactor (step 618). The identification information is provided to the PC and compared to information stored in memory to find a match (step 620). If no match is found, the microreactor is re-read. If matched, the PC determines what the appropriate next step is (step 622) and provides information regarding the X-Y location within the container tray at which the microreactor is to be deposited (step 624), and the microreactor is dropped into the dynamic dropper. If decapping of the microreactor is to be performed, the X- and Y- servos are activated to move to the decap point (step 626) after which the dynamic dropper is returned to the origin (step 628). In step 630, the X- and Y- servos are activated to move the dynamic dropper to the correct X-Y target. The dynamic dropper dwell timer is permitted to run down (step 632), at which time the microreactor is released into the designated container. The X- and Y- servos then return the dynamic dropper back to the origin (step 634).

A sorter server specification is provided for defining areas of memory in PLC 12710 which are used for communication to and from the PC 12701, including handshaking involved in reporting the memory of a microreactor and providing the location of the container within the X-Y axis into which the microreactor is to be placed. The sorter server also defines settings for the X- and Y- position control units (PCUs) and provides information for initializing them. This information should be customized for each sorter individually, and the information is stored in PC 12701 and downloaded to PLC 12710. Other functions of the sorter server include reporting on whether the sorter is connected and operating, enabling and disabling operation, switching to single cycle operation, reporting identity and validity of a microreactor and receiving instructions on what type of sorting targets are to be used. The sorter server causes the PLC 12710 to poll at a predetermined period to perform status checks of the sorter.

Sorter Command Test Utility 12707 is a debugging tool which allows the user to enter the command portion of Host-Link command strings, send it to logic controller 12710, then view the response from the logic controller 12710. Sorter test and calibration (CalTest) program 12708 is used for set-up and alignment of the sorter. The various configuration and calibration files are created, viewed and edited using program 12708. Access to the CalTest program 12708 is preferably controlled using a multi-tier password, limiting access to only those personnel who are sufficiently trained for making changes to the calibrated parameters. Configuration, template and calibration test files 12709 are created, edited and/or read using the CalTest program 12708. Configuration files, which are created, edited and viewed using the CalTest program, contain deck/X-Y arm calibration data as well as calibration data for any other deck-based features such as the reject and recycle bins. A separate configuration file is created for each sorter in set-ups where a host controller is used for controlling a network of sorting systems. The configuration file will include the identity of the specific sorter for which is was created.

Template files serve as templates for defining allowable sort target arrangements. Target arrangements will include variables of organization, size, and spacing for a plurality of containers, and can include sorting patterns for using less than a full tray or other array of containers. One template file will be created for each possible arrangement variation, however, in most cases, only a few template files will be required. Template files may be read, but are not modified, by the CalTest program 12708.

Calibration files are created by the template files and the configuration files in the course of calibrating the frames, carriers and other features of the sorter. The calibration files provide a translation from a template file location to a corresponding X-Y location for a selected sorting arrangement, thus mapping the features defined in the template file to the X-Y locations. Calibration files provide basic calibration and calibration verification for items including: the deck, deck features (recycle bin, reject bin, handoff point, decap points), frame and frame carriers, and bins. The user interface allows the user to select a target and command the X-,Y-translator to move to that target simply by moving a mouse or other pointer and clicking on the target. Up, down, left and right arrows on a keyboard attached to PC 12701 can also be used to move the X-,Y- translator. Calibration files provide means for checking the accuracy of the sorter's homing function and displaying any deviation from "home".

An optional program, the Simulator Utility program 12711 allows the user to send simulated commands to sorter server program 12706 and receive responses from it for testing the sorter server program 12706 and the sorter 12700. Simulator Utility program 12711 simulates a data base look-up of a data for a memory device and may include a user-settable delay to simulate the data base look up time.

Logic controller 12710 is generated by a PLC (programmable logic controller) and provides local control over all motion and functions of the sorter 12700. Logic controller 12710 operates as a slave to host controller 12701, responding only to received commands, and does not initiate transmissions. As in previous embodiments, the PLC is programmable in relay ladder logic using a personal computer with a ladder support software package, and is available from Omron Electronics, Inc. of Schaumburg, Ill. Communication between the host controller 12701 and logic controller 12710 is provided by RS-232 link 12704 using the serial communication protocol described in the Omron Sysmac C-Series Rack PC's Host Link Units System Manual, Catalog No. W143-E3-1. All interfacing between the PLC and the sorter system is transacted through the RS-232 port. The serial port parameters include a baud rate of 19,200, word length of seven bits, two stop bits and odd parity. The PLC 12710 contains battery backed-up memory, which is organized as 16 bit words. Special areas of data memory that are specifically designated for interfacing to the sorter including data regarding communications between the PC 12701 and PLC 12710, and the X- and Y- axis positioning control data.

PLC 12710 is permitted to query the state of the sorter. Information the is provided describes current conditions such as whether a motor is on, detection of microreactors by the sensors, whether a system door is open, or if a fuse has blown. PLC 12710 receives data from the RF tag scanner, validates its, then stores it in memory which PC 12701 may read. An indication of the validity of the tag data is generated.

PC 12701 may write data to the system memory as a means of specifying the location to which the sorter's X-Y arms should move. PC 12701 can also set a certain memory location to inform PLC 12710 that the X-,Y-coordinate registers contain valid data and it is okay to proceed with placing the current microreactor at that location. PC 12701 may contain memory locations to directly manipulate solenoids and other devices which may normally be under autonomous control of PLC 12710. This allows PC 12701 to perform special functions such as calibration, testing, and troubleshooting. PC 12701 may also have special memory locations designated for selectable options which can be enabled and disabled. Such options include decapping of the microreactors or microvessels. A single cycle command is provided in the event the user wishes to stop the sorting process after each microreactor is sorted.

Referring again to FIG. 57, as in the previous embodiments, vibratory feeder 12720 is used to feed the memory devices for reading and sorting. Briefly, feeder 12720 is a conventional vibratory bowl feeder which has a helical track 12721 climbing the inside wall of bowl 12722, generally in a counterclockwise direction. By applying a circular vibratory motion to bowl 12722, the memory devices that are dumped into bowl 12722 will climb helical track 12721 in single file. Feeder 12720 is connected to and receive control commands from PLC 12710 via connector 12724.

Once the memory devices reach the top of bowl 12722 they proceed through feed channel 12723 to orientator 12730. Depending on the configuration of the memory devices, e.g., single- or double-bodied microreactors, orientator 12730 may be one of the embodiments shown in and described with reference to FIGS. 53 and 54. After the memory devices are correctly oriented they fall through vertical channel or tube 12731 and into singulator 12740 for releasing the memory devices one-at-a-time for placement in the target containers.

Figure 59:
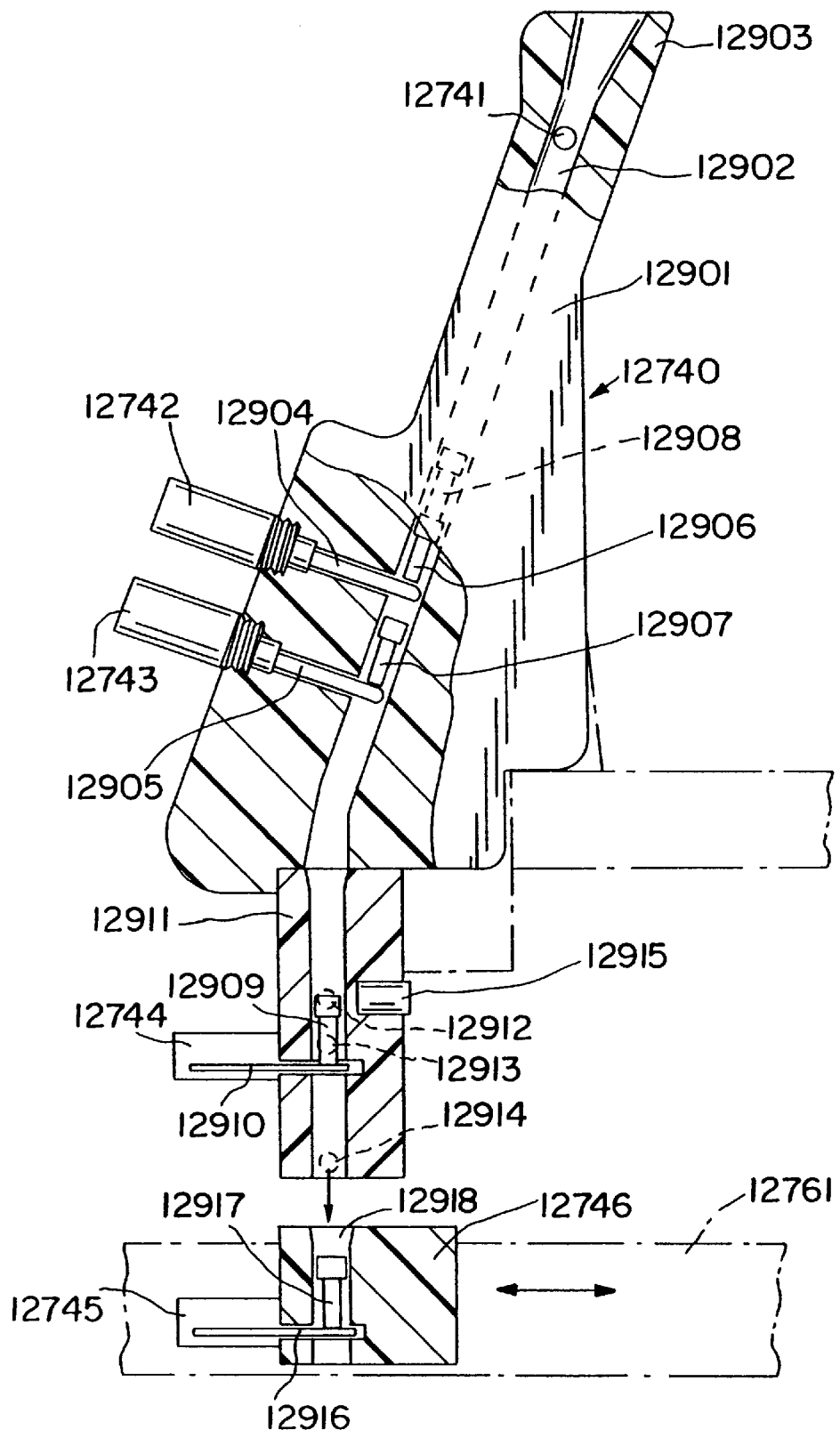
FIG. 59 is an enlarged side view, partially cut away, of the singulator for use in the automated sorting system shown in FIG. 57.

A detailed view of singulator 12740, which is mounted above and in a fixed relationship to X-axis arm 12765, is provided in FIG. 59. As shown, singulator 12740 comprises a body 12901 with a cylindrical bore 12902 running at a substantially vertical angle through the length of body 12901. Body 12901 is generally of solid construction except where bores are formed. In the exemplary embodiment, body 12901 is formed from one or more blocks of clear acrylic or Lucite material. Bore 12902 may be slightly flared at its entrance at upper end 12903 for mating with tube 12731 and to facilitate transition of the memory devices into the bore. The bore angle may be perpendicular to the surface on which the sorter is resting, or may be off-perpendicular by as much as 40°. An important consideration in selecting bore angle is that the force for advancement of the memory devices through bore 12902 is provided solely by gravity, therefore, the bore angle must be steep enough to allow gravity to overcome at least part of the friction or other possible adhesion forces between the inner walls of bore 12902 and the memory device. The bore angle must also be shallow enough to slow the progress of the memory devices to permit gating using solenoids 12742 and 12743, as described below. As illustrated, the bore angle is on the order of 25° to 30° from vertical.

At the upper end of body 12901 is sensor 12741 for monitoring the contents of bore 12902. If the memory devices becomes backed-up in bore 12902, sensor 12741 provides a signal to PLC 12710 which may then trigger a signal to pause operation of feeder 12720 until the bottleneck at the singulator is cleared to prevent jamming that may be caused by too many memory devices being fed into channel 12722 or orientator 12730. Sensor 12741 may be an optical sensor which detects changes in light reflection or transmission caused when a memory device dwells in front of sensor 12741 for a relatively extended period of time, indicating that the memory devices has stopped moving. Sensor 12741 may also be used to generate a signal every time a memory device passes it, allowing calculation of the feed rate.

Singulation, i.e., the controlled intermittent release of individual memory devices, is effected using gating solenoids 12742 and 12743 which are mounted on body 12901 so that pistons 12904 and 12905, which are driven by the two gating solenoids, project perpendicular to and at least partially into bore 12902. First gating solenoid 12742 and its corresponding piston 12904 are activated by a signal from PLC 12710 to halt memory devices as they are stacked one on top of the other within bore 12902. As shown, memory devices 12906 and 12908 are stopped above piston 12904. First gating solenoid 12742 is then quickly opened and closed to allow one memory device 12907 to pass, where it is trapped by piston 12905, driven by second gating solenoid 12743, activated by a signal from PLC 12710. The rate of opening and closing of second gating solenoid 12743 is governed by the amount of time required to read the memory devices to determine its identity and any other information pertinent to the sorting procedure. Due to the amount of heat that can be generated by the rapid and repeated activation of the two gating solenoids 12742 and 12743, it may be desirable to provide a heat sink or other cooling means to prevent the solenoids from burning out. Although not shown, in the preferred embodiment, metal radiating fins are placed in thermal communication with the two solenoids. Implementation of such heat sinks are within the level of skill in the art.

Following its release by second gating solenoid 12743, memory device 12909 is halted within the bore in the lower end 12911 of body 12901 by third gating solenoid 12744 and retractable gate 12910. Position sensors 12912 and 12913 monitoring the bore above gate 12910 to detect the presence of memory device 12909. First position sensor 12912 provides a signal to PLC 12710 to trigger the activation of a reading device 12915 which queries memory device 12909 to determine its identity and obtain any other pertinent information. In the exemplary embodiment, reading device 12915 is an RF antenna connected to an RF reader (not shown) which provides input to host computer 12701. Examples of such systems are described above. Other types of readers, including optical readers are also described above and may be utilized in the present embodiment with appropriate adaptations. Second position sensor 12913 provides a signal to PLC 12710 confirming the presence of memory device 12909 at the reading position. Once the reading operation is complete, host computer 12701 provides a signal to PLC 12710 which, in turn, causes solenoid 12744 to be activated, opening gate 12910, dropping the memory device past third position sensor 12914 to generate a signal to PLC 12710 to confirm release of the device.

After exiting from lower portion 12911 of body 12901, memory device 12917, which has now been identified by the reader, drops into bore 12918 within loading block 12746. While the calibration and set-up procedures will provide for alignment of singulator 12740 and loading block 12746, any minor offset can be alleviated by providing a slight flare in the entrance to bore 12918. Fourth gating solenoid 12745 and retractable gate 12916 retain memory device 12917 within bore 12918 until it is properly positioned over the target container.

Referring again to FIG. 57, loading block 12746 is slidably mounted on arm 12761 of X-Y positioner 12760. After memory device 12917 has been received in bore 12918 and the host computer 12701 and its associated software for managing the synthesis process, e.g., the SYNTHESIS MANAGER software, have determined the desired target location for memory device 12917, X-Y positioner 12760 will move loading block 12746 into position over the target container.

As described with regard to other embodiments of the automated sorter, X-Y positioner 12760 comprises an X-axis arm 12765, X-axis high speed stepper motor 12762 mounted on arm 12765, Y-axis mounting plate 12764 slidably mounted on X-axis arm 12765 and connected to X-axis motor 12762 for translation along the X-axis, and Y-axis arm 12761 attached to Y-axis mounting plate 12764. Loading block 12746 is movable along Y-axis arm 12761 and is driven by high speed Y-axis motor 12763. Movement of loading block 12746 is guided by X-Y position sensors, as previously described, the SYNTHESIS MANAGER software, the sorter server, and the calibration files to identify the exact target position.

As illustrated in FIG. 57, and as described with reference to other embodiments of the automated sorter, the containers 12781 into which the memory devices are to be placed are microreactor carriers. The carriers 12781 are retained within microreactor carrier tray 12780 which is supported on a tray frame (not shown). Only one carrier tray 12780 is illustrated in the figure for simplicity, however, configurations of multiple carrier trays 12780 may be used with an appropriate sorting template.

Once the position of the target microreactor carrier 12781 is determined, loading block 12746 is moved to the specified position and, after confirming the position, PLC 12710 sends a release signal to fourth gating solenoid 12745, causing gate 12916 to open, dropping memory device 12917 into the target microreactor carrier 12781. After placement of every memory device in its target microreactor carrier, loading block 12746 returns to its starting position below singulator 12740 to receive the next microreactor carrier.

B. Automated Cleaver (1) A first embodiment

Figure 68:
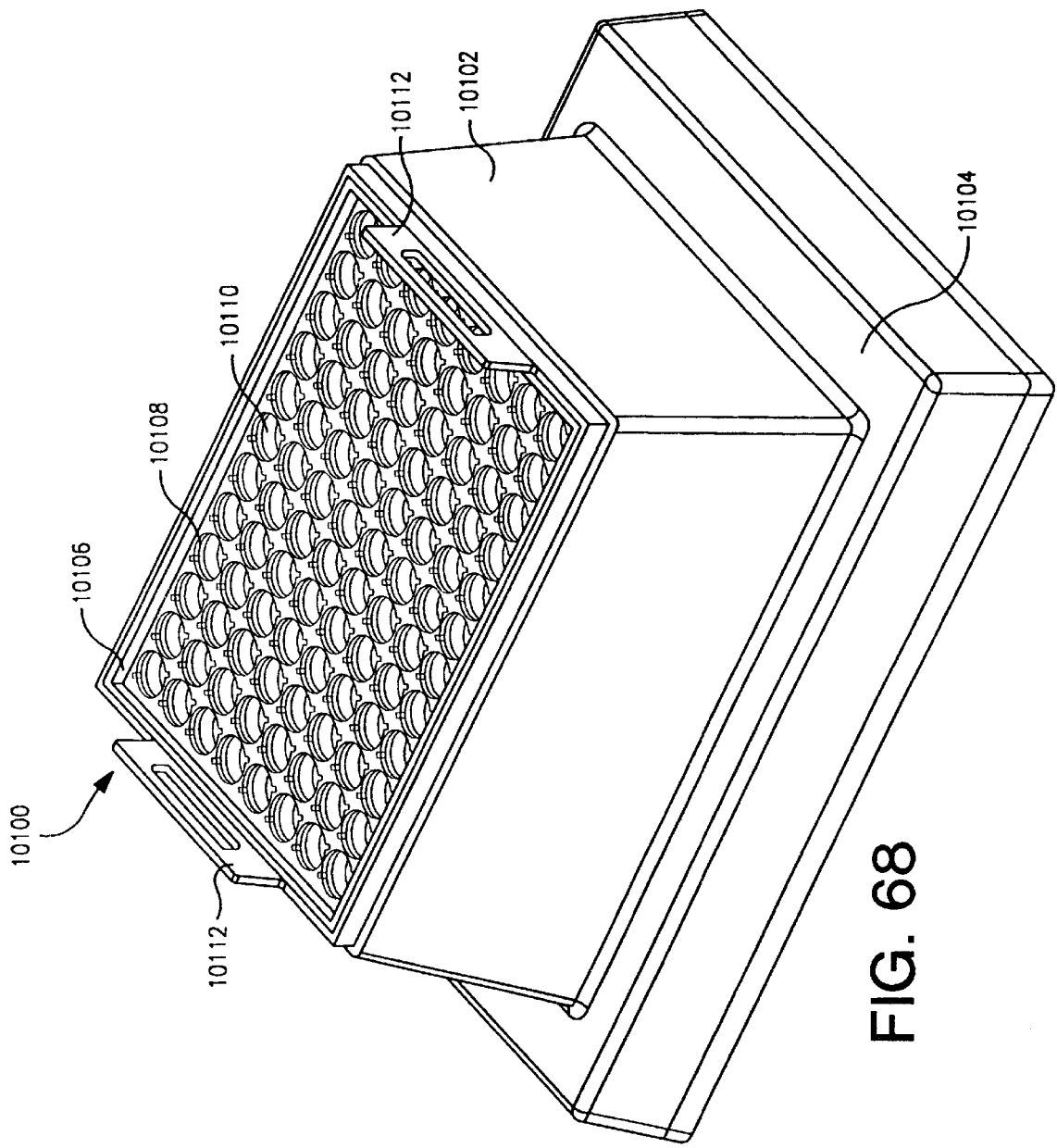
FIG. 68 is a perspective view of a first embodiment of an automated cleaving station.

FIG. 68 illustrates a first exemplary automated cleaving station 10100. Automated cleaving station 10100 includes a cleaving block 10102 mounted to a base 10104. A tray 10106 is attached to the top of the cleaving block 10102 and is formed with an array of holes 10108, with each hole being loaded with a disposable microreactor carrier 10110. Optional handles 10112 are provided for tray 10106 in order to easily raise and lower the tray from the cleaving block, as described in conjunction with the manual cleaving station shown in FIGS. 40–43, and to remove the microreactor carriers from the station 10100.

Figure 69:
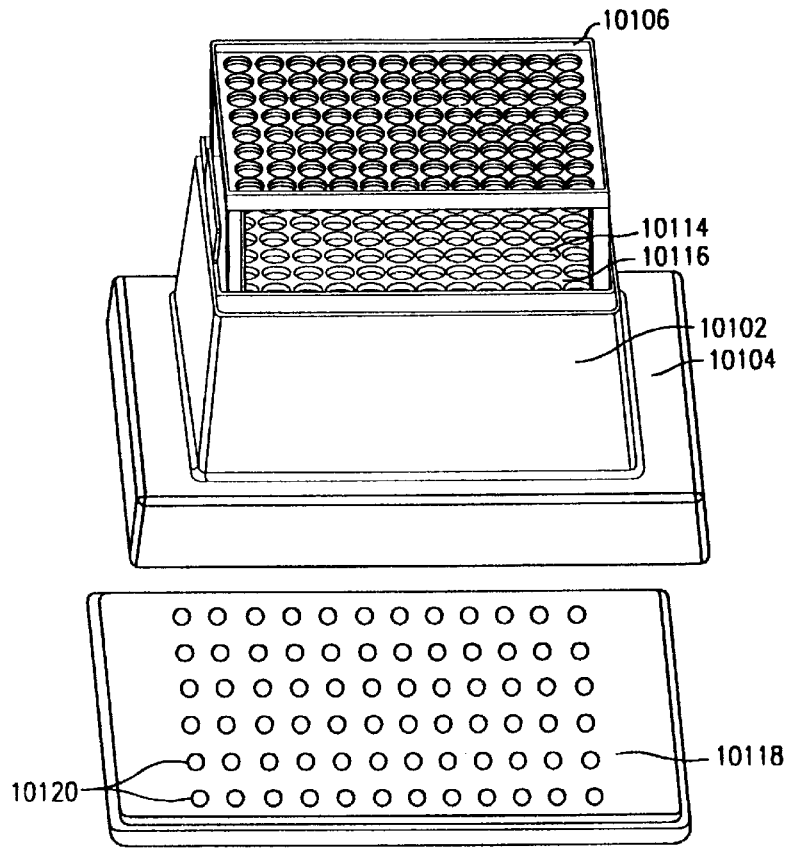
FIG. 69 is a perspective view of the automated cleaving station of FIG. 68 with the top plate raised, and the nozzle array interface plate separated from the cleaving block.

FIG. 69 shows the automated cleaving station 10100 in an exploded format detailing the movement of tray 10106 from the cleaving block 10102, and the interaction of the nozzle array interface plate 10118 to the base 10104. As shown, the nozzle array interface plate 10118 is attached to the base 10104 such that the outlets from each of the bores 10116 may be routed to the plate 10118 to accommodate a variety of patterns, as will be discussed in more detail in conjunction with FIGS. 72 and 73.

Figure 70:
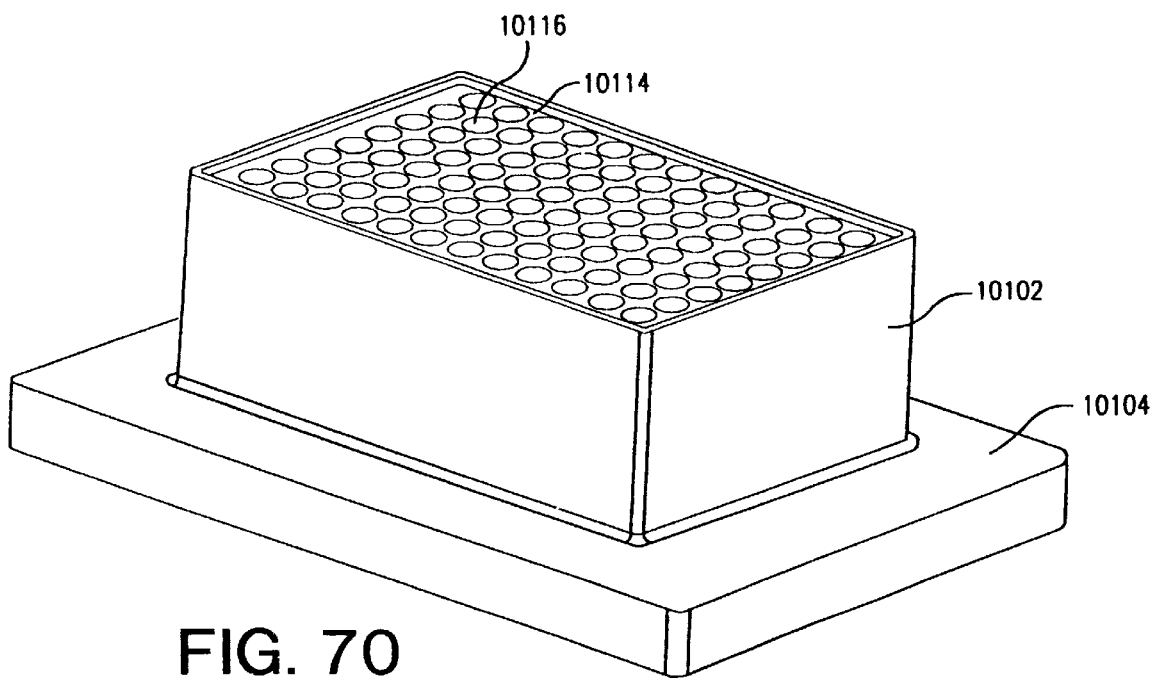
FIG. 70 is a perspective view of the cleaving block of the automated cleaving station of FIG. 68.
Figure 71:
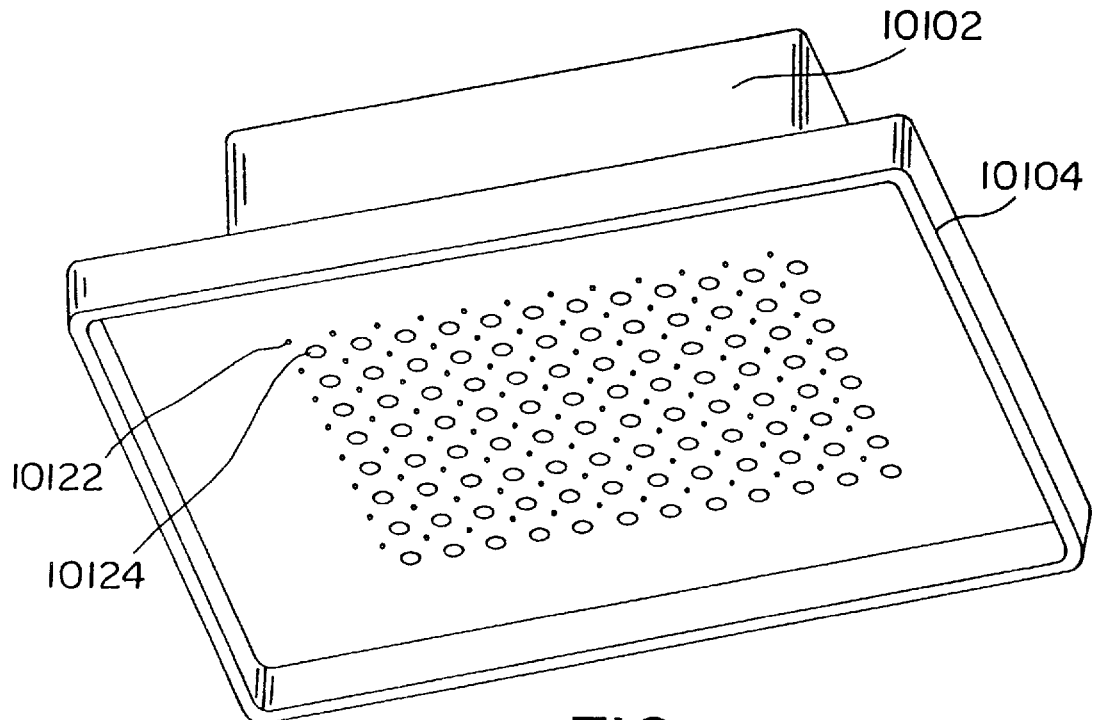
FIG. 71 is a perspective view of the bottom surface of the cleaving block of the automated cleaving station of FIG. 68 showing the exits from the cylinders and the U-tube insertion bores.

FIG. 70 illustrates the cleaving block 10102 with the tray 10106 removed from upper surface 10114. Cleaving block 10102 is formed with an array of ninety-six bores 10116 which are sized only slightly larger than disposable microreactor carriers 10110. Note that the ninety-six bore configuration is exemplary only, and any number of bores may be formed in the cleaving block to corresponding to standard or custom microtiter formats. FIG. 71 provides a view of the bottom side of base 10104 showing an array of drains 10122, and a corresponding array of tube bores 10124 which are formed in the cleaving block 10102. From this view it can be appreciated that the drain 10122 is axially aligned with the bore 10116, and that the tube bores 10124 are formed within the interstitial space between the bores 10116.

Figure 72:
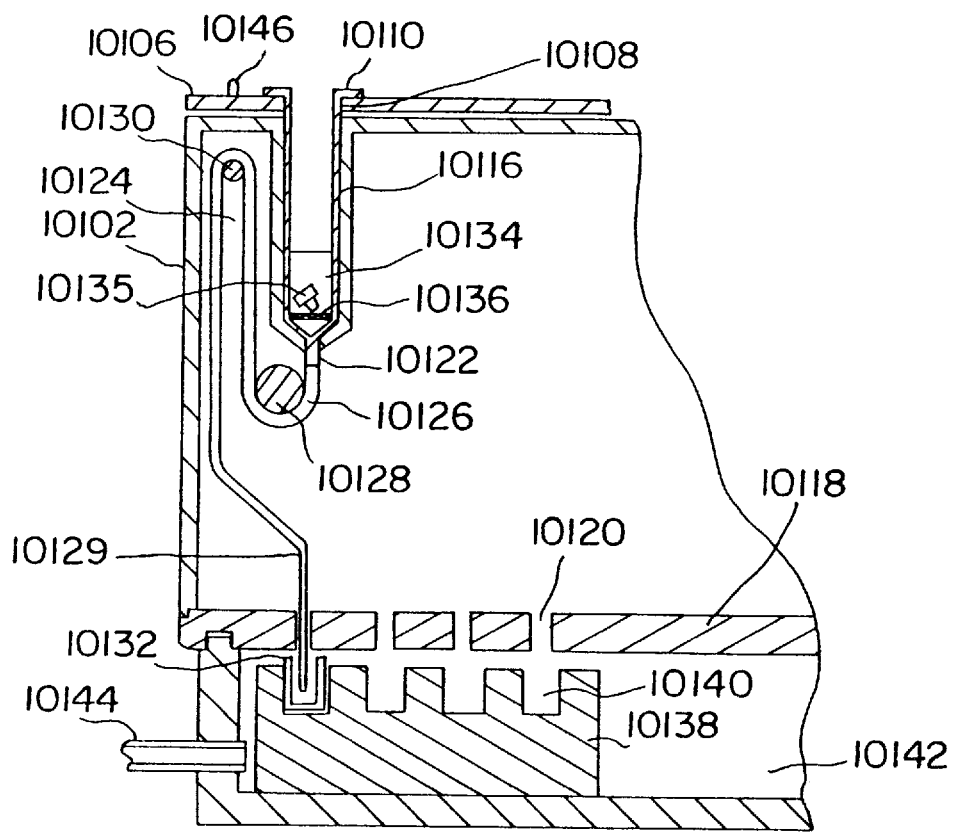
FIG. 72 is a cross-sectional view of an alternative embodiment of the automated cleaving station showing a U-tube which is routed over a pair of retaining pins to the nozzle array interface plate.

The internal construction of automated cleaving station 10100 is shown in FIG. 72. Cleaving block 10102 is formed with bores 10116 which are sized to receive microreactor carrier 10110 that is resting in hole 10108 in tray 10106. To assist in correct positioning of tray 10106 on cleaving block 10102, alignment pin 10146 is provided for mating with an alignment hole in the tray (not shown). As in the cleaver embodiment of FIG. 43, microreactor carrier 10100 includes a filter or frit 10136 at its lower end to prevent particles from microreactor 10135 from exiting through the opening in the lower end and passing into the cleaved solution.

Bore 10116 has drain 10122 which leads to U-tube 10126 which is routed in such a way as to form a trap. As illustrated, U-tube 10126 extends downward from the drain 10122 then around pin 10128, turning upward and then around pin 10130 at which point it leads to pigtail. Because the location of pin 10130 is substantially the same height of bore 10116, any fluid 10134 which is in the microreactor carrier and/or bore will be prevented from inadvertently escaping from the cleaving block. Typically, the U-tube is made of a TEFLON™ (PTFE) tubing which has an outer diameter of approximately 1–3 mm, preferably about 2 mm. The small diameter of the U-tube 10126 allows it to be easily routed to any number of locations underneath the cleaving block 10102.

Figure 74:
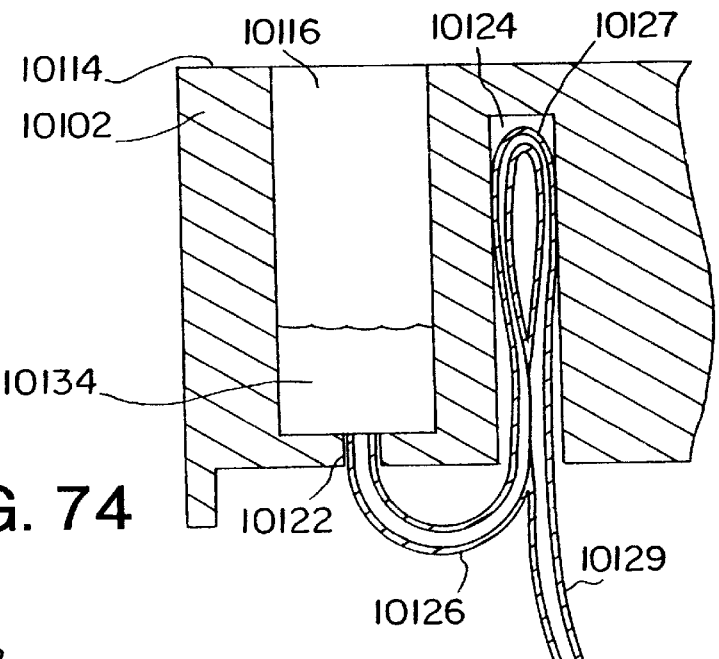
FIG. 74 is a detail view of an alternative embodiment of the automated cleaving station showing the placement of the U-tube within the cleaving block.

Referring back to FIG. 71 for an alternative to pins 10128 and 10130, bores 10124 are formed in the cleaving block 10102 and are sized to have an approximate diameter of 6 mm, which allows U-tube 10126 to be folded over and inserted into bore 10124. Because the diameter of hole 10124 is greater than twice the diameter of U-tube 10126, the sidewalls of U-tube 10126 will not be pinched together to restrict the flow of fluid through the U-tube. For example, as shown in FIG. 74, cleaving block 10102 is shown with bore 10116 having drain 10122 at its bottom. U-tube 10126 is attached to drain 10122, bent upon itself, then inserted into bore 10124 to form a trap. Bend 10127 has a smooth curvature as inserted into bore 10124 and does not experience any pinching or other restriction of the inner volume of the U-tube.

Regardless of whether pins 10128 and 10130 of FIG. 72, or bores 10124 of FIGS. 71 and 74 are used, following formation of the trap with U-tube 10126, pigtail 10129 is routed to port 10120 in the nozzle array interface plate 10118 shown in FIG. 69. The nozzle array interface plate 10118 is formed with an array of ports 10120 such that different routing options may be accommodated. For example, the routing from bores 10116 to interface plate 10118 may be such as to permit mapping to any of the standard microtiter plate footprints (3×4, 4×6, 6×8, or 8×12) or any other configuration of wells. Alternatively, the routing may be a format to accommodate a standard vial rack, or may be a custom routing. The flexibility of U-tube 10126, and the length of pigtail 10129 allow virtually any routing configuration to be created.

Referring again to FIG. 72, cleaving block 10102 is shown with its U-tube 10126 routed to a position on nozzle array interface plate 10118. Cleaving block 10102 and nozzle array interface 10118 are positioned over a vacuum chamber 10142. Seal 10131 establishes an airtight seal between the interface plate and vacuum chamber to prevent the entry of air into the vacuum chamber from anywhere but U-tubes 10126. Pigtail 10129 extends through interface plate 10118 for alignment with vessel 10132 in desired collection rack 10138. While it is not necessary to include a vessel 10132 in addition to wells 10140, both are shown as an example. Different types of containers can be utilized in a similar manner by positioning them within vacuum chamber for alignment with the interface plate and protruding pigtail 10129.

Once cleaving block 10102 is in position over vacuum chamber 10142, a vacuum is created within that chamber by activating a conventional vacuum generating device (not shown) which attached to vacuum hose 10144. The vacuum which is created within vacuum chamber 10142, in turn, draws fluid 10134 from microreactor carrier 10110 and/or bore 10116 through drain 10122, through U-tube 10126, and out pigtail 10129 into vessel 10132. Thus, the fluid within bore 10116 and microreactor carrier 10110 can be drawn into the appropriate vessel without manual intervention other than activation of the vacuum source. While not shown in FIG. 72, fluid 10134 from any number of bores 10116 may be drawn into a multi-well container simultaneously, effectively providing for automated one step fluid transfer, for example, from a cleaving station to a microtiter plate.

The vacuum transfer from cleaving station 10100 to the subsequent processing platform, such as a collection rack eliminates the need for manual transfer of the fluid. The valveless automated cleaving station is capable of cleaving ninety-six or more compounds simultaneously, eliminating the tedious step-and-repeat process of cleaving with a pipet, or pipet-like device. The pigtails can be mapped to any location within the nozzle array interface plate, making it possible to accommodate standard microtiter plate formats or a custom array of containers.

The U-tube design includes no connectors which can corrode over time, and thus the durability and reliability of the automated cleaving station is enhanced. Since the entire process is vacuum driven, there is also no need for valves in the system, thereby improving the performance and life of an automated cleaving station. In addition to eliminating the risk of leakage, the absence of valves and connectors also greatly decreases the chance of contamination of one solution from another is minimal. Cleaning of the automated cleaving station is also simplified. The cleaning process comprises the steps of filling the bores 10116 with a cleaning solution and drawing the solution through the system using the vacuum chamber, providing a cleaving station which is effectively self-washing.

Vacuum chamber 10142 may be made from glass to provide the ability to visually verify that the cleaving process is completed, as well as to resist corrosion arising from exposure to harsh chemicals such as the cleaving agents. In addition to vacuum chamber 10632, the vacuum generator (not shown) may include a vacuum trap (cold trap) to eliminate the potentially destructive effect of the cleaving agent on the vacuum generator. Such cold traps are well known in the art.

(2) A second embodiment

An alternative embodiment of the automated cleaving station 10600 is illustrated in FIG. 73. Automated cleaving station 10600 functions in a similar manner to station 10100 using a slightly different structure. Station 10600 includes cleaving block 10602 formed with well 10604 sized to receive microreactor carrier 10606. As in the cleaver embodiment of FIG. 43, microreactor carrier 10606 includes a filter or frit 10640 at its lower end to prevent particles from microreactor 10638 from exiting through the opening in the lower end and passing into the cleaved solution. Microreactor carrier 10606 has a flange at its upper end with a diameter greater than the openings in top plate 10608. Microreactor carrier 10606 is retained in top plate 10608 by inserting it through the opening in top plate 10608 so that the flange abuts the top surface of top plate 10608. Top plate 10608 is disposed on supports 10610 on the upper surface of cleaving block 10602, with microreactor carrier 10606 is suspended within well 10604. Reservoir 10614 extends laterally below well 10604 and first vertical bore 10612 to provide means for fluid communication between them. First vertical bore 10612 extends upward from reservoir 10614 to horizontal channel 10618. Horizontal channel 10618 connects first vertical bore 10612 to second vertical bore 10616 which extends downward and through cleaving block 10602 to create an opening at the lower surface of cleaving block 10602.

U-tube 10620 is inserted into both first and second vertical bores 10612 and 10616, and through horizontal channel 10618 with one end of the U-tube positioned near the reservoir 10614, and the other end, pigtail 10621, extending out the bottom of cleaving block 10602 for routing to an appropriate port on nozzle array interface plate 10622. U-tube 10620 may be pre-formed in a U-shape, or may assume the shape of the combined vertical bores and horizontal channel once inserted. In order to ensure that the end of the U-tube within first vertical bore 10612 does not seal itself against the bottom of reservoir 10614 when a vacuum is drawn, a small notch or an angle cut can be formed at the end of U-tube 10620, such a shown in FIG. 76.

Ports 10624 on nozzle array interface plate 10622 may be tapered to facilitate insertion of 10621 through the plate. In addition, support flange or nipple 10626 may be attached to or formed integrally with the interface plate 10622.

The operation of automated cleaving station 10600 is similar to the operation of other embodiments of the automated cleaving station, as discussed above. Operation includes the use of vacuum chamber 10632 to draw solution 10636 from microreactor carrier 10606 and/or well 10604 into a suitably positioned container, such as collection rack 10628, or a well 10630. Integration of the U-tube guides, i.e., bores 10612,10616 and channel 10618, into cleaving block 10602, makes the manufacturing of this embodiment relatively easy as compared to the other embodiments. For example, the cleaving block can be formed by injection molding. Well 10604, first vertical bore 10612, upper connecting channel 10618, and second vertical bore 10616 may be formed in a single injection molding step. Reservoir 10614 may also be formed during the injection molding process, or by an end-mill machining process following the injection molding. Once the U-tube guides have been formed, a pre-formed U-tube 10620 dropped into position within the bores. Pigtail 10621, which extends from the bottom surface of cleaving block 10602 is then mapped to the appropriate port on nozzle array interface adapter 10622. Because there are no pins through which the U-tube must be routed, or any bores into which the U-tube must be guided, the present embodiment can be more readily assembled, providing an advantage when large numbers of U-tubes are being used, such as in the case of nozzle array interface plate with ninety-six small diameter tubes.

In addition to the manufacturing advantages listed above, the automated cleaving station 10600 can utilize any available solution 10636 more efficiently. For example, instead of having drain 10122 which retains an amount of uncirculated solution, or "dead" solution, the automated cleaving station 10600 has reservoir 10614 which minimizes the uncirculated fluid. This is particularly important when attempting to cleave a microreactor 10638 with the least possible amount of solution.

(3) A third embodiment

Figure 75:
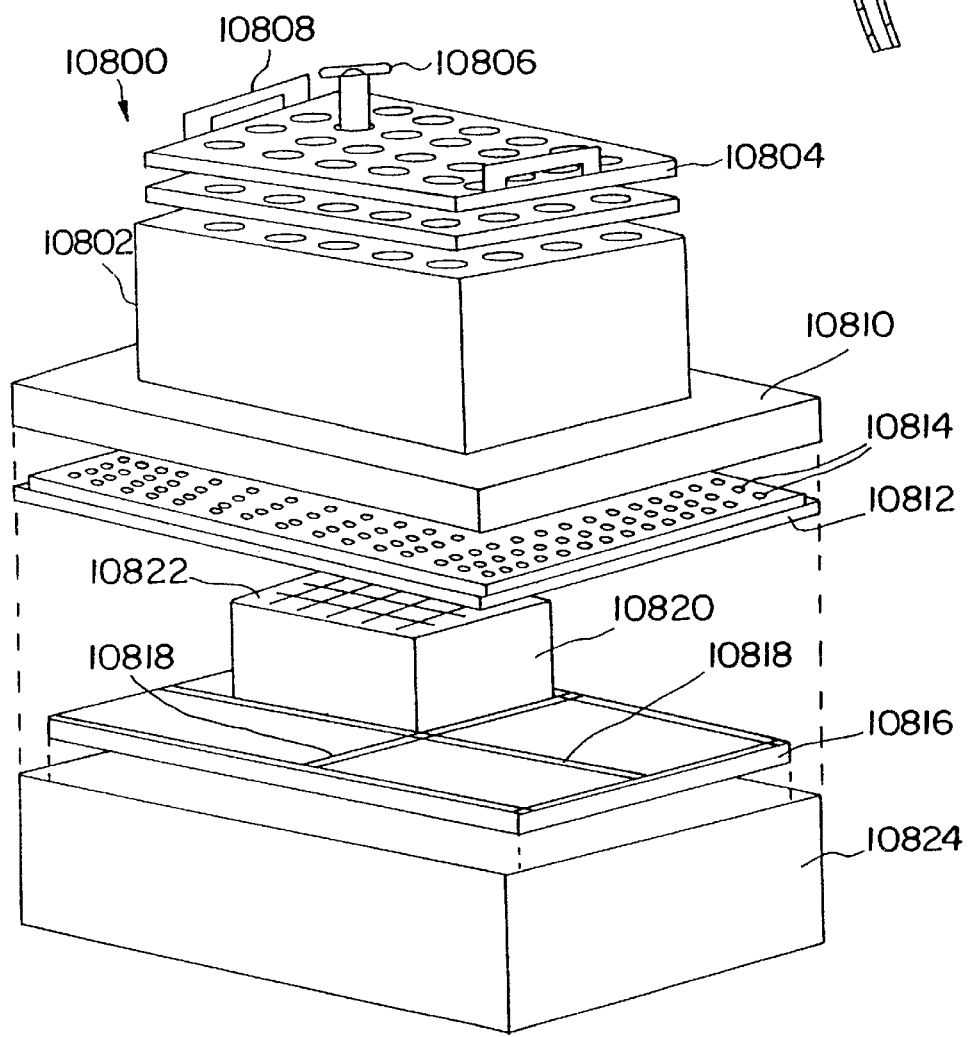
FIG. 75 is a perspective view of an alternative embodiment of the automated cleaving station shown in exploded format for clarity.

Referring now to FIG. 75, a third alternative embodiment of an automated cleaving station is shown. The cleaving station 10800 includes a cleaving block 10802 with a top plate 10804, or carrier trays, which are formed with an array of holes to receive microreactor carriers 10806. The top plate 10804 is equipped with handles 10808 to simplify the manual or robot-assisted movement and positioning of the tray on the cleaving block 10802. Cleaving block 10802 is attached to a base 10810 that fits together with a nozzle array interface plate 10812 having an array of ports 10814. The routing of the U-tubes for this embodiment is identical to the routing of the previously described embodiments, and will not be discussed again for this embodiment.

The automated cleaving station 10800 has a vacuum chamber 10824 which receives a collection rack locator plate 10816 which is formed with guide ridges 10818 which are sized to accept a variety of standard high-density collection racks, such as a 12, 24, 48, 96, and 384 microtiter plate. Collection rack locator plate 10816 can be customized for a particular application, or may be generic to a family of collection racks as shown.

The operation of the automated cleaving station 10800 includes placing the appropriate number of microreactor carriers 10806, or barrels, into carrier trays 10804, sorting the desired number of microreactors (not shown) into the appropriate microreactor carriers, place the carrier trays in onto cleaving block 10802, fill the wells with cleaving solvent, place any necessary upper and lower spill sheets onto station, cleave on a standard platform shaker for an appropriate period of time, draw a vacuum within the vacuum chamber to transfer the compounds to the collection rack of the proper format, such as a standard microtiter plate, or vial rack.

(4) A fourth embodiment

Figure 76:
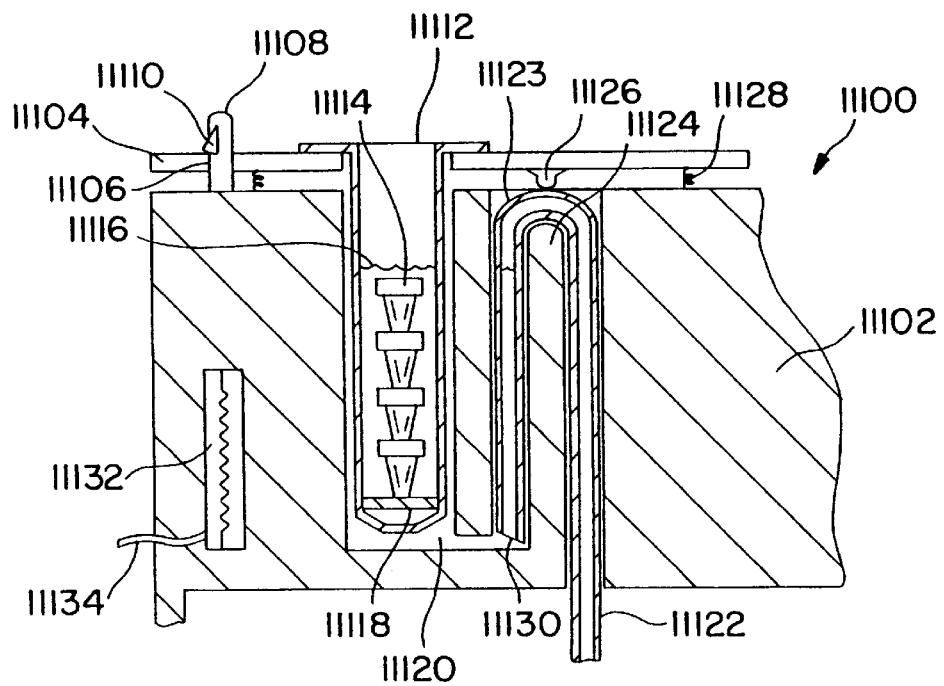
FIG. 76 is a cross-sectional view of an alterative embodiment of an automated cleaving station showing a U-tube having a valve assembly for use in inhibiting the flow of fluid through the U-tube, and a resistive heater for assisting in the maintenance of a particular temperature within the cleaving block.

Referring now to FIG. 76, an alternative embodiment of a cleaving block having a valve is shown and generally designated 11100. Cleaving block 11100 includes body 11102 formed with bores 11120 which are similar to those discussed in conjunction with FIG. 73. Microreactor carrier 11104 is formed with alignment holes 11106 to receive alignment and retaining pin 11108 to ensure the proper orientation and positioning of microreactors 11112. Moveable tab 11110 is formed on the upper portion of pin 11108 to allow for the positioning of the microreactor carrier tray 11104, and its associated microreactor carriers 11112 in a raised or lowered position. Each microreactor carrier 1112 may hold one or more microreactors, such as microreactors 11114 shown, and they may be immersed in a quantity of a cleaving agent 11116, such as TFA. As in the previous embodiments, microreactor carrier 11112 includes a filter or frit 11118 at its lower end to prevent particles from microreactor(s) 11112 from escaping through the opening in the lower end and passing into the cleaved solution.

Cleaving block 11102 has a U-tube guide formed therein with ascending and descending bores and a divider with curved portion 11124 dividing the two bores. U-tube 11122 with curved section 11123 is retained and supported within the U-tube guide. The spacing between curved portion 11124 and the top surface of cleaving block 11102 is slightly less than the outer diameter of U-tube 11122 so that curved section 11123 protrudes above the top surface. A plurality of nipples 11126 are formed or attached to the underside of microreactor carrier tray 11104 at positions which directly overlie the curved sections 11123. A number of springs 11128 may be disposed on the top surface of cleaving block 11102 to bias microreactor carrier 11104 at a predetermined height above the top surface of cleaving block 11102 so that no pressure is applied to curved section 11123 by nipple 11126.

Figure 77:
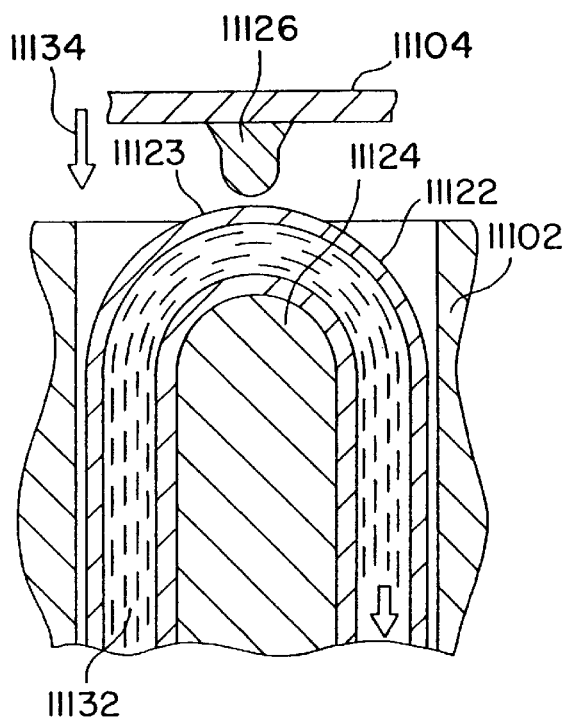
FIG. 77 is an enlarged view of the U-tube having a valve showing the valve in its open state allowing fluid to flow freely through the U-tube.
Figure 78:
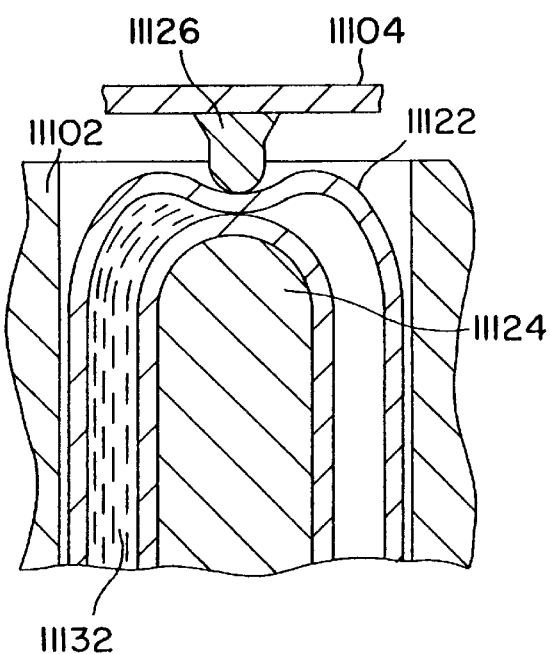
FIG. 78 is an enlarged view of the U-tube having a valve showing the valve in its closed state inhibiting the flow of fluid through the U-tube.

FIGS. 77 and 78 illustrate the implementation of the valving in more detail. In FIG. 77, microreactor carrier tray 11104 is shown in an upward-biased position, with nipple 11126 aligned with curved section 11123 of U-tube 11122. In this position, fluids 11132 or other compounds can easily flow through U-tube 11122 when a vacuum is applied to the vacuum chamber, as discussed elsewhere herein. As shown in FIG. 78, when pressure is applied to the top of carrier tray 11104 in direction 11134 to overcome the spring bias, nipple 11126 presses downward on curved section 11123 of U-tube 11122 so that the force between nipple 11126 and curved portion 11124 collapses the sidewalls of curved section 11123, thus preventing the flow of all fluid 11132 through U-tube 11122.

Alignment pin 11108 includes a spring-biased resilient tab 11110. When carrier tray 11104 is aligned over the top of cleaving block 11102 and alignment bore 11106 is slid over pin 11108, resilient tab 11110 is pressed so that it retracts into a spacing within the pin body. When sufficient pressure is applied to the top of carrier tray 11104 to prevent fluid flow in U-tube 11122, the upper surface of carrier tray 11104 is below the bottom edge of resilient tab 11110, allowing tab 11110 to resile outward, where it locks carrier tray 11104 in the lowered position. Once cleaving is completed, resilient tabs 11110 may be physically depressed into the pins 11108, either manually or robotically, allowing the microreactor carrier tray 11104 resile upward to its spring-biased position. As will be apparent to those skilled in the art, the movable tabs and springs discussed herein are exemplary only, and other biasing and locking methods may be used.

To assist in the cleaving process, cleaving block 11102 may be equipped with heaters 11132, as shown in FIG. 76, to increase its temperature during the cleaving process. Heater 11132 can be an electrically-controlled resistive heating element which is implemented by embedding or otherwise inserting wire 11134 into the block and applying a controlled electrical current to establish the proper temperature of the cleaving block. The heater as described and alternative heating elements are well known in the art and may be readily adapted for use in heating cleaving block 11102.

(5) A fifth embodiment

Figure 79:
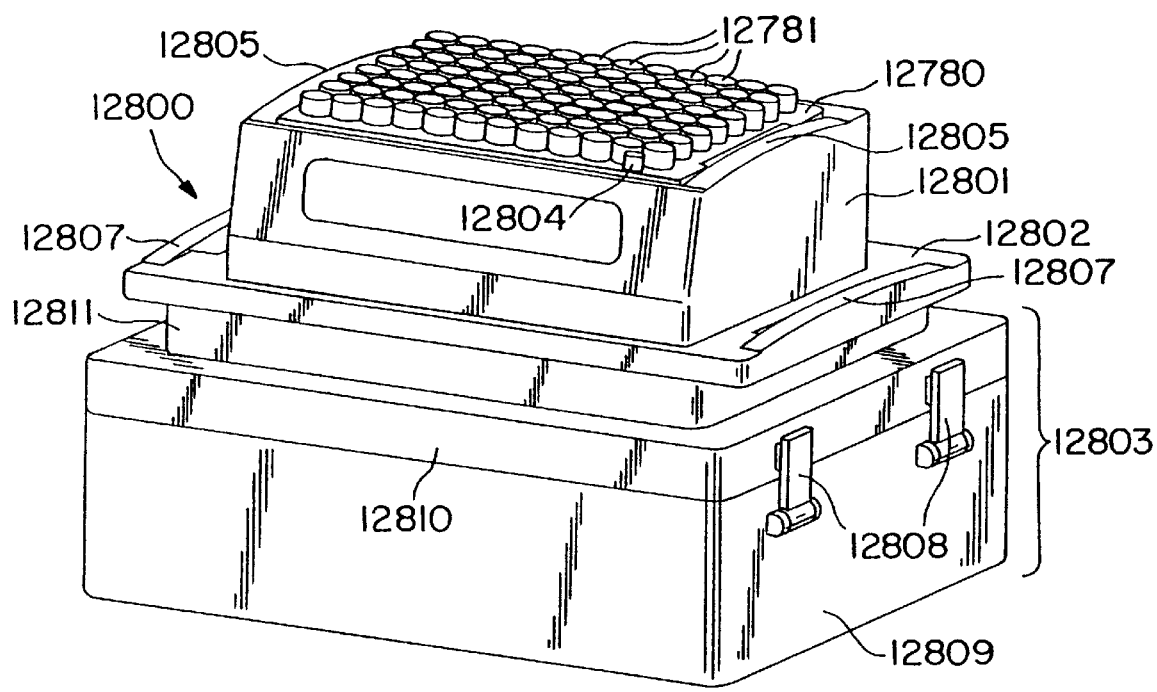
FIG. 79 is a perspective view of a second embodiment of the cleaving assembly for use with the automated sorting system.

The cleaving assembly 12800 illustrated in FIG. 79 provides an alternate embodiment for cleavage of synthetic compounds. The matrix-with-memory devices have already been sorted into microreactor carriers 12871 in microreactor carrier 12780. Microreactor carrier tray 12780 is then removed from sorter assembly 12700 and is placed on cleaving block 12801.

Cleaving block 12801 is shown with the tray 12780 disposed on its upper surface, positioned within the recessed area between guide rails 12805. As in the previous embodiment, exemplary cleaving block 12801 is formed with an array of ninety-six wells 13001 having dimensions to provide a small clearance fit between microreactor carriers 12780 and well walls 13002, the detail of which is shown in FIG. 81. Cleaving block 12780 may be formed with any number of wells 13001 for compatibility with standard microtiter formats or custom formats. The lower portion of cleaving block 12780 is formed as a flange 12802 which overhangs a recess 12811, to facilitate raising and lowering the upper portion of cleaving assembly 12800. Stepped or recessed areas 12807 in the outer side edges of flange 12802 may be formed to enhance the ability to grasp flange 12802. Below recess 12811 is a base portion 12810 which provides the upper sealing portion for vacuum chamber 12809. As shown in FIG. 80, cleaving block 12801 is formed as an outer shell 13001, which includes ridges 12805, flange 12802, recess 12811 and base portion 12810, which surrounds center block 13003 into which wells 13001 are formed. Wells 13001 may be formed by machining bores into the material from which center block 13003 is formed, which, as in the previous embodiment, may be TEFLON™ or polypropylene. Referring to FIG. 82, in addition to the bores, a lateral extension 13004 is created in the bottom of well 13001 to provide fluid communication with the lower end of a second bore 13017 into which the ascending portion 13008 of a U-tube is inserted. The bottoms of wells 13001 are sealed by plate 13006, which is attached to the lower surface of center block 13003.

As previously described with regard to other embodiments of the cleaving assembly, U-tubes are used to draw the cleaved fluid from wells 13001 into vials 13020 located within vacuum chamber 12809, as shown in FIG. 80. Referring again to FIG. 82, ascending portion 13008 of U-tube closely fits within second bore 13017. The relative dimensions of the lower end 13021 of the U-tube and the lower end of second bore 13017 are such that an interference fit is provided to create tight vacuum seal for drawing the liquid in the bottom of well 13001 through bore 13017 and into the U-tube. The details of the interference it and the slanted cut of lower end 13021 are provided in FIG. 83. Referring again to FIG. 82, at the top of bore 13017, U-tube 13014 bends and turns downward into third bore 13010, which continues through center block 13003 and lower plate 13006, allowing descending portion 13009 of the U-tube to extend beyond the bottom surface of the cleaving block. Using the same interrelationship described with reference to FIGS. 77 and 78, as shown in FIG. 82, the combination of the bend 13014 in the U-tube and the nipple 13023 which extends downward from the bottom of carrier tray 12780 provide a valve for preventing the flow of fluids through the U-tube when downward pressure is applied to the carrier tray 12780 by pinching bend 13014 between nipple 13023 and bridge 13015, which is located between the tops of second bore 13017 and third bore 13010. A top view showing the relative positioning of wells 13001 and bend 13014 in the U-tube for a plurality of wells 13001 is provided in FIG. 81. As previously described with reference to other embodiments, the U-tube is formed from resilient material which can be compressed under external pressure to prevent fluid flow therethrough, but resiles to re-open when the external pressure is released.

Referring again to FIG. 82, The descending portion 13012 of the U-tube extends beyond the bottom surface of plate 13006 via third bore 13010, across gap 13011, and through nozzle array interface plate 13022, in which is formed an array of ports 13023. Gap 13011 is provided to permit the routing of the exiting U-tubes 13012 to various ports 13033 in plate 13022, allowing a variety of routing options to be selected. It should be noted that the direct vertical correspondence between the exiting U-tubes 13012 and the feeding end 13016 of the U-tubes is shown for simplicity, and that exiting U-tubes may be passed laterally within gap 13011 so that it is directed toward a different vial or vials 13020 within vacuum chamber 12803. Vials 13020 are retained within vial tray 13025, which is positioned on the inside of vacuum chamber bottom 12809.

In order to provide a good quality seal against the loss of vacuum within vacuum chamber 12803, the upper inside edge 13024 of vacuum chamber 12809 should create an interference fit with the lower edge of interface place 13022. Referring back to FIG. 79, the vacuum seal is also enhanced by the use of latches 12808, which pull and lock base 12811 and vacuum chamber bottom 12809 together. The vacuum tubing 13026 is connected to a vacuum pump or other conventional means for drawing a vacuum on vacuum chamber 12803.

EXAMPLE 3
Preparation of a library and encoding the matrices with memories

A typical matrix-with-memory, such as the MICROKAN matrix-with-memory reactor will provide the following yield:

| | |
|---|---|
| Resin loading | 0.5–1.0 μmol/mg resin |
| Using 30 mg of resin: | 15–30 μmol compound |
| For a 500 MW compound: | 7.5–15 mg of compound. |

A pool of the matrices with memories prepared was split into two equal groups. Each group was then addressed and write-encoded with a unique radio frequency signal corresponding to the building block, in this instance an amino acid, to be added to that group.

The matrices with memories were then pooled, and common reactions and manipulations such as washing and drying, were performed. The pool was then re-split and each group was encoded with a second set of radio frequency signals corresponding to the next set of building blocks to be introduced, and the reactions were performed accordingly. This process was repeated until the synthesis was completed. The semiconductor devices also recorded temperature and can be modified to record other reaction conditions and parameters for each synthetic step for storage and future retrieval.

Ninety-six matrices with memories were used to construct a 24-member peptide library using a 3×2×2×2 "split and pool" strategy. The reactions, standard Fmoc peptide syntheses [see, e.g., Barany et al. (1987) *Int. J. Peptide Protein Res.* 30:705–739] were carried out separately with each group. All reactions were performed at ambient temperature; fmoc deprotection steps were run for 0.5 h; coupling steps were run for 1 h; and cleavage for 2 h. This number was selected to ensure the statistical formation of a 24-member library [see, Burgess et al. (1994) *J. Med. Chem.* 37:2985].

Each matrix with memory in the 96-member pool was decoded using a specifically designed radio frequency memory retrieving device [Bio Medic Data Systems Inc. DAS-5001 CONSOLE™ System, see, also U.S. Pat. No. 5,252,962 and U.S. Pat. No. 5,262,772] the identity of the peptide on each matrix with memory. The structural identity of each peptide was confirmed by mass spectrometry and $^1$H NMR spectroscopy. The content of peptide in each crude sample was determined by HPLC to be higher than 90% prior to any purification and could be increased further by standard chromatographic techniques.

Detailed exemplification of the use of matrix-with-memory combinations for synthesis of libraries, as well as for screening is described in co-pending, co-owned applications U.S. application Ser. Nos. 08/428,662, 08/480,147, 08/484,486, 08/484,504, 08/480,196, 08/473,660, 08/538,387, 08/567,746, 08/639,813, 08/711,426, 08/709,435, 08/723,423, 08/633,410, 08/669,252, 08/726,703, 08/743,984, 08/741,685, 08/857,800, 08/826,253 and 08/912,998, as well as published International PCT application Nos. WO 96/36436 and WO 97/12680.

EXAMPLE 4
Radiation grafting of a polymer on a insert surface for preparation of matrices with memories Matrices for use as supports for synthesis and for use in coupled [single platform] protocols have been prepared using radiation grafting. These supports include any inert surface, including PFTE [TEFLON®], which heretofore does not appear to have been used for radiation grafting. The methods exemplified below have been designed for use with PFTE as well as other surfaces. A method of radiation-induced crafted copolymerization of styrene to Teflon (PTFF) has been developed.

A. Scheme 1

1. Preparation of polymer

Polystyrene is radiation grafted onto polypropylene or TEFLON® tubes, an RF tag, such as the BMDS tag, or IDTAG transponder, was inserted into the tube to produce a microreactor (e.g., MICROTUBE™ microreactor, available from IRORI, La Jolla, Calif.). The polystyrene is then functionalized with selected functional groups. Scintillant is covalently linked onto the polystyrene though "A", and a bioactive molecules, such as, for example, biotin, can be synthesized on the surface using the remaining "A" functionalities.

2. Radiation

The teflon (PTFE) tube was radiated under a Co$^{60}$ source at a dose rate of $0.1 \times 10^5$ r/h; the total dose is typically $2.6–2.9 \times 10^6$ r.

3. Polymers

Using radiation-induced grafting polymerization techniques, a variety of monomers such as styrene, acrylic acid, methylacrylic acid, 2-hydroxymethylacrylate, and other such monomers can be used to produce different polymeric surfaces with different functional groups on polypropylene (PP), polyethylene (PE) and fluoropolymers. Polyethylene oxide (PEG) may be grafted onto the surface to change the hydrophilicity and reduce the steric-hindrance to antibodies or receptors. Functional groups such as amines, alcohols and phenols, carboxylic acids, halides, aldehydes, nitriles and other such groups. can be introduced.

It was found that dilution of monomers, such as styrene, with methanol enhanced the rate of grafting PP and PTFE tubes have demonstrated highest styrene grafting at styrene concentrations of about 25 to 50%.

4. Functionalization

The functionalization was performed using the readily available N-(hydroxymethyl) phthalimide, with trifluoromethanesulfonic acid as catalyst. The polystyrene grafted tubes is thoroughly washed before use to remove residual monomer, non-attached polystyrene and additives remaining from radiation grafting. The amidoalkylation proceeds smoothly in the 50% (v/v) trifluoroacetic acid—dichloromethane as solvent at room temperature for 24 hours. The predetermined loading can be obtained by changing the concentrations of reagent, catalyst and reaction time. The hydrazinolysis in refluxing ethanol gives the aminomethyl polystyrene grafted PTFE tube.

The MICROTUBE microreactors were prepared in different sizes (2–12 mm) with loading capacity range from 0.5–15 ymol per tube.

5. Fluorophores

The scintillants, which are chemical stable, were chosen to match the energy gap from radiation energy of radioisotopes. Scintillants such as 9-anthracenepropionoc acid, 1-pyrenebutanoic acid and their derivatives are matched to the energy transfer for different radioisotopes, in including $^{125}$I, $^{3}$H, $^{14}$C and others. Care should be taken when selecting combinations of scintillants and radioisotopes to match so that energy transfer from isotope to scintillant is matched.

A portion of the functional groups were covalently linked to the mixture of primary fluor (S1, molecules that emit light following interaction with radiation) and secondary fluor (S2, wavelength shifter). Experiments were performed with mixture of S1/S2 at the ratio ranging from 20:1 to 100:1 for S1 and S2 respectively, with optimum ratio of 40:1 for most of the experiments presented here. Conditions in which 20% to 80% of the functional groups were occupied with mixture of S1/S2 were evaluated. The optimum number of the functional group linked to primary and secondary fluors for most of the experiments was 50%.

The remaining of the functional groups (20% to 80%) were used for chemical synthesis. Small molecules (e.g., biotin) were synthesized on the solid support as described in the scheme 2.

6. Chemical synthesis on the surface of microreactor such as a MICROTUBE™ microreactor A variety of small molecules, such as biotin, peptides, and oligonucleotides, may be synthesized on the MICROTUBE (available from IRORI, La Jolla, Calif.) microreactor [see, e.g., scheme 2 (biotin), below]. In order to reduce steric hinderance and improve the interaction of labeled biological target (e.g. antibody, receptor, and complementary DNA or RNA, labeled probe), and depending on the size and nature of the small molecule, different percentages of the functional groups were used for chemical synthesis while the remaining functional group(s) were blocked with Boc. Conditions in which 0.25% to 100% of the functional groups were used for chemical synthesis were evaluated. The results indicated that use of 25% of the functional groups for chemical synthesis is optimal.

B. Scheme 2: Biotin synthesis

In order to reduce steric hinderance and improve the interaction of labeled biological target [e.g., $^{125}$I-receptor), and depending on the size and nature of the small molecule, a different percentage of the functional groups was utilized for chemical synthesis, while the remaining functional group were blocked with Boc. The experiments indicate that optimum results are obtainable with 25% of the functional group dedicated for chemical synthesis.

1. Synthesis

Fmoc (Fmoc-Gly-OH) and Boc(Boc-Gly-OH) linked amino acids were used to control the loading of scintillants and remaining amines. The Fmoc groups were removed using 20 piperidine in DMF, and Boc groups were removed using 1:1 ratio of TFA and dimethylmethane. 50% amine groups were covalently linked to scintillants. The remaining 50% amine were used to synthesis biotin.

2. Assays

As described elsewhere (see, e.g., International PCT application No. WO 96/35436) memories-with-matrices can be used in any screening assay, and particularly can be used in multi-analyte assays. Test compounds of interest are synthesized on the beads or linked thereto, the identity of the linked compounds is encoded in the memory either during or following synthesis, linkage or coating, and the resulting matrix-with-memory combination is used for screening. The matrix-with-memory combination is used or the linked biological particles are cleaved and used in screening assays. As described herein, they are cleaved into vessels that include memories so that their identities can be tracked.

The assays included receptor assays, cell-based assays, immunoassays, non-radioactive energy transfer reactions, such as FET or FRET, FP and HTRF assays (see, e.g., Cardullo et al. (1988) *Proc. Natl. Acad. Sci. U.S.A.* 85:8790–8794; Peerce et al. (1986) *Proc. Natl. Acad. Sci. U.S.A.* 83:8092–8096; U.S. Pat. No. 4,777,128; U.S. Pat. No. 5,162,508; U.S. Pat. No. 4,927,923; U.S. Pat. No. 5,279,943; and International PCT Application No. WO 92/01225), scintillation proximity assays, and any other assay of interest.

C. Radiation grafting

Teflon tube [19 mm, long, OD:5 mm, ID:2 mm] were radiation grafted. It was found that dilution of styrene with methanol enhances the rate of grafting. Dilutions of from 5% to 70% were tested. The PTFE tube has the highest styrene grafting at a 50% dilution. The polypropylene tube has the best performance at 35% dilution. The teflon (PTFE) tube is radiated under Co$^{60}$ source at a dose rate of $0.1 \times 10^6$ r/h; the total dose of $2.6–2.9 \times 10^6$ r.

Functionalization was performed using N-(hydroxymethyl) phthalimide, with trifluoromethane-sulfonic acid [TFMSA] as a catalyst. The polystyrene grafted PTFE tube is thoroughly washed before use to remove residual monomer, non-attached polystyrene and additives remaining from radiation grafting. The amidoalkylation proceeds smoothly in the 50% (v/v) trifluoroacetic acid—dichloromethane solvent at room temperature for 24 hours. The predetermined loading can be obtained by changing the concentrations of reagent, catalyst and reaction time. The hydrazinolysis in refluxing ethanol gives the aminomethyl polystyrene grafted PTFE tube.

Loading on the grafted tubes and balls is adjustable can was typically about 0.5–15 $\mu$mol per tube. The amount can be varied by altering the size of the tube or balls. A variety of selected functional groups are available. Any known to those of skill in the art may be used, including any described herein. PFTE devices are particularly suitable for high temperature reactions [loading was less than or about 3 $\mu$mol per device].

D. Protocol for Increasing Loading on Fluoropolymer

Dilution of styrene with methanol enhances the rate of grafting. In the radiation-induced grafted copolymerization of styrene to ETFE and Teflon (PTFE) tube (21 mm long, OD:6 mm, ID: 4 mm), dilutions of from 5% to 70% were tested. The PTFE tube had the highest styrene grafting at a 50% dilution. By adding a mineral acid such as sulfuric acid and nitric acid (concentrations from 0.01–0.5M), the polystyrene grafting was increased from 50–200%. See Table below. Loading was further improved by machining the ETFE/PTFE tubes from rods rather than extruding the tubes from ETFE/PTFE resin beads at high temperatures. The machined tubes, which as a result of the crimping introduced by machining are about 4 mm shorter than the extruded tubes, have more rough surfaces than the extruded tubes.

| Sulfuric Acid (M) | Polystyrene amount (mg) loaded per tube | | |
|---|---|---|---|
| | extruded ETFE tube | machined PTFE tube | machined ETFE tube |
| 0 | 17 | 10 | 19 |
| 0.05 | — | 12 | 32 |
| 0.1 | 38 | 24 | 48 |
| 0.2 | — | 38 | 56 |

In addition, adjusting the polystyrene concentration in combination with the use of acid increased the loading. The best increase was observed at a concentration of about 45% styrene in methanol. At 45% styrene grafted in the presence of acid, the amount of polystyrene loaded per tube was almost 70 mg, compared to in the absence of acid (less than about 20 mg loaded). At other concentrations of styrene in acid the amount loaded varied from about 30 mg to the high of 70 mg. In the absence of acid, loading is substantially independent of polystyrene concentration for the tested concentration range (25% to 50%).

The functionalization was performed as described above, using N- (hydroxymethyl) phthalimide, with trifluoromethanesulfonic acid as catalyst. The polystyrene grafted PTFE tube was thoroughly washed before use to remove residual monomer, non-attached polystyrene and additives remaining from radiation grafting. The amidoalkylation proceeded smoothly in the 50% (v/v) trifluoroacetic acid—dichloromethane as the solvent at room temperature for 24 hours.

A predetermined loading can be obtained by changing the concentrations of reagent catalyst and reaction time. The hydrazinolysis in refluxing ethanol gave the aminomethyl polystyrene grafted PTFE or ETFE tube. The loading of amine groups on a PTFE tube was about 41 micromol, and on an ETFE was as high as 52 micromol.

| Acid Concentration (M) | Polystyrene attached on tube surface (mg) PTFE | Polystyrene which attached on tube surface (mg) |
|---|---|---|
| 0 | 10 | 19 |
| 0.05 | 12 | 32 |
| 0.1 | 12 | 33 |
| 0.2 | 20 | 35 |

The two modifications to the procedure using acid and also machining the polymer substantially increased polystyrene radiation grafting loadings. Adding a mineral acid such as sulfuric or nitric (concentrations 0.01M to 0.5M) increased the the grafted polystyrene from about 20 to 200%. Using a rough surface further increased the loading.

EXAMPLE 5

Wash and SPA assay procedure using MICROTUBE microreactors

1. Covalently linking scintillant to the surface of the MICROTUBE microreactor

Scintillants (pyrenebutyric acid and 9-anthracenepropionic acid) were covalently linked to the grafted polystyrene on the surface of the polymer. The Fluorophore was linked to 50% of the available functional groups as described above (see polymer preparation).

2. Synthesizing biotin on the MICROTUBE™ microreactor

The remaining 50% functional amine groups on the surface of the MICROTUBE microreactor was estimated by Fmoc to be ≠1.8 $\mu$mol/tube. The amine group was covalently linked to biotin under conditions described below. 0.012M biotin, 0.024 MDIEA (diisopropylethylamine), 0.012M PYBOP (Benzotriazol-1-yl-oxy-tris-pyrrollidino-phophonium hexafluorophosphate) in DMF (N,N-Dimethyl foramide) at room temperature for 1 hour.

3. Washing protocol for MICROTUBE microreactors

A. Development and Optimization of wash procedure.

The MICROTUBE microreactors were washed with various detergents (SDS, CHAPS, Triton X-100, or Benzalchonium Chloride) or charcoal. The effects of detergents were evaluated by washing the microreactors with different concentrations of detergents (0.5 to 5% in PBS) for 24 hours on an orbital shaker at room temperature. The charcoal wash was done by dialysis against PBS containing 10–35% charcoal (4–8 mesh).

It was found that the MICROTUBE microreactors that had been washed with SDS, Benzalchonium Chloride or charcoal had an improved signal. Additional wash studies were performed with either SDS and/or charcoal in wash buffer. The effect of SDS concentration was assessed by washing the tube with 0.25, 0.5, 0.75, or 1% SDS in PBS for 24 hours. Results of this experiment indicated that microreactors that had been washed with 0.5%–0.75% SDS and/or charcoal in PBS yielded a better signal.

Finally, the optimal wash period was determined by washing microreactors with 0.75% SDS/charcoal for 1, 2, 3, 4, or 5 days at room temperature on an orbital shaker. The results of this experiment revealed that washing tubes for 2 days efficiently removes undesirable material which interfere with the SPA signal.

B. Optimized Wash Procedure.

After synthesis of small molecules (biotin) on the MICROTUBE microreactors were washed as described above. The MICROTUBE microreactors were placed in a dialysis bag and were dialyzed against PBS containing 0.75% SDS +/−35% charcoal for 2 days at room temperature on an orbital shaker. At the end of SDS wash, microreactors were rinsed with PBS (10 ml/MICROTUBE) 2 times.

Thus, performance of assays on solid supports can be improved by washing the solid support with linked biological particle or molecule with 0.75% SDS with or without 35% charcoal in PBS (pH 7.2) for about 2 days.

2. Blocking

The MICROTUBE microreactors were placed in PBS (pH 7.2) buffer containing 3% BSA (bovine serum albumin) and incubated overnight at 4° C.

3. SPA Detection.

Biotin was detected in the SPA format. MICROTUBE microreactors were placed in 24 well plate containing 1 ml of Assay Buffer [10 mM Sodium Phosphate pH 7.2, 150 mM NaCl, 0.5% BSA, 0.05% Tween 20, and $^{125}$I-streptavidin (244 ng/ml, specific activity 0.291 $\mu$Ci/$\mu$g)]. MICROTUBE microreactors were incubated at room temperature on an orbital shaker for 2 hours. The extent of $^{125}$I streptavidin binding on the MICROTUBE microreactors was assessed in a Wallac MicroBeta Trilux scintillation counter.

Since modifications will be apparent to those of skill in this art, it is intended that this invention be limited only by the scope of the appended claims.

What is claimed:

1. An apparatus for use in a cleaving reaction using compounds from a plurality of microreactors, wherein each microreactor is disposed within a carrier having an at least partially open lower end, and wherein a plurality of carriers are disposed in a first array within a carrier tray, the apparatus comprising:

a cleaving block comprising a plurality of bores adapted for receiving the plurality of carriers, wherein the plurality of bores is arranged to correspond to the first array within the carrier tray so that each carrier is disposed within a corresponding bore;

a drain means disposed at a lower end of each bore of the plurality of bores, the drain means comprising at least one drain tube which extends outside of the cleaving block and further comprising a valve means adapted for preventing flow through the at least one drain tube;

a plurality of wells arranged in a second array;

a vacuum chamber abutting the cleaving block to form a vacuum seal, the plurality of wells being disposed within the vacuum chamber so that the at least one drain tube is directed toward a well of the plurality of wells;

a vacuum source connected to the vacuum chamber; and a controller for activating the vacuum source to draw a vacuum on the vacuum chamber.

2. The apparatus of claim 1, wherein the drain means includes a trap for preventing a flow through the at least one drain tube when the vacuum is not being drawn.

3. The apparatus of claim 2, wherein the trap comprises a U-tube comprising an inverted U-shape.

4. The apparatus of claim 1, further comprising a plurality of well trays disposed within the vacuum chamber for retaining the wells.

5. The apparatus of claim 1, further comprising at least one alignment key for aligning the carrier tray with the cleavage block.

6. The apparatus of claim 1, wherein the carrier tray includes a remotely readable tag for identifying the carrier tray.

7. The apparatus of claim 1, wherein the well tray includes a remotely readable tag for identifying the well tray.

8. The apparatus of claim 1, wherein the cleaving block includes a remotely readable tag for identifying the cleaving block.

9. The apparatus of claim 1, wherein the drain tube is a U-tube and the valve means comprises a structure for collapsing a section of the drain tube.

10. The apparatus of claim 1, further comprising a shaker for accelerating the cleaving process.

11. The apparatus of claim 1, wherein the carrier tray is compatible with and fits within an automated sorter unit drawer.

12. The apparatus of claim 1, further comprising a heating element for heating the cleaving block to enhance cleavage.

13. An apparatus for use in a cleaving reaction simultaneously using a plurality of compounds from a plurality of microreactors using a cleaving agent, wherein each microreactor has been sorted into a plurality of open-bottom carriers disposed in a first array within a carrier tray, the apparatus comprising:

a cleaving block comprising a bore corresponding to each carrier of the plurality of carriers, each bore being adapted to receive at least a bottom portion of each carrier and for retaining the cleaving agent;

a plurality of wells for receiving a solution formed from the cleaving agent and the compound;

a plurality of drain tubes, each drain tube comprising a first end disposed adjacent a bottom of each bore and a second end disposed above or within a well of the plurality of wells;

a valve means for preventing flow through each drain tube;

a vacuum chamber comprising tray for holding the plurality of wells in a second array, the vacuum chamber abutting the cleaving block to form a vacuum seal so that a vacuum drawn on the vacuum chamber draws the solution through the plurality of drain tubes and into the plurality of wells.

14. The apparatus of claim 13, wherein each drain tube comprises a U-tube comprising an inverted U-shape.

15. The apparatus of claim 14, wherein the valve means comprises means for collapsing a section of the drain tube.

16. The apparatus of claim 13, wherein the carrier tray includes a remotely readable tag for identifying the carrier tray.

17. The apparatus of claim 13, wherein the plurality of wells are retained within a well tray, and the well tray includes a remotely readable tag for identifying the well tray.

18. The apparatus of claim 13, wherein the cleaving block includes a remotely readable tag for identifying the cleaving block.

* * * * *